(12) United States Patent
Zhao et al.

(10) Patent No.: US 11,738,047 B2
(45) Date of Patent: Aug. 29, 2023

(54) GENETICALLY MODIFIED IMMUNE CELLS TARGETING NY-ESO-1 AND METHODS OF USE THEREOF

(71) Applicant: The Trustees of the University of Pennsylvania, Philadelphia, PA (US)

(72) Inventors: Yangbing Zhao, Lumberton, NJ (US); Xiaojun Liu, Wallingford, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 16/216,774

(22) Filed: Dec. 11, 2018

(65) Prior Publication Data

US 2019/0247432 A1    Aug. 15, 2019

Related U.S. Application Data

(60) Provisional application No. 62/597,717, filed on Dec. 12, 2017.

(51) Int. Cl.
| | |
|---|---|
| *A61K 35/17* | (2015.01) |
| *C07K 19/00* | (2006.01) |
| *C07K 14/725* | (2006.01) |
| *C12N 5/10* | (2006.01) |
| *C07K 14/705* | (2006.01) |
| *A61P 35/00* | (2006.01) |
| *C12N 15/62* | (2006.01) |
| *A61K 38/00* | (2006.01) |

(52) U.S. Cl.
CPC .............. *A61K 35/17* (2013.01); *A61P 35/00* (2018.01); *C07K 14/7051* (2013.01); *C07K 14/70596* (2013.01); *C07K 19/00* (2013.01); *C12N 5/10* (2013.01); *C12N 15/62* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 9,663,763 B2 | 5/2017 | Sentman | |
| 2006/0200869 A1 | 9/2006 | Naldini et al. | |
| 2009/0053184 A1 | 2/2009 | Morgan et al. | |
| 2011/0027240 A1 | 2/2011 | Laer et al. | |
| 2014/0120622 A1* | 5/2014 | Gregory | A61K 35/26 435/462 |
| 2014/0301990 A1* | 10/2014 | Gregory | A61K 35/26 424/93.21 |
| 2014/0349402 A1* | 11/2014 | Cooper | A61K 39/001112 435/455 |
| 2015/0056705 A1* | 2/2015 | Conway | C12N 15/907 435/462 |
| 2015/0164954 A1 | 6/2015 | Bonini et al. | |
| 2015/0368316 A1* | 12/2015 | Lazar-Molnar | A61K 38/00 424/278.1 |
| 2016/0120905 A1 | 5/2016 | Galetto et al. | |
| 2016/0272999 A1 | 9/2016 | Duchateau et al. | |
| 2017/0152506 A1 | 6/2017 | Wagner et al. | |
| 2017/0175128 A1 | 6/2017 | Welstead et al. | |
| 2017/0211075 A1 | 7/2017 | Lee et al. | |
| 2017/0290858 A1 | 10/2017 | Zhao et al. | |

FOREIGN PATENT DOCUMENTS

| | | | | |
|---|---|---|---|---|
| CN | 201610226230 | * | 1/2016 | |
| WO | WO-2006031221 A1 | * | 3/2006 | ............ A61K 48/005 |
| WO | WO-2013019615 A2 | * | 2/2013 | ......... C07K 14/7051 |
| WO | 2013126726 A1 | | 8/2013 | |
| WO | 2014153470 A2 | | 9/2014 | |
| WO | 2016154596 A1 | | 9/2016 | |
| WO | 2017044661 A1 | | 3/2017 | |
| WO | 2017062451 A1 | | 4/2017 | |
| WO | 2017070429 A1 | | 4/2017 | |
| WO | 2017093969 A1 | | 6/2017 | |
| WO | WO-2017177575 A1 | * | 10/2017 | ............ C07K 14/705 |

OTHER PUBLICATIONS

UniProt No. P10747 Human CD28, sequence date 1989, 16 pages.*
UniProt No. 015116 Human PD-1, sequence date of 1997, 16 pages.*
Zhao et al. Primary Human Lymphocytes Transduced with NY-ESO-1 Antigen-Specific TCR Genes Recognize and Kill Diverse Human Tumor Cell Lines. The Journal of Immunology, 2005. 174:4415-4423.*
PDCD1 Entry from online database UniproKB, downloaded from https://www.uniprot.org/uniprot/Q15116#function on Sep. 1, 2021, 10 Pages.*
Neilsen et al. Alternative Splice Variants of the Human PD-1 Gene. Cellular Immunology, 2005. 235:109-116.*
Koehler et al. CD28 Costimulation Overcomes Transforming Growth Factor-β-Mediated Repression of Proliferation of Redirected Human CD4+ and CD8+ T cells in an Antitumor Cell Attack. Cancer Research, 2007. 67(5):2265-2273.*
Baumgaertner, et al., Ex vivo Detectable Human CD8 T-Cell Responses to Cancer-Testis Antigens, Cancer Research. 2006;66(4):1912-1916.

(Continued)

*Primary Examiner* — James D Schultz
*Assistant Examiner* — Kimberly A Aron
(74) *Attorney, Agent, or Firm* — Saul Ewing LLP; Kathryn Doyle

(57) ABSTRACT

The present disclosure provides modified immune cell (e.g., modified T cell) comprising an exogenous T cell receptor (TCR) having specificity for NY-ESO-1. The present disclosure provides modified immune cells or precursors thereof (e.g., modified T cells) comprising an exogenous TCR and a switch receptor. Gene edited modified cells are also provided, such that the expression of one or more of an endogenous T-cell receptor gene (e.g., TRAC, TRBC) or an endogenous immune checkpoint gene (e.g., PD-1 or TIM-3) is downregulated.

20 Claims, 62 Drawing Sheets

Specification includes a Sequence Listing.

(56) References Cited

OTHER PUBLICATIONS

Bunder, et al., Treatment of Metastatic Melanoma with Autologous CD4+ T Cells against NY-ESO-1, 2008, New England Journal of Medicine 358:2698-2703.

Odunsi, et al., Vaccination with an NY-ESO-1 peptide of HLA class I/II specificities induces integrated humoral and T cell responses in ovarian cancer, PNAS 104 (31) 12837-12842 (Jul. 31, 2007).

Rapoport, et al., NY-ESO-1 specific TCR engineered T-cells mediate sustained antigen-specific antitumor effects in myeloma, Rapoport et al. Nat Med. Aug. 2015; 21(8):914-921.

Robbins, et al., Tumor regression in patients with metastatic synovial cell sarcoma and melanoma using genetically engineered lymphocytes reactive with NY-ESO-1, 2011, J Clin Oncol 29:917-924.

Schumann, et al., Generation of knock-in primary human T cells using Cas9 ribonucleoproteins, PNAS 112 (33) 10437-10442 (Aug. 18, 2015).

Yuan, et al., CTLA-4 blockade enhances polyfunctional NY-ESO-1 specific T cell responses in metastatic melanoma patients with clinical benefit, PNAS 105(51):20410-20415 (Dec. 23, 2008).

PCT Application No. PCT/US2018/065020—International Search Report and Written Opinion dated Apr. 29, 2019.

\* cited by examiner

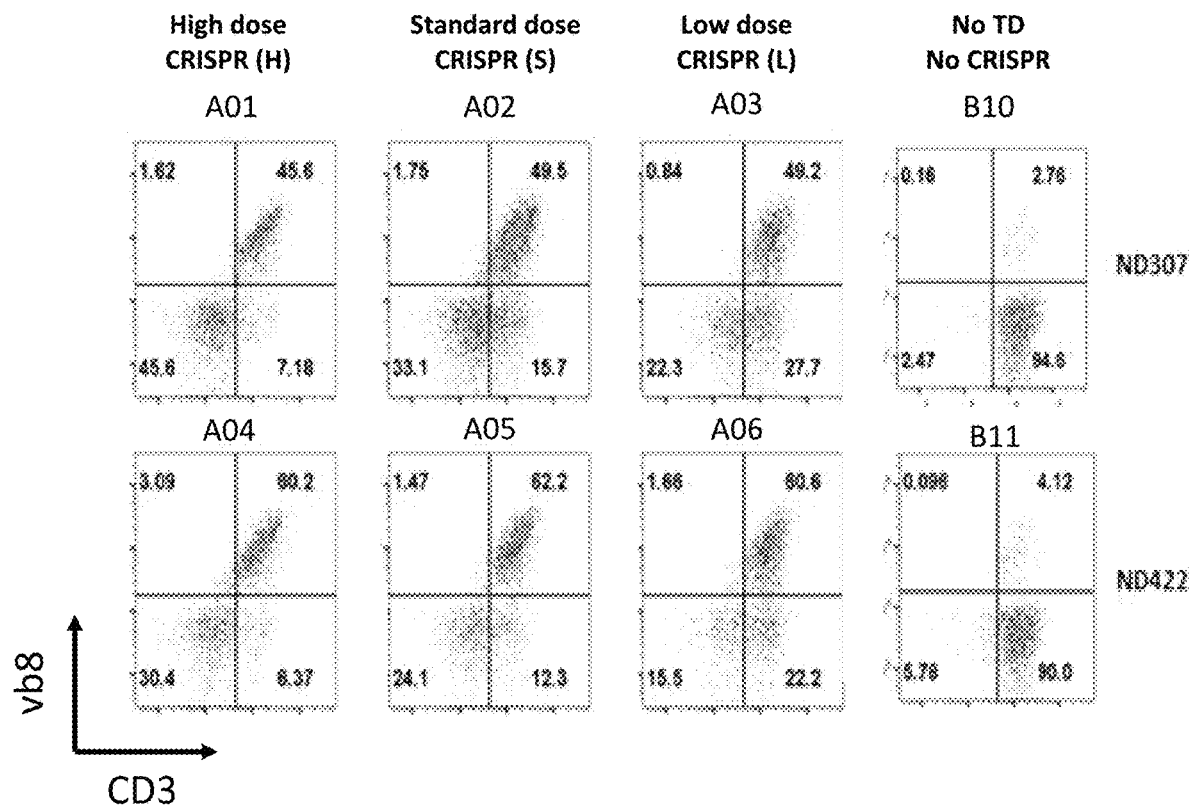
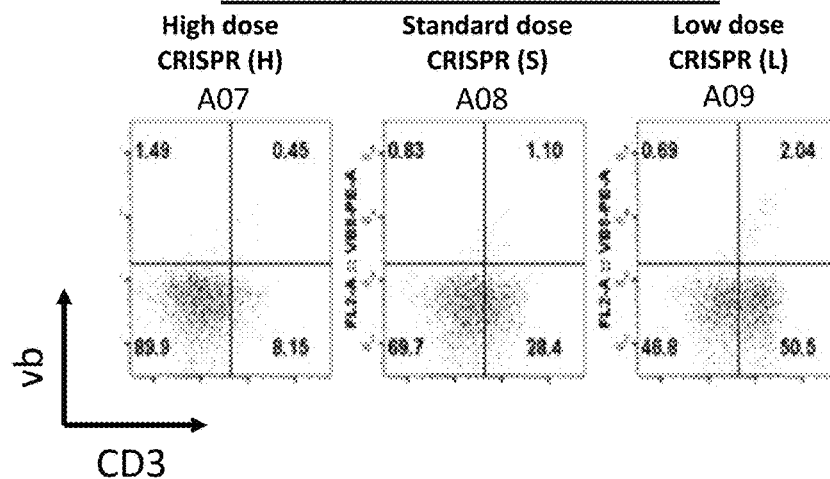
Figure 5

NY-ESO-1 TCR Transduced

Figure 8
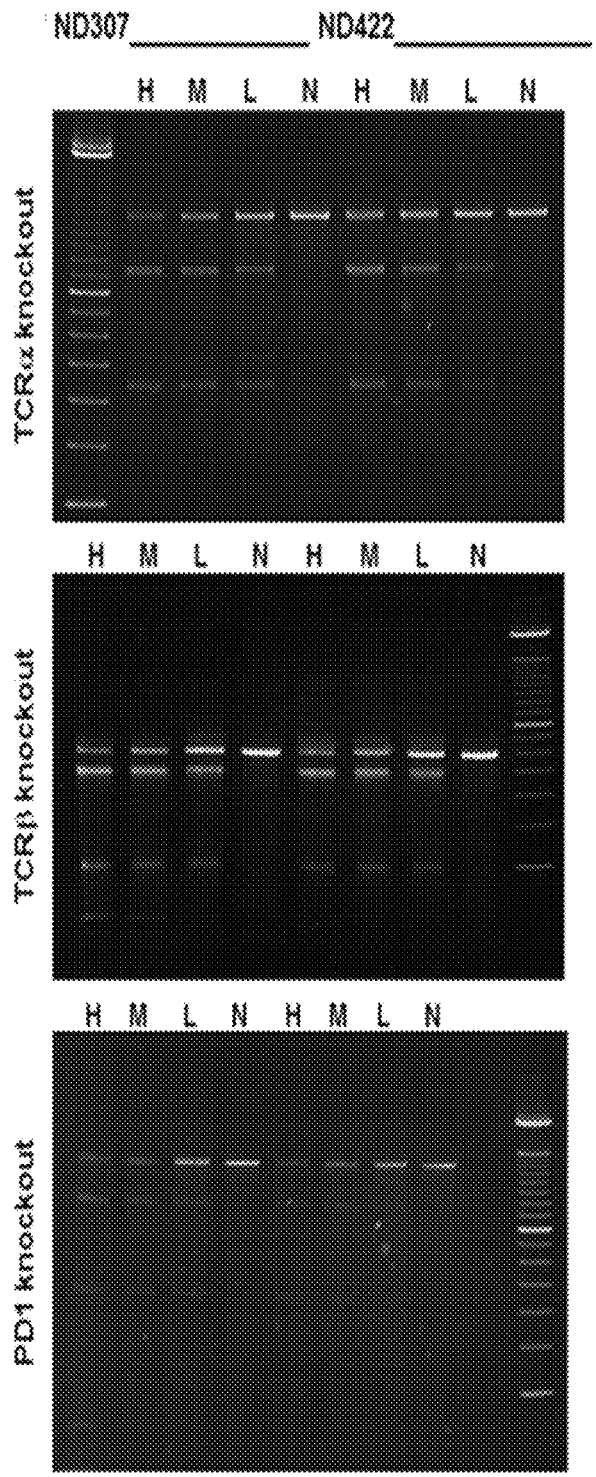
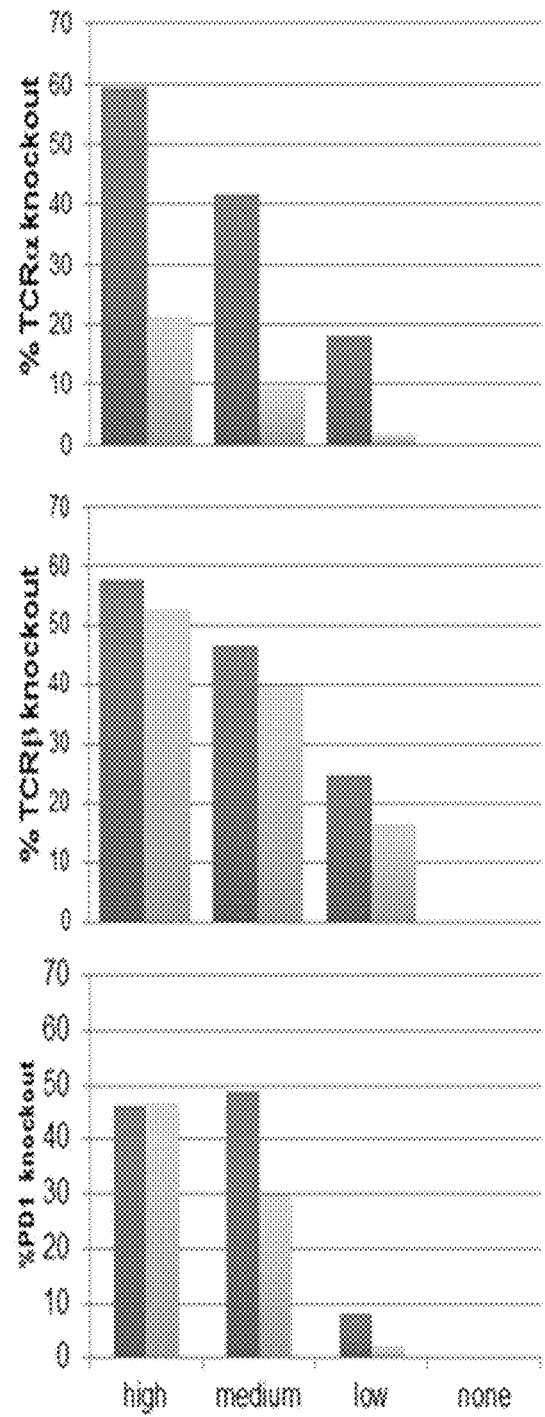

Figure 9
TD + CRISPR
| ND422H | ND422M | ND422L |
|---|---|---|
TD No CRISPR
ND422
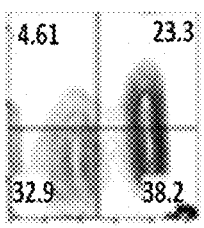 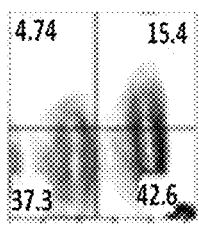 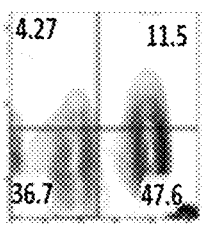 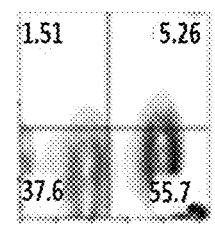 Naml6-ESO
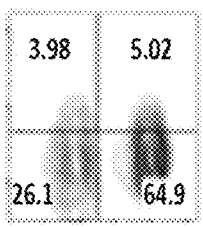 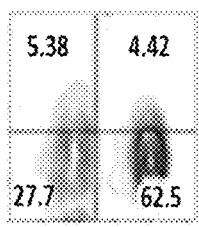 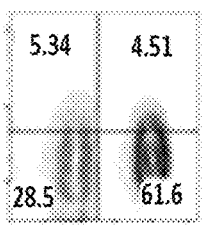 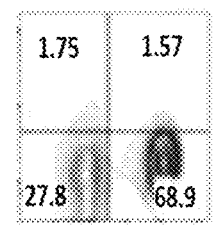 Naml6
TD + CRISPR
| ND307H | ND307M | ND307L |
|---|---|---|
TD No CRISPR
ND307
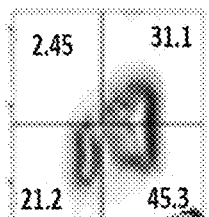 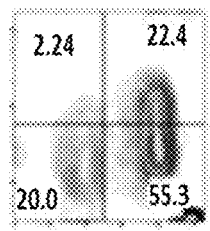 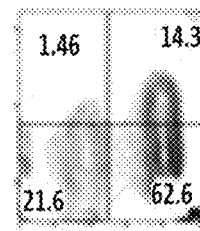 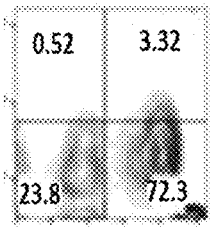 Naml6-ESO
CD107a ↑
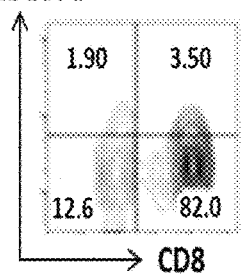 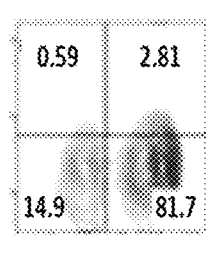 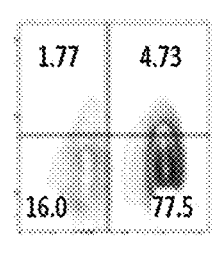 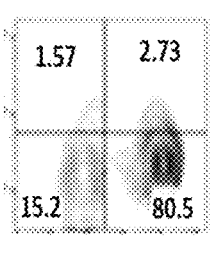 Naml6
→ CD8

Figure 16A
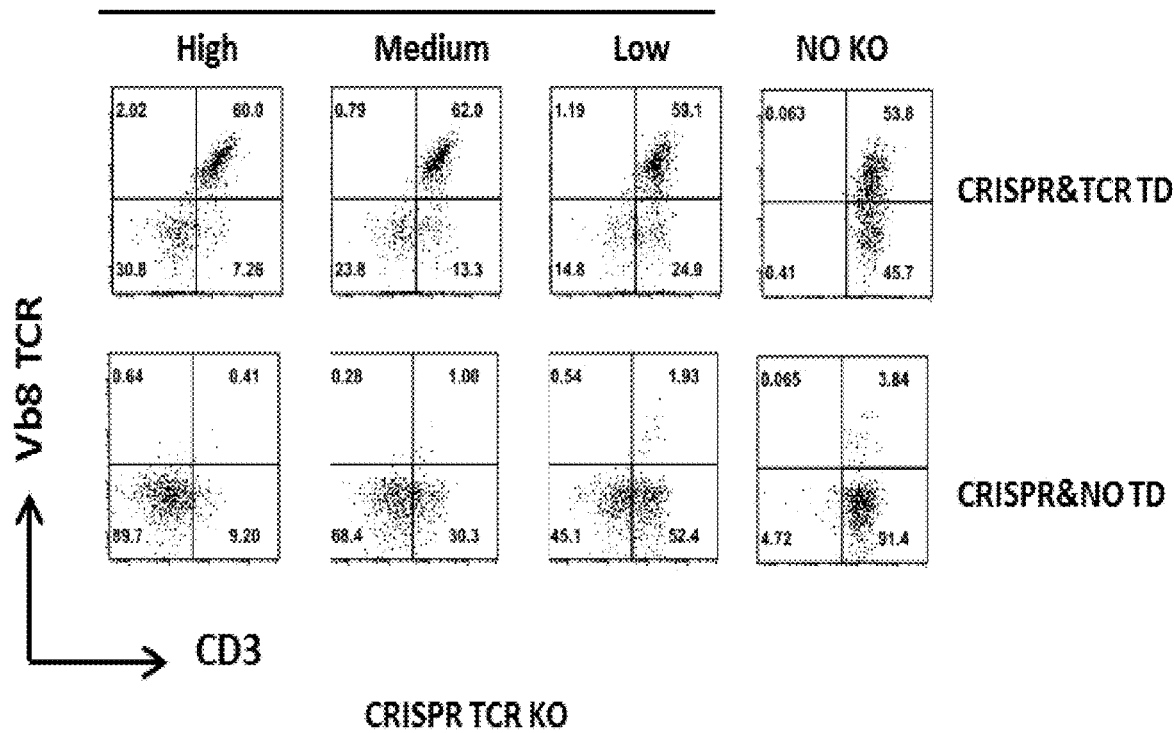
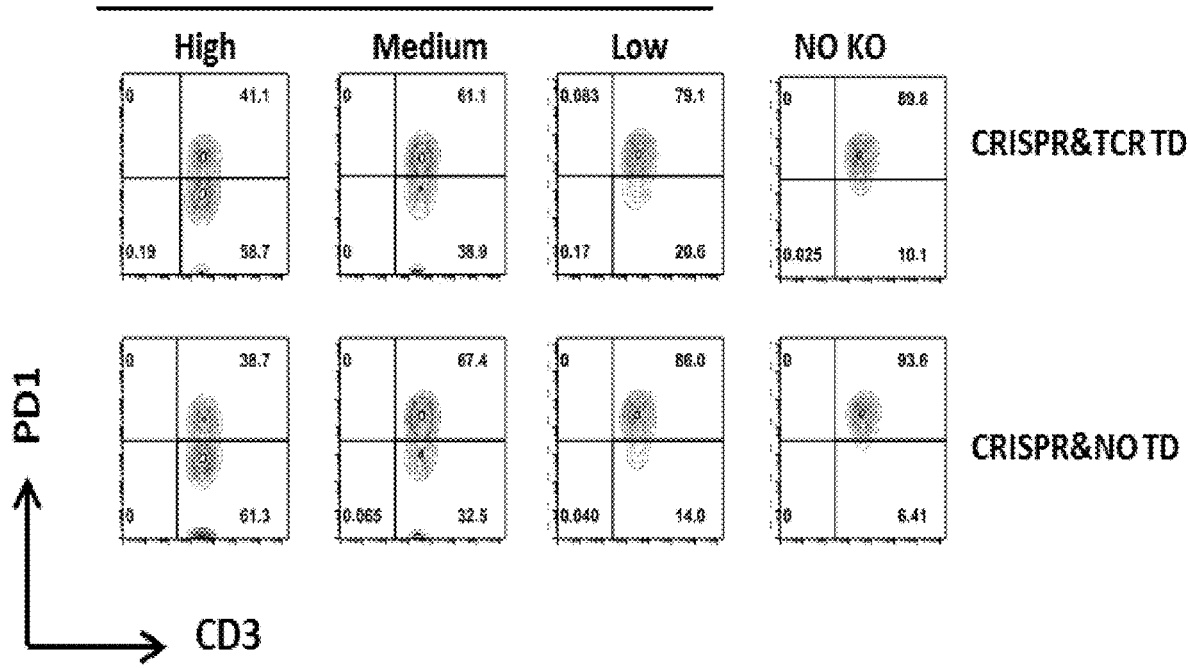

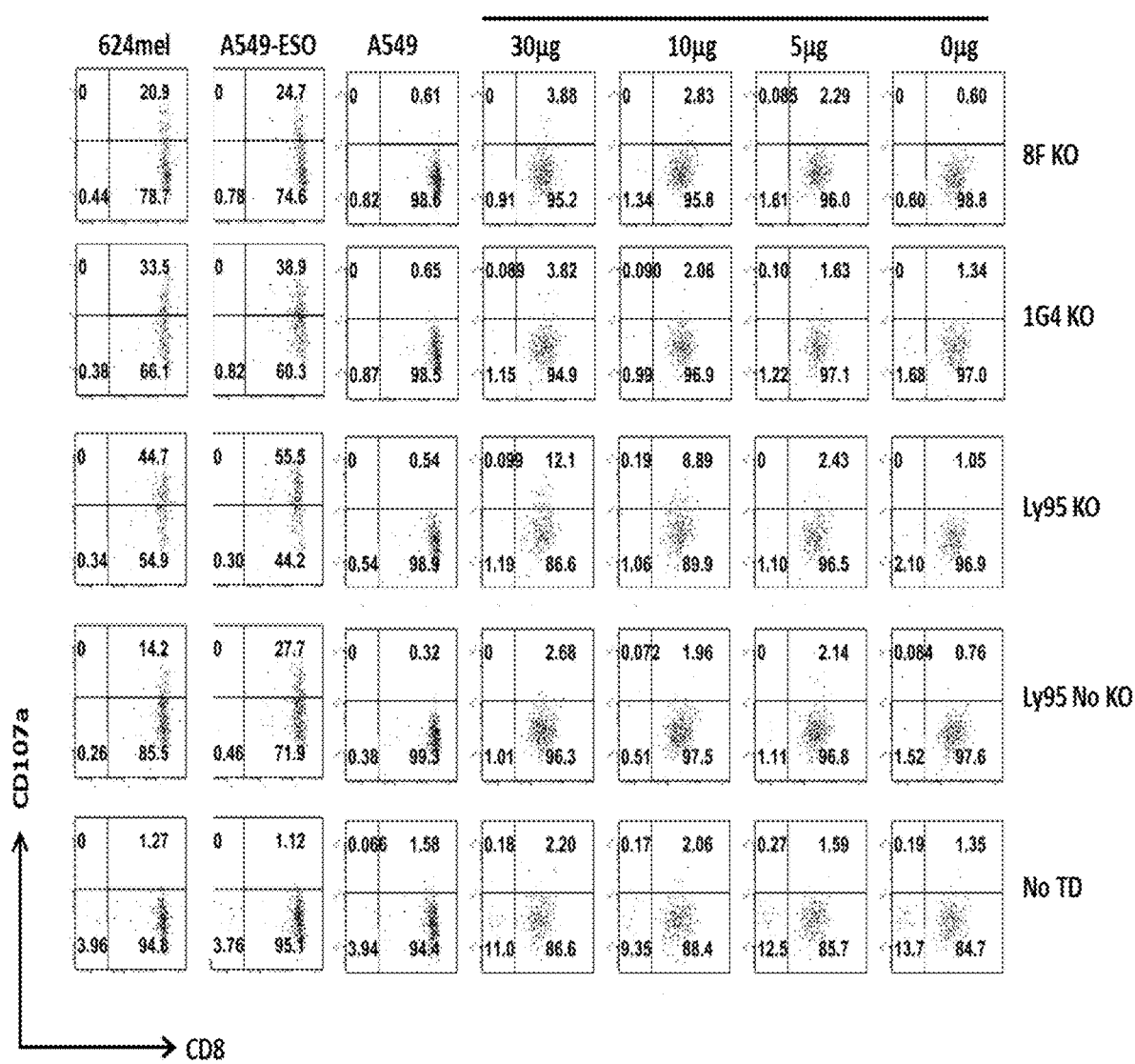

| Group # | | Treatment per Group | # cells | # mice |
|---|---|---|---|---|
| 1 | Control | PBS | - | 5 Females / 5 Males |
| 2 | Control | UTD T cells | 10^7 | 5 Females / 5 Males |
| 3 | Exp. | 8F; DKO (NY-ESO-1 TCR, TRAC/TRBC CRISPR Knockout) | 10^7 | 5 Females / 5 Males |
| 4 | Exp. | 8F; TKO (NY-ESO-1 TCR, TRAC/TRBC/PD1 CRISPR Knockout) | 10^7 | 5 Females / 5 Males |
| 5 | Exp. | PD1-CD28,8F, DKO (PD1-CD28 switch & NY-ESO-1 TCR, DKO) | 10^7 | 5 Females / 5 Males |

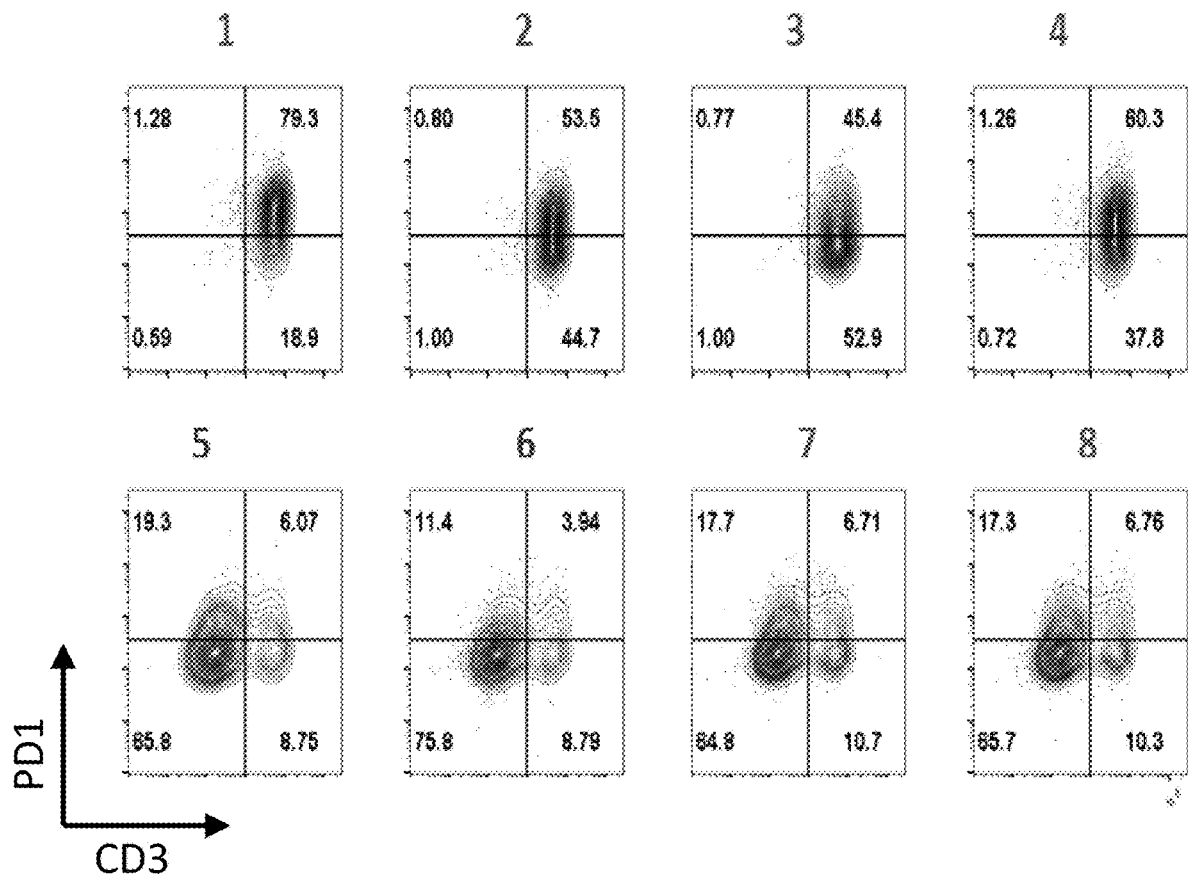

| | Group I | | | Group II | | |
|---|---|---|---|---|---|---|
| Guide RNA | PD1-3 | TRAC-5 | TRBC-4 | PD1.1-3 | TRAC3-4 | TRBC.12-12 |
| MIT SCORE | 84 | 73 | 72 | 81 | 89 | 75 |
| On-Target Sites | 1 | 1 | 2 | 1 | 1 | 2 |
| On-Target Read | 329,260 | 379,243 | 149,394 | 600,457 | 272,368 | 600,878 |
| Off-Target Reads | 5,344 | 13,538 | 12,270 | 4,993 | 3,506 | 8,003 |
| Onco-related Reads | | 3,124 | 569 | | 1,330 | 3,366 |
| Onco-related Templates | | 12 | 7 | | 2 | 3 |

Figure 28A

| Name | gRNA sequence |
|---|---|
| Tim3-1 | AATGTGACTCTAGCAGACAG |
| Tim3-2 | ATGAGAATACCCTAGTAAGG |
| Tim3-3 | TATGAGAATACCCTAGTAAG |
| Tim3-4 | TGGCCCAGGTAACTATGCAT |
| Tim3-5 | ATAGGCATCTACATCGGAGC |
| Tim3-6 | GCTGTGGAAATAAAGTGTTG |
| Tim3-7 | GTGGAATACAGAGCGGAGGT |
| Tim3-8 | ACAGTGGGATCTACTGCTGC |
| Tim3-9 | TCTCTCTGCCGAGTCGGTGC |
| Tim3-10 | TTATGCCTGGGATTTGGATC |
| Tim3-11 | ATCAGAATAGGCATCTACAT |
| Tim3-12 | TGAGTTACGGGACTCTAGAT |
| Tim3-13 | GCCAATGTGGATATTTGCTA |
| Tim3-14 | GTGAAGTCTCTCTGCCGAGT |
| Tim3-15 | TCAGGGACACATCTCCTTTG |
| Tim3-16 | GGGCACGAGGTTCCCTGGGG |
| Tim3-17 | AAATAAGGTGGTTGGATCTA |
| Tim3-18 | CTAAATGGGGATTTCCGCAA |
| Tim3-19 | AATGTGGCAACGTGGTGCTC |
| Tim3-20 | ATCCCCATTTAGCCAGTATC |
| Tim3-21 | TGCTGCCGGATCCAAATCCC |
| Tim3-22 | GAACCTCGTGCCCGTCTGCT |
| Tim3-23 | CAGACGGGCACGAGGTTCCC |
| Tim3-24 | AGACGGGCACGAGGTTCCCT |
| Tim3-25 | CTCTCTGCCGAGTCGGTGCA |
| Tim3-26 | TCTCTGCCGAGTCGGTGCAG |
| Tim3-27 | AGGTCACCCTGCACCGACT |
| Tim3-28 | TAGGCATCTACATCGGAGCA |
| Tim3-29 | TAGATTGGCCAATGACTTAC |

Tim-3 →

Figure 28C

| EP # | gRNA | % Tim3 | % KO |
|---|---|---|---|
| 1 | Tim3-1 | 31.1 | 40.2 |
| 2 | Tim3-2 | 53.8 | -3.5 |
| 3 | Tim3-3 | 52.6 | -1.2 |
| 4 | Tim3-4 | 33.9 | 34.8 |
| 5 | Tim3-5 | 45.8 | 11.9 |
| 6 | Tim3-6 | 20.9 | 59.8 |
| 7 | Tim3-7 | 4.6 | 91.2 |
| 8 | Tim3-8 | 18.2 | 65.0 |
| 9 | Tim3-9 | 49.1 | 5.6 |
| 10 | Tim3-10 | 44.9 | 13.7 |
| 11 | Tim3-11 | 20.7 | 60.2 |
| 12 | Tim3-12 | 47.0 | 9.6 |
| 13 | Tim3-13 | 18.1 | 65.2 |
| 14 | Tim3-14 | 52.9 | -1.7 |
| 15 | Tim3-15 | 40.7 | 21.7 |
| 16 | Tim3-16 | 30.0 | 42.3 |
| 17 | Tim3-17 | 34.4 | 33.8 |
| 18 | Tim3-18 | 23.7 | 54.4 |
| 19 | Tim3-19 | 25.1 | 51.7 |
| 20 | Tim3-20 | 45.8 | 11.9 |
| 21 | Tim3-21 | 23.2 | 55.4 |
| 22 | Tim3-22 | 21.8 | 58.1 |
| 23 | Tim3-23 | 31.2 | 40.0 |
| 24 | Tim3-24 | 11.9 | 77.1 |
| 25 | Tim3-25 | 51.8 | 0.4 |
| 26 | Tim3-26 | 44.0 | 15.4 |
| 27 | Tim3-27 | 55.5 | -6.7 |
| 28 | Tim3-28 | 44.7 | 14.0 |
| 29 | Tim3-29 | 42.8 | 17.7 |
| 30 | control1 | 51.4 | |

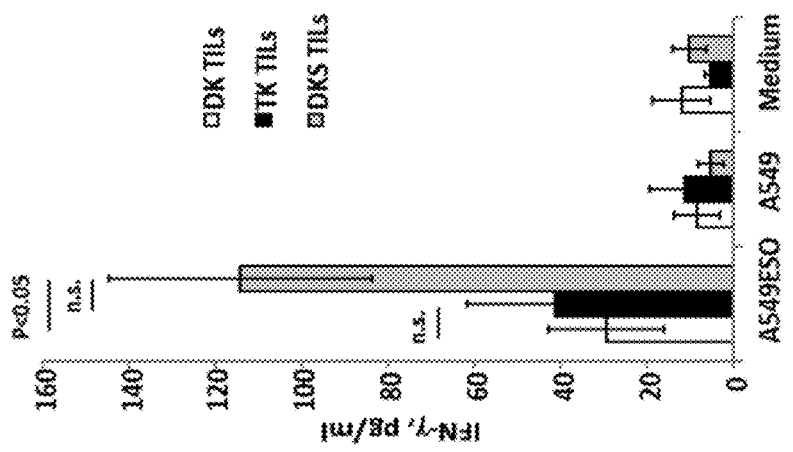
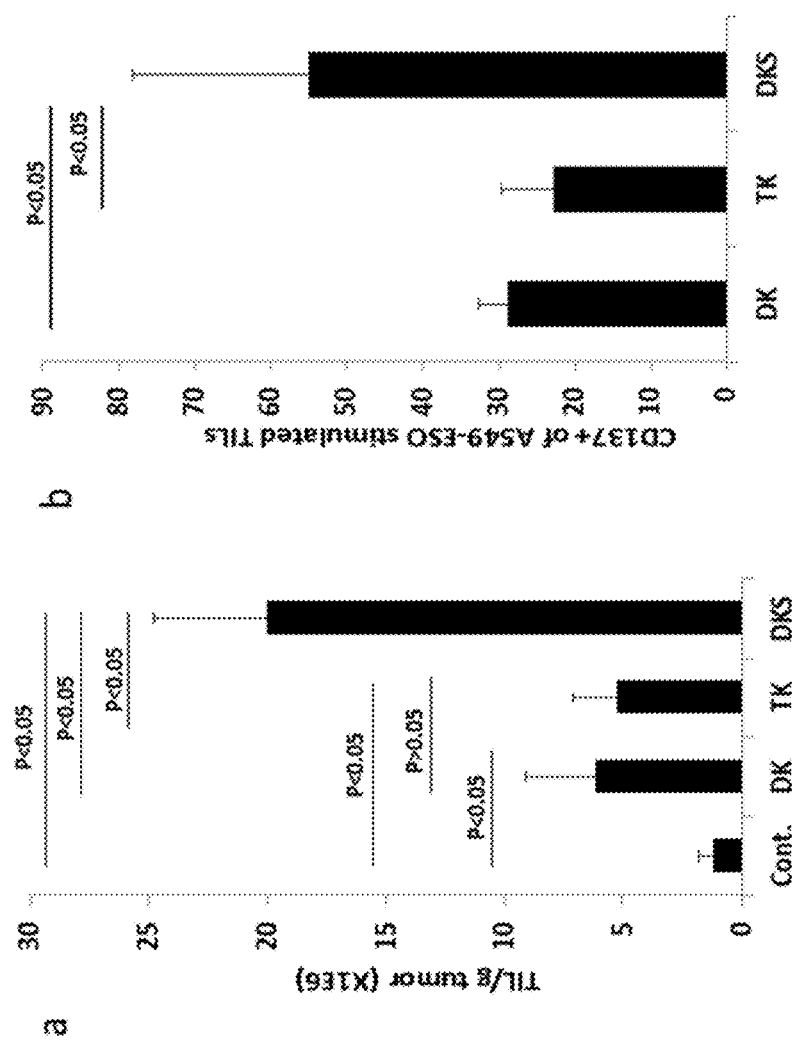

- 11 samples were subject to two lanes of Hi-Seq.
- The read depths are ranged from 56M reads to 94M reads.

Figure 31C

| Rank | GS DETAILS |
|---|---|
| 1 | IMMUNE_SYSTEM_PROCESS |
| 2 | IMMUNE_RESPONSE |
| 3 | NUCLEIC_ACID_METABOLIC_PROCESS |
| 4 | DEFENSE_RESPONSE |
| 5 | RNA_METABOLIC_PROCESS |
| 6 | TRANSCRIPTION |
| 7 | CELLULAR_DEFENSE_RESPONSE |
| 8 | REGULATION_OF_NUCLEIC_ACID_METABOLIC_PROCESS |
| 9 | LEUKOCYTE_ACTIVATION |
| 10 | LYMPHOCYTE_ACTIVATION |
| 11 | CELL_CYCLE_PROCESS |
| 12 | LOCOMOTORY_BEHAVIOR |
| 13 | T_CELL_ACTIVATION |
| 14 | CELL_CYCLE_GO_0007049 |
| 15 | REGULATION_OF_CELLULAR_METABOLIC_PROCESS |
| 16 | REGULATION_OF_METABOLIC_PROCESS |
| 17 | REGULATION_OF_GENE_EXPRESSION |
| 18 | RNA_BIOSYNTHETIC_PROCESS |
| 19 | TRANSCRIPTION_DNA_DEPENDENT |
| 20 | REGULATION_OF_TRANSCRIPTION |

Figure 31G
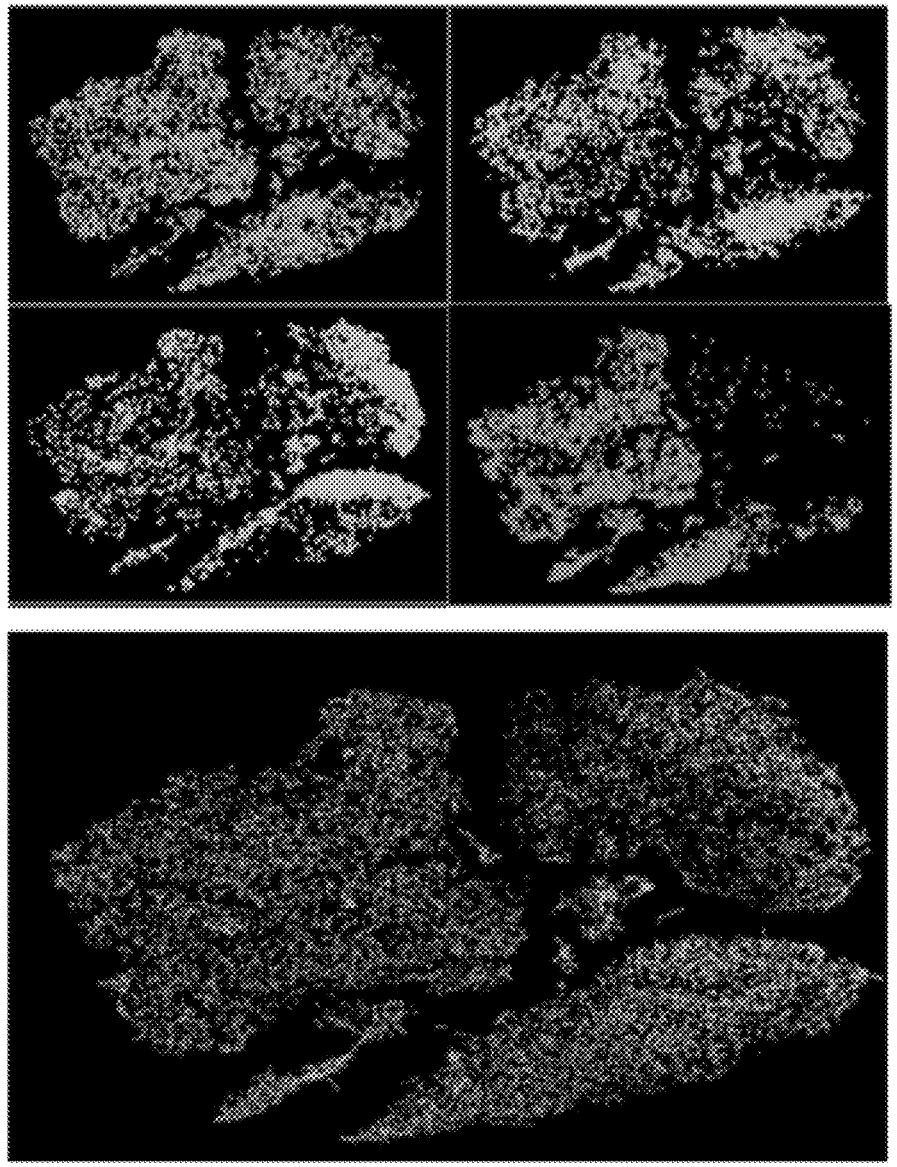
OK (5000) 
TK-PD1 (5000) 
DKS (5000) 
NTD (5000) 
DEG#: 770
Gene Sets: 474
FDR q-val <0.05: 139

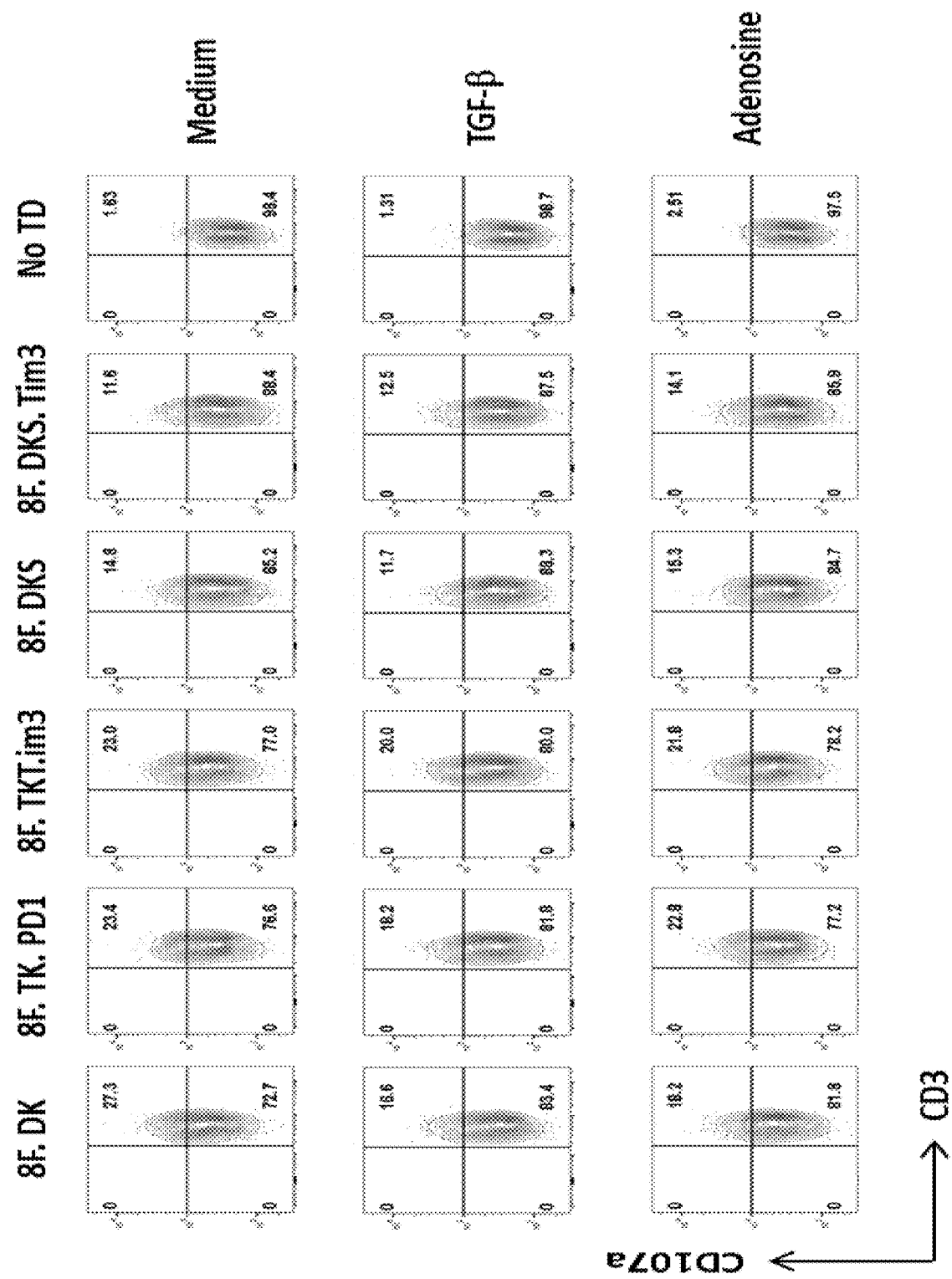

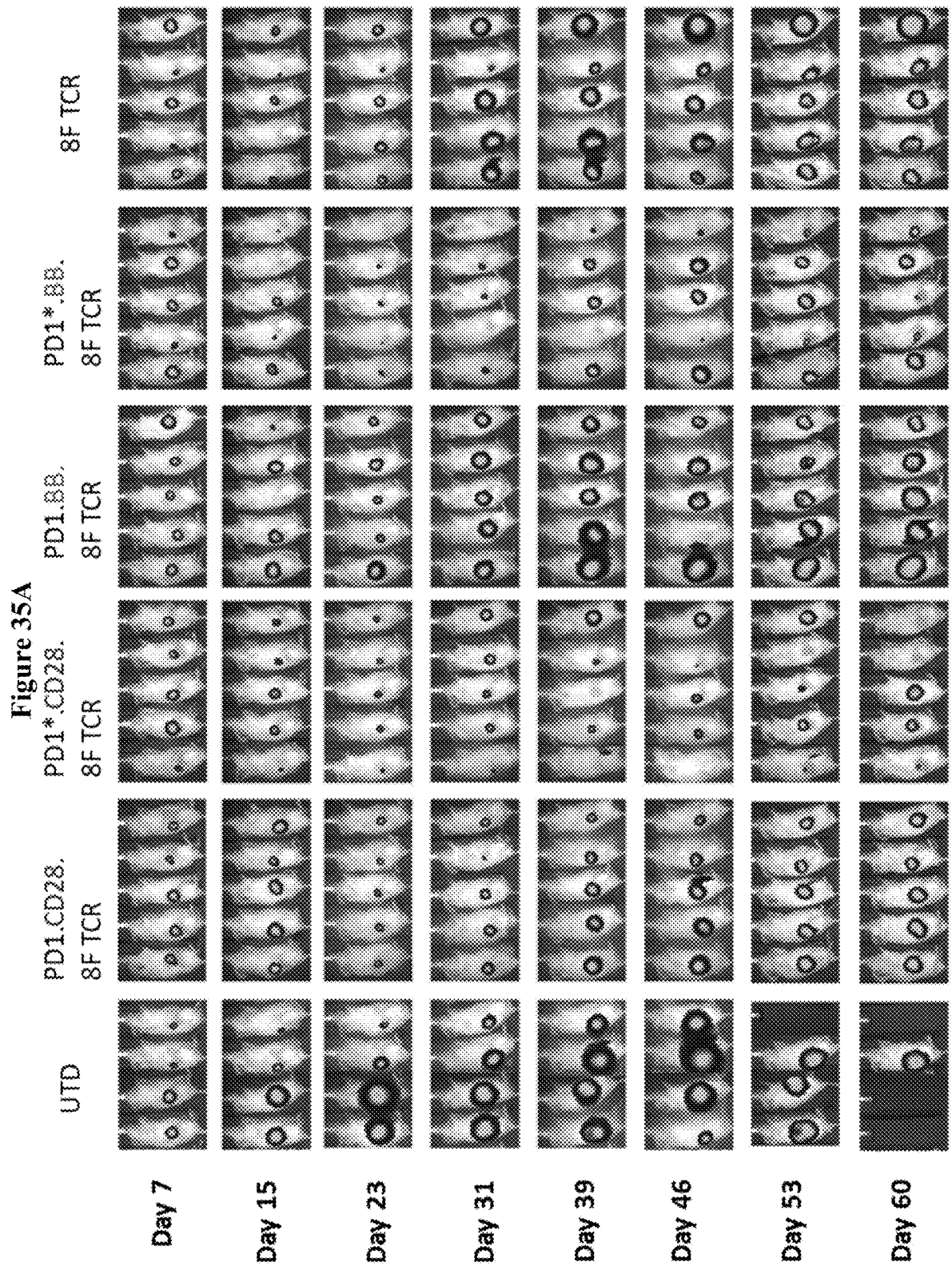

SEQUENCE LISTING

<160> NUMBER OF SEQ ID NOS: 292

<210> SEQ ID NO 1
<211> LENGTH: 9
<212> TYPE: PRT
<213> ORGANISM: Artificial Sequence
<220> FEATURE:
<223> OTHER INFORMATION: NY-ESO epitope

<400> SEQUENCE: 1

Ser Leu Leu Met Trp Ile Thr Gln Cys
1               5

<210> SEQ ID NO 2
<211> LENGTH: 106
<212> TYPE: PRT
<213> ORGANISM: Artificial Sequence
<220> FEATURE:
<223> OTHER INFORMATION: 8F TCR alpha chain variable region

<400> SEQUENCE: 2

Glu Glu Asp Pro Gln Ala Leu Ser Ile Gln Gly Glu Asn Ala Thr
1               5                   10                  15

Met Asn Cys Ser Tyr Lys Thr Ser Ile Asn Asn Leu Gln Trp Tyr Arg
            20                  25                  30

Gln Asn Ser Gly Arg Gly Leu Val His Leu Ile Leu Ile Arg Ser Asn
        35                  40                  45

Glu Arg Glu Lys His Ser Gly Arg Leu Arg Val Thr Leu Asp Thr Ser
    50                  55                  60

Lys Lys Ser Ser Ser Leu Leu Ile Thr Ala Ser Arg Ala Ala Asp Thr
65                  70                  75                  80

Ala Ser Tyr Phe Cys Ala Thr Asp Gly Ala Gly Lys Ser Thr Phe Gly
                85                  90                  95

Asp Gly Thr Thr Leu Thr Val Lys Pro Asn
                100                 105

<210> SEQ ID NO 3
<211> LENGTH: 318
<212> TYPE: DNA
<213> ORGANISM: Artificial Sequence
<220> FEATURE:
<223> OTHER INFORMATION: 8F TCR alpha chain

<400> SEQUENCE: 3
gaggaggacc cccaggccct gtccatccag gagggggaga atgccaccat gaattgcagt      60
tacaagactt ccataaacaa cctgcagtgg taccgccaga actccggccg cggcctggtg     120
cacctgatcc tcatccggtc gaatgaaagg gaaaagcact cgggacgcct gcgagtgact     180
ctggacacgt ccaagaagtc gtccagtctc ttaatcaccg cctctcgcgc agccgatacc     240
gcatcgtact tctgtgcaac cgacggggcg ggcaagagta cattcggcga cggcactacc     300
ctgaccgtga agccaaat                                                  318

<210> SEQ ID NO 4

-continued

```
<211> LENGTH: 5
<212> TYPE: PRT
<213> ORGANISM: Artificial Sequence
<220> FEATURE:
<223> OTHER INFORMATION: 8F TCR CDR1

<400> SEQUENCE: 4

Thr Ser Ile Asn Asn
1               5

<210> SEQ ID NO 5
<211> LENGTH: 270
<212> TYPE: PRT
<213> ORGANISM: Artificial Sequence
<220> FEATURE:
<223> OTHER INFORMATION: 8F TCR alpha chain

<400> SEQUENCE: 5

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Leu Leu Ile
                85                  90                  95

Thr Ala Ser Arg Ala Ala Asp Thr Ala Ser Tyr Phe Cys Ala Thr Asp
            100                 105                 110

Gly Ala Gly Lys Ser Thr Phe Gly Asp Gly Thr Thr Leu Thr Val Lys
        115                 120                 125

Pro Asn Ile Gln Lys Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Ala Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 6
<211> LENGTH: 924
<212> TYPE: DNA
<213> ORGANISM: Artificial Sequence
<220> FEATURE:
<223> OTHER INFORMATION: 8F TCR alpha chain
```

<400> SEQUENCE: 6

```
atggactcgt ggaccttatg ctgcgtgtcc ctgtgcatac tggttgccaa gcacacagac    60
gccggggtga tccagagccc ccggcacgaa gttaccgaga tgggccagga ggtgacgctc   120
cgatgcaagc ccatcagtgg ccacgattat ctcttctggt accgccaaac catgatgcgc   180
ggcttggaac tcctcatcta cttcaacaac aacgtcccca tcgatgactc cggcatgcct   240
gaggacaggt tcagtgcgaa gatgccaaat gcatccttct ccaccctgaa gatacagccg   300
agtgagcccc gcgactccgc tgtgtacttc tgcgcctcta ctatcggcgc ccagcctcaa   360
catttcggcg acggcacgcg cctcagtatc ctggaggacc tgaacaaggt gttccctccg   420
gaagtggctg tgtttgagcc ctccgaggca gaaatctcac acacacagaa ggcaaccctc   480
gtgtgtctgg caacaggttt cttcccagat cacgtggagc tgagttggtg ggtcaacggc   540
aaggaggtcc atagcggggt gagtaccgac ccacagcctc tcaaggagca gcctgccctc   600
aacgacagta ggtactgcct gtcctcgcgc ctccgcgtgt ccgcaacgtt ctggcagaat   660
ccccgcaacc acttccggtg ccaggtccaa ttctacggcc tgagtgagaa cgatgagtgg   720
acacaggata gggccaagcc cgtgacccag atcgtgtccg ccgaggcctg gggccgcgct   780
gactgcggct tcacctccgt gtcgtatcag cagggcgtat tatcagccac cattctttac   840
gaaatcctcc tcggcaaggc cacactatac gccgtgctgg tgtcggcgct ggtgttaatg   900
gcgatggtca agcgaaagga ttaa                                          924
```

<210> SEQ ID NO 7
<211> LENGTH: 110
<212> TYPE: PRT
<213> ORGANISM: Artificial Sequence
<220> FEATURE:
<223> OTHER INFORMATION: 8F TCR beta chain variable region

<400> SEQUENCE: 7

```
Val Ile Gln Ser Pro Arg His Glu Val Thr Glu Met Gly Gln Glu Val
1               5                   10                  15
Thr Leu Arg Cys Lys Pro Ile Ser Gly His Asp Tyr Leu Phe Trp Tyr
            20                  25                  30
Arg Gln Thr Met Met Arg Gly Leu Glu Leu Leu Ile Tyr Phe Asn Asn
        35                  40                  45
Asn Val Pro Ile Asp Asp Ser Gly Met Pro Glu Asp Arg Phe Ser Ala
    50                  55                  60
Lys Met Pro Asn Ala Ser Phe Ser Thr Leu Lys Ile Gln Pro Ser Glu
65                  70                  75                  80
Pro Arg Asp Ser Ala Val Tyr Phe Cys Ala Ser Thr Ile Gly Ala Gln
                85                  90                  95
Pro Gln His Phe Gly Asp Gly Thr Arg Leu Ser Ile Leu Glu
            100                 105                 110
```

<210> SEQ ID NO 8
<211> LENGTH: 330
<212> TYPE: DNA
<213> ORGANISM: Artificial Sequence
<220> FEATURE:
<223> OTHER INFORMATION: 8F TCR beta chain variable region

<400> SEQUENCE: 8

```
gtgatccaga gccccggca cgaagttacc gagatgggcc aggaggtgac gctccgatgc    60
aagcccatca gtggccacga ttatctcttc tggtaccgcc aaaccatgat gcgcggcttg   120
```

```
gaactcctca tctacttcaa caacaacgtc cccatcgatg actccggcat gcctgaggac      180
aggttcagtg cgaagatgcc gaatgcatcc ttctccaccc tgaagataca gccgagtgag      240
ccccgcgact ccgctgtgta cttctgcgcc tctactatcg gcgcccagcc tcaacatttc      300
ggcgacggca cgcgcctcag tatcctggag                                      330
```

```
<210> SEQ ID NO 9
<211> LENGTH: 5
<212> TYPE: PRT
<213> ORGANISM: Artificial Sequence
<220> FEATURE:
<223> OTHER INFORMATION: 8F TCR CDR1 VB

<400> SEQUENCE: 9

Ser Gly His Asp Tyr
1               5

<210> SEQ ID NO 10
<211> LENGTH: 6
<212> TYPE: PRT
<213> ORGANISM: Artificial Sequence
<220> FEATURE:
<223> OTHER INFORMATION: 8F TCR CDR2 VB

<400> SEQUENCE: 10

Phe Asn Asn Asn Val Pro
1               5

<210> SEQ ID NO 11
<211> LENGTH: 4
<212> TYPE: PRT
<213> ORGANISM: Artificial Sequence
<220> FEATURE:
<223> OTHER INFORMATION: 8F TCR CDR3 VB

<400> SEQUENCE: 11

Ala Ser Thr Ile
1

<210> SEQ ID NO 12
<211> LENGTH: 270
<212> TYPE: PRT
<213> ORGANISM: Artificial Sequence
<220> FEATURE:
<223> OTHER INFORMATION: 8F TCR beta chain

<400> SEQUENCE: 12

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Leu Leu Ile
                85                  90                  95

Thr Ala Ser Arg Ala Ala Asp Thr Ala Ser Tyr Phe Cys Ala Thr Asp
            100                 105                 110
```

Gly Ala Gly Lys Ser Thr Phe Gly Asp Gly Thr Thr Leu Thr Val Lys
            115                 120                 125

Pro Asn Ile Gln Lys Pro Asp Pro Ala Val Tyr Gln Leu Arg Asp Ser
        130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Ala Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 13
<211> LENGTH: 810
<212> TYPE: DNA
<213> ORGANISM: Artificial Sequence
<220> FEATURE:
<223> OTHER INFORMATION: 8F TCR beta chain

<400> SEQUENCE: 13
atggagaccc tgctcggggt ctcactggtc atcctgtggc tgcagctggc cagggtgaac      60
tcgcagcagg gggaggagga ccccccaggcc ctgtccatcc aggaggggga gaatgccacc    120
atgaattgca gttacaagac ttccataaac aacctgcagt ggtaccgcca gaactccggc    180
cgcggcctgg tgcacctgat cctcatccgg tcgaatgaaa gggaaaagca ctcgggacgc    240
ctgcgagtga ctctggacac gtccaagaag tcgtccagtc tcttaatcac cgcctctcgc    300
gcagccgata ccgcatcgta cttctgtgca accgacgggg cgggcaagag tacattcggc    360
gacggcacta cccthgaccgt gaagccaaat atccagaagc ctgatccagc tgtctatcag    420
ttgcgcgatt ccaaatcgtc tgacaaatct gtgtgcctgt tcaccgactt cgactcccag    480
acgaacgtgt cccagagtaa agacagcgac gtgtacatca ctgataagac cgtgctggac    540
atgcgctcca tggactttaa agtaacagc gctgtagcgt ggagcaacaa gagtgacttc     600
gcctgcgcca acgccttcaa taactctatc atacctgccg ataccttctt cccgagcccc    660
gaatccagtt gcgacgtgaa gctcgtggag aagagctttg agacagacac caacctgaac    720
ttccaaaacc tgtccgtcat tggcttcagg atcctcctcc tcaaggtggc cggcttcaac    780
ttgctcatga cgctgagact ctggagttca                                      810

<210> SEQ ID NO 14
<211> LENGTH: 238
<212> TYPE: PRT
<213> ORGANISM: Artificial Sequence
<220> FEATURE:
<223> OTHER INFORMATION: PD1-CD28 switch receptor

<400> SEQUENCE: 14

Met Gln Ile Pro Gln Ala Pro Trp Pro Val Val Trp Ala Val Leu Gln

```
 1               5                  10                 15
Leu Gly Trp Arg Pro Gly Trp Phe Leu Asp Ser Pro Asp Arg Pro Trp
                20                 25                 30

Asn Pro Pro Thr Phe Ser Pro Ala Leu Leu Val Val Thr Glu Gly Asp
                35                 40                 45

Asn Ala Thr Phe Thr Cys Ser Phe Ser Asn Thr Ser Glu Ser Phe Val
 50                 55                 60

Leu Asn Trp Tyr Arg Met Ser Pro Ser Asn Gln Thr Asp Lys Leu Ala
 65                 70                 75                 80

Ala Phe Pro Glu Asp Arg Ser Gln Pro Gly Gln Asp Cys Arg Phe Arg
                85                 90                 95

Val Thr Gln Leu Pro Asn Gly Arg Asp Phe His Met Ser Val Val Arg
                100                105                110

Ala Arg Arg Asn Asp Ser Gly Thr Tyr Leu Cys Gly Ala Ile Ser Leu
                115                120                125

Ala Pro Lys Ala Gln Ile Lys Glu Ser Leu Arg Ala Glu Leu Arg Val
                130                135                140

Thr Glu Arg Arg Ala Glu Val Pro Thr Ala His Pro Ser Pro Ser Pro
145                150                155                160

Arg Pro Ala Gly Gln Phe Gln Thr Leu Val Phe Trp Val Leu Val Val
                165                170                175

Val Gly Gly Val Leu Ala Cys Tyr Ser Leu Leu Val Thr Val Ala Phe
                180                185                190

Ile Ile Phe Trp Val Arg Ser Lys Arg Ser Arg Leu Leu His Ser Asp
                195                200                205

Tyr Met Asn Met Thr Pro Arg Arg Pro Gly Pro Thr Arg Lys His Tyr
 210                215                220

Gln Pro Tyr Ala Pro Pro Arg Asp Phe Ala Ala Tyr Arg Ser
225                230                235
```

<210> SEQ ID NO 15
<211> LENGTH: 714
<212> TYPE: DNA
<213> ORGANISM: Artificial Sequence
<220> FEATURE:
<223> OTHER INFORMATION: PD1-CD28 switch receptor

<400> SEQUENCE: 15

```
atgcagatcc cacaggcgcc ctggccagtc gtctgggcgg tgctacaact gggctggcgg      60
ccaggatggt tcttagactc cccagacagg ccctggaacc ccccaccttc tccccagcc     120
ctgctcgtgg tgaccgaagg ggacaacgcc accttcacct gcagcttctc caacacatcg     180
gagagcttcg tgctaaactg gtaccgcatg agcccagca accagacgga caagctggcc     240
gccttccccg aggaccgcag ccagcccggc caggactgcc gcttccgtgt cacacaactg     300
cccaacgggc gtgacttcca catgagcgtg tcagggccc ggcgcaatga cagcggcacc     360
tacctctgtg gggccatctc cctggccccc aaggcgcaga tcaaagagag cctgcgggca     420
gagctcaggg tgacagagag aagggcagaa gtgcccacag cccaccccag ccctcacccc     480
aggccagccg gccagttcca aaccctggtg ttttgggtgc tggtggtggt tggtggagtc     540
ctggcttgct atagcttgct agtaacagtg gcctttatta ttttctgggt gaggagtaag     600
aggagcaggc tcctgcacag tgactacatg aacatgactc ccgccgccc gggcccacc      660
cgcaagcatt accagcccta tgccccacca cgcgacttcg cagcctatcg ctcc           714
```

-continued

```
<210> SEQ ID NO 16
<211> LENGTH: 238
<212> TYPE: PRT
<213> ORGANISM: Artificial Sequence
<220> FEATURE:
<223> OTHER INFORMATION: TGFBRI-IL-12RB1 switch receptor

<400> SEQUENCE: 16
```

Leu Glu Ala Ala Val Ala Ala Pro Arg Pro Arg Leu Leu Leu Leu Val
1               5                   10                  15

Leu Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
        35                  40                  45

Val Thr Asp Gly Leu Cys Phe Val Ser Val Thr Glu Thr Thr Asp Lys
    50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Ala Ala
        115                 120                 125

Val Ile Ala Gly Pro Val Cys Phe Val Cys Ile Ser Leu Met Leu Met
    130                 135                 140

Val Tyr Ile Arg Ala Ala Arg His Leu Cys Pro Pro Leu Pro Thr Pro
145                 150                 155                 160

Cys Ala Ser Ser Ala Ile Glu Phe Pro Gly Gly Lys Glu Thr Trp Gln
                165                 170                 175

Trp Ile Asn Pro Val Asp Phe Gln Glu Ala Ser Leu Gln Glu Ala
            180                 185                 190

Leu Val Val Glu Met Ser Trp Asp Lys Gly Glu Arg Thr Glu Pro Leu
        195                 200                 205

Glu Lys Thr Glu Leu Pro Glu Gly Ala Pro Glu Leu Ala Leu Asp Thr
    210                 215                 220

Glu Leu Ser Leu Glu Asp Gly Asp Arg Cys Lys Ala Lys Met
225                 230                 235

```
<210> SEQ ID NO 17
<211> LENGTH: 717
<212> TYPE: DNA
<213> ORGANISM: Artificial Sequence
<220> FEATURE:
<223> OTHER INFORMATION: TGFBRI-IL-12RB1 switch receptor

<400> SEQUENCE: 17
```
ctggaggcgg cggtcgctgc tccgcgtccc cggctgctcc tcctcgtgct ggcggcggcg      60
gcggcggcgg cggcggcgct gctcccgggg gcgacggcgt acagtgtttt ctgccacctc    120
tgtacaaaag acaattttac ttgtgtgaca gatgggctct gctttgtctc tgtcacagag    180
accacagaca aagttataca caacagcatg tgtatagctg aaattgactt aattcctcga    240
gataggccgt ttgtatgtgc ccctcttca aaaactgggt ctgtgactac aacatattgc    300
tgcaatcagg accattgcaa taaaatagaa cttccaacta ctgtaaagtc atcacctggc    360
cttggtcctg tggaactggc agctgtcatt gctggaccag tgtgcttcgt ctgcatctca    420
ctcatgttga tggtctatat cagggccgca cggcacctgt gcccgccgct gcccacaccc    480

```
tgtgccagct ccgccattga gttccctgga gggaaggaga cttggcagtg gatcaaccca    540
gtggacttcc aggaagaggc atccctgcag gaggccctgg tggtagagat gtcctgggac    600
aaaggcgaga ggactgagcc tctcgagaag acagagctac ctgagggtgc ccctgagctg    660
gccctggata cagagttgtc cttggaggat ggagacaggt gcaaggccaa gatgtga       717
```

<210> SEQ ID NO 18
<211> LENGTH: 403
<212> TYPE: PRT
<213> ORGANISM: Artificial Sequence
<220> FEATURE:
<223> OTHER INFORMATION: TGFBRII-IL-12RB2 switch receptor

<400> SEQUENCE: 18

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
        50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Gln Gln Lys Val Phe
            180                 185                 190

Val Leu Leu Ala Ala Leu Arg Pro Gln Trp Cys Ser Arg Glu Ile Pro
        195                 200                 205

Asp Pro Ala Asn Ser Thr Cys Ala Lys Lys Tyr Pro Ile Ala Glu Glu
    210                 215                 220

Lys Thr Gln Leu Pro Leu Asp Arg Leu Leu Ile Asp Trp Pro Thr Pro
225                 230                 235                 240

Glu Asp Pro Glu Pro Leu Val Ile Ser Glu Val Leu His Gln Val Thr
                245                 250                 255

Pro Val Phe Arg His Pro Pro Cys Ser Asn Trp Pro Gln Arg Glu Lys
            260                 265                 270

Gly Ile Gln Gly His Gln Ala Ser Glu Lys Asp Met Met His Ser Ala
        275                 280                 285

Ser Ser Pro Pro Pro Pro Arg Ala Leu Gln Ala Glu Ser Arg Gln Leu
    290                 295                 300

Val Asp Leu Tyr Lys Val Leu Glu Ser Arg Gly Ser Asp Pro Lys Pro
305                 310                 315                 320
```

```
Glu Asn Pro Ala Cys Pro Trp Thr Val Leu Pro Ala Gly Asp Leu Pro
            325                 330                 335

Thr His Asp Gly Tyr Leu Pro Ser Asn Ile Asp Asp Leu Pro Ser His
        340                 345                 350

Glu Ala Pro Leu Ala Asp Ser Leu Glu Glu Leu Glu Pro Gln His Ile
                355                 360                 365

Ser Leu Ser Val Phe Pro Ser Ser Ser Leu His Pro Leu Thr Phe Ser
    370                 375                 380

Cys Gly Asp Lys Leu Thr Leu Asp Gln Leu Lys Met Arg Cys Asp Ser
385                 390                 395                 400

Leu Met Leu

<210> SEQ ID NO 19
<211> LENGTH: 1212
<212> TYPE: DNA
<213> ORGANISM: Artificial Sequence
<220> FEATURE:
<223> OTHER INFORMATION: TGFBRII-IL-12RB2 switch receptor

<400> SEQUENCE: 19
atgggtcggg ggctgctcag gggcctgtgg ccgctgcaca tcgtcctgtg gacgcgtatc      60
gccagcacga tcccaccgca cgttcagaag tcggttaata cgacatgat agtcactgac     120
aacaacggtg cagtcaagtt tccacaactg tgtaaatttt gtgatgtgag atttccacc     180
tgtgacaacc agaaatcctg catgagcaac tgcagcatca cctccatctg tgagaagcca     240
caggaagtct gtgtggctgt atggagaaag aatgacgaga acataacact agagacagtt     300
tgccatgacc ccaagctccc ctaccatgac tttattctgg aagatgctgc ttctccaaag     360
tgcattatga aggaaaaaaa aaagcctggt gagactttct tcatgtgttc ctgtagctct     420
gatgagtgca atgacaacat catcttctca gaagaatata caccagcaa tcctgacttg     480
ttgctagtca tatttcaagt gacaggcatc agcctcctgc caccactggg agttgccata     540
tctgtcatca tcatcttcta ccagcaaaag gtgtttgttc cctagcagc cctcagacct     600
cagtggtgta gcagagaaat tccagatcca gcaaatagca cttgcgctaa gaaatatccc     660
attgcagagg agaagacaca gctgcccttg acaggctcc tgatagactg gcccacgcct     720
gaagatcctg aaccgctggt catcagtgaa gtccttcatc aagtgacccc agttttcaga     780
catccccccct gctccaactg gccacaaagg gaaaaggaa tccaaggtca tcaggcctct     840
gagaaagaca tgatgcacag tgcctcaagc ccaccacctc aagagctct ccaagctgag     900
agcagacaac tggtggatct gtacaaggtg ctggagagca ggggctccga cccaaagcca     960
gaaaacccag cctgtccctg gacggtgctc ccagcaggtg accttcccac ccatgatggc    1020
tacttaccct ccaacataga tgacctcccc tcacatgagg cacctctcgc tgactctctg    1080
gaagaactgg agcctcagca catctcccctt tctgtttttcc cctcaagttc tcttcaccca    1140
ctcaccttct cctgtggtga taagctgact ctggatcagt taaagatgag gtgtgactcc    1200
ctcatgctct ga                                                        1212

<210> SEQ ID NO 20
<211> LENGTH: 201
<212> TYPE: PRT
<213> ORGANISM: Artificial Sequence
<220> FEATURE:
<223> OTHER INFORMATION: TGFBRIIDN switch receptor

<400> SEQUENCE: 20
```

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
            115                 120                 125

Pro Gly Glu Thr Phe Phe Met Cys Ser Cys Ser Ser Asp Glu Cys Asn
        130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
                180                 185                 190

Arg Gln Gln Lys Leu Ser Ser Ser Gly
        195                 200

<210> SEQ ID NO 21
<211> LENGTH: 603
<212> TYPE: DNA
<213> ORGANISM: Artificial Sequence
<220> FEATURE:
<223> OTHER INFORMATION: TGFBRIIDN switch receptor

<400> SEQUENCE: 21
atgggtcggg ggctgctcag gggcctgtgg ccgctgcaca tcgtcctgtg gacgcgtatc      60
gccagcacga tcccaccgca cgttcagaag tcggttaata cgacatgat agtcactgac     120 aacaacggtg cagtcaagtt tccacaactg tgtaaatttt gtgatgtgag attttccacc     180
tgtgacaacc agaaatcctg catgagcaac tgcagcatca cctccatctg tgagaagcca     240
caggaagtct gtgtggctgt atggagaaag aatgacgaga acataacact agagacagtt     300
tgccatgacc ccaagctccc ctaccatgac tttattctgg aagatgctgc ttctccaaag     360
tgcattatga ggaaaaaaa aaagcctggt gagactttct tcatgtgttc ctgtagctct     420
gatgagtgca atgacaacat catcttctca gaagaatata caccagcaa tcctgacttg     480 ttgctagtca tatttcaagt gacaggcatc agcctcctgc caccactggg agttgccata     540
tctgtcatca tcatcttcta ctgctaccgc gttaaccggc agcagaagct gagttcatcc     600
gga                                                                   603

<210> SEQ ID NO 22
<211> LENGTH: 4
<212> TYPE: PRT
<213> ORGANISM: Artificial Sequence
<220> FEATURE:
<223> OTHER INFORMATION: furin cleavage sites
<220> FEATURE:

```
<221> NAME/KEY: misc_feature
<222> LOCATION: (2)..(2)
<223> OTHER INFORMATION: Xaa can be any naturally occurring amino acid

<400> SEQUENCE: 22

Arg Xaa Lys Arg
1

<210> SEQ ID NO 23
<211> LENGTH: 4
<212> TYPE: PRT
<213> ORGANISM: Artificial Sequence
<220> FEATURE:
<223> OTHER INFORMATION: furin cleavage sites
<220> FEATURE:
<221> NAME/KEY: misc_feature
<222> LOCATION: (2)..(2)
<223> OTHER INFORMATION: Xaa can be any naturally occurring amino acid

<400> SEQUENCE: 23

Arg Xaa Arg Arg
1

<210> SEQ ID NO 24
<211> LENGTH: 5
<212> TYPE: PRT
<213> ORGANISM: Artificial Sequence
<220> FEATURE:
<223> OTHER INFORMATION: furin cleavage sites
<220> FEATURE:
<221> NAME/KEY: misc_feature
<222> LOCATION: (1)..(1)
<223> OTHER INFORMATION: Xaa can be K or R
<220> FEATURE:
<221> NAME/KEY: misc_feature
<222> LOCATION: (3)..(3)
<223> OTHER INFORMATION: Xaa can be any naturally occuring amino acid
<220> FEATURE:
<221> NAME/KEY: misc_feature
<222> LOCATION: (4)..(4)
<223> OTHER INFORMATION: Xaa can be K or R

<400> SEQUENCE: 24

Xaa Arg Xaa Xaa Arg
1               5

<210> SEQ ID NO 25
<211> LENGTH: 4
<212> TYPE: PRT
<213> ORGANISM: Artificial Sequence
<220> FEATURE:
<223> OTHER INFORMATION: furin cleavage sites
<220> FEATURE:
<221> NAME/KEY: misc_feature
<222> LOCATION: (2)..(3)
<223> OTHER INFORMATION: Xaa can be any naturally occurring amino acid

<400> SEQUENCE: 25

Arg Xaa Xaa Arg
1

<210> SEQ ID NO 26
<211> LENGTH: 4
<212> TYPE: PRT
<213> ORGANISM: Artificial Sequence
<220> FEATURE:
<223> OTHER INFORMATION: furin cleavage sites

<400> SEQUENCE: 26

Arg Gln Lys Arg
```

```
<210> SEQ ID NO 27
<211> LENGTH: 5
<212> TYPE: PRT
<213> ORGANISM: Artificial Sequence
<220> FEATURE:
<223> OTHER INFORMATION: spacer sequence
<220> FEATURE:
<221> NAME/KEY: REPEAT
<222> LOCATION: (1)..(5)
<223> OTHER INFORMATION: repeat n times, where n represents an integer
      of at least 1

<400> SEQUENCE: 27

Gly Ser Gly Gly Ser
1               5

<210> SEQ ID NO 28
<211> LENGTH: 4
<212> TYPE: PRT
<213> ORGANISM: Artificial Sequence
<220> FEATURE:
<223> OTHER INFORMATION: spacer sequence
<220> FEATURE:
<221> NAME/KEY: REPEAT
<222> LOCATION: (1)..(4)
<223> OTHER INFORMATION: repeat n times, where n represents an integer
      of at least 1

<400> SEQUENCE: 28

Gly Gly Gly Ser
1

<210> SEQ ID NO 29
<211> LENGTH: 4
<212> TYPE: PRT
<213> ORGANISM: Artificial Sequence
<220> FEATURE:
<223> OTHER INFORMATION: spacer sequence

<400> SEQUENCE: 29

Gly Gly Ser Gly
1

<210> SEQ ID NO 30
<211> LENGTH: 5
<212> TYPE: PRT
<213> ORGANISM: Artificial Sequence
<220> FEATURE:
<223> OTHER INFORMATION: spacer sequence

<400> SEQUENCE: 30

Gly Gly Ser Gly Gly
1               5

<210> SEQ ID NO 31
<211> LENGTH: 5
<212> TYPE: PRT
<213> ORGANISM: Artificial Sequence
<220> FEATURE:
<223> OTHER INFORMATION: spacer sequence

<400> SEQUENCE: 31

Gly Ser Gly Ser Gly
1               5

<210> SEQ ID NO 32
```

```
<211> LENGTH: 5
<212> TYPE: PRT
<213> ORGANISM: Artificial Sequence
<220> FEATURE:
<223> OTHER INFORMATION: spacer sequence

<400> SEQUENCE: 32

Gly Ser Gly Gly Gly
1               5

<210> SEQ ID NO 33
<211> LENGTH: 5
<212> TYPE: PRT
<213> ORGANISM: Artificial Sequence
<220> FEATURE:
<223> OTHER INFORMATION: spacer sequence

<400> SEQUENCE: 33

Gly Gly Gly Ser Gly
1               5

<210> SEQ ID NO 34
<211> LENGTH: 5
<212> TYPE: PRT
<213> ORGANISM: Artificial Sequence
<220> FEATURE:
<223> OTHER INFORMATION: spacer sequence

<400> SEQUENCE: 34

Gly Ser Ser Ser Gly
1               5

<210> SEQ ID NO 35
<211> LENGTH: 96
<212> TYPE: DNA
<213> ORGANISM: Artificial Sequence
<220> FEATURE:
<223> OTHER INFORMATION: F-GS2-T2A linker

<400> SEQUENCE: 35
cgtgcgaaga ggggcggcgg gggctccggc gggggaggca gtgagggccg cggctccctg    60
ctgacctgcg gagatgtaga agagaaccca ggcccc                              96

<210> SEQ ID NO 36
<211> LENGTH: 32
<212> TYPE: PRT
<213> ORGANISM: Artificial Sequence
<220> FEATURE:
<223> OTHER INFORMATION: F-GS2-T2A linker

<400> SEQUENCE: 36

Arg Ala Lys Arg Gly Gly Gly Gly Ser Gly Gly Gly Gly Ser Glu Gly
1               5                   10                  15

Arg Gly Ser Leu Leu Thr Cys Gly Asp Val Glu Glu Asn Pro Gly Pro
            20                  25                  30

<210> SEQ ID NO 37
<211> LENGTH: 20
<212> TYPE: DNA
<213> ORGANISM: Artificial Sequence
<220> FEATURE:
<223> OTHER INFORMATION: gRNA

<400> SEQUENCE: 37
gagaatcaaa atcggtgaat                                                20
```

```
<210> SEQ ID NO 38
<211> LENGTH: 20
<212> TYPE: DNA
<213> ORGANISM: Artificial Sequence
<220> FEATURE:
<223> OTHER INFORMATION: gRNA

<400> SEQUENCE: 38
tgtgctagac atgaggtcta                                               20

<210> SEQ ID NO 39
<211> LENGTH: 20
<212> TYPE: DNA
<213> ORGANISM: Artificial Sequence
<220> FEATURE:
<223> OTHER INFORMATION: gRNA

<400> SEQUENCE: 39
aaagtcagat ttgttgctcc                                               20

<210> SEQ ID NO 40
<211> LENGTH: 20
<212> TYPE: DNA
<213> ORGANISM: Artificial Sequence
<220> FEATURE:
<223> OTHER INFORMATION: gRNA

<400> SEQUENCE: 40
agagtctctc agctggtaca                                               20

<210> SEQ ID NO 41
<211> LENGTH: 20
<212> TYPE: DNA
<213> ORGANISM: Artificial Sequence
<220> FEATURE:
<223> OTHER INFORMATION: gRNA

<400> SEQUENCE: 41
agctggtaca cggcagggtc                                               20

<210> SEQ ID NO 42
<211> LENGTH: 20
<212> TYPE: DNA
<213> ORGANISM: Artificial Sequence
<220> FEATURE:
<223> OTHER INFORMATION: gRNA

<400> SEQUENCE: 42
acaaaactgt gctagacatg                                               20

<210> SEQ ID NO 43
<211> LENGTH: 20
<212> TYPE: DNA
<213> ORGANISM: Artificial Sequence
<220> FEATURE:
<223> OTHER INFORMATION: gRNA

<400> SEQUENCE: 43
ctcgaccagc ttgacatcac                                               20

<210> SEQ ID NO 44
<211> LENGTH: 20
<212> TYPE: DNA
<213> ORGANISM: Artificial Sequence
<220> FEATURE:
<223> OTHER INFORMATION: gRNA
```

```
<400> SEQUENCE: 44
aagttcctgt gatgtcaagc                                        20

<210> SEQ ID NO 45
<211> LENGTH: 20
<212> TYPE: DNA
<213> ORGANISM: Artificial Sequence
<220> FEATURE:
<223> OTHER INFORMATION: gRNA

<400> SEQUENCE: 45
ttcggaaccc aatcactgac                                        20

<210> SEQ ID NO 46
<211> LENGTH: 20
<212> TYPE: DNA
<213> ORGANISM: Artificial Sequence
<220> FEATURE:
<223> OTHER INFORMATION: gRNA

<400> SEQUENCE: 46
ttaatctgct catgacgctg                                        20

<210> SEQ ID NO 47
<211> LENGTH: 20
<212> TYPE: DNA
<213> ORGANISM: Artificial Sequence
<220> FEATURE:
<223> OTHER INFORMATION: gRNA

<400> SEQUENCE: 47
gattaaaccc ggccactttc                                        20

<210> SEQ ID NO 48
<211> LENGTH: 20
<212> TYPE: DNA
<213> ORGANISM: Artificial Sequence
<220> FEATURE:
<223> OTHER INFORMATION: gRNA

<400> SEQUENCE: 48
cgtcatgagc agattaaacc                                        20

<210> SEQ ID NO 49
<211> LENGTH: 20
<212> TYPE: DNA
<213> ORGANISM: Artificial Sequence
<220> FEATURE:
<223> OTHER INFORMATION: gRNA

<400> SEQUENCE: 49
taaacccggc cactttcagg                                        20

<210> SEQ ID NO 50
<211> LENGTH: 20
<212> TYPE: DNA
<213> ORGANISM: Artificial Sequence
<220> FEATURE:
<223> OTHER INFORMATION: gRNA

<400> SEQUENCE: 50
caaacacagc gacctcgggt                                        20

<210> SEQ ID NO 51
```

```
<211> LENGTH: 20
<212> TYPE: DNA
<213> ORGANISM: Artificial Sequence
<220> FEATURE:
<223> OTHER INFORMATION: gRNA

<400> SEQUENCE: 51
ggctcaaaca cagcgacctc                                                    20

<210> SEQ ID NO 52
<211> LENGTH: 20
<212> TYPE: DNA
<213> ORGANISM: Artificial Sequence
<220> FEATURE:
<223> OTHER INFORMATION: gRNA

<400> SEQUENCE: 52
tcaaacacag cgacctcggg                                                    20

<210> SEQ ID NO 53
<211> LENGTH: 20
<212> TYPE: DNA
<213> ORGANISM: Artificial Sequence
<220> FEATURE:
<223> OTHER INFORMATION: gRNA

<400> SEQUENCE: 53
tggctcaaac acagcgacct                                                    20

<210> SEQ ID NO 54
<211> LENGTH: 20
<212> TYPE: DNA
<213> ORGANISM: Artificial Sequence
<220> FEATURE:
<223> OTHER INFORMATION: gRNA

<400> SEQUENCE: 54
tctccgagag cccgtagaac                                                    20

<210> SEQ ID NO 55
<211> LENGTH: 20
<212> TYPE: DNA
<213> ORGANISM: Artificial Sequence
<220> FEATURE:
<223> OTHER INFORMATION: gRNA

<400> SEQUENCE: 55
ggctctcgga gaatgacgag                                                    20

<210> SEQ ID NO 56
<211> LENGTH: 20
<212> TYPE: DNA
<213> ORGANISM: Artificial Sequence
<220> FEATURE:
<223> OTHER INFORMATION: gRNA

<400> SEQUENCE: 56
tgacagcgga agtggttgcg                                                    20

<210> SEQ ID NO 57
<211> LENGTH: 20
<212> TYPE: DNA
<213> ORGANISM: Artificial Sequence
<220> FEATURE:
<223> OTHER INFORMATION: gRNA

<400> SEQUENCE: 57
```
agtccagttc tacgggctct        20

<210> SEQ ID NO 58
<211> LENGTH: 20
<212> TYPE: DNA
<213> ORGANISM: Artificial Sequence
<220> FEATURE:
<223> OTHER INFORMATION: gRNA

<400> SEQUENCE: 58
cgctgtcaag tccagttcta        20

<210> SEQ ID NO 59
<211> LENGTH: 20
<212> TYPE: DNA
<213> ORGANISM: Artificial Sequence
<220> FEATURE:
<223> OTHER INFORMATION: gRNA

<400> SEQUENCE: 59
agctcagctc cacgtggtcg        20

<210> SEQ ID NO 60
<211> LENGTH: 20
<212> TYPE: DNA
<213> ORGANISM: Artificial Sequence
<220> FEATURE:
<223> OTHER INFORMATION: gRNA

<400> SEQUENCE: 60
actggacttg acagcggaag        20

<210> SEQ ID NO 61
<211> LENGTH: 20
<212> TYPE: DNA
<213> ORGANISM: Artificial Sequence
<220> FEATURE:
<223> OTHER INFORMATION: gRNA

<400> SEQUENCE: 61
ttgacagcgg aagtggttgc        20

<210> SEQ ID NO 62
<211> LENGTH: 20
<212> TYPE: DNA
<213> ORGANISM: Artificial Sequence
<220> FEATURE:
<223> OTHER INFORMATION: gRNA

<400> SEQUENCE: 62
gacagcggaa gtggttgcgg        20

<210> SEQ ID NO 63
<211> LENGTH: 20
<212> TYPE: DNA
<213> ORGANISM: Artificial Sequence
<220> FEATURE:
<223> OTHER INFORMATION: gRNA

<400> SEQUENCE: 63
tgacgagtgg acccaggata        20

<210> SEQ ID NO 64
<211> LENGTH: 20
<212> TYPE: DNA

```
<213> ORGANISM: Artificial Sequence
<220> FEATURE:
<223> OTHER INFORMATION: gRNA

<400> SEQUENCE: 64
cgtagaactg gacttgacag                                                    20

<210> SEQ ID NO 65
<211> LENGTH: 20
<212> TYPE: DNA
<213> ORGANISM: Artificial Sequence
<220> FEATURE:
<223> OTHER INFORMATION: gRNA

<400> SEQUENCE: 65
atgacgagtg gacccaggat                                                    20

<210> SEQ ID NO 66
<211> LENGTH: 20
<212> TYPE: DNA
<213> ORGANISM: Artificial Sequence
<220> FEATURE:
<223> OTHER INFORMATION: gRNA

<400> SEQUENCE: 66
cttgacagcg gaagtggttg                                                    20

<210> SEQ ID NO 67
<211> LENGTH: 20
<212> TYPE: DNA
<213> ORGANISM: Artificial Sequence
<220> FEATURE:
<223> OTHER INFORMATION: gRNA

<400> SEQUENCE: 67
gctgtcaagt ccagttctac                                                    20

<210> SEQ ID NO 68
<211> LENGTH: 20
<212> TYPE: DNA
<213> ORGANISM: Artificial Sequence
<220> FEATURE:
<223> OTHER INFORMATION: gRNA

<400> SEQUENCE: 68
aggcctcggc gctgacgatc                                                    20

<210> SEQ ID NO 69
<211> LENGTH: 20
<212> TYPE: DNA
<213> ORGANISM: Artificial Sequence
<220> FEATURE:
<223> OTHER INFORMATION: gRNA

<400> SEQUENCE: 69
ggcctcggcg ctgacgatct                                                    20

<210> SEQ ID NO 70
<211> LENGTH: 20
<212> TYPE: DNA
<213> ORGANISM: Artificial Sequence
<220> FEATURE:
<223> OTHER INFORMATION: gRNA

<400> SEQUENCE: 70
cacccagatc gtcagcgccg                                                    20
```

```
<210> SEQ ID NO 71
<211> LENGTH: 20
<212> TYPE: DNA
<213> ORGANISM: Artificial Sequence
<220> FEATURE:
<223> OTHER INFORMATION: gRNA

<400> SEQUENCE: 71
gacgatctgg gtgacgggtt                                              20

<210> SEQ ID NO 72
<211> LENGTH: 20
<212> TYPE: DNA
<213> ORGANISM: Artificial Sequence
<220> FEATURE:
<223> OTHER INFORMATION: gRNA

<400> SEQUENCE: 72
gatcgtcagc gccgaggcct                                              20

<210> SEQ ID NO 73
<211> LENGTH: 20
<212> TYPE: DNA
<213> ORGANISM: Artificial Sequence
<220> FEATURE:
<223> OTHER INFORMATION: gRNA

<400> SEQUENCE: 73
agatcgtcag cgccgaggcc                                              20

<210> SEQ ID NO 74
<211> LENGTH: 20
<212> TYPE: DNA
<213> ORGANISM: Artificial Sequence
<220> FEATURE:
<223> OTHER INFORMATION: gRNA

<400> SEQUENCE: 74
tgtagcaccg cccagacgac                                              20

<210> SEQ ID NO 75
<211> LENGTH: 20
<212> TYPE: DNA
<213> ORGANISM: Artificial Sequence
<220> FEATURE:
<223> OTHER INFORMATION: gRNA

<400> SEQUENCE: 75
cgtctgggcg gtgctacaac                                              20

<210> SEQ ID NO 76
<211> LENGTH: 20
<212> TYPE: DNA
<213> ORGANISM: Artificial Sequence
<220> FEATURE:
<223> OTHER INFORMATION: gRNA

<400> SEQUENCE: 76
gtctgggcgg tgctacaact                                              20

<210> SEQ ID NO 77
<211> LENGTH: 20
<212> TYPE: DNA
<213> ORGANISM: Artificial Sequence
<220> FEATURE:
```

<223> OTHER INFORMATION: gRNA

<400> SEQUENCE: 77
aggcgccctg gccagtcgtc                                          20

<210> SEQ ID NO 78
<211> LENGTH: 20
<212> TYPE: DNA
<213> ORGANISM: Artificial Sequence
<220> FEATURE:
<223> OTHER INFORMATION: gRNA

<400> SEQUENCE: 78
caccgcccag acgactggcc                                          20

<210> SEQ ID NO 79
<211> LENGTH: 20
<212> TYPE: DNA
<213> ORGANISM: Artificial Sequence
<220> FEATURE:
<223> OTHER INFORMATION: gRNA

<400> SEQUENCE: 79
atgtggaagt cacgcccgtt                                          20

<210> SEQ ID NO 80
<211> LENGTH: 20
<212> TYPE: DNA
<213> ORGANISM: Artificial Sequence
<220> FEATURE:
<223> OTHER INFORMATION: gRNA

<400> SEQUENCE: 80
catgtggaag tcacgcccgt                                          20

<210> SEQ ID NO 81
<211> LENGTH: 20
<212> TYPE: DNA
<213> ORGANISM: Artificial Sequence
<220> FEATURE:
<223> OTHER INFORMATION: gRNA

<400> SEQUENCE: 81
cacgaagctc tccgatgtgt                                          20

<210> SEQ ID NO 82
<211> LENGTH: 20
<212> TYPE: DNA
<213> ORGANISM: Artificial Sequence
<220> FEATURE:
<223> OTHER INFORMATION: gRNA

<400> SEQUENCE: 82
cggagagctt cgtgctaaac                                          20

<210> SEQ ID NO 83
<211> LENGTH: 20
<212> TYPE: DNA
<213> ORGANISM: Artificial Sequence
<220> FEATURE:
<223> OTHER INFORMATION: gRNA

<400> SEQUENCE: 83
cctgctcgtg gtgaccgaag                                          20

-continued

<210> SEQ ID NO 84
<211> LENGTH: 20
<212> TYPE: DNA
<213> ORGANISM: Artificial Sequence
<220> FEATURE:
<223> OTHER INFORMATION: gRNA

<400> SEQUENCE: 84
ccccttcggt caccacgagc                                               20

<210> SEQ ID NO 85
<211> LENGTH: 20
<212> TYPE: DNA
<213> ORGANISM: Artificial Sequence
<220> FEATURE:
<223> OTHER INFORMATION: gRNA

<400> SEQUENCE: 85
aggcggccag cttgtccgtc                                               20

<210> SEQ ID NO 86
<211> LENGTH: 20
<212> TYPE: DNA
<213> ORGANISM: Artificial Sequence
<220> FEATURE:
<223> OTHER INFORMATION: gRNA

<400> SEQUENCE: 86
gccctgctcg tggtgaccga                                               20

<210> SEQ ID NO 87
<211> LENGTH: 20
<212> TYPE: DNA
<213> ORGANISM: Artificial Sequence
<220> FEATURE:
<223> OTHER INFORMATION: gRNA

<400> SEQUENCE: 87
cccttcggtc accacgagca                                               20

<210> SEQ ID NO 88
<211> LENGTH: 20
<212> TYPE: DNA
<213> ORGANISM: Artificial Sequence
<220> FEATURE:
<223> OTHER INFORMATION: gRNA

<400> SEQUENCE: 88
ccctgctcgt ggtgaccgaa                                               20

<210> SEQ ID NO 89
<211> LENGTH: 20
<212> TYPE: DNA
<213> ORGANISM: Artificial Sequence
<220> FEATURE:
<223> OTHER INFORMATION: gRNA

<400> SEQUENCE: 89
gcgtgacttc cacatgagcg                                               20

<210> SEQ ID NO 90
<211> LENGTH: 20
<212> TYPE: DNA
<213> ORGANISM: Artificial Sequence
<220> FEATURE:
<223> OTHER INFORMATION: gRNA

```
<400> SEQUENCE: 90
aggtgccgct gtcattgcgc                                           20

<210> SEQ ID NO 91
<211> LENGTH: 20
<212> TYPE: DNA
<213> ORGANISM: Artificial Sequence
<220> FEATURE:
<223> OTHER INFORMATION: gRNA

<400> SEQUENCE: 91
acttccacat gagcgtggtc                                           20

<210> SEQ ID NO 92
<211> LENGTH: 20
<212> TYPE: DNA
<213> ORGANISM: Artificial Sequence
<220> FEATURE:
<223> OTHER INFORMATION: gRNA

<400> SEQUENCE: 92
ggtgccgctg tcattgcgcc                                           20

<210> SEQ ID NO 93
<211> LENGTH: 20
<212> TYPE: DNA
<213> ORGANISM: Artificial Sequence
<220> FEATURE:
<223> OTHER INFORMATION: gRNA

<400> SEQUENCE: 93
accctggtgg ttggtgtcgt                                           20

<210> SEQ ID NO 94
<211> LENGTH: 20
<212> TYPE: DNA
<213> ORGANISM: Artificial Sequence
<220> FEATURE:
<223> OTHER INFORMATION: gRNA

<400> SEQUENCE: 94
agggtttgga actggccggc                                           20

<210> SEQ ID NO 95
<211> LENGTH: 20
<212> TYPE: DNA
<213> ORGANISM: Artificial Sequence
<220> FEATURE:
<223> OTHER INFORMATION: gRNA

<400> SEQUENCE: 95
attgtctttc ctagcggaat                                           20

<210> SEQ ID NO 96
<211> LENGTH: 20
<212> TYPE: DNA
<213> ORGANISM: Artificial Sequence
<220> FEATURE:
<223> OTHER INFORMATION: gRNA

<400> SEQUENCE: 96
tcagtggctg ggcactccga                                           20

<210> SEQ ID NO 97
<211> LENGTH: 20
```

```
<212> TYPE: DNA
<213> ORGANISM: Artificial Sequence
<220> FEATURE:
<223> OTHER INFORMATION: gRNA

<400> SEQUENCE: 97
cattgtcttt cctagcggaa                                              20

<210> SEQ ID NO 98
<211> LENGTH: 20
<212> TYPE: DNA
<213> ORGANISM: Artificial Sequence
<220> FEATURE:
<223> OTHER INFORMATION: gRNA

<400> SEQUENCE: 98
aatgtgactc tagcagacag                                              20

<210> SEQ ID NO 99
<211> LENGTH: 20
<212> TYPE: DNA
<213> ORGANISM: Artificial Sequence
<220> FEATURE:
<223> OTHER INFORMATION: gRNA

<400> SEQUENCE: 99
atgagaatac cctagtaagg                                              20

<210> SEQ ID NO 100
<211> LENGTH: 20
<212> TYPE: DNA
<213> ORGANISM: Artificial Sequence
<220> FEATURE:
<223> OTHER INFORMATION: gRNA

<400> SEQUENCE: 100
tatgagaata ccctagtaag                                              20

<210> SEQ ID NO 101
<211> LENGTH: 20
<212> TYPE: DNA
<213> ORGANISM: Artificial Sequence
<220> FEATURE:
<223> OTHER INFORMATION: gRNA

<400> SEQUENCE: 101
tggcccaggt aactatgcat                                              20

<210> SEQ ID NO 102
<211> LENGTH: 20
<212> TYPE: DNA
<213> ORGANISM: Artificial Sequence
<220> FEATURE:
<223> OTHER INFORMATION: gRNA

<400> SEQUENCE: 102
ataggcatct acatcggagc                                              20

<210> SEQ ID NO 103
<211> LENGTH: 20
<212> TYPE: DNA
<213> ORGANISM: Artificial Sequence
<220> FEATURE:
<223> OTHER INFORMATION: gRNA

<400> SEQUENCE: 103
```

```
gctgtggaaa taaagtgttg                                                 20

<210> SEQ ID NO 104
<211> LENGTH: 20
<212> TYPE: DNA
<213> ORGANISM: Artificial Sequence
<220> FEATURE:
<223> OTHER INFORMATION: gRNA

<400> SEQUENCE: 104
gtggaataca gagcggaggt                                                 20

<210> SEQ ID NO 105
<211> LENGTH: 20
<212> TYPE: DNA
<213> ORGANISM: Artificial Sequence
<220> FEATURE:
<223> OTHER INFORMATION: gRNA

<400> SEQUENCE: 105
acagtgggat ctactgctgc                                                 20

<210> SEQ ID NO 106
<211> LENGTH: 20
<212> TYPE: DNA
<213> ORGANISM: Artificial Sequence
<220> FEATURE:
<223> OTHER INFORMATION: gRNA

<400> SEQUENCE: 106
tctctctgcc gagtcggtgc                                                 20

<210> SEQ ID NO 107
<211> LENGTH: 20
<212> TYPE: DNA
<213> ORGANISM: Artificial Sequence
<220> FEATURE:
<223> OTHER INFORMATION: gRNA

<400> SEQUENCE: 107
ttatgcctgg gatttggatc                                                 20

<210> SEQ ID NO 108
<211> LENGTH: 20
<212> TYPE: DNA
<213> ORGANISM: Artificial Sequence
<220> FEATURE:
<223> OTHER INFORMATION: gRNA

<400> SEQUENCE: 108
atcagaatag gcatctacat                                                 20

<210> SEQ ID NO 109
<211> LENGTH: 20
<212> TYPE: DNA
<213> ORGANISM: Artificial Sequence
<220> FEATURE:
<223> OTHER INFORMATION: gRNA

<400> SEQUENCE: 109
tgagttacgg gactctagat                                                 20

<210> SEQ ID NO 110
<211> LENGTH: 20
<212> TYPE: DNA
<213> ORGANISM: Artificial Sequence
```

```
<220> FEATURE:
<223> OTHER INFORMATION: gRNA

<400> SEQUENCE: 110
gccaatgtgg atatttgcta                                              20

<210> SEQ ID NO 111
<211> LENGTH: 20
<212> TYPE: DNA
<213> ORGANISM: Artificial Sequence
<220> FEATURE:
<223> OTHER INFORMATION: gRNA

<400> SEQUENCE: 111
gtgaagtctc tctgccgagt                                              20

<210> SEQ ID NO 112
<211> LENGTH: 20
<212> TYPE: DNA
<213> ORGANISM: Artificial Sequence
<220> FEATURE:
<223> OTHER INFORMATION: gRNA

<400> SEQUENCE: 112
tcagggacac atctcctttg                                              20

<210> SEQ ID NO 113
<211> LENGTH: 20
<212> TYPE: DNA
<213> ORGANISM: Artificial Sequence
<220> FEATURE:
<223> OTHER INFORMATION: gRNA

<400> SEQUENCE: 113
gggcacgagg ttccctgggg                                              20

<210> SEQ ID NO 114
<211> LENGTH: 20
<212> TYPE: DNA
<213> ORGANISM: Artificial Sequence
<220> FEATURE:
<223> OTHER INFORMATION: gRNA

<400> SEQUENCE: 114
aaataaggtg gttggatcta                                              20

<210> SEQ ID NO 115
<211> LENGTH: 20
<212> TYPE: DNA
<213> ORGANISM: Artificial Sequence
<220> FEATURE:
<223> OTHER INFORMATION: gRNA

<400> SEQUENCE: 115
ctaaatgggg atttccgcaa                                              20

<210> SEQ ID NO 116
<211> LENGTH: 20
<212> TYPE: DNA
<213> ORGANISM: Artificial Sequence
<220> FEATURE:
<223> OTHER INFORMATION: gRNA

<400> SEQUENCE: 116
aatgtggcaa cgtggtgctc                                              20
```

<210> SEQ ID NO 117
<211> LENGTH: 20
<212> TYPE: DNA
<213> ORGANISM: Artificial Sequence
<220> FEATURE:
<223> OTHER INFORMATION: gRNA

<400> SEQUENCE: 117
atccccattt agccagtatc								20

<210> SEQ ID NO 118
<211> LENGTH: 20
<212> TYPE: DNA
<213> ORGANISM: Artificial Sequence
<220> FEATURE:
<223> OTHER INFORMATION: gRNA

<400> SEQUENCE: 118
tgctgccgga tccaaatccc								20

<210> SEQ ID NO 119
<211> LENGTH: 20
<212> TYPE: DNA
<213> ORGANISM: Artificial Sequence
<220> FEATURE:
<223> OTHER INFORMATION: gRNA

<400> SEQUENCE: 119
gaacctcgtg cccgtctgct								20

<210> SEQ ID NO 120
<211> LENGTH: 20
<212> TYPE: DNA
<213> ORGANISM: Artificial Sequence
<220> FEATURE:
<223> OTHER INFORMATION: gRNA

<400> SEQUENCE: 120
cagacgggca cgaggttccc								20

<210> SEQ ID NO 121
<211> LENGTH: 20
<212> TYPE: DNA
<213> ORGANISM: Artificial Sequence
<220> FEATURE:
<223> OTHER INFORMATION: gRNA

<400> SEQUENCE: 121
agacgggcac gaggttccct								20

<210> SEQ ID NO 122
<211> LENGTH: 20
<212> TYPE: DNA
<213> ORGANISM: Artificial Sequence
<220> FEATURE:
<223> OTHER INFORMATION: gRNA

<400> SEQUENCE: 122
ctctctgccg agtcggtgca								20

<210> SEQ ID NO 123
<211> LENGTH: 20
<212> TYPE: DNA
<213> ORGANISM: Artificial Sequence
<220> FEATURE:
<223> OTHER INFORMATION: gRNA

<400> SEQUENCE: 123
tctctgccga gtcggtgcag                                         20

<210> SEQ ID NO 124
<211> LENGTH: 20
<212> TYPE: DNA
<213> ORGANISM: Artificial Sequence
<220> FEATURE:
<223> OTHER INFORMATION: gRNA

<400> SEQUENCE: 124
aggtcacccc tgcaccgact                                         20

<210> SEQ ID NO 125
<211> LENGTH: 20
<212> TYPE: DNA
<213> ORGANISM: Artificial Sequence
<220> FEATURE:
<223> OTHER INFORMATION: gRNA

<400> SEQUENCE: 125
taggcatcta catcggagca                                         20

<210> SEQ ID NO 126
<211> LENGTH: 20
<212> TYPE: DNA
<213> ORGANISM: Artificial Sequence
<220> FEATURE:
<223> OTHER INFORMATION: gRNA

<400> SEQUENCE: 126
tagattggcc aatgacttac                                         20

<210> SEQ ID NO 127
<211> LENGTH: 20
<212> TYPE: DNA
<213> ORGANISM: Artificial Sequence
<220> FEATURE:
<223> OTHER INFORMATION: gRNA

<400> SEQUENCE: 127
ggcgccctgg ccagtcgtct                                         20

<210> SEQ ID NO 128
<211> LENGTH: 101
<212> TYPE: DNA
<213> ORGANISM: Homo sapiens

<400> SEQUENCE: 128
aacaaatgtg tcacaaagta aggattctga tgtgtatatc acagacaaaa ctgtgctaga    60
catgaggtct atggacttca agagcaacag tgctgtggcc t                      101

<210> SEQ ID NO 129
<211> LENGTH: 101
<212> TYPE: DNA
<213> ORGANISM: Homo sapiens

<400> SEQUENCE: 129
gcagaacccc cgcaaccact tccgctgtca agtccagttc tacgggctct cggagaatga    60
cgagtggacc caggataggg ccaaacctgt cacccagatc g                      101

<210> SEQ ID NO 130

```
<211> LENGTH: 101
<212> TYPE: DNA
<213> ORGANISM: Homo sapiens

<400> SEQUENCE: 130
gctgctccag gcatgcagat cccacaggcg ccctggccag tcgtctgggc ggtgctacaa    60
ctgggctggc ggccaggatg gttcttaggt aggtggggtc g                       101

<210> SEQ ID NO 131
<211> LENGTH: 20
<212> TYPE: DNA
<213> ORGANISM: Artificial Sequence
<220> FEATURE:
<223> OTHER INFORMATION: gRNA

<400> SEQUENCE: 131
ggagaatgac gagtggaccc                                                20

<210> SEQ ID NO 132
<211> LENGTH: 268
<212> TYPE: PRT
<213> ORGANISM: Artificial Sequence
<220> FEATURE:
<223> OTHER INFORMATION: TIM3-CD28 switch receptor

<400> SEQUENCE: 132
```

Met Phe Ser His Leu Pro Phe Asp Cys Val Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Phe Trp Val Leu Val Val Val Gly
        195                 200                 205

Gly Val Leu Ala Cys Tyr Ser Leu Leu Val Thr Val Ala Phe Ile Ile
    210                 215                 220

Phe Trp Val Arg Ser Lys Arg Ser Arg Leu Leu His Ser Asp Tyr Met
225                 230                 235                 240

Asn Met Thr Pro Arg Arg Pro Gly Pro Thr Arg Lys His Tyr Gln Pro
                245                 250                 255

Tyr Ala Pro Pro Arg Asp Phe Ala Ala Tyr Arg Ser
            260                 265

<210> SEQ ID NO 133
<211> LENGTH: 804
<212> TYPE: DNA
<213> ORGANISM: Artificial Sequence
<220> FEATURE:
<223> OTHER INFORMATION: TIM3-CD28 switch receptor

<400> SEQUENCE: 133

```
atgttttcac atcttccctt tgactgtgtc ctgctgctgc tgctgctact acttacaagg      60
tcctcagaag tggaatacag agcggaggtc ggtcagaatg cctatctgcc ctgcttctac     120
accccagccg ccccagggaa cctcgtgccc gtctgctggg gcaaaggagc ctgtcctgtg     180
tttgaatgtg gcaacgtggt gctcaggact gatgaaaggg atgtgaatta ttggacatcc     240
agatactggc taaatgggga tttccgcaaa ggagatgtgt ccctgaccat agagaatgtg     300
actctagcag acagtgggat ctactgctgc cgaatccaaa tcccaggcat aatgaatgat     360
gaaaaattta acctgaagtt ggtcatcaaa ccagccaagg tcacccctgc accgactcgg     420
cagagagact tcactgcagc ctttccaagg atgcttacca ccaggggaca tggcccagca     480
gagacacaga cactggggag cctccctgac ataaatctaa cacaaatatc cacattggcc     540
aatgagttac gggactctag gttggccaat gacttacggg actccggagc aaccatcaga     600
ttttgggtgc tggtggtggt tggtggagtc ctggcttgct atagcttact agtaacagtg     660
gcctttatta ttttctgggt gaggagtaag aggagcaggc tcctgcacag tgactacatg     720
aacatgactc cccgccgccc cgggcccacc cgcaagcatt accagcccta tgccccacca     780
cgcgacttcg cagcctatcg ctcc                                            804
```

<210> SEQ ID NO 134
<211> LENGTH: 237
<212> TYPE: PRT
<213> ORGANISM: Artificial Sequence
<220> FEATURE:
<223> OTHER INFORMATION: PD1-41BB switch receptor

<400> SEQUENCE: 134

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Ile Tyr Ile Trp Ala Pro
            165                 170                 175

Leu Ala Gly Thr Cys Gly Val Leu Leu Leu Ser Leu Val Ile Thr Leu
        180                 185                 190

Tyr Cys Lys Lys Arg Gly Arg Lys Lys Leu Leu Tyr Ile Phe Lys Gln
    195                 200                 205

Pro Phe Met Arg Pro Val Gln Thr Thr Gln Glu Glu Asp Gly Cys Ser
210                 215                 220

Cys Arg Phe Pro Glu Glu Glu Glu Gly Gly Cys Glu Leu
225                 230                 235

<210> SEQ ID NO 135
<211> LENGTH: 711
<212> TYPE: DNA
<213> ORGANISM: Artificial Sequence
<220> FEATURE:
<223> OTHER INFORMATION: PD1-41BB switch receptor

<400> SEQUENCE: 135
atgcagatcc cacaggcgcc ctggccagtc gtctgggcgg tgctacaact gggctggcgg       60
ccaggatggt tcttagactc cccagacagg ccctggaacc cccccacctt ctccccagcc      120
ctgctcgtgg tgaccgaagg ggacaacgcc accttcacct gcagcttctc caacacatcg      180
gagagcttcg tgctaaactg gtaccgcatg agccccagca accagacgga caagctggcc      240
gccttccccg aggaccgcag ccagcccggc caggactgcc gcttccgtgt cacacaactg      300
cccaacgggc gtgacttcca catgagcgtg gtcagggccc ggcgcaatga cagcggcacc      360
tacctctgtg ggccatctct cctggccccc aaggcgcaga tcaaagagag cctgcgggca      420
gagctcaggg tgacagagag aagggcagaa gtgcccacag cccaccccag ccctcacccc      480
aggccagccg gccagttcca aaccctggtt atctacatct gggcgccctt ggccgggact      540 tgtgggggtcc ttctcctgtc actggttatc accctttact gcaaaaaacg gggcagaaag      600
aaactcctgt atatattcaa acaaccattt atgagaccag tacaaactac tcaagaggaa      660
gatggctgta gctgccgatt ccagaagaa gaagaaggag gatgtgaact g              711

<210> SEQ ID NO 136
<211> LENGTH: 237
<212> TYPE: PRT
<213> ORGANISM: Artificial Sequence
<220> FEATURE:
<223> OTHER INFORMATION: PD1A132L-41BB switch receptor

<400> SEQUENCE: 136

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Leu Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Ile Tyr Ile Trp Ala Pro
                165                 170                 175

Leu Ala Gly Thr Cys Gly Val Leu Leu Leu Ser Leu Val Ile Thr Leu
            180                 185                 190

Tyr Cys Lys Lys Arg Gly Arg Lys Lys Leu Leu Tyr Ile Phe Lys Gln
                195                 200                 205

Pro Phe Met Arg Pro Val Gln Thr Thr Gln Glu Glu Asp Gly Cys Ser
            210                 215                 220

Cys Arg Phe Pro Glu Glu Glu Glu Gly Gly Cys Glu Leu
225                 230                 235

<210> SEQ ID NO 137
<211> LENGTH: 711
<212> TYPE: DNA
<213> ORGANISM: Artificial Sequence
<220> FEATURE:
<223> OTHER INFORMATION: PD1A132L-41BB switch receptor

<400> SEQUENCE: 137

```
atgcagatcc cacaggcgcc ctggccagtc gtctgggcgg tgctacaact gggctggcgg      60
ccaggatggt tcttagactc cccagacagg ccctggaacc ccccaccttt ctccccagcc     120
ctgctcgtgg tgaccgaagg ggacaacgcc accttcacct gcagcttctc caacacatcg     180
gagagcttcg tgctaaactg gtaccgcatg agccccagca accagacgga caagctggcc     240
gccttccccg aggaccgcag ccagcccggc caggactgcc gcttccgtgt cacacaactg     300
cccaacgggc gtgacttcca catgagcgtg gtcagggccc ggcgcaatga cagcggcacc     360
tacctctgtg gggccatctc cctggccccc aagctgcaga tcaaagagag cctgcgggca     420
gagctcaggg tgacagagag aagggcagaa gtgcccacag cccaccccag cccctcaccc     480
aggccagccg gccagttcca aaccctggtt atctacatct gggcgccctt ggccgggact     540
tgtggggtcc ttctcctgtc actggttatc acccttttact gcaaaaaacg ggcagaaaag     600
aaactcctgt atatattcaa acaaccattt atgagaccag tacaaactac tcaagaggaa     660
gatggctgta gctgccgatt ccagaagaa gaagaaggag atgtgaact g                711
```

<210> SEQ ID NO 138
<211> LENGTH: 238
<212> TYPE: PRT
<213> ORGANISM: Artificial Sequence
<220> FEATURE:
<223> OTHER INFORMATION: PD1A132L-CD28 switch receptor

<400> SEQUENCE: 138

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp

```
                35                  40                  45
Asn Ala Thr Phe Thr Cys Ser Phe Ser Asn Thr Ser Glu Ser Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Leu Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Phe Trp Val Leu Val Val
                165                 170                 175

Val Gly Gly Val Leu Ala Cys Tyr Ser Leu Leu Val Thr Val Ala Phe
            180                 185                 190

Ile Ile Phe Trp Val Arg Ser Lys Arg Ser Arg Leu Leu His Ser Asp
        195                 200                 205

Tyr Met Asn Met Thr Pro Arg Arg Pro Gly Pro Thr Arg Lys His Tyr
    210                 215                 220

Gln Pro Tyr Ala Pro Pro Arg Asp Phe Ala Ala Tyr Arg Ser
225                 230                 235
```

<210> SEQ ID NO 139
<211> LENGTH: 714
<212> TYPE: DNA
<213> ORGANISM: Artificial Sequence
<220> FEATURE:
<223> OTHER INFORMATION: PD1A132L-CD28 switch receptor

<400> SEQUENCE: 139

```
atgcagatcc acaggcgcc ctggccagtc gtctgggcgg tgctacaact gggctggcgg      60
ccaggatggt tcttagactc cccagacagg ccctggaacc cccccacctt ctccccagcc    120
ctgctcgtgg tgaccgaagg ggacaacgcc accttcacct gcagcttctc caacacatcg    180
gagagcttcg tgctaaactg gtaccgcatg agccccagca accagacgga caagctggcc    240
gccttccccg aggaccgcag ccagcccggc caggactgcc gcttccgtgt cacacaactg    300
cccaacgggc gtgacttcca catgagcgtg gtcagggccc ggcgcaatga cagcggcacc    360
tacctctgtg gggccatctc cctggccccc aagctgcaga tcaaagagag cctgcgggca    420
gagctcaggg tgacagagag aagggcagaa gtgcccacag cccaccccag ccctcaccc    480
aggccagccg gccagttcca aaccctggtg ttttgggtgc tggtggtggt tggtggagtc    540
ctggcttgct atagcttgct agtaacagtg gcctttatta ttttctgggt gaggagtaag    600
aggagcaggc tcctgcacag tgactacatg aacatgactc ccgccgccc gggcccacc      660
cgcaagcatt accagcccta tgccccacca cgcgacttcg cagcctatcg ctcc           714
```

<210> SEQ ID NO 140
<211> LENGTH: 101
<212> TYPE: DNA
<213> ORGANISM: Artificial Sequence
<220> FEATURE:
<223> OTHER INFORMATION: Illustrative sequence from Fig. 1

<400> SEQUENCE: 140
aacaaatgtg tcacaaagta aggattctga tgtgtatatc acagacaaaa ctgtgctaga     60
catgaggtct atggacttca agagcaacag tgctgtggcc t                        101

<210> SEQ ID NO 141
<211> LENGTH: 100
<212> TYPE: DNA
<213> ORGANISM: Artificial Sequence
<220> FEATURE:
<223> OTHER INFORMATION: Illustrative sequence from Fig. 1

<400> SEQUENCE: 141
aacaaatgtg tcacaaagta aggattctga tgttatatca cagacaaact gtgctagaca     60
tgaggtctat ggacttcaag agcaacagtg gctgtggcct                          100

<210> SEQ ID NO 142
<211> LENGTH: 99
<212> TYPE: DNA
<213> ORGANISM: Artificial Sequence
<220> FEATURE:
<223> OTHER INFORMATION: Illustrative sequence from Fig. 1

<400> SEQUENCE: 142
aacaaatgtg tcacaaagta aggattctga tgtgtatatc acagcaaaac tgtgctagac     60
atgaggtcta tggattcaag agcaacagtg ctgtggcct                           99

<210> SEQ ID NO 143
<211> LENGTH: 100
<212> TYPE: DNA
<213> ORGANISM: Artificial Sequence
<220> FEATURE:
<223> OTHER INFORMATION: Illustrative sequence from Fig. 1

<400> SEQUENCE: 143
aacaaatgtg tcacaaagta aggattctga tgtgtatatc acagacaaac tgtgctagac     60
atgaggtcta tggacttcaa gagcaacagt gctgtggcct                          100

<210> SEQ ID NO 144
<211> LENGTH: 101
<212> TYPE: DNA
<213> ORGANISM: Artificial Sequence
<220> FEATURE:
<223> OTHER INFORMATION: Illustrative sequence from Fig. 1

<400> SEQUENCE: 144
aacaaatgtg tcacaaagta aggattctga tgtgtatatc acagacaaaa ctgtgctaga     60
catgaggtct atggacttca agagcaacag tgctgtggcc t                        101

<210> SEQ ID NO 145
<211> LENGTH: 99
<212> TYPE: DNA
<213> ORGANISM: Artificial Sequence
<220> FEATURE:
<223> OTHER INFORMATION: Illustrative sequence from Fig. 1

<400> SEQUENCE: 145
aacaaatgtg tcacaaagta aggattctga tgtgtatatc acagacaaaa ctgtgctaga     60
catgatctat ggacttcaag agcaacagtg ctgtggcct                           99

<210> SEQ ID NO 146

```
<211> LENGTH: 94
<212> TYPE: DNA
<213> ORGANISM: Artificial Sequence
<220> FEATURE:
<223> OTHER INFORMATION: Illustrative sequence from Fig. 1

<400> SEQUENCE: 146
aacaaatgtg tcacaaagta aggattctga tgtgtatatc acagacaaaa ctgtgctaga      60
catgaggact tcaagagcaa cagtgctgtg gcct                                  94

<210> SEQ ID NO 147
<211> LENGTH: 97
<212> TYPE: DNA
<213> ORGANISM: Artificial Sequence
<220> FEATURE:
<223> OTHER INFORMATION: Illustrative sequence from Fig. 1

<400> SEQUENCE: 147
aacaaatgtg tcacaaagta aggattctga tgtgtatatc acagacaaaa ctgtgctaga      60
catgctatgg acttcaagag caacagtgct gtggcct                               97

<210> SEQ ID NO 148
<211> LENGTH: 99
<212> TYPE: DNA
<213> ORGANISM: Artificial Sequence
<220> FEATURE:
<223> OTHER INFORMATION: Illustrative sequence from Fig. 1

<400> SEQUENCE: 148
aacaaatgtg tcacaaagta aggattctga tgtgtatatc acagacaaaa ctgtgctaga      60
catgagctat ggacttcaag agcaacagtg ctgtggcct                             99

<210> SEQ ID NO 149
<211> LENGTH: 100
<212> TYPE: DNA
<213> ORGANISM: Artificial Sequence
<220> FEATURE:
<223> OTHER INFORMATION: Illustrative sequence from Fig. 1

<400> SEQUENCE: 149
aacaaatgtg tcacaaagta aggattctga tgtgtatatc acagacaaaa ctgtgctaga      60
catgaggtta tggacttcaa gagcaacagt gctgtggcct                           100

<210> SEQ ID NO 150
<211> LENGTH: 92
<212> TYPE: DNA
<213> ORGANISM: Artificial Sequence
<220> FEATURE:
<223> OTHER INFORMATION: Illustrative sequence from Fig. 1

<400> SEQUENCE: 150
aacaaatgtg tcacaaagta aggattctga tgtgtatatc acagacaaaa ctgtgctaga      60
catggacttc aagagcaaca gtgctgtggc ct                                    92

<210> SEQ ID NO 151
<211> LENGTH: 99
<212> TYPE: DNA
<213> ORGANISM: Artificial Sequence
<220> FEATURE:
<223> OTHER INFORMATION: Illustrative sequence from Fig. 1

<400> SEQUENCE: 151
aacaaatgtg tcacaaagta aggattctga tgtgtatatc acagacaaaa ctgtgctaga      60
```
catgaggtat ggacttcaag agcaacagtg ctgtggcct        99

<210> SEQ ID NO 152
<211> LENGTH: 83
<212> TYPE: DNA
<213> ORGANISM: Artificial Sequence
<220> FEATURE:
<223> OTHER INFORMATION: Illustrative sequence from Fig. 1

<400> SEQUENCE: 152
aacaaatgtg tcacaaagta aggattctga tgtgtatatc acagacaaaa ctgtgctaga        60
catgagcaac agtgctgtgg cct        83

<210> SEQ ID NO 153
<211> LENGTH: 86
<212> TYPE: DNA
<213> ORGANISM: Artificial Sequence
<220> FEATURE:
<223> OTHER INFORMATION: Illustrative sequence from Fig. 1

<400> SEQUENCE: 153
aacaaatgtg tcacaaagta aggattctga tgtgtatatc acagacaaaa ctgtgctaga        60
cttcaagagc aacagtgctg tggcct        86

<210> SEQ ID NO 154
<211> LENGTH: 88
<212> TYPE: DNA
<213> ORGANISM: Artificial Sequence
<220> FEATURE:
<223> OTHER INFORMATION: Illustrative sequence from Fig. 1

<400> SEQUENCE: 154
aacaaatgtg tcacaaagta aggattctga tgtgtatatc acagacaaaa ctgtgctatg        60
gacttcaaga gcaacagtgc tgtggcct        88

<210> SEQ ID NO 155
<211> LENGTH: 98
<212> TYPE: DNA
<213> ORGANISM: Artificial Sequence
<220> FEATURE:
<223> OTHER INFORMATION: Illustrative sequence from Fig. 1

<400> SEQUENCE: 155
aacaaatgtg tcacaaagta aggattctga tgtgtatatc acagacaaaa ctgtgctaga        60
catgactatg gacttcaaga gcaacagtgc tgtggcct        98

<210> SEQ ID NO 156
<211> LENGTH: 98
<212> TYPE: DNA
<213> ORGANISM: Artificial Sequence
<220> FEATURE:
<223> OTHER INFORMATION: Illustrative sequence from Fig. 1

<400> SEQUENCE: 156
aacaaatgtg tcacaaagta aggattctga tgtgtatatc acagacaaaa ctgtgctaga        60
catgtctatg gacttcaaga gcaacagtgc tgtggcct        98

<210> SEQ ID NO 157
<211> LENGTH: 91
<212> TYPE: DNA
<213> ORGANISM: Artificial Sequence
<220> FEATURE:

```
<223> OTHER INFORMATION: Illustrative sequence from Fig. 1

<400> SEQUENCE: 157
aacaaatgtg tcacaaagta aggattctga tgtgtatatc acagacaaaa ctgtgctaga      60
catgacttca agagcaacag tgctgtggcc t                                     91

<210> SEQ ID NO 158
<211> LENGTH: 96
<212> TYPE: DNA
<213> ORGANISM: Artificial Sequence
<220> FEATURE:
<223> OTHER INFORMATION: Illustrative sequence from Fig. 1

<400> SEQUENCE: 158
aacaaatgtg tcacaaagta aggattctga tgtgtatatc acagacaaaa ctgtgctaga      60
catctatgga cttcaagagc aacagtgctg tggcct                               96

<210> SEQ ID NO 159
<211> LENGTH: 100
<212> TYPE: DNA
<213> ORGANISM: Artificial Sequence
<220> FEATURE:
<223> OTHER INFORMATION: Illustrative sequence from Fig. 1

<400> SEQUENCE: 159
aacaaatgtg tcacaaagta aggattctga tgtgtatatc acagacaaaa ctgtgctaga      60
catgagtcta tggacttcaa gagcaacagt gctgtggcct                           100

<210> SEQ ID NO 160
<211> LENGTH: 100
<212> TYPE: DNA
<213> ORGANISM: Artificial Sequence
<220> FEATURE:
<223> OTHER INFORMATION: Illustrative sequence from Fig. 1

<400> SEQUENCE: 160
aacaaatgtg tcacaaagta aggattctga tgtgtatatc acagacaaaa ctgtgctaga      60
catgaggcta tggacttcaa gagcaacagt gctgtggcct                           100

<210> SEQ ID NO 161
<211> LENGTH: 64
<212> TYPE: DNA
<213> ORGANISM: Artificial Sequence
<220> FEATURE:
<223> OTHER INFORMATION: Illustrative sequence from Fig. 1

<400> SEQUENCE: 161
aacaaatgtg tcacaaagta aggattctga tgtgtatatc acagacaaaa ctgtgctgtg      60
gcct                                                                  64

<210> SEQ ID NO 162
<211> LENGTH: 83
<212> TYPE: DNA
<213> ORGANISM: Artificial Sequence
<220> FEATURE:
<223> OTHER INFORMATION: Illustrative sequence from Fig. 1

<400> SEQUENCE: 162
aacaaatgtg tcacaaagta aggattctga tgtgtatatc acagacaaaa ctgtgctaga      60
caagagcaac agtgctgtgg cct                                             83
```

```
<210> SEQ ID NO 163
<211> LENGTH: 95
<212> TYPE: DNA
<213> ORGANISM: Artificial Sequence
<220> FEATURE:
<223> OTHER INFORMATION: Illustrative sequence from Fig. 1

<400> SEQUENCE: 163
aacaaatgtg tcacaaagta aggattctga tgtgtatatc acagacaaaa ctgtgctaga     60
cactatggac ttcaagagca acagtgctgt ggcct                                95

<210> SEQ ID NO 164
<211> LENGTH: 97
<212> TYPE: DNA
<213> ORGANISM: Artificial Sequence
<220> FEATURE:
<223> OTHER INFORMATION: Illustrative sequence from Fig. 1

<400> SEQUENCE: 164
aacaaatgtg tcacaaagta aggattctga tgtgtatatc acagacaaaa ctgtgctaga     60
catgaggtgg acttcaagag caacagtgct gtggcct                              97

<210> SEQ ID NO 165
<211> LENGTH: 93
<212> TYPE: DNA
<213> ORGANISM: Artificial Sequence
<220> FEATURE:
<223> OTHER INFORMATION: Illustrative sequence from Fig. 1

<400> SEQUENCE: 165
aacaaatgtg tcacaaagta aggattctga tgtgtatatc acagacaaaa ctgtgctaga     60
ctatggactt caagagcaac agtgctgtgg cct                                  93

<210> SEQ ID NO 166
<211> LENGTH: 95
<212> TYPE: DNA
<213> ORGANISM: Artificial Sequence
<220> FEATURE:
<223> OTHER INFORMATION: Illustrative sequence from Fig. 1

<400> SEQUENCE: 166
aacaaatgtg tcacaaagta aggattctga tgtgtatatc acagacaaaa ctgtgctaga     60
catgatggac ttcaagagca acagtgctgt ggcct                                95

<210> SEQ ID NO 167
<211> LENGTH: 91
<212> TYPE: DNA
<213> ORGANISM: Artificial Sequence
<220> FEATURE:
<223> OTHER INFORMATION: Illustrative sequence from Fig. 1

<400> SEQUENCE: 167
aacaaatgtg tcacaaagta aggattctga tgtgtatatc acagacaaaa ctgtgctaga     60
catgaggtca agagcaacag tgctgtggcc t                                    91

<210> SEQ ID NO 168
<211> LENGTH: 78
<212> TYPE: DNA
<213> ORGANISM: Artificial Sequence
<220> FEATURE:
<223> OTHER INFORMATION: Illustrative sequence from Fig. 1

<400> SEQUENCE: 168
```
aacaaatgtg tcacaaagta aggattctga tgtgtatatc acagacaaaa ctgtgctaga    60
gcaacagtgc tgtggcct    78

<210> SEQ ID NO 169
<211> LENGTH: 101
<212> TYPE: DNA
<213> ORGANISM: Artificial Sequence
<220> FEATURE:
<223> OTHER INFORMATION: Illustrative sequence from Fig. 1

<400> SEQUENCE: 169
aacaaatgtg tcacaaagta aggattctga tgtgtatatc acagacaaaa ctgtgctaga    60
catgaggtct atggacttca agagcaacag tgctgtggcc t    101

<210> SEQ ID NO 170
<211> LENGTH: 95
<212> TYPE: DNA
<213> ORGANISM: Artificial Sequence
<220> FEATURE:
<223> OTHER INFORMATION: Illustrative sequence from Fig. 1

<400> SEQUENCE: 170
aacaaatgtg tcacaaagta aggattctga tgtgtatatc acagacaaaa ctgtgctaga    60
ctctatggac ttcaagagca agagtgctgt ggcct    95

<210> SEQ ID NO 171
<211> LENGTH: 95
<212> TYPE: DNA
<213> ORGANISM: Artificial Sequence
<220> FEATURE:
<223> OTHER INFORMATION: Illustrative sequence from Fig. 1

<400> SEQUENCE: 171
aacaaatgtg tcacaaagta aggattctga tgtgtatatc acagacaaaa ctgtgctaga    60
catgagggac ttcaagagca acagtgctgt ggcct    95

<210> SEQ ID NO 172
<211> LENGTH: 64
<212> TYPE: DNA
<213> ORGANISM: Artificial Sequence
<220> FEATURE:
<223> OTHER INFORMATION: Illustrative sequence from Fig. 1

<400> SEQUENCE: 172
aacaaatgtg tcacaaagta aggattctga tgtgtatatc acagacaaaa cagtgctgtg    60
gcct    64

<210> SEQ ID NO 173
<211> LENGTH: 93
<212> TYPE: DNA
<213> ORGANISM: Artificial Sequence
<220> FEATURE:
<223> OTHER INFORMATION: Illustrative sequence from Fig. 1

<400> SEQUENCE: 173
aacaaatgtg tcacaaagta aggattctga tgtgtatatc acagacaaaa ctgtgctagt    60
ctatggactt caagagcaac agtgctgtgg cct    93

<210> SEQ ID NO 174
<211> LENGTH: 76
<212> TYPE: DNA
<213> ORGANISM: Artificial Sequence

```
<220> FEATURE:
<223> OTHER INFORMATION: Illustrative sequence from Fig. 1

<400> SEQUENCE: 174
aacaaatgtg tcacaaagta aggattctga tgtgtatatc acagacaaaa cttcaagagc    60
aacagtgctg tggcct                                                    76

<210> SEQ ID NO 175
<211> LENGTH: 94
<212> TYPE: DNA
<213> ORGANISM: Artificial Sequence
<220> FEATURE:
<223> OTHER INFORMATION: Illustrative sequence from Fig. 1

<400> SEQUENCE: 175
aacaaatgtg tcacaaagta aggattctga tgtgtatatc acagacaaaa ctgtgctaga    60
cctatggact caagagcaa cagtgctgtg gcct                                 94

<210> SEQ ID NO 176
<211> LENGTH: 92
<212> TYPE: DNA
<213> ORGANISM: Artificial Sequence
<220> FEATURE:
<223> OTHER INFORMATION: Illustrative sequence from Fig. 1

<400> SEQUENCE: 176
aacaaatgtg tcacaaagta aggattctga tgtgtatatc acagacaaaa ctgtgctaga    60
catgaggttc aagagcaaca gtgctgtggc ct                                  92

<210> SEQ ID NO 177
<211> LENGTH: 83
<212> TYPE: DNA
<213> ORGANISM: Artificial Sequence
<220> FEATURE:
<223> OTHER INFORMATION: Illustrative sequence from Fig. 1

<400> SEQUENCE: 177
aacaaatgtg tcacaaagta aggattctga tgtgtatatc acagacaaaa ctatggactt    60
caagagcaac agtgctgtgg cct                                            83

<210> SEQ ID NO 178
<211> LENGTH: 95
<212> TYPE: DNA
<213> ORGANISM: Artificial Sequence
<220> FEATURE:
<223> OTHER INFORMATION: Illustrative sequence from Fig. 1

<400> SEQUENCE: 178
aacaaatgtg tcacaaagta aggattctga tgtgtatatc acagacaaaa cgtgctagac    60
atgaggtgac ttcaagagca acagtgctgt ggcct                               95

<210> SEQ ID NO 179
<211> LENGTH: 85
<212> TYPE: DNA
<213> ORGANISM: Artificial Sequence
<220> FEATURE:
<223> OTHER INFORMATION: Illustrative sequence from Fig. 1

<400> SEQUENCE: 179
aacaaatgtg tcacaaagta aggattctga tgtgtatatc acagacaaaa ctctatggac    60
ttcaagagca acagtgctgt ggcct                                          85
```

<210> SEQ ID NO 180
<211> LENGTH: 71
<212> TYPE: DNA
<213> ORGANISM: Artificial Sequence
<220> FEATURE:
<223> OTHER INFORMATION: Illustrative sequence from Fig. 1

<400> SEQUENCE: 180
aacaaatgtg tcacaaagta aggattctga tgtgtatatc acagacttca agagcaacag    60
tgctgtggcc t                                                         71

<210> SEQ ID NO 181
<211> LENGTH: 94
<212> TYPE: DNA
<213> ORGANISM: Artificial Sequence
<220> FEATURE:
<223> OTHER INFORMATION: Illustrative sequence from Fig. 1

<400> SEQUENCE: 181
aacaaatgtg tcacaaagta aggattctga tgtgtatatc acagacaaaa ctgtgctaga    60
catatggact tcaagagcaa cagtgctgtg gcct                                94

<210> SEQ ID NO 182
<211> LENGTH: 62
<212> TYPE: DNA
<213> ORGANISM: Artificial Sequence
<220> FEATURE:
<223> OTHER INFORMATION: Illustrative sequence from Fig. 1

<400> SEQUENCE: 182
aacaaatgtg tcacaaagta aggattctga tgtgtatatc acagacaaca gtgctgtggc    60
ct                                                                   62

<210> SEQ ID NO 183
<211> LENGTH: 63
<212> TYPE: DNA
<213> ORGANISM: Artificial Sequence
<220> FEATURE:
<223> OTHER INFORMATION: Illustrative sequence from Fig. 1

<400> SEQUENCE: 183
aacaaatgtg tcacaaagta aggattctga tgtgtatatc acagagcaac agtgctgtgg    60
cct                                                                  63

<210> SEQ ID NO 184
<211> LENGTH: 97
<212> TYPE: DNA
<213> ORGANISM: Artificial Sequence
<220> FEATURE:
<223> OTHER INFORMATION: Illustrative sequence from Fig. 1

<400> SEQUENCE: 184
aacaaatgtg tcacaaagta aggattctga tgtgtatatc acagacaaaa ctgtgctaga    60
catgatatgg acttcaagag caacagtgct gtggcct                             97

<210> SEQ ID NO 185
<211> LENGTH: 68
<212> TYPE: DNA
<213> ORGANISM: Artificial Sequence
<220> FEATURE:
<223> OTHER INFORMATION: Illustrative sequence from Fig. 1

<400> SEQUENCE: 185
aacaaatgtg tcacaaagta aggattctga tgtgtatatc acagacaaga gcaacagtgc    60
tgtggcct                                                             68

<210> SEQ ID NO 186
<211> LENGTH: 101
<212> TYPE: DNA
<213> ORGANISM: Artificial Sequence
<220> FEATURE:
<223> OTHER INFORMATION: Illustrative sequence from Fig. 1

<400> SEQUENCE: 186
aacaaatgtg tcacaaagta aggattctga tgtgtatatc acagacaaaa ctgtgctaga    60
catgaggact atggacttca agagcaacag tgctgtggcc t                       101

<210> SEQ ID NO 187
<211> LENGTH: 81
<212> TYPE: DNA
<213> ORGANISM: Artificial Sequence
<220> FEATURE:
<223> OTHER INFORMATION: Illustrative sequence from Fig. 1

<400> SEQUENCE: 187
aacaaatgtg tcacaaagta aggattctga tgtgtatatc acagacaaaa ctgtgcttca    60
agagcaacag tgctgtggcc t                                              81

<210> SEQ ID NO 188
<211> LENGTH: 93
<212> TYPE: DNA
<213> ORGANISM: Artificial Sequence
<220> FEATURE:
<223> OTHER INFORMATION: Illustrative sequence from Fig. 1

<400> SEQUENCE: 188
aacaaatgtg tcacaaagta aggattctga tgtgtatatc acagacaaaa ctgtgctaga    60
catgagactt caagagcaac agtgctgtgg cct                                 93

<210> SEQ ID NO 189
<211> LENGTH: 99
<212> TYPE: DNA
<213> ORGANISM: Artificial Sequence
<220> FEATURE:
<223> OTHER INFORMATION: Illustrative sequence from Fig. 1

<400> SEQUENCE: 189
aacaaatgtg tcacaaagta aggattctga tgtgtatatc acagacaaaa ctgtgctaga    60
catggactat ggacttcaag agcaacagtg ctgtggcct                           99

<210> SEQ ID NO 190
<211> LENGTH: 101
<212> TYPE: DNA
<213> ORGANISM: Artificial Sequence
<220> FEATURE:
<223> OTHER INFORMATION: Illustrative sequence from Fig. 1

<400> SEQUENCE: 190
aacaaatgtg tcacaaagta aggattctga tgtgtatatc acagacaaaa ctgtgctaga    60
catgaggtct atggacttca agagcaacag tgctgtggcc t                       101

<210> SEQ ID NO 191
<211> LENGTH: 101
<212> TYPE: DNA

<213> ORGANISM: Artificial Sequence
<220> FEATURE:
<223> OTHER INFORMATION: Illustrative sequence from Fig. 2

<400> SEQUENCE: 191
gcagaacccc cgcaaccact tccgctgtca agtccagttc tacgggctct cggagaatga    60
cgagtggacc caggataggg ccaaacctgt cacccagatc g                        101

<210> SEQ ID NO 192
<211> LENGTH: 101
<212> TYPE: DNA
<213> ORGANISM: Artificial Sequence
<220> FEATURE:
<223> OTHER INFORMATION: Illustrative sequence from Fig. 2

<400> SEQUENCE: 192
gcagaacccc cgcaaccact tccgctgtca agtccagttc tacgggctct cggagaatga    60
cgagtggacc caggataggg ccaaacccgt cacccagatc g                        101

<210> SEQ ID NO 193
<211> LENGTH: 101
<212> TYPE: DNA
<213> ORGANISM: Artificial Sequence
<220> FEATURE:
<223> OTHER INFORMATION: Illustrative sequence from Fig. 2

<400> SEQUENCE: 193
gcagaacccc cgcaaccact tccgctgtca agtccagttc tacgggctct cggagaatga    60
cgagtggacc caggataggg ccaaacccgt cacccagatc g                        101

<210> SEQ ID NO 194
<211> LENGTH: 99
<212> TYPE: DNA
<213> ORGANISM: Artificial Sequence
<220> FEATURE:
<223> OTHER INFORMATION: Illustrative sequence from Fig. 2

<400> SEQUENCE: 194
gcagaacccc cgcaaccact tccgctgtca agtccagttc tacgggctct cggagaatga    60
cgagtggaca ggatagggcc aaacctgtca cccagatcg                           99

<210> SEQ ID NO 195
<211> LENGTH: 100
<212> TYPE: DNA
<213> ORGANISM: Artificial Sequence
<220> FEATURE:
<223> OTHER INFORMATION: Illustrative sequence from Fig. 2

<400> SEQUENCE: 195
gcagaacccc cgcaaccact tccgctgtca agtccagttc tacgggctct cggagaatga    60
cgagtggccc aggatagggc caaacccgtc acccagatcg                          100

<210> SEQ ID NO 196
<211> LENGTH: 100
<212> TYPE: DNA
<213> ORGANISM: Artificial Sequence
<220> FEATURE:
<223> OTHER INFORMATION: Illustrative sequence from Fig. 2

<400> SEQUENCE: 196
gcagaacccc cgcaaccact tccgctgtca agtccagttc tacgggctct cggagaatga    60
cgagtggacc aggatagggc caaacccgtc acccagatcg                          100

```
<210> SEQ ID NO 197
<211> LENGTH: 94
<212> TYPE: DNA
<213> ORGANISM: Artificial Sequence
<220> FEATURE:
<223> OTHER INFORMATION: Illustrative sequence from Fig. 2

<400> SEQUENCE: 197
gcagaacccc cgcaaccact tccgctgtca agtccagttc tacgggctct cggagaatga      60
cgagtggata gggccaaacc cgtcacccag atcg                                  94

<210> SEQ ID NO 198
<211> LENGTH: 97
<212> TYPE: DNA
<213> ORGANISM: Artificial Sequence
<220> FEATURE:
<223> OTHER INFORMATION: Illustrative sequence from Fig. 2

<400> SEQUENCE: 198
gcagaacccc cgcaaccact tccgctgtca agtccagttc tacgggctct cggagaatga      60
cgagtggagg atagggccaa acccgtcacc cagatcg                               97

<210> SEQ ID NO 199
<211> LENGTH: 99
<212> TYPE: DNA
<213> ORGANISM: Artificial Sequence
<220> FEATURE:
<223> OTHER INFORMATION: Illustrative sequence from Fig. 2

<400> SEQUENCE: 199
gcagaacccc cgcaaccact tccgctgtca agtccagttc tacgggctct cggagaatga      60
cgagtgccca ggatagggcc aaacccgtca cccagatcg                             99

<210> SEQ ID NO 200
<211> LENGTH: 96
<212> TYPE: DNA
<213> ORGANISM: Artificial Sequence
<220> FEATURE:
<223> OTHER INFORMATION: Illustrative sequence from Fig. 2

<400> SEQUENCE: 200
gcagaacccc cgcaaccact tccgctgtca agtccagttc tacgggctct cggagaatga      60
cgagtggaga tagggccaaa cccgtcaccc agatcg                                96

<210> SEQ ID NO 201
<211> LENGTH: 95
<212> TYPE: DNA
<213> ORGANISM: Artificial Sequence
<220> FEATURE:
<223> OTHER INFORMATION: Illustrative sequence from Fig. 2

<400> SEQUENCE: 201
gcagaacccc cgcaaccact tccgctgtca agtccagttc tacgggctct cggagaatga      60
cgagtggaat agggccaaac ccgtcaccca gatcg                                 95

<210> SEQ ID NO 202
<211> LENGTH: 80
<212> TYPE: DNA
<213> ORGANISM: Artificial Sequence
<220> FEATURE:
<223> OTHER INFORMATION: Illustrative sequence from Fig. 2
```

```
<400> SEQUENCE: 202
gcagaacccc cgcaaccact tccgctgtca agtccagttc tacgggctct cggatagggc     60
caaacccgtc acccagatcg                                                 80

<210> SEQ ID NO 203
<211> LENGTH: 92
<212> TYPE: DNA
<213> ORGANISM: Artificial Sequence
<220> FEATURE:
<223> OTHER INFORMATION: Illustrative sequence from Fig. 2

<400> SEQUENCE: 203
gcagaacccc cgcaaccact tccgctgtca agtccagttc tacgggctct cggagaatga     60
cgaggatagg gccaaacccg tcacccagat cg                                   92

<210> SEQ ID NO 204
<211> LENGTH: 91
<212> TYPE: DNA
<213> ORGANISM: Artificial Sequence
<220> FEATURE:
<223> OTHER INFORMATION: Illustrative sequence from Fig. 2

<400> SEQUENCE: 204
gcagaacccc cgcaaccact tccgctgtca agtccagttc tacgggctct cggagaatga     60 cgagatagggc ccaaacccgt cacccagatc g                                   91

<210> SEQ ID NO 205
<211> LENGTH: 67
<212> TYPE: DNA
<213> ORGANISM: Artificial Sequence
<220> FEATURE:
<223> OTHER INFORMATION: Illustrative sequence from Fig. 2

<400> SEQUENCE: 205
gcagaacccc cgcaaccact tccgctgtca agtccagttc tacgggccaa acccgtcacc     60
cagatcg                                                               67

<210> SEQ ID NO 206
<211> LENGTH: 97
<212> TYPE: DNA
<213> ORGANISM: Artificial Sequence
<220> FEATURE:
<223> OTHER INFORMATION: Illustrative sequence from Fig. 2

<400> SEQUENCE: 206
gcagaacccc cgcaaccact tccgctgtca agtccagttc tacgggctct cggagaatga     60
cgagtcccag datagggcaa acccgtcacc cagatcg                              97

<210> SEQ ID NO 207
<211> LENGTH: 100
<212> TYPE: DNA
<213> ORGANISM: Artificial Sequence
<220> FEATURE:
<223> OTHER INFORMATION: Illustrative sequence from Fig. 2

<400> SEQUENCE: 207
gcagaacccc cgcaaccact tccgctgtca agtccagttc tacgggctct cggagaatga     60
cgagtggaag gataggggcc aaacccgtc acccagatcg                            100

<210> SEQ ID NO 208
<211> LENGTH: 101
```

```
<212> TYPE: DNA
<213> ORGANISM: Artificial Sequence
<220> FEATURE:
<223> OTHER INFORMATION: Illustrative sequence from Fig. 2

<400> SEQUENCE: 208
gcagaacccc cgcaaccact tccgctgtca agtccagttc tacgggctct cggagaatga        60
cgagtggacc caggataggg ccaaacccgt cacccagatc g                           101

<210> SEQ ID NO 209
<211> LENGTH: 86
<212> TYPE: DNA
<213> ORGANISM: Artificial Sequence
<220> FEATURE:
<223> OTHER INFORMATION: Illustrative sequence from Fig. 2

<400> SEQUENCE: 209
gcagaacccc cgcaaccact tccgctgtca agtccagttc tacgggctct cggagaatga        60
tagggccaaa cccgtcaccc agatcg                                             86

<210> SEQ ID NO 210
<211> LENGTH: 101
<212> TYPE: DNA
<213> ORGANISM: Artificial Sequence
<220> FEATURE:
<223> OTHER INFORMATION: Illustrative sequence from Fig. 2

<400> SEQUENCE: 210
gcagaacccc cgcaaccact tccgctgtca agtccagttc tacgggctct cggagaatga        60
cgagtggacc caggataggg ccaaacccgt cacccagatc g                           101

<210> SEQ ID NO 211
<211> LENGTH: 97
<212> TYPE: DNA
<213> ORGANISM: Artificial Sequence
<220> FEATURE:
<223> OTHER INFORMATION: Illustrative sequence from Fig. 2

<400> SEQUENCE: 211
gcagaacccc cgcaaccact tccgctgtca agtccagttc tacgggctct cggagaatga        60
cgagcccagg atagggccaa acccgtcacc cagatcg                                 97

<210> SEQ ID NO 212
<211> LENGTH: 74
<212> TYPE: DNA
<213> ORGANISM: Artificial Sequence
<220> FEATURE:
<223> OTHER INFORMATION: Illustrative sequence from Fig. 2

<400> SEQUENCE: 212
gcagaacccc cgcaaccact tccgctgtca agtccagttc tacgggctct cggagaatga        60
cgtcacccag atcg                                                          74

<210> SEQ ID NO 213
<211> LENGTH: 79
<212> TYPE: DNA
<213> ORGANISM: Artificial Sequence
<220> FEATURE:
<223> OTHER INFORMATION: Illustrative sequence from Fig. 2

<400> SEQUENCE: 213
gcagaacccc cgcaaccact tccgctgtca agtccagttc tacgggctct cgatagggcc        60
```

```
aaacccgtca cccagatcg                                              79

<210> SEQ ID NO 214
<211> LENGTH: 99
<212> TYPE: DNA
<213> ORGANISM: Artificial Sequence
<220> FEATURE:
<223> OTHER INFORMATION: Illustrative sequence from Fig. 2

<400> SEQUENCE: 214
gcagaacccc cgcaaccact tccgctgtca agtccagttc tacgggctct cggagaatga   60
cgagtggcca ggatagggcc aaacccgtca cccagatcg                          99

<210> SEQ ID NO 215
<211> LENGTH: 88
<212> TYPE: DNA
<213> ORGANISM: Artificial Sequence
<220> FEATURE:
<223> OTHER INFORMATION: Illustrative sequence from Fig. 2

<400> SEQUENCE: 215
gcagaacccc cgcaaccact tccgctgtca agtccagttc tacgggctct cggagaatga   60
cgagtggcca aacccgtcac ccagatcg                                      88

<210> SEQ ID NO 216
<211> LENGTH: 82
<212> TYPE: DNA
<213> ORGANISM: Artificial Sequence
<220> FEATURE:
<223> OTHER INFORMATION: Illustrative sequence from Fig. 2

<400> SEQUENCE: 216
gcagaacccc cgcaaccact tccgctgtca agtccagttc tacgggctct cggagatagg   60
gccaaacccg tcacccagat cg                                            82

<210> SEQ ID NO 217
<211> LENGTH: 79
<212> TYPE: DNA
<213> ORGANISM: Artificial Sequence
<220> FEATURE:
<223> OTHER INFORMATION: Illustrative sequence from Fig. 2

<400> SEQUENCE: 217
gcagaacccc cgcaaccact tccgctgtca agtccagttc tacgggccca ggatagggcc   60
aaacccgtca cccagatcg                                                79

<210> SEQ ID NO 218
<211> LENGTH: 88
<212> TYPE: DNA
<213> ORGANISM: Artificial Sequence
<220> FEATURE:
<223> OTHER INFORMATION: Illustrative sequence from Fig. 2

<400> SEQUENCE: 218
gcagaacccc cgcaaccact tccgctgtca agtccagttc tacgggctct cggagcccag   60
gatagggcca aacccgtcac ccagatgg                                      88

<210> SEQ ID NO 219
<211> LENGTH: 93
<212> TYPE: DNA
<213> ORGANISM: Artificial Sequence
<220> FEATURE:
<223> OTHER INFORMATION: Illustrative sequence from Fig. 2
```

<400> SEQUENCE: 219
gcagaacccc cgcaaccact tccgctgtca agtccagttc tacgggctct cggagaatga    60
cccaggatag ggccaaaccc gtcacccaga tcg                                 93

<210> SEQ ID NO 220
<211> LENGTH: 65
<212> TYPE: DNA
<213> ORGANISM: Artificial Sequence
<220> FEATURE:
<223> OTHER INFORMATION: Illustrative sequence from Fig. 2

<400> SEQUENCE: 220
gcagaacccc cgcaaccact tccgctgtca agtccaggat agggccaaac ccgtcaccca    60
gatcg                                                                65

<210> SEQ ID NO 221
<211> LENGTH: 97
<212> TYPE: DNA
<213> ORGANISM: Artificial Sequence
<220> FEATURE:
<223> OTHER INFORMATION: Illustrative sequence from Fig. 2

<400> SEQUENCE: 221
gcagaacccc cgcaaccact tccgctgtca agtccagttc tacgggctct cggagaatga    60
cgagcccagg atagggccaa acccgtcacc cagatcg                             97

<210> SEQ ID NO 222
<211> LENGTH: 100
<212> TYPE: DNA
<213> ORGANISM: Artificial Sequence
<220> FEATURE:
<223> OTHER INFORMATION: Illustrative sequence from Fig. 2

<400> SEQUENCE: 222
gcagaacccc cgcaaccact tccgctgtca agtccagttc tacgggctct cggagaatga    60
cgagtgaccc aggatagggc caaacccgtc acccagatcg                          100

<210> SEQ ID NO 223
<211> LENGTH: 94
<212> TYPE: DNA
<213> ORGANISM: Artificial Sequence
<220> FEATURE:
<223> OTHER INFORMATION: Illustrative sequence from Fig. 2

<400> SEQUENCE: 223
gcagaacccc cgcaaccact tccgctgtca agtccagttc tacgggctct cggagaatga    60
cgagtgcata gggccaaacc cgtcacccag atcg                                94

<210> SEQ ID NO 224
<211> LENGTH: 89
<212> TYPE: DNA
<213> ORGANISM: Artificial Sequence
<220> FEATURE:
<223> OTHER INFORMATION: Illustrative sequence from Fig. 2

<400> SEQUENCE: 224
gcagaacccc cgcaaccact tccgctgtca agtccagttc tacgggctct cggagaatga    60
cgatagggcc aaacccgtca cccagatcg                                      89

<210> SEQ ID NO 225

```
<211> LENGTH: 87
<212> TYPE: DNA
<213> ORGANISM: Artificial Sequence
<220> FEATURE:
<223> OTHER INFORMATION: Illustrative sequence from Fig. 2

<400> SEQUENCE: 225
gcagaacccc cgcaaccact tccgctgtca agtccagttc tacgggctct cggagaatga      60
cgagtggaaa acccgtcacc cagatcg                                          87

<210> SEQ ID NO 226
<211> LENGTH: 84
<212> TYPE: DNA
<213> ORGANISM: Artificial Sequence
<220> FEATURE:
<223> OTHER INFORMATION: Illustrative sequence from Fig. 2

<400> SEQUENCE: 226
gcagaacccc cgcaaccact tccgctgtca agtccagttc tacgggctct cggagaatga      60
cgagcaaacc cgtcacccag atcg                                             84

<210> SEQ ID NO 227
<211> LENGTH: 95
<212> TYPE: DNA
<213> ORGANISM: Artificial Sequence
<220> FEATURE:
<223> OTHER INFORMATION: Illustrative sequence from Fig. 2

<400> SEQUENCE: 227
gcagaacccc cgcaaccact tccgctgtca agtccagttc tacgggctct cggagaatga      60
cgcccaggat agggccaaac ccgtcaccca gatcg                                 95

<210> SEQ ID NO 228
<211> LENGTH: 87
<212> TYPE: DNA
<213> ORGANISM: Artificial Sequence
<220> FEATURE:
<223> OTHER INFORMATION: Illustrative sequence from Fig. 2

<400> SEQUENCE: 228
gcagaacccc cgcaaccact tccgctgtca agtccagttc tacgggctct cggagaatga      60
cgagagccaa acccgtcacc cagatcg                                          87

<210> SEQ ID NO 229
<211> LENGTH: 92
<212> TYPE: DNA
<213> ORGANISM: Artificial Sequence
<220> FEATURE:
<223> OTHER INFORMATION: Illustrative sequence from Fig. 2

<400> SEQUENCE: 229
gcagaacccc cgcaaccact tccgctgtca agtccagttc tacgggctct cggagaatga      60
ccaggatagg gccaaacccg tcacccagat cg                                    92

<210> SEQ ID NO 230
<211> LENGTH: 76
<212> TYPE: DNA
<213> ORGANISM: Artificial Sequence
<220> FEATURE:
<223> OTHER INFORMATION: Illustrative sequence from Fig. 2

<400> SEQUENCE: 230
gcagaacccc cgcaaccact tccgctgtca agtccagttc tacgggctct cggagaatga      60
```

```
cccgtcaccc agatcg                                                    76

<210> SEQ ID NO 231
<211> LENGTH: 95
<212> TYPE: DNA
<213> ORGANISM: Artificial Sequence
<220> FEATURE:
<223> OTHER INFORMATION: Illustrative sequence from Fig. 2

<400> SEQUENCE: 231
gcagaacccc cgcaaccact tccgctgtca agtccagttc tacgggctct cggagaatga    60
cgagtgggat agggccaaac ccgtcaccca gatcg                               95

<210> SEQ ID NO 232
<211> LENGTH: 98
<212> TYPE: DNA
<213> ORGANISM: Artificial Sequence
<220> FEATURE:
<223> OTHER INFORMATION: Illustrative sequence from Fig. 2

<400> SEQUENCE: 232
gcagaacccc cgcaaccact tccgctgtca agtccagttc tacgggctct cggagaatga    60
cgagtggcag gatagggcca aacccgtcac ccagatcg                            98

<210> SEQ ID NO 233
<211> LENGTH: 76
<212> TYPE: DNA
<213> ORGANISM: Artificial Sequence
<220> FEATURE:
<223> OTHER INFORMATION: Illustrative sequence from Fig. 2

<400> SEQUENCE: 233
gcagaacccc cgcaaccact tccgctgtca agtccagttc tacgggctct cggagaatga    60
cgagtcaccc agatcg                                                    76

<210> SEQ ID NO 234
<211> LENGTH: 88
<212> TYPE: DNA
<213> ORGANISM: Artificial Sequence
<220> FEATURE:
<223> OTHER INFORMATION: Illustrative sequence from Fig. 2

<400> SEQUENCE: 234
gcagaacccc cgcaaccact tccgctgtca agtccagttc tacgggctct cggagaatga    60
cgagtggcca aacccgtcac ccagatcg                                       88

<210> SEQ ID NO 235
<211> LENGTH: 77
<212> TYPE: DNA
<213> ORGANISM: Artificial Sequence
<220> FEATURE:
<223> OTHER INFORMATION: Illustrative sequence from Fig. 2

<400> SEQUENCE: 235
gcagaacccc cgcaaccact tccgctgtca agtccagttc tacgggcagg atagggccaa    60
acccgtcacc cagatcg                                                   77

<210> SEQ ID NO 236
<211> LENGTH: 94
<212> TYPE: DNA
<213> ORGANISM: Artificial Sequence
<220> FEATURE:
```

<223> OTHER INFORMATION: Illustrative sequence from Fig. 2

<400> SEQUENCE: 236
gcagaacccc cgcaaccact tccgctgtca agtccagttc tacgggctct cggagaatga    60
cgagaggata gggccaaacc cgtcacccag atcg    94

<210> SEQ ID NO 237
<211> LENGTH: 98
<212> TYPE: DNA
<213> ORGANISM: Artificial Sequence
<220> FEATURE:
<223> OTHER INFORMATION: Illustrative sequence from Fig. 2

<400> SEQUENCE: 237
gcagaacccc cgcaaccact tccgctgtca agtccagttc tacgggctct cggagaatga    60
cgagtgccag gatagggcca aacccgtcac ccagatcg    98

<210> SEQ ID NO 238
<211> LENGTH: 54
<212> TYPE: DNA
<213> ORGANISM: Artificial Sequence
<220> FEATURE:
<223> OTHER INFORMATION: Illustrative sequence from Fig. 2

<400> SEQUENCE: 238
gcagaacccc cgcaaccact tccgctgtca agtccaaacc cgtcacccag atcg    54

<210> SEQ ID NO 239
<211> LENGTH: 93
<212> TYPE: DNA
<213> ORGANISM: Artificial Sequence
<220> FEATURE:
<223> OTHER INFORMATION: Illustrative sequence from Fig. 2

<400> SEQUENCE: 239
gcagaacccc cgcaaccact tccgctgtca agtccagttc tacgggctct cggagaatga    60
cgagtggaag ggccaaaccc gtcacccaga tcg    93

<210> SEQ ID NO 240
<211> LENGTH: 57
<212> TYPE: DNA
<213> ORGANISM: Artificial Sequence
<220> FEATURE:
<223> OTHER INFORMATION: Illustrative sequence from Fig. 2

<400> SEQUENCE: 240
gcagaacccc cgcaaccact tccgctgtca agtccagttc tacgggctct cggatcg    57

<210> SEQ ID NO 241
<211> LENGTH: 97
<212> TYPE: DNA
<213> ORGANISM: Artificial Sequence
<220> FEATURE:
<223> OTHER INFORMATION: Illustrative sequence from Fig. 2

<400> SEQUENCE: 241
gcagaacccc cgcaaccact tccgctgtca agtccagttc tacgggctct cggagaatga    60
cgagtggacg atagggccaa acccgtcacc cagatcg    97

<210> SEQ ID NO 242
<211> LENGTH: 101
<212> TYPE: DNA
<213> ORGANISM: Artificial Sequence
<220> FEATURE:
<223> OTHER INFORMATION: Illustrative sequence from Fig. 3

<400> SEQUENCE: 242
cgaccccacc tacctaagaa ccatcctggc cgccagccca gttgtagcac cgcccagacg    60
actggccagg gcgcctgtgg gatctgcatg cctggagcag c                       101

<210> SEQ ID NO 243
<211> LENGTH: 101
<212> TYPE: DNA
<213> ORGANISM: Artificial Sequence
<220> FEATURE:
<223> OTHER INFORMATION: Illustrative sequence from Fig. 3

<400> SEQUENCE: 243
cgaccccacc tacctaagaa ccatcctggc cgccagccca gttgtagcac cgcccagacg    60
actggccagg gcgcctgtgg gatctgcatg cctggagcag c                       101

<210> SEQ ID NO 244
<211> LENGTH: 99
<212> TYPE: DNA
<213> ORGANISM: Artificial Sequence
<220> FEATURE:
<223> OTHER INFORMATION: Illustrative sequence from Fig. 3

<400> SEQUENCE: 244
cgaccccacc tacctaagaa ccatcctggc cgccagccca gttgtagccc gcccagacga    60
ctggccaggg cgcctgtggg atcgcatgcc tggagcagc                          99

<210> SEQ ID NO 245
<211> LENGTH: 101
<212> TYPE: DNA
<213> ORGANISM: Artificial Sequence
<220> FEATURE:
<223> OTHER INFORMATION: Illustrative sequence from Fig. 3

<400> SEQUENCE: 245
cgaccccacc tacctaagaa ccatcctggc cgccagccca gttgcagcac cgcccagacg    60
actggccagg gcgcctgtgg gatctgcatg cctggagcag c                       101

<210> SEQ ID NO 246
<211> LENGTH: 98
<212> TYPE: DNA
<213> ORGANISM: Artificial Sequence
<220> FEATURE:
<223> OTHER INFORMATION: Illustrative sequence from Fig. 3

<400> SEQUENCE: 246
cgaccccacc tacctaagaa ccatcctggc cgccagccca gttgtagcac cgcccagact    60
ggccagggcg cctgtgggat ctgcatgcct ggagcagc                           98

<210> SEQ ID NO 247
<211> LENGTH: 100
<212> TYPE: DNA
<213> ORGANISM: Artificial Sequence
<220> FEATURE:
<223> OTHER INFORMATION: Illustrative sequence from Fig. 3

<400> SEQUENCE: 247
cgaccccacc tacctaagaa ccatcctggc cgccagccca gttgtagcac cgcccagaga    60
ctggccaggg cgcctgtggg atctgcatgc ctggagcagc                         100

<210> SEQ ID NO 248
<211> LENGTH: 89
<212> TYPE: DNA
<213> ORGANISM: Artificial Sequence
<220> FEATURE:
<223> OTHER INFORMATION: Illustrative sequence from Fig. 3

<400> SEQUENCE: 248
cgaccccacc tacctaagaa ccatcctggc cgccagccca gttgtagcac cgcccagggc      60
gcctgtggga tctgcatccc tggagcagc                                       89

<210> SEQ ID NO 249
<211> LENGTH: 101
<212> TYPE: DNA
<213> ORGANISM: Artificial Sequence
<220> FEATURE:
<223> OTHER INFORMATION: Illustrative sequence from Fig. 3

<400> SEQUENCE: 249
cgaccccacc tacctaagaa ccatcctggc cgccagccca gttgtagcac cgcccagacg      60
actggccagg gcgcctgtgg gatctgcatg cctggagcag c                        101

<210> SEQ ID NO 250
<211> LENGTH: 73
<212> TYPE: DNA
<213> ORGANISM: Artificial Sequence
<220> FEATURE:
<223> OTHER INFORMATION: Illustrative sequence from Fig. 3

<400> SEQUENCE: 250
cgaccccacc tacctaagaa ccatcctggc cgccagccca gggcgcctgt gggatctgca      60
tgcctggagc agc                                                        73

<210> SEQ ID NO 251
<211> LENGTH: 100
<212> TYPE: DNA
<213> ORGANISM: Artificial Sequence
<220> FEATURE:
<223> OTHER INFORMATION: Illustrative sequence from Fig. 3

<400> SEQUENCE: 251
cgaccccacc tacctaagaa ccatcctggc cgccagccca gttgtagcac cgcccagcga      60
ctggccaggg cgcctgtggg atctgcatgc ctggagcagc                          100

<210> SEQ ID NO 252
<211> LENGTH: 101
<212> TYPE: DNA
<213> ORGANISM: Artificial Sequence
<220> FEATURE:
<223> OTHER INFORMATION: Illustrative sequence from Fig. 3

<400> SEQUENCE: 252
cgaccccacc tacctaagaa ccatcctggc cgccagccca gttgtagcac cgcccagacg      60
actggccagg gcgcctgtgg gatctgcatg cctggagcag c                        101

<210> SEQ ID NO 253
<211> LENGTH: 89
<212> TYPE: DNA
<213> ORGANISM: Artificial Sequence
<220> FEATURE:
<223> OTHER INFORMATION: Illustrative sequence from Fig. 3

<400> SEQUENCE: 253
cgaccccacc tacctaagaa ccatcctggc cgccagccca gttgtagcac tggccagggc    60
gcctgtggga tctgcatgcc tggagcagc                                       89

<210> SEQ ID NO 254
<211> LENGTH: 94
<212> TYPE: DNA
<213> ORGANISM: Artificial Sequence
<220> FEATURE:
<223> OTHER INFORMATION: Illustrative sequence from Fig. 3

<400> SEQUENCE: 254
cgaccccacc tacctaagaa ccatcctggc cgccagccca gttgtagcac cgccctggcc    60
agggcgcctg tgggatctgc atgcctggag cagc                                 94

<210> SEQ ID NO 255
<211> LENGTH: 93
<212> TYPE: DNA
<213> ORGANISM: Artificial Sequence
<220> FEATURE:
<223> OTHER INFORMATION: Illustrative sequence from Fig. 3

<400> SEQUENCE: 255
cgaccccacc tacctaagaa ccatcctggc cgccagccca gttgtagcac cgactggcca    60
gggcgcctgt gggatctgca tgcctggagc agc                                  93

<210> SEQ ID NO 256
<211> LENGTH: 99
<212> TYPE: DNA
<213> ORGANISM: Artificial Sequence
<220> FEATURE:
<223> OTHER INFORMATION: Illustrative sequence from Fig. 3

<400> SEQUENCE: 256
cgaccccacc tacctaagaa ccatcctggc cgccagccca gttgtagcac cgcccagaac    60
tggccagggc gcctgtggga tctgcatgcc tggagcagc                            99

<210> SEQ ID NO 257
<211> LENGTH: 99
<212> TYPE: DNA
<213> ORGANISM: Artificial Sequence
<220> FEATURE:
<223> OTHER INFORMATION: Illustrative sequence from Fig. 3

<400> SEQUENCE: 257
cgaccccacc tacctaagaa ccatcctggc cgccagccca gttgtagcac cgcccacgac    60
tggccagggc gcctgtggga tctgcatgcc tggagcagc                            99

<210> SEQ ID NO 258
<211> LENGTH: 93
<212> TYPE: DNA
<213> ORGANISM: Artificial Sequence
<220> FEATURE:
<223> OTHER INFORMATION: Illustrative sequence from Fig. 3

<400> SEQUENCE: 258
cgaccccacc tacctaagaa ccatcctggc cgccagccca gttgtagcac cgcccagaca    60
gggcgcctgt gggatctgca tgcctggagc agc                                  93

<210> SEQ ID NO 259
<211> LENGTH: 94
<212> TYPE: DNA

<213> ORGANISM: Artificial Sequence
<220> FEATURE:
<223> OTHER INFORMATION: Illustrative sequence from Fig. 3

<400> SEQUENCE: 259
cgaccccacc tacctaagaa ccatcctggc cgccagccca gttgtagcac cgcccagacc    60
agggcgcctg tgggatctgc atgcctgaga cagc    94

<210> SEQ ID NO 260
<211> LENGTH: 83
<212> TYPE: DNA
<213> ORGANISM: Artificial Sequence
<220> FEATURE:
<223> OTHER INFORMATION: Illustrative sequence from Fig. 3

<400> SEQUENCE: 260
cgaccccacc tacctaagaa ccatcctggc cgccagccca gttgtagcca gggcccttgt    60
gggatctgca tgcctggagc agc    83

<210> SEQ ID NO 261
<211> LENGTH: 88
<212> TYPE: DNA
<213> ORGANISM: Artificial Sequence
<220> FEATURE:
<223> OTHER INFORMATION: Illustrative sequence from Fig. 3

<400> SEQUENCE: 261
cgaccccacc tacctaagaa ccatcctggc cgccagccca gttgtagcac cgccagggcg    60
cctgtgggat ctgcatgcct ggagcagc    88

<210> SEQ ID NO 262
<211> LENGTH: 91
<212> TYPE: DNA
<213> ORGANISM: Artificial Sequence
<220> FEATURE:
<223> OTHER INFORMATION: Illustrative sequence from Fig. 3

<400> SEQUENCE: 262
cgaccccacc tacctaagaa ccatcctggc cgccagccca gttgtagcac cgcccagagg    60
gcgcctgtgg gatctgcatg cctggagcag c    91

<210> SEQ ID NO 263
<211> LENGTH: 80
<212> TYPE: DNA
<213> ORGANISM: Artificial Sequence
<220> FEATURE:
<223> OTHER INFORMATION: Illustrative sequence from Fig. 3

<400> SEQUENCE: 263
cgaccccacc tacctaagaa ccatcctggc cgccagccca gttgtagcac cgcctgtggg    60
atctgcatgc ctggagcagc    80

<210> SEQ ID NO 264
<211> LENGTH: 85
<212> TYPE: DNA
<213> ORGANISM: Artificial Sequence
<220> FEATURE:
<223> OTHER INFORMATION: Illustrative sequence from Fig. 3

<400> SEQUENCE: 264
cgaccccacc tacctaagaa ccatcctggc cgccagccca gttgtagcac cagggcgcct    60
gtgggatctg catgcctgga gcagc    85

<210> SEQ ID NO 265
<211> LENGTH: 88
<212> TYPE: DNA
<213> ORGANISM: Artificial Sequence
<220> FEATURE:
<223> OTHER INFORMATION: Illustrative sequence from Fig. 3

<400> SEQUENCE: 265
cgaccccacc tacctaagaa ccatcctggc cgccagccca gttgtagcac cgcccagacg    60
cctgtgggat ctgcatgcct ggagcagc                                       88

<210> SEQ ID NO 266
<211> LENGTH: 77
<212> TYPE: DNA
<213> ORGANISM: Artificial Sequence
<220> FEATURE:
<223> OTHER INFORMATION: Illustrative sequence from Fig. 3

<400> SEQUENCE: 266
cgaccccacc tacctaagaa ccatcctggc cgccagccca gttgtagcac cgcccagatc    60
tgcatgcctg gagcagc                                                   77

<210> SEQ ID NO 267
<211> LENGTH: 71
<212> TYPE: DNA
<213> ORGANISM: Artificial Sequence
<220> FEATURE:
<223> OTHER INFORMATION: Illustrative sequence from Fig. 3

<400> SEQUENCE: 267
cgaccccacc tacctaagaa ccatcctggc cgccagccca gcgcctgtgg gatctgcatg    60
cctggagcag c                                                         71

<210> SEQ ID NO 268
<211> LENGTH: 64
<212> TYPE: DNA
<213> ORGANISM: Artificial Sequence
<220> FEATURE:
<223> OTHER INFORMATION: Illustrative sequence from Fig. 3

<400> SEQUENCE: 268
cgaccccacc tacctaagaa ccatcctggc cgccagcctg tgggatctgc atgcctggag    60
cagc                                                                 64

<210> SEQ ID NO 269
<211> LENGTH: 98
<212> TYPE: DNA
<213> ORGANISM: Artificial Sequence
<220> FEATURE:
<223> OTHER INFORMATION: Illustrative sequence from Fig. 3

<400> SEQUENCE: 269
cgaccccacc tacctaagaa ccatcctggc cgccagccca gttgtagcac cgccccgact    60
ggccagggcg cctgtgggat ctgcatgcct ggagcagc                            98

<210> SEQ ID NO 270
<211> LENGTH: 87
<212> TYPE: DNA
<213> ORGANISM: Artificial Sequence
<220> FEATURE:
<223> OTHER INFORMATION: Illustrative sequence from Fig. 3

<400> SEQUENCE: 270
cgaccccacc tacctaagaa ccatcctggc cgccagccca gttgtagcac cgccaggcgc  60
ctgtgggatc tgcatgcctg gagcagc  87

<210> SEQ ID NO 271
<211> LENGTH: 96
<212> TYPE: DNA
<213> ORGANISM: Artificial Sequence
<220> FEATURE:
<223> OTHER INFORMATION: Illustrative sequence from Fig. 3

<400> SEQUENCE: 271
cgaccccacc tacctaagaa ccatcctggc cgccagccca gttgtagcac cgcccagagg  60
ccagggcgcc tgtgggatct gcatgcctgg agcagc  96

<210> SEQ ID NO 272
<211> LENGTH: 77
<212> TYPE: DNA
<213> ORGANISM: Artificial Sequence
<220> FEATURE:
<223> OTHER INFORMATION: Illustrative sequence from Fig. 3

<400> SEQUENCE: 272
cgaccccacc tacctaagaa ccatcctggc cgccagccca gttgtagcac ctgtgggatc  60
tgcatgcctg gagcagc  77

<210> SEQ ID NO 273
<211> LENGTH: 97
<212> TYPE: DNA
<213> ORGANISM: Artificial Sequence
<220> FEATURE:
<223> OTHER INFORMATION: Illustrative sequence from Fig. 3

<400> SEQUENCE: 273
cgaccccacc tacctaagaa ccatcctggc cgccagccca gttgtagcac cgcccagatg  60
gccagggcgc ctgtgggatc tgcatgcctg gagcagc  97

<210> SEQ ID NO 274
<211> LENGTH: 94
<212> TYPE: DNA
<213> ORGANISM: Artificial Sequence
<220> FEATURE:
<223> OTHER INFORMATION: Illustrative sequence from Fig. 3

<400> SEQUENCE: 274
cgaccccacc tacctaagaa ccatcctggc cgccagccca gttgtagcac cgcccaggcc  60
agggcgcctg tgggatctgc atgcctggag cagc  94

<210> SEQ ID NO 275
<211> LENGTH: 74
<212> TYPE: DNA
<213> ORGANISM: Artificial Sequence
<220> FEATURE:
<223> OTHER INFORMATION: Illustrative sequence from Fig. 3

<400> SEQUENCE: 275
cgaccccacc tacctaagaa ccatcctggc cgccagccca gttgcgcctg tgggatctgc  60
atgcctggag cagc  74

<210> SEQ ID NO 276
<211> LENGTH: 87

```
<212> TYPE: DNA
<213> ORGANISM: Artificial Sequence
<220> FEATURE:
<223> OTHER INFORMATION: Illustrative sequence from Fig. 3

<400> SEQUENCE: 276
cgaccccacc tacctaagaa ccatcctggc cgccagccca gttgtagctg gccagggcgc      60
ctgtgggatc tgcattcctg gagcagc                                         87

<210> SEQ ID NO 277
<211> LENGTH: 95
<212> TYPE: DNA
<213> ORGANISM: Artificial Sequence
<220> FEATURE:
<223> OTHER INFORMATION: Illustrative sequence from Fig. 3

<400> SEQUENCE: 277
cgaccccacc tacctaagaa ccatcctggc cgccagccca gttgtagcac cgcgactggc      60
cagggcgcct gtgggatctg catgcctgga gcagc                                95

<210> SEQ ID NO 278
<211> LENGTH: 77
<212> TYPE: DNA
<213> ORGANISM: Artificial Sequence
<220> FEATURE:
<223> OTHER INFORMATION: Illustrative sequence from Fig. 3

<400> SEQUENCE: 278
cgaccccacc tacctaagaa ccatcctggc cgccagccca gttgtagcgc ctgtgggatc      60
tgcatgcctg gagcagc                                                    77

<210> SEQ ID NO 279
<211> LENGTH: 78
<212> TYPE: DNA
<213> ORGANISM: Artificial Sequence
<220> FEATURE:
<223> OTHER INFORMATION: Illustrative sequence from Fig. 3

<400> SEQUENCE: 279
cgaccccacc tacctaagaa ccatcctggc cgccagccct ggccagggcg cctgtgggat      60
ctgcatgcct ggagcagc                                                   78

<210> SEQ ID NO 280
<211> LENGTH: 68
<212> TYPE: DNA
<213> ORGANISM: Artificial Sequence
<220> FEATURE:
<223> OTHER INFORMATION: Illustrative sequence from Fig. 3

<400> SEQUENCE: 280
cgaccccacc tacctaagaa ccatcctggc cgccagggcg cctgtgggat ctgcatgcct      60
ggagcagc                                                              68

<210> SEQ ID NO 281
<211> LENGTH: 79
<212> TYPE: DNA
<213> ORGANISM: Artificial Sequence
<220> FEATURE:
<223> OTHER INFORMATION: Illustrative sequence from Fig. 3

<400> SEQUENCE: 281
cgaccccacc tacctaagaa ccatcctggc cgccagccca gttgtagggc gcctgtggga      60
```

```
tctgcatgcc tggagcagc                                              79
```

<210> SEQ ID NO 282
<211> LENGTH: 81
<212> TYPE: DNA
<213> ORGANISM: Artificial Sequence
<220> FEATURE:
<223> OTHER INFORMATION: Illustrative sequence from Fig. 3

<400> SEQUENCE: 282

```
cgaccccacc tacctaagaa ccatcctggc cgccagccca gttgtagcag ggcgcctgtg   60
ggatctgcat gcctgggcag c                                            81
```

<210> SEQ ID NO 283
<211> LENGTH: 84
<212> TYPE: DNA
<213> ORGANISM: Artificial Sequence
<220> FEATURE:
<223> OTHER INFORMATION: Illustrative sequence from Fig. 3

<400> SEQUENCE: 283

```
cgaccccacc tacctaagaa ccatcctggc cgccagccca gttgtagcac cgcccagatg   60
tgggatctgc atgcctggag cagc                                         84
```

<210> SEQ ID NO 284
<211> LENGTH: 60
<212> TYPE: DNA
<213> ORGANISM: Artificial Sequence
<220> FEATURE:
<223> OTHER INFORMATION: Illustrative sequence from Fig. 3

<400> SEQUENCE: 284

```
cgaccccacc tacctaagaa ccatcctggc cgcctgtggg atctgcatgc ctggagcagc   60
```

<210> SEQ ID NO 285
<211> LENGTH: 66
<212> TYPE: DNA
<213> ORGANISM: Artificial Sequence
<220> FEATURE:
<223> OTHER INFORMATION: Illustrative sequence from Fig. 3

<400> SEQUENCE: 285

```
cgaccccacc tacctaagaa ccatcctggc cgccagccca gttgggatct gcatgcctgg   60
agcagc                                                             66
```

<210> SEQ ID NO 286
<211> LENGTH: 92
<212> TYPE: DNA
<213> ORGANISM: Artificial Sequence
<220> FEATURE:
<223> OTHER INFORMATION: Illustrative sequence from Fig. 3

<400> SEQUENCE: 286

```
cgaccccacc tacctaagaa ccatcctggc cgccagccca gttgtagcac cgccggccag   60
ggcgcctgtg ggatctgcat gcctggagca gc                                92
```

<210> SEQ ID NO 287
<211> LENGTH: 90
<212> TYPE: DNA
<213> ORGANISM: Artificial Sequence
<220> FEATURE:
<223> OTHER INFORMATION: Illustrative sequence from Fig. 3

<400> SEQUENCE: 287
cgaccccacc tacctaagaa ccatcctggc cgccagccca gttgtagcac ctggccaggg    60
cgcctgtggg atctgcatgc ctggagcagc                                     90

<210> SEQ ID NO 288
<211> LENGTH: 86
<212> TYPE: DNA
<213> ORGANISM: Artificial Sequence
<220> FEATURE:
<223> OTHER INFORMATION: Illustrative sequence from Fig. 3

<400> SEQUENCE: 288
cgaccccacc tacctaagaa ccatcctggc cgccagccca gtgtagcacc gcccagaggc    60
cgtgggatct gcatgcctgg agcagc                                         86

<210> SEQ ID NO 289
<211> LENGTH: 64
<212> TYPE: DNA
<213> ORGANISM: Artificial Sequence
<220> FEATURE:
<223> OTHER INFORMATION: Illustrative sequence from Fig. 3

<400> SEQUENCE: 289
cgaccccacc tacctaagaa ccatcctggc cagggcgcct gtgggatctc atgcctggag    60
cagc                                                                 64

<210> SEQ ID NO 290
<211> LENGTH: 47
<212> TYPE: DNA
<213> ORGANISM: Artificial Sequence
<220> FEATURE:
<223> OTHER INFORMATION: Illustrative sequence from Fig. 3

<400> SEQUENCE: 290
cgaccccacc tcctaagaac catcctggcc gccagcccag ttgtagc                  47

<210> SEQ ID NO 291
<211> LENGTH: 92
<212> TYPE: DNA
<213> ORGANISM: Artificial Sequence
<220> FEATURE:
<223> OTHER INFORMATION: Illustrative sequence from Fig. 3

<400> SEQUENCE: 291
cgaccccacc tacctaagaa ccatcctggc cgccagccca gttgtagcac cgcccagaag    60
ggcgcctgtg ggatctgcat gcctggagca gc                                  92

<210> SEQ ID NO 292
<211> LENGTH: 100
<212> TYPE: DNA
<213> ORGANISM: Artificial Sequence
<220> FEATURE:
<223> OTHER INFORMATION: Illustrative sequence from Fig. 3

<400> SEQUENCE: 292
cgaccccacc tacctaagaa ccatcctggc cgccagccca gttgtagcac cgcccagaca    60
ctggccaggg cgcctgtggg atctgcatgc ctggagcagc                         100

GENETICALLY MODIFIED IMMUNE CELLS TARGETING NY-ESO-1 AND METHODS OF USE THEREOF

CROSS-REFERENCE TO RELATED APPLICATIONS

The present application claims priority under 35 U.S.C. § 119(e) to U.S. Provisional Patent Application No. 62/597,717, filed Dec. 12, 2017, which is incorporated herein by reference in its entirety.

BACKGROUND

New York esophageal squamous cell carcinoma 1 (NY-ESO-1) protein is encoded by the CTAG1B gene, and was originally identified as a human tumor antigen by a method called serological expression (SEREX) cloning of recombinant cDNA libraries from human tumors. NY-ESO-1 belongs to the cancer-testis (CT) antigen group of proteins and its function remains unknown.

Expression is restricted to the testis and ovaries as NY-ESO-1 has not been detected in other normal tissues by RT-PCR. On the other hand, NY-ESO-1 expression has been observed in various tumor types, including myelomas, sarcomas, melanomas and other solid tumors at both molecular and protein levels.

In multiple myeloma, detection of NY-ESO-1 varies depending on the study. Molecular and immunohistochemical analyses have demonstrated NY-ESO-1 expression ranges from approximately 7% to 56% of all multiple myeloma samples tested. Overall, increased NY-ESO-1 has been observed in advanced disease stages as well as myelomas with abnormal cytogenetic profiles (approximately a third of the total patient population) across multiple reports.

Expression of NY-ESO-1 protein in sarcoma samples has been reported to be ≥80%. Synovial sarcoma (SS) and Myxoid/Round Cell Liposarcoma (MRCL) show the highest levels of expression. Results show strong and homogeneous staining patterns, with more than 70% of SS and MRCL samples demonstrating intense signal in over half of the malignant cells. In samples that are positive, NY-ESO-1 expression is intracellular and expression is primarily cytoplasmic.

Melanoma samples have been shown to have varying degrees of NY-ESO-1 expression depending on the study and metastatic status. One report has shown that NY-ESO-1 is not expressed in primary tumors but detected in 28% of metastatic samples, while two others demonstrated that ~45% of melanoma samples were NY-ESO-1 positive, with no relationship between expression and tumor stage. Furthermore, differential expression of NY-ESO-1 has been observed in morphologically distinct metastases. It has also been suggested that NY-ESO-1 expression is positively correlated with tumor thickness and negatively correlated with tumor-infiltrating lymphocytes.

Thus, there is a need in the art for novel tumor therapies targeting NY-ESO-1. The present invention addresses and satisfies this need.

SUMMARY OF THE INVENTION

The present invention is based on the discovery that genetically modified immune cells (e.g., T cells) comprising an exogenous target specific TCR (e.g., NY-ESO-1 TCR) demonstrate enhanced efficacy in killing target tumor cells in the tumor microenvironment. The immune cells may be genetically modified to comprise an exogenous receptor (e.g., a switch receptor) and/or may be genetically edited to disrupt expression of one or more endogenous receptors (e.g., a T-cell receptor gene and/or immune checkpoint protein) which suppress immune cell proliferation in the tumor microenvironment.

Accordingly, in certain aspects, the instant disclosure provides a modified T cell comprising an exogenous T cell receptor (TCR) having affinity for NY-ESO-1 on a target tumor cell, wherein the expression of an endogenous receptor (e.g., a TCR alpha chain coding sequence, an endogenous TCR beta chain coding sequence, and/or an endogenous PD1 coding sequence) is downregulated. In other aspects, the instant disclosure provides a modified T cell comprising an exogenous T cell receptor (TCR) having affinity for NY-ESO-1 on a target cell and a switch receptor, wherein the expression of an endogenous TCR alpha chain coding sequence, and an endogenous TCR beta chain coding sequence is downregulated.

In one aspect, a modified T cell comprising an exogenous T cell receptor (TCR) having affinity for NY-ESO-1 on a target cell, wherein the expression of an endogenous TCR coding sequence and/or an endogenous immune checkpoint coding sequence is downregulated, is provided.

In certain exemplary embodiments, the immune checkpoint coding sequence encodes an immune checkpoint protein selected from the group consisting of PD1, A2AR, B7-H3 (CD276), B7-H4 (VTCN1), BTLA (CD272), CD96, CTLA-4 (CD152), IDO, KIR, LAG3, TIGIT, TIM-3, and VISTA.

In certain exemplary embodiments, the endogenous TCR coding sequence is TRAC or TRBC.

In certain exemplary embodiments, at least one nucleotide substitution, deletion, insertion, and/or insertion/deletion (indel) is in the endogenous TCR alpha chain coding sequence comprising the nucleic acid sequence set forth in SEQ ID NO:128, thereby resulting in downregulated expression of the endogenous TCR alpha chain coding sequence.

In certain exemplary embodiments, at least one nucleotide substitution, deletion, insertion, and/or insertion/deletion is in the endogenous TCR beta chain coding sequence comprising the nucleic acid sequence set forth in SEQ ID NO:129, thereby resulting in downregulated expression of the endogenous TCR beta chain coding sequence.

In certain exemplary embodiments, at least one nucleotide substitution, deletion, insertion, and/or insertion/deletion is in the endogenous PD1 coding sequence comprising the nucleic acid sequence set forth in SEQ ID NO:130, thereby resulting in downregulated expression of the endogenous PD1 coding sequence.

In certain exemplary embodiments, optionally, at least one nucleotide substitution, deletion, insertion, and/or insertion/deletion is in the endogenous coding sequence selected from A2AR, B7-H3 (CD276), B7-H4 (VTCN1), BTLA (CD272), CD96, CTLA-4 (CD152), IDO, KIR, LAG3, TIGIT, TIM-3, and VISTA, thereby resulting in downregulated expression of the endogenous A2AR, B7-H3 (CD276), B7-H4 (VTCN1), BTLA (CD272), CD96, CTLA-4 (CD152), IDO, KIR, LAG3, TIGIT, TIM-3, and/or VISTA coding sequence.

In certain exemplary embodiments, the exogenous TCR comprises a TCR alpha chain comprising the amino acid sequence set forth in SEQ ID NO:5.

In certain exemplary embodiments, the exogenous TCR comprises a TCR beta chain comprising the amino acid sequence set forth in SEQ ID NO:12.

In another aspect, a modified T cell comprising: a) an exogenous T cell receptor (TCR) having affinity for NY-ESO-1 on a target cell, wherein the exogenous TCR comprises: (i) a TCR alpha chain comprising the amino acid sequence set forth in SEQ ID NO:5; and (ii) a TCR beta chain comprising the amino acid sequence set forth in SEQ ID NO:12; b) at least one nucleotide substitution, deletion, insertion, and/or insertion/deletion in an endogenous TCR alpha chain coding sequence comprising the nucleic acid sequence set forth in SEQ ID NO:128; and c) at least one nucleotide substitution, deletion, insertion, and/or insertion/deletion in an endogenous TCR beta chain coding sequence comprising the nucleic acid sequence set forth in SEQ ID NO:129, wherein the expression of the endogenous TCR alpha and beta chain coding sequences are downregulated, is provided.

In certain exemplary embodiments, the modified T cell further comprises at least one nucleotide substitution, deletion, insertion, and/or insertion/deletion in an endogenous coding sequence selected from PD1, A2AR, B7-H3 (CD276), B7-H4 (VTCN1), BTLA (CD272), CD96, CTLA-4 (CD152), IDO, KIR, LAG3, TIGIT, TIM-3, and VISTA.

In certain exemplary embodiments, the modified T cell further comprises d) at least one nucleotide substitution, deletion, insertion, and/or insertion/deletion in an endogenous PD1 coding sequence comprising the nucleic acid sequence set forth in SEQ ID NO:130.

In certain exemplary embodiments, the modified T cell is an autologous T cell.

In certain exemplary embodiments, the autologous T cell is derived from a human.

In certain exemplary embodiments, the autologous T cell is a CD3+ T cell.

In another aspect, a modified T cell comprising an exogenous T cell receptor (TCR) having affinity for NY-ESO-1 on a target cell, wherein the expression of an endogenous TCR alpha chain coding sequence, and the expression of an endogenous TCR beta chain coding sequence are downregulated, is provided.

In certain exemplary embodiments, at least one nucleotide substitution, deletion, insertion, and/or insertion/deletion is in the endogenous TCR alpha chain coding sequence comprising the nucleic acid sequence set forth in SEQ ID NO:128, thereby resulting in downregulated expression of the endogenous TCR alpha chain coding sequence.

In certain exemplary embodiments, at least one nucleotide substitution, deletion, insertion, and/or insertion/deletion is in the endogenous TCR beta chain coding sequence comprising the nucleic acid sequence set forth in SEQ ID NO:129, thereby resulting in downregulated expression of the endogenous TCR beta chain coding sequence.

In another aspect, a modified T cell comprising: a) an exogenous T cell receptor (TCR) having affinity for NY-ESO-1 on a target cell, wherein the exogenous TCR comprises: (i) a TCR alpha chain comprising the amino acid sequence set forth in SEQ ID NO:5; and (ii) a TCR beta chain comprising the amino acid sequence set forth in SEQ ID NO:12; b) at least one nucleotide substitution, deletion, insertion, and/or insertion/deletion in an endogenous TCR alpha chain coding sequence comprising the nucleic acid sequence set forth in SEQ ID NO:128; c) at least one nucleotide substitution, deletion, insertion, and/or insertion/deletion in an endogenous TCR beta chain coding sequence comprising the nucleic acid sequence set forth in SEQ ID NO:129; and d) at at least one nucleotide substitution, deletion, insertion, and/or insertion/deletion in an endogenous PD1 coding sequence comprising the nucleic acid sequence set forth in SEQ ID NO:130; wherein the expression of the endogenous TCR alpha chain, TCR beta chain coding sequence, and PD1 coding sequences are downregulated, is provided.

In certain exemplary embodiments, the modified T cell further comprises at least one nucleotide substitution, deletion, insertion, and/or insertion/deletion in an endogenous coding sequence selected from A2AR, B7-H3 (CD276), B7-H4 (VTCN1), BTLA (CD272), CD96, CTLA-4 (CD152), IDO, KIR, LAG3, TIGIT, TIM-3, and VISTA.

In certain exemplary embodiments, the modified T cell further comprises a switch receptor.

In certain exemplary embodiments, the switch receptor comprises: a first domain, wherein the first domain is derived from a first polypeptide that is associated with a negative signal; and a second domain, wherein the second domain is derived from a second polypeptide that is associated with a positive signal.

In certain exemplary embodiments, the first domain comprises at least a portion of an extracellular domain of the first polypeptide that is associated with a negative signal, and wherein the second domain comprises at least a portion of an intracellular domain of the second polypeptide that is associated with a positive signal.

In certain exemplary embodiments, the switch receptor further comprises a switch receptor transmembrane domain.

In certain exemplary embodiments, the switch receptor transmembrane domain comprises: a transmembrane domain of a first polypeptide that is associated with a negative signal; or a transmembrane domain of a second polypeptide that is associated with a positive signal.

In certain exemplary embodiments, the first polypeptide that is associated with a negative signal is selected from the group consisting of TIM-3, CTLA4, PD-1, BTLA, and TGFβR.

In certain exemplary embodiments, the first polypeptide that is associated with a negative signal is a variant of PD-1 having an alanine-to-leucine substitution at amino acid position 132 relative to the wild-type PD-1 amino acid sequence.

In certain exemplary embodiments, the second polypeptide that is associated with a positive signal is selected from the group consisting of 41BB, CD28, ICOS, and IL-12R.

In certain exemplary embodiments, the switch receptor comprises: a first domain comprising at least a portion of the extracellular domain of PD1; a switch receptor transmembrane domain comprising at least a portion of the transmembrane domain of CD28; and a second domain comprising at least a portion of the intracellular domain of CD28.

In certain exemplary embodiments, the switch receptor comprises a first domain comprising at least a portion of the extracellular domain of PD-1, wherein the PD-1 is a variant having an alanine-to-leucine substitution at amino acid position 132 relative to the wild-type PD-1 amino acid sequence; a second domain comprising a switch receptor transmembrane domain comprising at least a portion of the transmembrane domain of CD28; and a third domain comprising at least a portion of the intracellular domain of CD28.

In certain exemplary embodiments, the switch receptor comprises a first domain comprising at least a portion of the extracellular domain of PD-1; a second domain comprising a switch receptor transmembrane domain comprising at least a portion of the transmembrane domain of CD8alpha; and a third domain comprising at least a portion of the intracellular domain of 4-1BB.

In certain exemplary embodiments, the switch receptor comprises a first domain comprising at least a portion of the extracellular domain of PD-1, wherein the PD-1 is a variant having an alanine-to-leucine substitution at amino acid position 132 relative to the wild-type PD-1 amino acid sequence; a second domain comprising a switch receptor transmembrane domain comprising at least a portion of the transmembrane domain of CD8alpha; and a third domain comprising at least a portion of the intracellular domain of CD28.

In certain exemplary embodiments, the switch receptor comprises the amino acid sequence set forth in any one of SEQ ID NOs:14, 134, 136, or 138.

In certain exemplary embodiments, the switch receptor comprises: a first domain comprising at least a portion of the extracellular domain of TIM3; a switch receptor transmembrane domain comprising at least a portion of the transmembrane domain of CD28; and a second domain comprising at least a portion of the intracellular domain of CD28. In certain exemplary embodiments, the switch receptor comprises the amino acid sequence set forth in SEQ ID NO:132.

In certain exemplary embodiments, the switch receptor comprises: a first domain comprising at least a portion of the extracellular domain of a TGFβR; a second domain comprising at least a portion of the intracellular domain of a IL-12R.

In certain exemplary embodiments, the switch receptor comprises the amino acid sequence set forth in SEQ ID NO:16.

In certain exemplary embodiments, the switch receptor comprises the amino acid sequence set forth in SEQ ID NO:18.

In certain exemplary embodiments, the switch receptor comprises a truncated variant of a wild-type protein associated with a negative signal.

In certain exemplary embodiments, the switch receptor comprises the amino acid sequence set forth in SEQ ID NO:20.

In another aspect, a modified T cell comprising: a) an exogenous T cell receptor (TCR) having affinity for NY-ESO-1 on a target cell, wherein the exogenous TCR comprises: (i) a TCR alpha chain comprising the amino acid sequence set forth in SEQ ID NO:5; and (ii) a TCR beta chain comprising the amino acid sequence set forth in SEQ ID NO:12; b) at least one nucleotide substitution, deletion, insertion, and/or insertion/deletion in an endogenous TCR alpha chain coding sequence comprising the nucleic acid sequence set forth in SEQ ID NO:128; c) at least one nucleotide substitution, deletion, insertion, and/or insertion/deletion in an endogenous TCR beta chain coding sequence comprising the nucleic acid sequence set forth in SEQ ID NO:129; and d) a switch receptor comprising the amino acid sequence set forth in SEQ ID NO:14, wherein the expression of the endogenous TCR alpha chain coding sequence and the expression of the endogenous TCR beta chain coding sequence are downregulated, is provided.

In another aspect, a modified T cell comprising: a) an exogenous T cell receptor (TCR) having affinity for NY-ESO-1 on a target cell, wherein the exogenous TCR comprises: (i) a TCR alpha chain comprising the amino acid sequence set forth in SEQ ID NO:5; and (ii) a TCR beta chain comprising the amino acid sequence set forth in SEQ ID NO:12; b) at least one nucleotide substitution, deletion, insertion, and/or insertion/deletion in an endogenous TCR alpha chain coding sequence comprising the nucleic acid sequence set forth in SEQ ID NO:128; c) at least one nucleotide substitution, deletion, insertion, and/or insertion/deletion in an endogenous TCR beta chain coding sequence comprising the nucleic acid sequence set forth in SEQ ID NO:129; and d) a switch receptor comprising the amino acid sequence set forth in SEQ ID NO:136, wherein the expression of the endogenous TCR alpha chain coding sequence and the expression of the endogenous TCR beta chain coding sequence are downregulated.

In another aspect, a modified T cell comprising: a) an exogenous T cell receptor (TCR) having affinity for NY-ESO-1 on a target cell, wherein the exogenous TCR comprises: (i) a TCR alpha chain comprising the amino acid sequence set forth in SEQ ID NO:5; and (ii) a TCR beta chain comprising the amino acid sequence set forth in SEQ ID NO:12; b) at least one nucleotide substitution, deletion, insertion, and/or insertion/deletion in an endogenous TCR alpha chain coding sequence comprising the nucleic acid sequence set forth in SEQ ID NO:128; c) at least one nucleotide substitution, deletion, insertion, and/or insertion/deletion in an endogenous TCR beta chain coding sequence comprising the nucleic acid sequence set forth in SEQ ID NO:129; d) at least one nucleotide substitution, deletion, insertion, and/or insertion/deletion in an endogenous TIM-3 coding sequence; and e) a switch receptor comprising the amino acid sequence set forth in SEQ ID NO:14, wherein the expression of the endogenous TCR alpha chain coding sequence, the expression of the endogenous TCR beta chain coding sequence, and the expression of the endogenous TIM-3 coding sequence are downregulated, is provided.

In another aspect, a modified T cell comprising: a) an exogenous T cell receptor (TCR) having affinity for NY-ESO-1 on a target cell, wherein the exogenous TCR comprises: (i) a TCR alpha chain comprising the amino acid sequence set forth in SEQ ID NO:5; and (ii) a TCR beta chain comprising the amino acid sequence set forth in SEQ ID NO:12; b) at least one nucleotide substitution, deletion, insertion, and/or insertion/deletion in an endogenous TCR alpha chain coding sequence comprising the nucleic acid sequence set forth in SEQ ID NO:128; c) at least one nucleotide substitution, deletion, insertion, and/or insertion/deletion in an endogenous TCR beta chain coding sequence comprising the nucleic acid sequence set forth in SEQ ID NO:129; d) at least one nucleotide substitution, deletion, insertion, and/or insertion/deletion in an endogenous coding sequence selected from A2AR, B7-H3 (CD276), B7-H4 (VTCN1), BTLA (CD272), CD96, CTLA-4 (CD152), IDO, KIR, LAG3, PD1, TIGIT, TIM-3, and VISTA; and e) a switch receptor comprising the amino acid sequence set forth in any one of SEQ ID NOs:14, 16, 18, 20, 132, 134, 136, and 138, wherein the expressions of the endogenous TCR alpha chain coding sequence, the endogenous TCR beta chain coding sequence, and/or the endogenous coding sequence selected from A2AR, B7-H3 (CD276), B7-H4 (VTCN1), BTLA (CD272), CD96, CTLA-4 (CD152), IDO, KIR, LAG3, PD1, TIGIT, TIM-3, or VISTA are downregulated, is provided.

In another aspect, a method for generating a modified T cell comprising: a) introducing into a T cell a first nucleic acid comprising a nucleic acid sequence encoding an exogenous T cell receptor (TCR) having affinity for NY-ESO-1 on a target cell; and b) introducing into the T cell one or more nucleic acids capable of downregulating gene expression of one or more endogenous genes selected from the group consisting of TCR alpha chain, TCR beta chain, A2AR, B7-H3 (CD276), B7-H4 (VTCN1), BTLA (CD272), CD96, CTLA-4 (CD152), IDO, KIR, LAG3, PD1, TIGIT, TIM-3, and VISTA, is provided.

In certain exemplary embodiments, the first nucleic acid comprises a TCR alpha chain coding sequence and a TCR beta chain coding sequence.

In certain exemplary embodiments, the TCR alpha chain coding sequence and the TCR beta chain coding sequence are separated by a linker.

In certain exemplary embodiments, the linker comprises a nucleic acid sequence encoding an internal ribosome entry site (IRES).

In certain exemplary embodiments, the linker comprises a nucleic acid sequence encoding a self-cleaving peptide.

In certain exemplary embodiments, the self-cleaving peptide is a 2A peptide.

In certain exemplary embodiments, the 2A peptide is selected from the group consisting of porcine teschovirus-1 2A (P2A), Thoseaasigna virus 2A (T2A), equine rhinitis A virus 2A (E2A), and foot-and-mouth disease virus 2A (F2A).

In certain exemplary embodiments, the 2A peptide is T2A.

In certain exemplary embodiments, the linker comprises a furin cleavage site.

In certain exemplary embodiments, the linker comprises a furin cleavage site and T2A.

In certain exemplary embodiments, the first nucleic acid comprises from 5' to 3' the TCR alpha chain coding sequence, the linker, and the TCR beta chain coding sequence.

In certain exemplary embodiments, the first nucleic acid comprises from 5' to 3' the TCR beta chain coding sequence, the linker, and the TCR alpha chain coding sequence.

In certain exemplary embodiments, the TCR alpha chain coding sequence comprises the nucleic acid sequence set forth in SEQ ID NO:6.

In certain exemplary embodiments, the TCR beta chain coding sequence comprises the nucleic acid sequence set forth in SEQ ID NO:13.

In certain exemplary embodiments, the first nucleic acid is introduced by viral transduction.

In certain exemplary embodiments, the viral transduction comprises contacting the cell with a viral vector comprising the first nucleic acid.

In certain exemplary embodiments, the viral vector is selected from the group consisting of a retroviral vector, a lentiviral vector, an adenoviral vector, and an adeno-associated viral vector.

In certain exemplary embodiments, the viral vector is a lentiviral vector.

In certain exemplary embodiments, the lentiviral vector further comprises an EF-1α promoter.

In certain exemplary embodiments, the lentiviral vector further comprises a rev response element (RRE).

In certain exemplary embodiments, the lentiviral vector further comprises a woodchuck hepatitis virus posttranscriptional regulatory element (WPRE).

In certain exemplary embodiments, the lentiviral vector further comprises a cPPT sequence.

In certain exemplary embodiments, the lentiviral vector further comprises an EF-1α promoter, a rev response element (RRE), a woodchuck hepatitis virus posttranscriptional regulatory element (WPRE), and a cPPT sequence.

In certain exemplary embodiments, the lentiviral vector is a self-inactivating lentiviral vector.

In certain exemplary embodiments, each of the one or more nucleic acids capable of downregulating gene expression comprises an antisense RNA, an antagomir RNA, siRNA, shRNA, and a CRISPR system, or any combination thereof.

In certain exemplary embodiments, the CRISPR system comprises a Cas9 RNA and a guide RNA (gRNA).

In certain exemplary embodiments, the CRISPR system comprises a Cas9/gRNA ribonucleoprotein complex.

In certain exemplary embodiments, the CRISPR system comprises a gRNA comprising a nucleic acid sequence set forth in any one of SEQ ID NOs:37-127 and 131.

In certain exemplary embodiments, each of the one or more nucleic acids capable of downregulating gene expression is introduced by electroporation.

In another aspect, a method for generating a modified T cell comprising: a) introducing into a T cell a first nucleic acid comprising a nucleic acid sequence encoding an exogenous T cell receptor (TCR) having affinity for NY-ESO-1 on a target cell; and b) introducing into the T cell one or more nucleic acids capable of downregulating gene expression of one or more endogenous genes selected from the group consisting of TCR alpha chain, and TCR beta chain, is provided.

In certain exemplary embodiments, the first nucleic acid further comprises a nucleic acid sequence encoding a switch receptor.

In certain exemplary embodiments, the nucleic acid sequence encoding the switch receptor comprises the nucleic acid sequence set forth in SEQ ID NO:15.

In certain exemplary embodiments, the nucleic acid sequence encoding the switch receptor comprises the nucleic acid sequence set forth in SEQ ID NO: 137.

In certain exemplary embodiments, the nucleic acid sequence encoding the switch receptor comprises the nucleic acid sequence set forth in SEQ ID NO: 139.

In certain exemplary embodiments, the method further comprises: c) introducing into the T cell one or more nucleic acids capable of downregulating gene expression of one or more endogenous genes selected from the group consisting A2AR, B7-H3 (CD276), B7-H4 (VTCN1), BTLA (CD272), CD96, CTLA-4 (CD152), IDO, KIR, LAG3, TIGIT, TIM-3, and VISTA.

In another aspect, a method for generating a modified T cell comprising: a) introducing into a T cell a first nucleic acid comprising a nucleic acid sequence encoding an exogenous T cell receptor (TCR) having affinity for NY-ESO-1 on a target cell, and a nucleic acid sequence encoding a switch receptor; and b) introducing into the T cell one or more nucleic acids capable of downregulating gene expression of one or more endogenous genes selected from the group consisting of TCR alpha chain, TCR beta chain, A2AR, B7-H3 (CD276), B7-H4 (VTCN1), BTLA (CD272), CD96, CTLA-4 (CD152), IDO, KIR, LAG3, PD1, TIGIT, TIM-3, and VISTA, is provided.

In certain exemplary embodiments, the nucleic acid sequence encoding the exogenous TCR comprises a TCR alpha chain coding sequence and a TCR beta chain coding sequence.

In certain exemplary embodiments, the TCR alpha chain coding sequence comprises the nucleic acid sequence set forth in SEQ ID NO:6.

In certain exemplary embodiments, the TCR beta chain coding sequence comprises the nucleic acid sequence set forth in SEQ ID NO:13.

In certain exemplary embodiments, the nucleic acid sequence encoding the switch receptor comprises the nucleic acid sequence set forth in SEQ ID NO:15, 17, 19, or 21, 133, 135, 137 or 139.

In certain exemplary embodiments, the nucleic acid sequence encoding the exogenous TCR and the nucleic acid sequence encoding the switch receptor are separated by a first linker.

In certain exemplary embodiments, the TCR alpha chain coding sequence and the TCR beta chain coding sequence are separated by a second linker.

In certain exemplary embodiments, each of the first and second linkers independently comprise a nucleic acid sequence encoding an internal ribosome entry site (IRES).

In certain exemplary embodiments, each of the first and second linkers independently comprise a nucleic acid sequence encoding a self-cleaving peptide.

In certain exemplary embodiments, the self-cleaving peptide is a 2A peptide.

In certain exemplary embodiments, the 2A peptide is selected from the group consisting of porcine teschovirus-1 2A (P2A), Thoseaasigna virus 2A (T2A), equine rhinitis A virus 2A (E2A), and foot-and-mouth disease virus 2A (F2A).

In certain exemplary embodiments, the 2A peptide is T2A.

In certain exemplary embodiments, the first linker and the second linker are different.

In certain exemplary embodiments, the second linker comprises a nucleic acid sequence encoding a furin cleavage site.

In certain exemplary embodiments, the second linker comprises a nucleic acid sequence encoding a furin cleavage site and T2A.

In certain exemplary embodiments, the first linker comprises a nucleic acid sequence encoding F2A.

In certain exemplary embodiments, the first nucleic acid comprises from 5' to 3' the nucleic acid sequence encoding the switch receptor, the first linker, the TCR alpha chain coding sequence, the second linker, and the TCR beta chain coding sequence.

In certain exemplary embodiments, the first nucleic acid comprises from 5' to 3' the TCR beta chain coding sequence, the second linker, the TCR alpha chain coding sequence, the first linker, and the nucleic acid sequence encoding the switch receptor.

In certain exemplary embodiments, the first nucleic acid is introduced by viral transduction.

In certain exemplary embodiments, the viral transduction comprises contacting the cell with a viral vector comprising the first nucleic acid.

In certain exemplary embodiments, the viral vector is selected from the group consisting of a retroviral vector, a lentiviral vector, an adenoviral vector, and an adeno-associated viral vector.

In certain exemplary embodiments, the viral vector is a lentiviral vector.

In certain exemplary embodiments, the lentiviral vector further comprises an EF-1α promoter.

In certain exemplary embodiments, the lentiviral vector further comprises a rev response element (RRE).

In certain exemplary embodiments, the lentiviral vector further comprises a woodchuck hepatitis virus posttranscriptional regulatory element (WPRE).

In certain exemplary embodiments, the lentiviral vector further comprises a cPPT sequence.

In certain exemplary embodiments, the lentiviral vector further comprises an EF-1α promoter, a rev response element (RRE), a woodchuck hepatitis virus posttranscriptional regulatory element (WPRE), and a cPPT sequence.

In certain exemplary embodiments, the lentiviral vector is a self-inactivating lentiviral vector.

In certain exemplary embodiments, each of the one or more nucleic acids capable of downregulating gene expression comprises an antisense RNA, an antagomir RNA, siRNA, shRNA, and a CRISPR system, or any combination thereof.

In certain exemplary embodiments, the CRISPR system is a Cas9 RNA and a gRNA.

In certain exemplary embodiments, the CRISPR system is a Cas9/gRNA RNP complex.

In certain exemplary embodiments, the CRISPR system comprises a gRNA comprising a nucleic acid sequence set forth in any one of SEQ ID NOs: 37-127, and 131.

In certain exemplary embodiments, each of the one or more nucleic acids capable of downregulating gene expression is introduced by electroporation.

In another aspect, a method of treating cancer in a subject in need thereof, the method comprising administering a therapeutically effective composition comprising a modified immune cell described herein to the subject, is provided.

In another aspect, a method of treating multiple myeloma in a subject in need thereof, comprising: a) administering to the subject a lymphodepleting chemotherapy comprising administering to the subject an effective amount of cyclophosphamide; b) administering to the subject a modified T cell comprising: i) an exogenous T cell receptor (TCR) having affinity for NY-ESO-1 on a target cell, wherein the exogenous TCR comprises: (1) a TCR alpha chain comprising the amino acid sequence set forth in SEQ ID NO:5; and (2) a TCR beta chain comprising the amino acid sequence set forth in SEQ ID NO:12; ii) at least one nucleotide substitution, deletion, insertion, and/or insertion/deletion in an endogenous TCR alpha chain coding sequence comprising the nucleic acid sequence set forth in SEQ ID NO:128; iii) at least one nucleotide substitution, deletion, insertion, and/or insertion/deletion in an endogenous TCR beta chain coding sequence comprising the nucleic acid sequence set forth in SEQ ID NO:129; and iv) at least one nucleotide substitution, deletion, insertion, and/or insertion/deletion in an endogenous PD1 coding sequence comprising the nucleic acid sequence set forth in SEQ ID NO:130, wherein the expression of the endogenous TCR alpha chain coding sequence, the endogenous TCR beta chain coding sequence, and endogenous PD1 coding sequence are downregulated, is provided.

In another aspect, a method of treating melanoma, synovial sarcoma, or myxoid/round cell liposarcoma in a subject in need thereof, comprising: a) administering to the subject a lymphodepleting chemotherapy comprising administering to the subject an effective amount of cyclophosphamide, and an effective amount of fludarabine; b) administering to the subject a modified T cell comprising: i) an exogenous T cell receptor (TCR) having affinity for NY-ESO-1 on a target cell, wherein the exogenous TCR comprises: (1) a TCR alpha chain comprising the amino acid sequence set forth in SEQ ID NO:5; and (2) a TCR beta chain comprising the amino acid sequence set forth in SEQ ID NO:12; ii) at least one nucleotide substitution, deletion, insertion, and/or insertion/deletion in an endogenous TCR alpha chain coding sequence comprising the nucleic acid sequence set forth in SEQ ID NO:128; iii) at least one nucleotide substitution, deletion, insertion, and/or insertion/deletion in an endogenous TCR beta chain coding sequence comprising the nucleic acid sequence set forth in SEQ ID NO:129; and iv) at least one nucleotide substitution, deletion, insertion, and/or insertion/deletion in an endogenous PD1 coding sequence comprising the nucleic acid sequence set forth in SEQ ID NO:130, wherein the expression of the endogenous TCR alpha chain coding sequence, the endogenous TCR beta chain coding sequence, and endogenous PD1 coding sequence are downregulated, is provided.

BRIEF DESCRIPTION OF THE DRAWINGS

The foregoing and other features and advantages of the present invention will be more fully understood from the following detailed description of illustrative embodiments taken in conjunction with the accompanying drawings.

FIG. 5 depicts flow cytometry analysis demonstrating the efficiency of gene editing of endogenous TCR.

FIG. 8 depicts results from a Surveyor assay for detection of percent gene editing.

FIG. 9 depicts flow cytometry analysis demonstrating the ability of NY-ESO-1 transduced T cell with $TCR^{endo}$ and PD1 gene edited to degranulate in response to tumor.

FIGS. 16A-16B depict results of stress tests that were performed on CRISPR gene edited NY-ESO-1 TCR transduced T cells.

FIGS. 21A-21B depict data showing that disruption of TRAC and TRBC disruption improves function of NY-ESO-1 TCR transduced T cells.

FIG. 25D shows a graph of tumor size that was measured one day prior to the T cell treatment, and weekly post-treatment.

FIGS. 27A-27D depict the off-target detection of gRNAs using Guide-seq.

FIGS. 28A-28D depict a series of plots illustrating CRISPR/Cas9 gene disruption efficiency of T cells. FIG. 28A further depicts 29 gRNA sequences spanning Tim3-1 to Tim3-29, which correspond to SEQ ID Nos: 98-126, respectively.

FIGS. 30A-30C depict data showing improved anti-tumor function of NY-ESO-1 TCR transduced T cells with PD1-CD28 switch receptor.

FIGS. 31A-31F depict data showing massive gene expression profile changes in transduced T cells.

FIGS. 31G-31H depict data showing gene expression distribution and profile changes in various T cells as indicated.

FIGS. 32A-32B depict data showing that T cells transduced with NY-ESO-1 TCR (8F) and PD1-CD28 switch receptor exhibit increased resistance to TGFβ and adenosine.

FIGS. 35A-35C depict data showing that a high affinity PD1 switch receptor enhances NY-ESO-1 TCR anti-tumor activity. Bioluminescence images are shown in FIG. 35A, and corresponding quantification of radiance is shown in FIG. 35B. FIG. 35C is a plot showing change in tumor size over time for the various groups as indicated. UTD: untransduced; CD28: NY-ESO-1 TCR (8F) and PD1.CD28 switch (PD1-CD28); CD28 #: NY-ESO-1 TCR (8F) and PD1*.CD28 switch ($PD1^{A132L}$-CD28); BB: NY-ESO-1 TCR (8F) and PD1.BB switch (PD1-41BB); BB #: NY-ESO-1 TCR (8F) and PD1*.BB switch ($PD1^{A132L}$-41BB); 8F: NY-ESO-1 TCR.

FIG. 36A shows bioluminescence images, and corresponding quantification of radiance is shown in FIG. 36B. FIG. 36C is a plot showing change in tumor size over time for the various groups as indicated. A: untransduced, TRAC/TRBC disrupted T cells (UTD DKO); B: NY-ESO-1 TCR (8F), TRAC/TRBC disrupted T cells (8F DKO); C: NY-ESO-1 TCR (8F), TRAC/TRBC/PDCD1/TIM3 disrupted T cells (8F DKO+PD1 & Tim3 KO); D: NY-ESO-1 TCR (8F), TIM3-CD28 switch, TRAC/TRBC disrupted T cells (Tim3CD28.8F DKO); E: NY-ESO-1 TCR (8F), TIM3-CD28 switch, TRAC/TRBC/PDCD1 disrupted T cells (Tim3CD28.8F DKO+PD1 KO); F: NY-ESO-1 TCR (8F), PD1$^{A132L}$-41BB switch, TRAC/TRBC disrupted T cells (PD1*BB.8F DKO); G: NY-ESO-1 TCR (8F), PD1$^{A132L}$-41BB switch, TRAC/TRBC/TIM3 disrupted T cells (PD1*BB.8F DKO+Tim3 KO); H: NY-ESO-1 TCR (8F), PD1$^{A132L}$-41BB switch, TIM3-CD28 switch, TRAC/TRBC disrupted T cells (PD1*BB.Tim3CD28.8F DKO); and I: NY-ESO-1 TCR (8F), PD1-CD28 switch, TRAC/TRBC/TIM3 disrupted T cells (PD1CD28.8F DKO+Tim3 KO). FIG. 36D shows BLI of mice injected with T cells as indicated. FIG. 36E shows a plot of tumor size measured at various time points as indicated post-injection with T cells for the various groups as indicated. In FIGS. 36D and 36E: UTD: untransduced T cells; PD1.CD28.8F (CD28 in FIG. 36E): 8F NY-ESO-1 TCR T cells with PD1-CD28 switch; PD1*.CD28.8F (CD28 # in FIG. 36E): 8F NY-ESO-1 TCR T cells with PD1$^{A132L}$-CD28 switch; PD1.BB.8F (BB in FIG. 36E): 8F NY-ESO-1 TCR T cells with PD1-41BB switch; PD1*.BB.8F (BB # in FIG. 36E): 8F NY-ESO-1 TCR T cells with PD1$^{A132L}$-41BB switch; 8F: 8F NY-ESO-1 TCR T cells.

DETAILED DESCRIPTION

Figure 1:
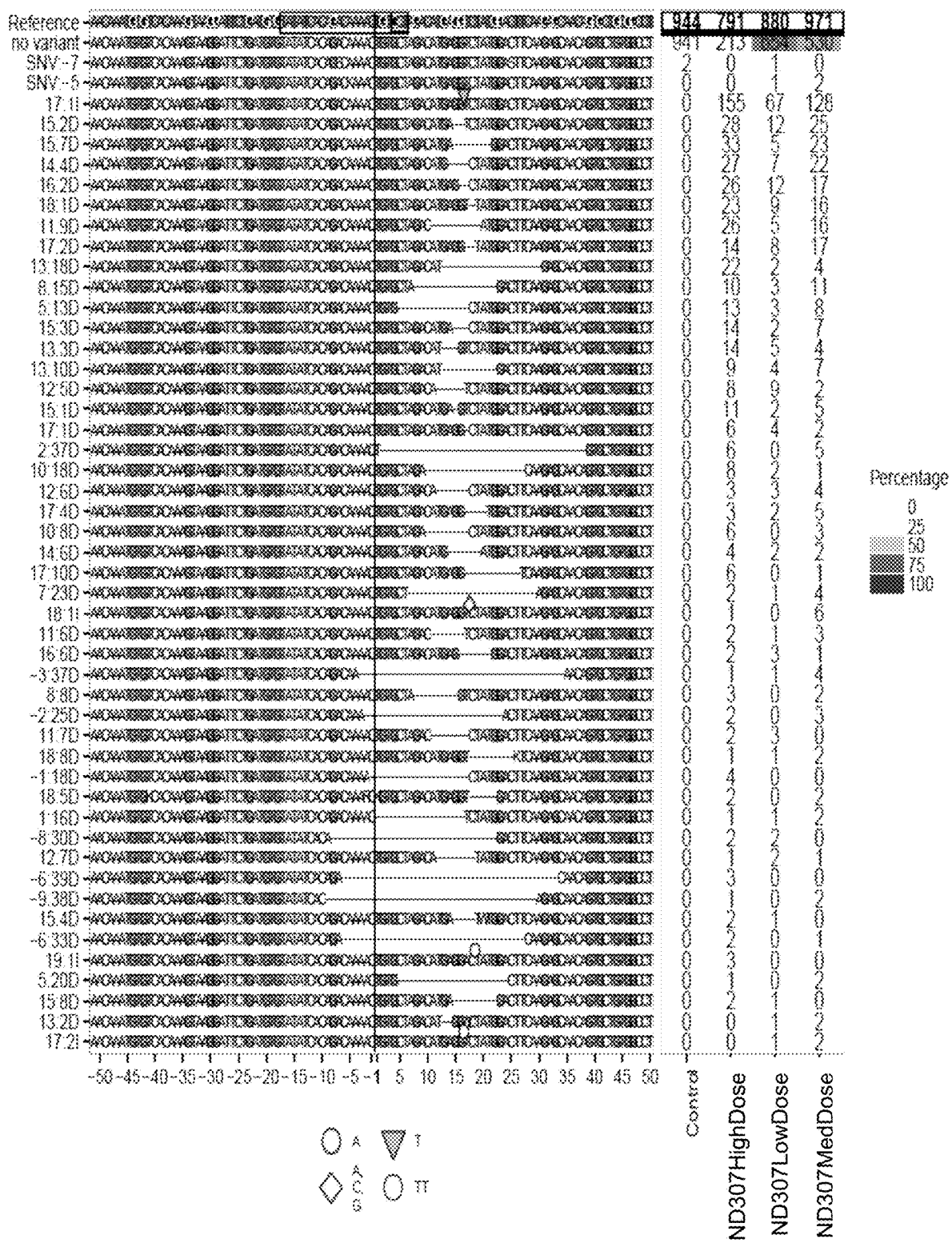
FIG. 1 depicts sequencing of a portion of the endogenous TRAC gene in cell clones targeted by the Group I TRAC gRNA (SEQ ID NOs: 140-190).

The present invention provides compositions and methods for modified immune cells (e.g., T cells and NK cells) or precursors thereof (e.g., modified T cells) comprising an exogenous (e.g., recombinant, transgenic or engineered) T cell receptor (TCR). In some embodiments, the exogenous TCR is a TCR having affinity for NY-ESO-1 on a target cell (NY-ESO-1 TCR), particularly melanoma and other solid tumor cells. The provided cells comprise additional genetic modifications to enhance the efficacy of the immune cell in the tumor microenvironment. In certain embodiments, the immune cells have a genetic disruption of a gene encoding endogenous TCR polypeptide (e.g., TRAC or TRBC) or an endogenous immune checkpoint protein (e.g., PD1 or TIM3). In additional or alternative embodiments, the immune cell comprises an exogenous switch molecule. In some embodiments, the modified immune cell or precursor thereof (e.g., modified T cell) further comprises a switch receptor. In some embodiments, the modified immune cell or precursor thereof (e.g., modified T cell comprising an NY-ESO-1 TCR) is further modified such that the expression of one or more of TRAC and/or TRBC is downregulated. In additional or alternative embodiments, the modified immune cell is further modified such that expression of an immune checkpoint protein (e.g., PD1 or TIM3) is downregulated. In one embodiment, the present invention provides a modified T cell comprising an exogenous TCR having affinity for NY-ESO-1 on a target cell, wherein the T cell is further modified such that the expression of TRAC, TRBC, and PD-1 is downregulated. In another embodiment, the present invention provides a modified T cell comprising an exogenous TCR having affinity for NY-ESO-1 on a target cell, and a switch receptor, wherein the T cell is further modified such that the expression of TRAC and TRBC is downregulated. Also provided are methods of producing such genetically engineered cells. In some embodiments, the cells and compositions can be used in adoptive cell therapy, e.g. adoptive tumor immunotherapy.

In some embodiments, the provided immune cells, compositions and methods alter or reduce the effects of T cell inhibitory pathways or signals in the tumor microenvironment. The modified immune cells of the invention counteract the upregulation and/or expression of inhibitory receptor or ligands that can negatively control T cell activation and T cell function. For example, expression of certain immune checkpoint proteins (e.g., PD-1 or PD-LI) on T cells and/or in the tumor microenvironment can reduce the potency and efficacy of adoptive T cell therapy. Such inhibitory pathways may otherwise impair certain desirable effector functions in the context of adoptive cell therapy. Tumor cells and/or cells in the tumor microenvironment often upregulate certain inhibitory proteins (such as PD-L1 and PD-L2) delivering an inhibitory signal. Such proteins may also be upregulated on T cells in the tumor microenvironment, e.g., on tumor-infiltrating T cells, which can occur following signaling through the antigen receptor or certain other activating signals. Such events may contribute to genetically engineered immune cells (e.g., NY-ESO-1 targeting T cells) acquiring an exhausted phenotype, such as when present in proximity with other cells that express such protein, which in turn can lead to reduced functionality. Thus, the modified immune cells of the invention address the T cell exhaustion and/or the lack of T cell persistence that is a barrier to the efficacy and therapeutic outcomes of conventional adoptive cell therapies.

It is to be understood that the methods described in this disclosure are not limited to particular methods and experimental conditions disclosed herein as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by M R Green and J. Sambrook and Harlow et al., Antibodies: A Laboratory Manual, Chapter 14, Cold Spring Harbor Laboratory, Cold Spring Harbor (2013, 2nd edition).

A. Definitions

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclature used in connection with cell and tissue culture, molecular biology, immunology, microbiology, genetics and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

As used herein, to "alleviate" a disease means reducing the severity of one or more symptoms of the disease.

The term "antigen" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen.

Furthermore, antigens can be derived from recombinant or genomic DNA. A skilled artisan will understand that any DNA, which comprises a nucleotide sequence or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to an amount that when administered to a mammal, causes a detectable level of immune suppression or tolerance compared to the immune response detected in the absence of the composition of the invention. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly about 10 amino acids and/or sugars in size. Preferably, the epitope is about 4-18 amino acids, more preferably about 5-16 amino acids, and even more most preferably 6-14 amino acids, more preferably about 7-12, and most preferably about 8-10 amino acids. One skilled in the art understands that generally the overall three-dimensional structure, rather than the specific linear sequence of the molecule, is the main criterion of antigenic specificity and therefore distinguishes one epitope from another. Based on the present disclosure, a peptide of the present invention can be an epitope.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immune response" as used herein is defined as a cellular response to an antigen that occurs when lymphocytes identify antigenic molecules as foreign and induce the formation of antibodies and/or activate lymphocytes to remove the antigen.

The term "immunosuppressive" is used herein to refer to reducing overall immune response.

"Insertion/deletion", commonly abbreviated "indel," is a type of genetic polymorphism in which a specific nucleotide sequence is present (insertion) or absent (deletion) in a genome.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "knockdown" as used herein refers to a decrease in gene expression of one or more genes.

The term "knockout" as used herein refers to the ablation of gene expression of one or more genes.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

A "target site" or "target sequence" refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha (α) and beta (β) chain, although in some cells the TCR consists of gamma and delta (γ/δ) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

"Transplant" refers to a biocompatible lattice or a donor tissue, organ or cell, to be transplanted. An example of a transplant may include but is not limited to skin cells or tissue, bone marrow, and solid organs such as heart, pancreas, kidney, lung and liver. A transplant can also refer to any material that is to be administered to a host. For example, a transplant can refer to a nucleic acid or a protein.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

B. T Cell Receptors

The present invention provides compositions and methods for modified immune cells or precursors thereof (e.g., modified T cells) comprising an exogenous T cell receptor (TCR). Thus, in some embodiments, the target cell has been altered to contain specific T cell receptor (TCR) genes (e.g., a TRAC and TRBC gene). TCRs or antigen-binding portions thereof include those that recognize a peptide epitope or T cell epitope of a target polypeptide, such as an antigen of a tumor, viral or autoimmune protein. In some embodiments, the TCR has binding specificity for a tumor associated antigen, e.g., human NY-ESO-1.

A TCR is a disulfide-linked heterodimeric protein comprised of six different membrane bound chains that participate in the activation of T cells in response to an antigen. There exists alpha/beta TCRs and gamma/delta TCRs. An alpha/beta TCR comprises a TCR alpha chain and a TCR beta chain. T cells expressing a TCR comprising a TCR alpha chain and a TCR beta chain are commonly referred to as alpha/beta T cells. Gamma/delta TCRs comprise a TCR gamma chain and a TCR delta chain. T cells expressing a TCR comprising a TCR gamma chain and a TCR delta chain are commonly referred to as gamma/delta T cells. A TCR of the present disclosure is a TCR comprising a TCR alpha chain and a TCR beta chain.

The TCR alpha chain and the TCR beta chain are each comprised of two extracellular domains, a variable region and a constant region. The TCR alpha chain variable region and the TCR beta chain variable region are required for the affinity of a TCR to a target antigen. Each variable region comprises three hypervariable or complementarity-determining regions (CDRs) which provide for binding to a target antigen. The constant region of the TCR alpha chain and the constant region of the TCR beta chain are proximal to the cell membrane. A TCR further comprises a transmembrane region and a short cytoplasmic tail. CD3 molecules are assembled together with the TCR heterodimer. CD3 molecules comprise a characteristic sequence motif for tyrosine phosphorylation, known as immunoreceptor tyrosine-based activation motifs (ITAMs). Proximal signaling events are mediated through the CD3 molecules, and accordingly, TCR-CD3 complex interaction plays an important role in mediating cell recognition events.

Stimulation of TCR is triggered by major histocompatibility complex molecules (MHCs) on antigen presenting cells that present antigen peptides to T cells and interact with TCRs to induce a series of intracellular signaling cascades. Engagement of the TCR initiates both positive and negative signaling cascades that result in cellular proliferation, cytokine production, and/or activation-induced cell death.

A TCR of the present invention can be a wild-type TCR, a high affinity TCR, and/or a chimeric TCR. A high affinity TCR may be the result of modifications to a wild-type TCR that confers a higher affinity for a target antigen compared to the wild-type TCR. A high affinity TCR may be an affinity-matured TCR. Methods for modifying TCRs and/or the affinity-maturation of TCRs are known to those of skill in the art. Techniques for engineering and expressing TCRs include, but are not limited to, the production of TCR heterodimers which include the native disulphide bridge which connects the respective subunits (Garboczi, et al., (1996), Nature 384(6605): 134-41; Garboczi, et al., (1996), J Immunol 157(12): 5403-10; Chang et al., (1994), PNAS USA 91: 11408-11412; Davodeau et al., (1993), J. Biol. Chem. 268(21): 15455-15460; Golden et al., (1997), J. Imm. Meth. 206: 163-169; U.S. Pat. No. 6,080,840).

In some embodiments, the exogenous TCR is a full TCR or antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable a chain and variable β chain of a TCR, sufficient to form a binding site for binding to a specific MHC-peptide complex. Generally, the variable chains of a TCR contain complementarity determining regions (CDRs) involved in recognition of the peptide, MHC and/or MHC-peptide complex.

In some embodiments, the variable domains of the TCR contain hypervariable loops, or CDRs, which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al, Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR contains a variable alpha domain ($V_\alpha$) and/or a variable beta domain ($V_\beta$) or antigen-binding fragments thereof. In some embodiments, the a-chain and/or β-chain of a TCR also can contain a constant domain, a transmembrane domain and/or a short cytoplasmic tail (see, e.g., Janeway et al., Immunobiology: The Immune System in Health and Disease, 3 Ed., Current Biology Publications, p. 4:33, 1997). In some embodiments, the a chain constant domain is encoded by the TRAC gene (IMGT nomenclature) or is a variant thereof. In some embodiments, the β chain constant region is encoded by TRBC1 or TRBC2 genes (IMGT nomenclature) or is a variant thereof. In some embodiments, the constant domain is adjacent to the cell membrane. For example, in some cases, the extracellular portion of the TCR formed by the two chains contains two membrane-proximal constant domains, and two membrane-distal variable domains, which variable domains each contain CDRs.

It is within the level of a skilled artisan to determine or identify the various domains or regions of a TCR. In some aspects, residues of a TCR are known or can be identified according to the International Immunogenetics Information System (IMGT) numbering system (see e.g. wwwdotimgt-dotorg; see also, Lefranc et al. (2003) Developmental and Comparative Immunology, 27:55-77; and The T Cell Factsbook 2nd Edition, Lefranc and LeFranc Academic Press 2001). Using this system, the CDR1 sequences within a TCR Vα chain and/or vβ chain correspond to the amino acids present between residue numbers 27-38, inclusive, the CDR2 sequences within a TCR Vα chain and/or vβ chain correspond to the amino acids present between residue numbers 56-65, inclusive, and the CDR3 sequences within a TCR Vα chain and/or vβ chain correspond to the amino acids present between residue numbers 105-117, inclusive.

In some embodiments, the TCR may be a heterodimer of two chains a and β (or optionally γ and δ) that are linked, such as by a disulfide bond or disulfide bonds. In some embodiments, the constant domain of the TCR may contain short connecting sequences in which a cysteine residue forms a disulfide bond, thereby linking the two chains of the TCR. In some embodiments, a TCR may have an additional cysteine residue in each of the a and β chains, such that the TCR contains two disulfide bonds in the constant domains. In some embodiments, each of the constant and variable domains contain disulfide bonds formed by cysteine residues.

In some embodiments, the TCR for engineering cells as described is one generated from a known TCR sequence(s), such as sequences of vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences. In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the T-cells can be a cultured T-cell hybridoma or clone. In some embodiments, the TCR or antigen-binding portion thereof can be synthetically generated from knowledge of the sequence of the TCR. In some embodiments, a high-affinity T cell clone for a target antigen (e.g., a cancer antigen) is identified, isolated from a patient, and introduced into the cells. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) Clin Cancer Res. 15: 169-180 and Cohen et al. (2005) J Immunol. 175:5799-5808. In some embodiments, phage display is used to isolate TCRs against a target antigen (see, e.g., Varela-Rohena et al. (2008) Nat Med. 14: 1390-1395 and Li (2005) Nat Biotechnol. 23:349-354.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), or T cell display (Chervin et al. (2008) J Immunol Methods, 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments as described, the TCR can contain an introduced disulfide bond or bonds. In some embodiments, the native disulfide bonds are not present. In some embodiments, the one or more of the native cysteines (e.g. in the constant domain of the a chain and β chain) that form a native interchain disulfide bond are substituted to another residue, such as to a serine or alanine. In some embodiments, an introduced disulfide bond can be formed by mutating non-cysteine residues on the alpha and beta chains, such as in the constant domain of the a chain and β chain, to cysteine. Exemplary non-native disulfide bonds of a TCR are described in published International PCT No. WO2006/000830 and WO2006037960. In some embodiments, cysteines can be introduced at residue Thr48 of the a chain and Ser57 of the β chain, at residue Thr45 of the a chain and Ser77 of the β chain, at residue Tyr10 of the a chain and Ser17 of the β chain, at residue Thr45 of the a chain and Asp59 of the β chain and/or at residue Ser15 of the a chain and Glu15 of the β chain. In some embodiments, the presence of non-native cysteine residues (e.g. resulting in one or more non-native disulfide bonds) in a recombinant TCR can favor production of the desired recombinant TCR in a cell in which it is introduced over expression of a mismatched TCR pair containing a native TCR chain.

In some embodiments, the TCR chains contain a transmembrane domain. In some embodiments, the transmembrane domain is positively charged. In some cases, the TCR chain contains a cytoplasmic tail. In some aspects, each chain (e.g. alpha or beta) of the TCR can possess one N-terminal immunoglobulin variable domain, one immunoglobulin constant domain, a transmembrane region, and a short cytoplasmic tail at the C-terminal end. In some embodiments, a TCR, for example via the cytoplasmic tail, is associated with invariant proteins of the CD3 complex involved in mediating signal transduction. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ζ chains) contain one or more immunoreceptor tyrosine-based activation motifs or ITAMs that are involved in the signaling capacity of the TCR complex.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). A TCR may be cell-bound or in soluble form. In some embodiments, for purposes of the provided methods, the TCR is in cell-bound form expressed on the surface of a cell. In some embodiments a dTCR contains a first polypeptide wherein a sequence corresponding to a TCR a chain variable region sequence is fused to the N terminus of a sequence corresponding to a TCR a chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native interchain disulfide bond present in native dimeric αδ TCRs. In some embodiments, the interchain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane. In some embodiments, a dTCR contains a TCR a chain containing a variable a domain, a constant a domain and a first dimerization motif attached to the C-terminus of the constant a domain, and a TCR β chain comprising a variable β domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR a chain and TCR β chain together.

In some embodiments, the TCR is a scTCR, which is a single amino acid strand containing an a chain and a β chain that is able to bind to MHC-peptide complexes. Typically, a scTCR can be generated using methods known to those of skill in the art, See e.g., International published PCT Nos. WO 96/13593, WO 96/18105, WO99/18129, WO04/033685, WO2006/037960, WO2011/044186; U.S. Pat. No. 7,569,664; and Schlueter, C. J. et al. J. Mol. Biol. 256, 859 (1996). In some embodiments, a scTCR contains a first segment constituted by an amino acid sequence corresponding to a TCR a chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment. In some embodiments, a scTCR contains a first segment constituted by an amino acid sequence corresponding to a TCR β chain variable region, a second segment constituted by an amino acid sequence corresponding to a TCR a chain variable region sequence fused to the N terminus of an amino acid sequence corresponding to a TCR a chain constant domain extracellular sequence, and a linker sequence linking the C terminus of the first segment to the N terminus of the second segment. In some embodiments, a scTCR contains a first segment constituted by an a chain variable region sequence fused to the N terminus of an a chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment. In some embodiments, a scTCR contains a first segment constituted by a TCR β chain variable region sequence fused to the N terminus of a β chain extracellular constant domain sequence, and a second segment constituted by an a chain variable region sequence fused to the N terminus of a sequence a chain extracellular constant and transmembrane sequence, and, optionally, a linker sequence linking the C terminus of the first segment to the N terminus of the second segment. In some embodiments, for the scTCR to bind an MHC-peptide complex, the a and β chains must be paired so that the variable region sequences thereof are orientated for such binding. Various methods of promoting pairing of an a and β in a scTCR are well known in the art. In some embodiments, a linker sequence is included that links the a and β chains to form the single polypeptide strand. The linker should have sufficient length to span the distance between the C terminus of the a chain and the N terminus of the β chain, or vice versa, while also ensuring that the linker length is not so long so that it blocks or reduces bonding of the scTCR to the target peptide-MHC complex. In some embodiments, the linker of a scTCRs that links the first and second TCR segments can be any linker capable of forming a single polypeptide strand, while retaining TCR binding specificity. In some embodiments, the linker sequence may, for example, have the formula -P-AA-P-, wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, a scTCR contains a disulfide bond between residues of the single amino acid strand, which, in some cases, can promote stability of the pairing between the a and β regions of the single chain molecule (see e.g. U.S. Pat. No. 7,569,664). In some embodiments, the scTCR contains a covalent disulfide bond linking a residue of the immunoglobulin region of the constant domain of the a chain to a residue of the immunoglobulin region of the constant domain of the β chain of the single chain molecule. In some embodiments, the disulfide bond corresponds to the native disulfide bond present in a native dTCR. In some embodiments, the disulfide bond in a native TCR is not present. In some embodiments, the disulfide bond is an introduced non-native disulfide bond, for example, by incorporating one or more cysteines into the constant region extracellular sequences of the first and second chain regions of the scTCR polypeptide. Exemplary cysteine mutations include any as described above. In some cases, both a native and a non-native disulfide bond may be present.

In some embodiments, any of the TCRs, including a dTCR or scTCR, can be linked to signaling domains that yield an active TCR on the surface of a T cell. In some embodiments, the TCR is expressed on the surface of cells. In some embodiments, the TCR does contain a sequence corresponding to a transmembrane sequence. In some embodiments, the transmembrane domain can be a Ca or Cβ transmembrane domain. In some embodiments, the transmembrane domain can be from a non-TCR origin, for example, a transmembrane region from CD3z, CD28 or B7.1. In some embodiments, the TCR does contain a sequence corresponding to cytoplasmic sequences. In some embodiments, the TCR contains a CD3z signaling domain. In some embodiments, the TCR is capable of forming a TCR complex with CD3. In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal.

In some embodiments, the TCR comprises affinity to a target antigen on a target cell. The target antigen may include any type of protein, or epitope thereof, associated with the target cell. For example, the TCR may comprise affinity to a target antigen on a target cell that indicates a particular disease state of the target cell. In some embodiments, the target antigen is processed and presented by MHCs.

In an exemplary embodiment, the target cell antigen is a New York esophageal-1 (NY-ESO-1) peptide. NY-ESO-1 belongs to the cancer-testis (CT) antigen group of proteins. NY-ESO-1 is a highly immunogenic antigen in vitro and is presented to T cells via the MHC. CTLs recognizing the A2 presented epitope NY-ESO$_{157-165}$, SLLMWITQC (SEQ ID NO:1), have been grown from the blood and lymph nodes of myeloma patients. T cell clones specific for this epitope have been shown to kill tumor cells. A high affinity TCR recognizing the NY-ESO$_{157-165}$ epitope may recognize HLA-A2-positive, NY-ESO-1 positive cell lines (but not cells that lack either HLA-A2 or NY-ESO). Accordingly, a TCR of the present disclosure may be a HLA-A2-restricted NY-ESO-1 (SLLMWITQC; SEQ ID NO:1)-specific TCR. In one embodiment, an NY-ESO-1 TCR of the present disclosure is a wild-type NY-ESO-1 TCR. A wild-type NY-ESO-1 TCR may include, without limitation, the 8F NY-ESO-1 TCR (also referred to herein as "8F" or "8F TCR"), and the 1G4 NY-ESO-1 TCR (also referred to herein as "1G4" or "1G4 TCR"). In one embodiment, an NY-ESO-1 TCR of the present disclosure is an affinity enhanced 1G4 TCR, also called Ly95. 1G4 TCR and affinity enhanced 1G4 TCR is described in U.S. Pat. No. 8,143,376.

As described herein a TCR of the present disclosure may comprise a TCR alpha chain and a TCR beta chain. For example, a TCR having affinity for NY-ESO-1 comprises a TCR alpha chain and a TCR beta chain that together, contribute to the affinity of the TCR for NY-ESO-1. In one embodiment, a TCR having affinity for NY-ESO-1 comprises an 8F TCR alpha chain comprising an 8F TCR alpha chain variable region comprising the amino acid sequence set forth below:

```
                                      (SEQ ID NO: 2)
EEDPQALSIQEGENATMNCSYKTSINNLQWYRQNSGRGLVHLILIRSNER

EKHSGRLRVTLDTSKKSSSLLITASRAADTASYFCATDGAGKSTFGDGTT

LTVKPN,
``` which is encoded by the nucleic acid sequence set forth below:

```
                                      (SEQ ID NO: 3)
GAGGAGGACCCCCAGGCCCTGTCCATCCAGGAGGGGAGAATGCCACCA

TGAATTGCAGTTACAAGACTTCCATAAACAACCTGCAGTGGTACCGCCA

GAACTCCGGCCGCGGCCTGGTGCACCTGATCCTCATCCGGTCGAATGAA

AGGGAAAAGCACTCGGGACGCCTGCGAGTGACTCTGGACACGTCCAAGA

AGTCGTCCAGTCTCTTAATCACCGCCTCTCGCGCAGCCGATACCGCATC

GTACTTCTGTGCAACCGACGGGGCGGGCAAGAGTACATTCGGCGACGGC

ACTACCCTGACCGTGAAGCCAAAT.
```

Tolerable variations of the 8F TCR alpha chain of a TCR having affinity for NY-ESO-1 will be known to those of skill in the art, while maintaining affinity to NY-ESO-1. For example, a TCR having affinity for NY-ESO-1 comprises an 8F TCR alpha chain variable region comprising an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the 8F TCR alpha chain variable region amino acid sequence set forth in SEQ ID NO:2. In one embodiment, the TCR having affinity for NY-ESO-1 comprises the 8F TCR alpha chain variable region comprising the amino acid sequence set forth in SEQ ID NO:2.

A TCR having affinity for NY-ESO-1 may comprise an 8F TCR alpha chain variable region encoded by a nucleic acid sequence that has at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99% sequence identity to the 8F TCR alpha chain variable region nucleic acid sequence set forth in SEQ ID NO:3. In one embodiment, the TCR having affinity for NY-ESO-1 comprises the 8F TCR alpha chain variable region comprising the nucleic acid sequence set forth in SEQ ID NO:3.

The TCR alpha chain variable region of a TCR having affinity for NY-ESO-1 comprises three complementarity-determining regions (CDRs). As used herein, a "complementarity-determining region" or "CDR" refers to a region of the variable chain of an antigen binding molecule (such as immunoglobulins and TCRs) that binds to a specific antigen. Accordingly, a TCR having affinity for NY-ESO-1 may comprise an 8F TCR alpha chain variable region that comprises a CDR1 represented by the amino acid sequence TSINN (SEQ ID NO:4); a CDR2 represented by the amino acid sequence IRS; and a CDR3 represented by the amino acid sequence ATD. Tolerable variations to the CDRs of the TCR alpha chain variable region of a TCR having affinity for NY-ESO-1 will be known to those of skill in the art, while maintaining affinity to NY-ESO-1. For example, a TCR having affinity for NY-ESO-1 may comprise an 8F TCR alpha chain variable region comprising a CDR1 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR1 amino acid sequence set forth in SEQ ID NO:4. For example, a TCR having affinity for NY-ESO-1 may comprise an 8F TCR alpha chain variable region comprising a CDR2 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR2 represented by the amino acid sequence IRS. For example, a TCR having affinity for NY-ESO-1 may comprise an 8F TCR alpha chain variable region comprising a CDR3 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR3 represented by the amino acid sequence ATD. In one embodiment, the TCR alpha chain variable region of a TCR having affinity for NY-ESO-1 comprises the three aforementioned 8F TCR alpha chain variable region complementarity-determining regions (CDRs).

An 8F TCR alpha chain of a TCR having affinity for NY-ESO-1 may comprise the amino acid sequence set forth below:

(SEQ ID NO: 5)
METLLGVSLVILWLQLARVNSQQGEEDPQALSIQEGENATMNCSYKTSI

NNLQWYRQNSGRGLVHLILIRSNEREKHSGRLRVTLDTSKKSSSLLITA

SRAADTASYFCATDGAGKSTFGDGTTLTVKPNIQKPDPAVYQLRDSKSS

DKSVCLFTDFDSQTNVSQSKDSDVYITDKTVLDMRSMDFKSNSAVAWSN

KSDFACANAFNNSIIPADTFFPSPESSCDVKLVEKSFETDTNLNFQNLS

VIGFRILLLKVAGFNLLMTLRLWSS, which is encoded by the nucleic acid sequence set forth below:

(SEQ ID NO: 6)
ATGGACTCGTGGACCTTATGCTGCGTGTCCCTGTGCATACTGGTTGCCA

AGCACACAGACGCCGGGGTGATCCAGAGCCCCCGGCACGAAGTTACCGA

GATGGGCCAGGAGGTGACGCTCCGATGCAAGCCCATCAGTGGCCACGAT

TATCTCTTCTGGTACCGCCAAACCATGATGCGCGGCTTGGAACTCCTCA

TCTACTTCAACAACAACGTCCCCATCGATGACTCCGGCATGCCTGAGGA

CAGGTTCAGTGCGAAGATGCCGAATGCATCCTTCTCCACCCTGAAGATA

CAGCCGAGTGAGCCCCGCGACTCCGCTGTGTACTTCTGCGCCTCTACTA

TCGGCGCCCAGCCTCAACATTTCGGCGACGGCACGCGCCTCAGTATCCT

GGAGGACCTGAACAAGGTGTTCCCTCCGGAAGTGGCTGTGTTTGAGCCC

TCCGAGGCAGAAATCTCACACACACAGAAGGCAACCCTCGTGTGTCTGG

CAACAGGTTTCTTCCCAGATCACGTGGAGCTGAGTTGGTGGGTCAACGG

CAAGGAGGTCCATAGCGGGGTGAGTACCGACCCACAGCCTCTCAAGGAG

CAGCCTGCCCTCAACGACAGTAGGTACTGCCTGTCCTCGCGCCTCCGCG

TGTCCGCAACGTTCTGGCAGAATCCCCGCAACCACTTCCGGTGCCAGGT

CCAATTCTACGGCCTGAGTGAGAACGATGAGTGGACACAGGATAGGGCC

AAGCCCGTGACCCAGATCGTGTCCGCCGAGGCCTGGGGCCGCGCTGACT

GCGGCTTCACCTCCGTGTCGTATCAGCAGGGCGTATTATCAGCCACCAT

TCTTTACGAAATCCTCCTCGGCAAGGCCACACTATACGCCGTGCTGGTG

TCGGCGCTGGTGTTAATGGCGATGGTCAAGCGAAAGGATTAA.

An 8F TCR alpha chain having affinity for NY-ESO-1 may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the 8F TCR alpha chain amino acid sequence set forth in SEQ ID NO:5. In one embodiment, the TCR having affinity for NY-ESO-1 comprises the 8F TCR alpha chain comprising the amino acid sequence set forth in SEQ ID NO:5. A TCR having affinity for NY-ESO-1 may comprise an 8F TCR alpha chain encoded by a nucleic acid sequence that has at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99% sequence identity to the 8F TCR alpha chain nucleic acid sequence set forth in SEQ ID NO:6. In one embodiment, the TCR having affinity for NY-ESO-1 comprises the 8F TCR alpha chain comprising the nucleic acid sequence set forth in SEQ ID NO:6.

As described herein, a TCR of the present disclosure may comprise a TCR alpha chain and a TCR beta chain. In one embodiment, a TCR having affinity for NY-ESO-1 comprises an 8F TCR beta chain comprising an 8F TCR beta chain variable region comprising the amino acid sequence set forth below:

(SEQ ID NO: 7)
VIQSPRHEVTEMGQEVTLRCKPISGHDYLFWYRQTMMRGLELLIYFNNN

VPIDDSGMPEDRFSAKMPNASFSTLKIQPSEPRDSAVYFCASTIGAQPQ

HFGDGTRLSILE, which is encoded by the nucleic acid sequence set forth below:

(SEQ ID NO: 8)
GTGATCCAGAGCCCCCGGCACGAAGTTACCGAGATGGGCCAGGAGGTGA

CGCTCCGATGCAAGCCCATCAGTGGCCACGATTATCTCTTCTGGTACCG

CCAAACCATGATGCGCGGCTTGGAACTCCTCATCTACTTCAACAACAAC

GTCCCCATCGATGACTCCGGCATGCCTGAGGACAGGTTCAGTGCGAAGA

TGCCGAATGCATCCTTCTCCACCCTGAAGATACAGCCGAGTGAGCCCCG

CGACTCCGCTGTGTACTTCTGCGCCTCTACTATCGGCGCCCAGCCTCAA

CATTTCGGCGACGGCACGCGCCTCAGTATCCTGGAG.

Tolerable variations of the TCR alpha chain of a TCR having affinity for NY-ESO-1 will be known to those of skill in the art, while maintaining affinity to NY-ESO-1. For example, a TCR having affinity for NY-ESO-1 comprises an 8F TCR beta chain variable region comprising an amino acid sequence that has at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99% sequence identity to the 8F TCR beta chain variable region amino acid sequence set forth in SEQ ID NO:7. In one embodiment, the TCR having affinity for NY-ESO-1 comprises the 8F TCR beta chain variable region comprising the amino acid sequence set forth in SEQ ID NO:7.

A TCR having affinity for NY-ESO-1 may comprise an 8F TCR beta chain variable region encoded by a nucleic acid sequence that has at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99% sequence identity to the 8F TCR beta chain variable region nucleic acid sequence set forth in SEQ ID NO:8. In one embodiment, the TCR having affinity for NY-ESO-1 comprises the 8F TCR beta chain variable region comprising the nucleic acid sequence set forth in SEQ ID NO:8.

The TCR beta chain variable region of a TCR having affinity for NY-ESO-1 comprises three complementarity-determining regions (CDRs). Accordingly, a TCR having affinity for NY-ESO-1 may comprise an 8F TCR beta chain variable region that comprises a CDR1 represented by the amino acid sequence SGHDY (SEQ ID NO:9); a CDR2 represented by the amino acid sequence FNNNVP (SEQ ID NO:10); and a CDR3 represented by the amino acid sequence ASTI (SEQ ID NO:11). Tolerable variations to the CDRs of the TCR beta chain variable region of a TCR having affinity for NY-ESO-1 will be known to those of skill in the art, while maintaining affinity to NY-ESO-1. For example, a TCR having affinity for NY-ESO-1 may comprise an 8F TCR beta chain variable region comprising a CDR1 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR1 amino acid sequence set forth in SEQ ID NO:9. For example, a TCR having affinity for NY-ESO-1 may comprise an 8F TCR beta chain variable region comprising a CDR2 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR2 amino acid sequence set forth in SEQ ID NO:10. For example, a TCR having affinity for NY-ESO-1 may comprise an 8F TCR beta chain variable region comprising a CDR3 that comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the CDR3 amino acid sequence set forth in SEQ ID NO:11. In one embodiment, the TCR beta chain variable region of an 8F TCR having affinity for NY-ESO-1 comprises the three aforementioned TCR beta chain variable region complementarity-determining regions (CDRs).

An 8F TCR beta chain of a TCR having affinity for NY-ESO-1 may comprise the amino acid sequence set forth below:

```
                                            (SEQ ID NO: 12)
METLLGVSLVILWLQLARVNSQQGEEDPQALSIQEGENATMNCSYKTSI

NNLQWYRQNSGRGLVHLILIRSNEREKHSGRLRVTLDTSKKSSSLLITA

SRAADTASYFCATDGAGKSTFGDGTTLTVKPNIQKPDPAVYQLRDSKSS

DKSVCLFTDFDSQTNVSQSKDSDVYITDKTVLDMRSMDFKSNSAVAWSN

KSDFACANAFNNSIIPADTFFPSPESSCDVKLVEKSFETDTNLNFQNLS

VIGFRILLLKVAGFNLLMTLRLWSS,
``` which is encoded by the nucleic acid sequence set forth below:

```
                                            (SEQ ID NO: 13)
ATGGAGACCCTGCTCGGGGTCTCACTGGTCATCCTGTGGCTGCAGCTGG

CCAGGGTGAACTCGCAGCAGGGGGAGGAGGACCCCCAGGCCCTGTCCAT

CCAGGAGGGGGAGAATGCCACCATGAATTGCAGTTACAAGACTTCCATA

AACAACCTGCAGTGGTACCGCCAGAACTCCGGCCGCGGCCTGGTGCACC

TGATCCTCATCCGGTCGAATGAAAGGGAAAAGCACTCGGGACGCCTGCG

AGTGACTCTGGACACGTCCAAGAAGTCGTCCAGTCTCTTAATCACCGCC

TCTCGCGCAGCCGATACCGCATCGTACTTCTGTGCAACCGACGGGGCGG

GCAAGAGTACATTCGGCGACGGCACTACCCTGACCGTGAAGCCAAATAT

CCAGAAGCCTGATCCAGCTGTCTATCAGTTGCGCGATTCCAAATCGTCT

GACAAATCTGTGTGCCTGTTCACCGACTTCGACTCCCAGACGAACGTGT

CCCAGAGTAAAGACAGCGACGTGTACATCACTGATAAGACCGTGCTGGA

CATGCGCTCCATGGACTTTAAAAGTAACAGCGCTGTAGCGTGGAGCAAC

AAGAGTGACTTCGCCTGCGCCAACGCCTTCAATAACTCTATCATACCTG

CCGATACCTTCTTCCCGAGCCCCGAATCCAGTTGCGACGTGAAGCTCGT

GGAGAAGAGCTTTGAGACAGACACCAACCTGAACTTCCAAAACCTGTCC

GTCATTGGCTTCAGGATCCTCCTCCTCAAGGTGGCCGGCTTCAACTTGC

TCATGACGCTGAGACTCTGGAGTTCA.
```

An 8F TCR beta chain having affinity for NY-ESO-1 may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the 8F TCR beta chain amino acid sequence set forth in SEQ ID NO:12. In one embodiment, the TCR having affinity for NY-ESO-1 comprises the 8F TCR beta chain comprising the amino acid sequence set forth in SEQ ID NO:12. A TCR having affinity for NY-ESO-1 may comprise an 8F TCR beta chain encoded by a nucleic acid sequence that has at least 60%, at least 65%, at least 70%, at least 75%, at least 80%, at least 82%, at least 84%, at least 86%, at least 88%, at least 90%, at least 91%, at least 92%, at least 93%, at least 94%, at least 95%, at least 96%, at least 97%, at least 98%, at least 99% sequence identity to the 8F TCR beta chain nucleic acid sequence set forth in SEQ ID NO:13. In one embodiment, the TCR having affinity for NY-ESO-1 comprises the 8F TCR beta chain comprising the nucleic acid sequence set forth in SEQ ID NO:13.

C. Switch Receptors

The present invention provides a switch receptor for use in the modified cell of the invention. As used herein, the term "switch receptor" or "chimeric switch receptor" refers to a molecule designed to switch a negative signal transduction signal into a positive signal. In some embodiments, the switch receptor is a chimeric protein comprising a first protein or fragment thereof associated with a negative signal, and a second protein or fragment thereof associated with a positive signal. Examples of proteins associated with a negative signal include, without limitation, CTLA-4, PD-1, BTLA, TIM-3 and the like. Examples of proteins associated with a positive signal include, without limitation, CD28, ICOS, 4-1BB, TGFβR and the like.

Accordingly, a switch receptor, when expressed in a cell (e.g., mammalian cell), converts a negative signal into a positive signal in the cell. In some embodiments, a switch receptor of the present disclosure comprises a first domain derived from a protein or fragment thereof that delivers a negative signal; and a second domain derived from a protein or fragment thereof that delivers a positive signal.

Suitable first domains derived from a protein or fragment thereof that delivers a negative signal include, variants or derivatives of wild-type CTLA-4. In one embodiment, the first domain of the switch receptor comprises at least a portion of the extracellular domain of the CTLA-4 protein, specifically that portion of the extracellular domain which is necessary for binding to the natural ligand of CTLA-4. Variants of the wild-type form of the extracellular domain, or the portion of the extracellular domain responsible for binding to the natural ligand of CTLA-4, are also included in the present invention. Suitable first domains derived from a protein or fragment thereof that delivers a negative signal include, variants or derivatives of wild-type PD-1. In one embodiment, the first domain of the switch receptor comprises at least a portion of the extracellular domain of the PD-1 protein, specifically that portion of the extracellular domain which is necessary for binding to the natural ligand of PD-1. Variants of the wild-type form of the extracellular domain, or the portion of the extracellular domain responsible for binding to the natural ligand of PD-1, are also included in the present invention. For example, a variant PD1 extracellular domain having an A132L substitution relative to the full length amino acid sequence of PD1, is included in the present invention. Suitable first domains derived from a protein or fragment thereof that delivers a negative signal include, variants or derivatives of wild-type BTLA. In one embodiment, the first domain of the switch receptor comprises at least a portion of the extracellular domain of the BTLA protein, specifically that portion of the extracellular domain which is necessary for binding to the natural ligand of BTLA. Variants of the wild-type form of the extracellular domain, or the portion of the extracellular domain responsible for binding to the natural ligand of BTLA, are also included in the present invention. Suitable first domains derived from a protein or fragment thereof that delivers a negative signal include, variants or derivatives of wild-type TGFβR (e.g., TGFβRI or TGFβRII). In one embodiment, the first domain of the switch receptor comprises at least a portion of the extracellular domain of the TGFβR protein (e.g., TGFβRI or TGFβRII), specifically that portion of the extracellular domain which is necessary for binding to the natural ligand of TGFβR (e.g., TGFβRI or TGFβRII). Variants of the wild-type form of the extracellular domain, or the portion of the extracellular domain responsible for binding to the natural ligand of TGFβR (e.g., TGFβRI or TGFβRII), are also included in the present invention. Suitable first domains derived from a protein or fragment thereof that delivers a negative signal include, variants or derivatives of wild-type TIM3. In one embodiment, the first domain of the switch receptor comprises at least a portion of the extracellular domain of the TIM3 protein, specifically that portion of the extracellular domain which is necessary for binding to the natural ligand of TIM3. Variants of the wild-type form of the extracellular domain, or the portion of the extracellular domain responsible for binding to the natural ligand of TIM3, are also included in the present invention.

Suitable second domains derived from a protein or fragment thereof that delivers a negative signal include, variants or derivatives of the ICOS protein. In one embodiment, the second domain of the switch receptor comprises at least a portion of the intracellular domain (also referred to as endodomain or cytoplasmic domain) of the ICOS protein, specifically that portion which is necessary for triggering a signal to intracellular components of the cell. Variants of the wild-type form of the intracellular domain of the ICOS protein, or the portion of the intracellular domain responsible for signaling, are also included in the present invention. Suitable second domains derived from a protein or fragment thereof that delivers a negative signal include, variants or derivatives of the CD28 protein. In one embodiment, the second domain of the switch receptor comprises at least a portion of the intracellular domain (also referred to as endodomain or cytoplasmic domain) of the CD28 protein, specifically that portion which is necessary for triggering a signal to intracellular components of the cell. Variants of the wild-type form of the intracellular domain of the CD28 protein, or the portion of the intracellular domain responsible for signaling, are also included in the present invention. Suitable second domains derived from a protein or fragment thereof that delivers a negative signal include, variants or derivatives of IL-12R (e.g., IL-12Rβ1 or IL-12Rβ2). In one embodiment, the second domain of the switch receptor comprises at least a portion of the intracellular domain (also referred to as endodomain or cytoplasmic domain) of IL-12R (e.g., IL-12Rβ1 or IL-12Rβ2), specifically that portion which is necessary for triggering a signal to intracellular components of the cell. Variants of the wild-type form of the intracellular domain of IL-12R (e.g., IL-12Rβ1 or IL-12Rβ2), or the portion of the intracellular domain responsible for signaling, are also included in the present invention. Suitable second domains derived from a protein or fragment thereof that delivers a negative signal include, variants or derivatives of the 4-1BB protein. In one embodiment, the second domain of the switch receptor comprises at least a portion of the intracellular domain (also referred to as endodomain or cytoplasmic domain) of the 4-1BB protein, specifically that portion which is necessary for triggering a signal to intracellular components of the cell. Variants of the wild-type form of the intracellular domain of the 4-1BB protein, or the portion of the intracellular domain responsible for signaling, are also included in the present invention.

A switch receptor suitable for use in the present invention comprises a polypeptide corresponding to a cytoplasmic, transmembrane and extracellular domain, as well as polypeptides corresponding to smaller portions of the cytoplasmic, transmembrane and extracellular domain. In one embodiment the switch receptor comprises the transmembrane domain of the protein or fragment thereof that delivers a negative signal. In another embodiment, the switch receptor comprises the transmembrane domain of the protein or fragment thereof that delivers a positive signal.

In one embodiment, a switch receptor suitable for use in the present invention is a PD1-CD28 switch receptor. The PD1-CD28 switch receptor comprises a variant of the PD1 extracellular domain, a CD28 transmembrane domain, and a CD28 cytoplasmic domain. In one embodiment, the PD1-CD28 switch receptor comprises an amino acid sequence set forth below:

```
                                          (SEQ ID NO: 14)
MQIPQAPWPVVWAVLQLGWRPGWFLDSPDRPWNPPTFSPALLVVTEGDN

ATFTCSFSNTSESFVLNWYRMSPSNQTDKLAAFPEDRSQPGQDCRFRVT

QLPNGRDFHMSVVRARRNDSGTYLCGAISLAPKAQIKESLRAELRVTER

RAEVPTAHPSPSPRPAGQFQTLVFWVLVVVGGVLACYSLLVTVAFIIFW

VRSKRSRLLHSDYMNMTPRRPGPTRKHYQPYAPPRDFAAYRS,
``` encoded by the nucleic acid sequence set forth below:

```
                                          (SEQ ID NO: 15)
ATGCAGATCCCACAGGCGCCCTGGCCAGTCGTCTGGGCGGTGCTACAAC

TGGGCTGGCGGCCAGGATGGTTCTTAGACTCCCCAGACAGGCCCTGGAA
```

```
CCCCCCCACCTTCTCCCCAGCCCTGCTCGTGGTGACCGAAGGGGACAAC

GCCACCTTCACCTGCAGCTTCTCCAACACATCGGAGAGCTTCGTGCTAA

ACTGGTACCGCATGAGCCCCAGCAACCAGACGGACAAGCTGGCCGCCTT

CCCCGAGGACCGCAGCCAGCCCGGCCAGGACTGCCGCTTCCGTGTCACA

CAACTGCCCAACGGGCGTGACTTCCACATGAGCGTGGTCAGGGCCCGGC

GCAATGACAGCGGCACCTACCTCTGTGGGGCCATCTCCCTGGCCCCCAA

GGCGCAGATCAAAGAGAGCCTGCGGGCAGAGCTCAGGGTGACAGAGAGA

AGGGCAGAAGTGCCCACAGCCCACCCCAGCCCCTCACCCAGGCCAGCCG

GCCAGTTCCAAACCCTGGTGTTTTGGGTGCTGGTGGTGGTTGGTGGAGT

CCTGGCTTGCTATAGCTTGCTAGTAACAGTGGCCTTTATTATTTTCTGG

GTGAGGAGTAAGAGGAGCAGGCTCCTGCACAGTGACTACATGAACATGA

CTCCCCGCCGCCCCGGGCCCACCCGCAAGCATTACCAGCCCTATGCCCC

ACCACGCGACTTCGCAGCCTATCGCTCC.
```

Tolerable variations of the PD1-CD28 switch receptor will be known to those of skill in the art, while maintaining its intended biological activity (e.g., converting a negative PD1 signal into a positive CD28 signal when expressed in a cell). Accordingly, a PD1-CD28 switch receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1-CD28 switch receptor amino acid sequence set forth in SEQ ID NO:14. Accordingly, a PD1-CD28 switch receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1-CD28 switch receptor nucleic acid sequence set forth in SEQ ID NO:15.

In one embodiment, a switch receptor suitable for use in the present invention is a TIM3-CD28 switch receptor. The TIM3-CD28 switch receptor comprises a TIM3 extracellular domain, a CD28 transmembrane domain, and a CD28 cytoplasmic domain. In one embodiment, the TIM3-CD28 switch receptor comprises an amino acid sequence set forth below:

```
                                        (SEQ ID NO: 132)
MFSHLPFDCVLLLLLLLLTRSSEVEYRAEVGQNAYLPCFYTPAAPGNLV

PVCWGKGACPVFECGNVVLRTDERDVNYWTSRYWLNGDFRKGDVSLTIE

NVTLADSGIYCCRIQIPGIMNDEKFNLKLVIKPAKVTPAPTRQRDFTAA

FPRMLTTRGHGPAETQTLGSLPDINLTQISTLANELRDSRLANDLRDSG

ATIRFWVLVVVGGVLACYSLLVTVAFIIFWVRSKRSRLLHSDYMNMTPR

RPGPTRKHYQPYAPPRDFAAYRS,
``` encoded by the nucleic acid sequence set forth below:

```
                                        (SEQ ID NO: 133)
ATGTTTTCACATCTTCCCTTTGACTGTGTCCTGCTGCTGCTGCTGCTAC

TACTTACAAGGTCCTCAGAAGTGGAATACAGAGCGGAGGTCGGTCAGAA

TGCCTATCTGCCCTGCTTCTACACCCCAGCCGCCCCAGGGAACCTCGTG

CCCGTCTGCTGGGGCAAAGGAGCCTGTCCTGTGTTTGAATGTGGCAACG

TGGTGCTCAGGACTGATGAAAGGGATGTGAATTATTGGACATCCAGATA

CTGGCTAAATGGGGATTTCCGCAAAGGAGATGTGTCCCTGACCATAGAG

AATGTGACTCTAGCAGACAGTGGGATCTACTGCTGCCGAATCCAAATCC

CAGGCATAATGAATGATGAAAAATTTAACCTGAAGTTGGTCATCAAACC

AGCCAAGGTCACCCCTGCACCGACTCGGCAGAGAGACTTCACTGCAGCC

TTTCCAAGGATGCTTACCACCAGGGGACATGGCCCAGCAGAGACACAGA

CACTGGGGAGCCTCCCTGACATAAATCTAACACAAATATCCACATTGGC

CAATGAGTTACGGGACTCTAGGTTGGCCAATGACTTACGGGACTCCGGA

GCAACCATCAGATTTTGGGTGCTGGTGGTGGTTGGTGGAGTCCTGGCTT

GCTATAGCTTACTAGTAACAGTGGCCTTTATTATTTTCTGGGTGAGGAG

TAAGAGGAGCAGGCTCCTGCACAGTGACTACATGAACATGACTCCCCGC

CGCCCCGGGCCCACCCGCAAGCATTACCAGCCCTATGCCCCACCACGCG

ACTTCGCAGCCTATCGCTCC.
```

Tolerable variations of the TIM3-CD28 switch receptor will be known to those of skill in the art, while maintaining its intended biological activity (e.g., converting a negative TIM3 signal into a positive CD28 signal when expressed in a cell). Accordingly, a TIM3-CD28 switch receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TIM3-CD28 switch receptor amino acid sequence set forth in SEQ ID NO:132. Accordingly, a TIM3-CD28 switch receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TIM3-CD28 switch receptor nucleic acid sequence set forth in SEQ ID NO:133.

In one embodiment, a switch receptor suitable for use in the present invention is a PD1-41BB switch receptor (also referred to herein as PD1.BB). The PD1-41BB switch receptor comprises a PD1 extracellular domain, a CD8alpha transmembrane domain, and a 4-1BB cytoplasmic domain. In one embodiment, the PD1-41BB switch receptor comprises an amino acid sequence set forth below:

```
                                        (SEQ ID NO: 134)
MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL
```

-continued

PNGRDFHMSVVRARRNDSGTYLCGAISLAPKAQIKESLRAELRVTERRAE

VPTAHPSPSPRPAGQFQTLVIYIWAPLAGTCGVLLLSLVITLYCKKRGRK

KLLYIFKQPFMRPVQTTQEEDGCSCRFPEEEEGGCEL, encoded by the nucleic acid sequence set forth below:

(SEQ ID NO: 135)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCCAAGGCGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTTATCTACATCTGGGCGCCCTTGGCCGGGACTTGTGGGGTCC

TTCTCCTGTCACTGGTTATCACCCTTTACTGCAAAAAACGGGGCAGAAAG

AAACTCCTGTATATATTCAAACAACCATTTATGAGACCAGTACAAACTAC

TCAAGAGGAAGATGGCTGTAGCTGCCGATTTCCAGAAGAAGAAGAAGGAG

GATGTGAACTG.

Tolerable variations of the PD1-41BB switch receptor will be known to those of skill in the art, while maintaining its intended biological activity (e.g., converting a negative PD1 signal into a positive 4-1BB signal when expressed in a cell). Accordingly, a PD1-41BB switch receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1-41BB switch receptor amino acid sequence set forth in SEQ ID NO:134. Accordingly, a PD1-41BB switch receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1-41BB switch receptor nucleic acid sequence set forth in SEQ ID NO:135.

In one embodiment, a switch receptor suitable for use in the present invention is a PD1$^{A132L}$-41BB switch receptor (also referred to herein as PD1$^{A132L}$PTM.BB or PD1*.BB). The PD1$^{A132L}$-41BB switch receptor comprises a variant PD1 extracellular domain having a A132L substitution relative to the full length amino acid sequence of PD1, a CD8alpha transmembrane domain, and a 4-1BB cytoplasmic domain. The PD1 A132L substitution increases its affinity with PD-L1. See, e.g., Zhang et al. *Immunity* 2004, 20:337-347. In one embodiment, the PD1$^{A132L}$-41BB switch receptor comprises an amino acid sequence set forth below:

(SEQ ID NO: 136)
MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL

PNGRDFHMSVVRARRNDSGTYLCGAISLAPKLQIKESLRAELRVTERRAE

VPTAHPSPSPRPAGQFQTLVIYIWAPLAGTCGVLLLSLVITLYCKKRGRK

KLLYIFKQPFMRPVQTTQEEDGCSCRFPEEEEGGCEL, encoded by the nucleic acid sequence set forth below:

(SEQ ID NO: 137)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCCAAGCTGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTTATCTACATCTGGGCGCCCTTGGCCGGGACTTGTGGGGTCC

TTCTCCTGTCACTGGTTATCACCCTTTACTGCAAAAAACGGGGCAGAAAG

AAACTCCTGTATATATTCAAACAACCATTTATGAGACCAGTACAAACTAC

TCAAGAGGAAGATGGCTGTAGCTGCCGATTTCCAGAAGAAGAAGAAGGAG

GATGTGAACTG.

Tolerable variations of the PD1$^{A132L}$-41BB switch receptor will be known to those of skill in the art, while maintaining its intended biological activity (e.g., converting a negative PD1 signal into a positive 4-1BB signal when expressed in a cell). Accordingly, a PD1$^{A132L}$-41BB switch receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1$^{A132L}$-41BB switch receptor amino acid sequence set forth in SEQ ID NO:136. Accordingly, a PD1$^{A132L}$-41BB switch receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1$^{A132L}$-41BB switch receptor nucleic acid sequence set forth in SEQ ID NO:137.

In one embodiment, a switch receptor suitable for use in the present invention is a PD1$^{A132L}$-CD28 switch receptor (also referred to herein as PD1$^{A132L}$-PTM.CD28 or PD1*.CD28). The PD1$^{A132L}$-CD28 switch receptor comprises a variant PD1 extracellular domain having a A132L substitution relative to the full length amino acid sequence of PD1, a CD28 transmembrane domain, and a CD28 cytoplasmic domain. The PD1 A132L substitution increases its affinity with PD-L1. See, e.g., Zhang et al. *Immunity* 2004, 20:337-347. In one embodiment, the PD1$^{A132L}$-CD28 switch receptor comprises an amino acid sequence set forth below:

(SEQ ID NO: 138)
MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL

PNGRDFHMSVVRARRNDSGTYLCGAISLAPKLQIKESLRAELRVTERRAE

VPTAHPSPSPRPAGQFQTLVFWVLVVVGGVLACYSLLVTVAFIIFWVRSK

RSRLLHSDYMNMTPRRPGPTRKHYQPYAPPRDFAAYRS, encoded by the nucleic acid sequence set forth below:

(SEQ ID NO: 139)
ATGCAGATCCCACAGGCGCCCTGGCCAGTCGTCTGGGCGGTGCTACAACT

GGGCTGGCGGCCAGGATGGTTCTTAGACTCCCCAGACAGGCCCTGGAACC

CCCCCACCTTCTCCCCAGCCCTGCTCGTGGTGACCGAAGGGGACAACGCC

ACCTTCACCTGCAGCTTCTCCAACACATCGGAGAGCTTCGTGCTAAACTG

GTACCGCATGAGCCCCAGCAACCAGACGGACAAGCTGGCCGCCTTCCCCG

AGGACCGCAGCCAGCCCGGCCAGGACTGCCGCTTCCGTGTCACACAACTG

CCCAACGGGCGTGACTTCCACATGAGCGTGGTCAGGGCCCGGCGCAATGA

CAGCGGCACCTACCTCTGTGGGGCCATCTCCCTGGCCCCCAAGCTGCAGA

TCAAAGAGAGCCTGCGGGCAGAGCTCAGGGTGACAGAGAGAAGGGCAGAA

GTGCCCACAGCCCACCCCAGCCCCTCACCCAGGCCAGCCGGCCAGTTCCA

AACCCTGGTGTTTTGGGTGCTGGTGGTGGTTGGTGGAGTCCTGGCTTGCT

ATAGCTTGCTAGTAACAGTGGCCTTTATTATTTTCTGGGTGAGGAGTAAG

AGGAGCAGGCTCCTGCACAGTGACTACATGAACATGACTCCCCGCCGCCC

CGGGCCCACCCGCAAGCATTACCAGCCCTATGCCCCACCACGCGACTTCG

CAGCCTATCGCTCC.

Tolerable variations of the PD1$^{A132L}$-CD28 switch receptor will be known to those of skill in the art, while maintaining its intended biological activity (e.g., converting a negative PD1 signal into a positive CD28 signal when expressed in a cell). Accordingly, a PD1$^{A132L}$-CD28 switch receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1$^{A132L}$-CD28 switch receptor amino acid sequence set forth in SEQ ID NO:138. Accordingly, a PD1$^{A132L}$-CD28 switch receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the PD1$^{A132L}$-CD28 switch receptor nucleic acid sequence set forth in SEQ ID NO:139.

In one embodiment, a switch receptor suitable for use in the present invention is a TGFβRI-IL-12Rβ1 switch receptor. In one embodiment, the TGFβRI-IL-12Rβ1 switch receptor comprises an amino acid sequence set forth below:

(SEQ ID NO: 16)
LEAAVAAPRPRLLLLVLAAAAAAAAALLPGATALQCFCHLCTKDNFTCVT

DGLCFVSVTETTDKVIHNSMCIAEIDLIPRDRPFVCAPSSKTGSVTTTYC

CNQDHCNKIELPTTVKSSPGLGPVELAAVIAGPVCFVCISLMLMVYIRAA

RHLCPPLPTPCASSAIEFPGGKETWQWINPVDFQEEASLQEALVVEMSWD

KGERTEPLEKTELPEGAPELALDTELSLEDGDRCKAKM, encoded by the nucleic acid sequence set forth below:

(SEQ ID NO: 17)
CTGGAGGCGGCGGTCGCTGCTCCGCGTCCCCGGCTGCTCCTCCTCGTGCT

GGCGGCGGCGGCGGCGGCGGCGGCGGCGCTGCTCCCGGGGGCGACGGCGT

TACAGTGTTTCTGCCACCTCTGTACAAAAGACAATTTTACTTGTGTGACA

GATGGGCTCTGCTTTGTCTCTGTCACAGAGACCACAGACAAAGTTATACA

CAACAGCATGTGTATAGCTGAAATTGACTTAATTCCTCGAGATAGGCCGT

TTGTATGTGCACCCTCTTCAAAAACTGGGTCTGTGACTACAACATATTGC

TGCAATCAGGACCATTGCAATAAAATAGAACTTCCAACTACTGTAAAGTC

ATCACCTGGCCTTGGTCCTGTGGAACTGGCAGCTGTCATTGCTGGACCAG

TGTGCTTCGTCTGCATCTCACTCATGTTGATGGTCTATATCAGGGCCGCA

CGGCACCTGTGCCCGCCGCTGCCCACACCCTGTGCCAGCTCCGCCATTGA

GTTCCCTGGAGGGAAGGAGACTTGGCAGTGGATCAACCCAGTGGACTTCC

AGGAAGAGGCATCCCTGCAGGAGGCCCTGGTGGTAGAGATGTCCTGGGAC

AAAGGCGAGAGGACTGAGCCTCTCGAGAAGACAGAGCTACCTGAGGGTGC

CCCTGAGCTGGCCCTGGATACAGAGTTGTCCTTGGAGGATGGAGACAGGT

GCAAGGCCAAGATGTGA.

Tolerable variations of the TGFβRI-IL-12Rβ1 switch receptor will be known to those of skill in the art, while maintaining its intended biological activity (e.g., converting a negative TGF-β signal into a positive IL-12 signal when expressed in a cell). Accordingly, a TGFβRI-IL-12Rβ1 switch receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TGFβRI-IL-12Rβ1 switch receptor amino acid sequence set forth in SEQ ID NO:16. Accordingly, a TGFβRI-IL-12Rβ1 switch receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TGFβRI-IL-12Rβ1 switch receptor nucleic acid sequence set forth in SEQ ID NO:17.

In one embodiment, a switch receptor suitable for use in the present invention is a TGFβRII-IL-12Rβ2 switch receptor. In one embodiment, the TGFβRII-IL-12Rβ2 switch receptor comprises an amino acid sequence set forth below:

(SEQ ID NO: 18)
MGRGLLRGLWPLHIVLWTRIASTIPPHVQKSVNNDMIVTDNNGAVKFPQL

CKFCDVRFSTCDNQKSCMSNCSITSICEKPQEVCVAVWRKNDENITLETV

CHDPKLPYHDFILEDAASPKCIMKEKKKPGETFFMCSCSSDECNDNIIFS

EEYNTSNPDLLLVIFQVTGISLLPPLGVAISVIIIFYQQKVFVLLAALRP

QWCSREIPDPANSTCAKKYPIAEEKTQLPLDRLLIDWPTPEDPEPLVISE

VLHQVTPVFRHPPCSNWPQREKGIQGHQASEKDMMHSASSPPPPRALQAE

SRQLVDLYKVLESRGSDPKPENPACPWTVLPAGDLPTHDGYLPSNIDDLP

SHEAPLADSLEELEPQHISLSVFPSSSLHPLTFSCGDKLTLDQLKMRCDS

LML, encoded by the nucleic acid sequence set forth below:

(SEQ ID NO: 19)
ATGGGTCGGGGGCTGCTCAGGGGCCTGTGGCCGCTGCACATCGTCCTGTG

GACGCGTATCGCCAGCACGATCCCACCGCACGTTCAGAAGTCGGTTAATA

ACGACATGATAGTCACTGACAACAACGGTGCAGTCAAGTTTCCACAACTG

TGTAAATTTTGTGATGTGAGATTTTCCACCTGTGACAACCAGAAATCCTG

CATGAGCAACTGCAGCATCACCTCCATCTGTGAGAAGCCACAGGAAGTCT

GTGTGGCTGTATGGAGAAGAATGACGAGAACATAACACTAGAGACAGTT

TGCCATGACCCCAAGCTCCCCTACCATGACTTTATTCTGGAAGATGCTGC

TTCTCCAAAGTGCATTATGAAGGAAAAAAAAAAGCCTGGTGAGACTTTCT

TCATGTGTTCCTGTAGCTCTGATGAGTGCAATGACAACATCATCTTCTCA

GAAGAATATAACACCAGCAATCCTGACTTGTTGCTAGTCATATTTCAAGT

GACAGGCATCAGCCTCCTGCCACCACTGGGAGTTGCCATATCTGTCATCA

TCATCTTCTACCAGCAAAAGGTGTTTGTTCTCCTAGCAGCCCTCAGACCT

CAGTGGTGTAGCAGAGAAATTCCAGATCCAGCAAATAGCACTTGCGCTAA

GAAATATCCCATTGCAGAGGAGAAGACACAGCTGCCCTTGGACAGGCTCC

TGATAGACTGGCCCACGCCTGAAGATCCTGAACCGCTGGTCATCAGTGAA

GTCCTTCATCAAGTGACCCCAGTTTTCAGACATCCCCCCTGCTCCAACTG

GCCACAAAGGGAAAAAGGAATCCAAGGTCATCAGGCCTCTGAGAAAGACA

TGATGCACAGTGCCTCAAGCCCACCACCTCCAAGAGCTCTCCAAGCTGAG

AGCAGACAACTGGTGGATCTGTACAAGGTGCTGGAGAGCAGGGGCTCCGA

CCCAAAGCCAGAAAACCCAGCCTGTCCCTGGACGGTGCTCCCAGCAGGTG

ACCTTCCCACCCATGATGGCTACTTACCCTCCAACATAGATGACCTCCCC

TCACATGAGGCACCTCTCGCTGACTCTCTGGAAGAACTGGAGCCTCAGCA

CATCTCCCTTTCTGTTTTCCCCTCAAGTTCTCTTCACCCACTCACCTTCT

CCTGTGGTGATAAGCTGACTCTGGATCAGTTAAAGATGAGGTGTGACTCC

CTCATGCTCTGA.

Tolerable variations of the TGFβRII-IL-121Rβ2 switch receptor will be known to those of skill in the art, while maintaining its intended biological activity (e.g., converting a negative TGF-β signal into a positive IL-12 signal when expressed in a cell). Accordingly, a TGFβRII-IL-12Rβ2 switch receptor of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TGFβRII-IL-12Rβ2 switch receptor amino acid sequence set forth in SEQ ID NO:18. Accordingly, a TGFβRII-IL-12Rβ2 switch receptor of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TGFβRII-IL-12Rβ2 switch receptor nucleic acid sequence set forth in SEQ ID NO:19.

Other TGFβ signal converters or inhibitors are suitable for use in the present invention. In one embodiment, a dominant negative TGFβRII "switch receptor" (TGFβRIIDN) is suitable for use in the present invention. In such embodiment, the switch receptor is a truncated variant of a protein associated with a negative signal (e.g., TGFβRII). In one embodiment, the TGFβRIIDN comprises an amino acid sequence set forth below:

(SEQ ID NO: 20)

```
MGRGLLRGLWPLHIVLWTRIASTIPPHVQKSVNNDMIVTDNNGAVKFPQL
CKFCDVRFSTCDNQKSCMSNCSITSICEKPQEVCVAVWRKNDENITLETV
CHDPKLPYHDFILEDAASPKCIMKEKKKPGETFFMCSCSSDECNDNIIFS
EEYNTSNPDLLLVIFQVTGISLLPPLGVAISVIIIFYCYRVNRQQKLSSS
G,
``` encoded by the nucleic acid sequence set forth below:

(SEQ ID NO: 21)

```
ATGGGTCGGGGGCTGCTCAGGGGCCTGTGGCCGCTGCACATCGTCCTGT
GGACGCGTATCGCCAGCACGATCCCACCGCACGTTCAGAAGTCGGTTAA
TAACGACATGATAGTCACTGACAACAACGGTGCAGTCAAGTTTCCACAA
CTGTGTAAATTTTGTGATGTGAGATTTTCCACCTGTGACAACCAGAAAT
CCTGCATGAGCAACTGCAGCATCACCTCCATCTGTGAGAAGCCACAGGA
AGTCTGTGTGGCTGTATGGAGAAAGAATGACGAGAACATAACACTAGAG
ACAGTTTGCCATGACCCCAAGCTCCCCTACCATGACTTTATTCTGGAAG
ATGCTGCTTCTCCAAAGTGCATTATGAAGGAAAAAAAAAAGCCTGGTGA
GACTTTCTTCATGTGTTCCTGTAGCTCTGATGAGTGCAATGACAACATC
```

-continued

ATCTTCTCAGAAGAATATAACACCAGCAATCCTGACTTGTTGCTAGTCA

TATTTCAAGTGACAGGCATCAGCCTCCTGCCACCACTGGGAGTTGCCAT

ATCTGTCATCATCATCTTCTACTGCTACCGCGTTAACCGGCAGCAGAAG

CTGAGTTCATCCGGA.

Tolerable variations of the TGFβRIIDN will be known to those of skill in the art, while maintaining its intended biological activity. Accordingly, a TGFβRIIDN of the present invention may comprise an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TGFβRIIDN amino acid sequence set forth in SEQ ID NO:20. Accordingly, a TGFβRIIDN of the present invention may be encoded by a nucleic acid comprising a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the TGFβRIIDN nucleic acid sequence set forth in SEQ ID NO:21.

Other suitable switch receptors for use in the present invention are described in PCT Publication No. WO2013019615A2, the disclosure of which is incorporated herein by reference.

D. Nucleic Acids and Expression Vectors

The present disclosure provides a nucleic acid encoding an exogenous TCR and/or a switch receptor. In one embodiment, a nucleic acid of the present disclosure comprises a nucleic acid sequence encoding an exogenous TCR (e.g., an NY-ESO-1 TCR). In one embodiment, a nucleic acid of the present disclosure comprises a nucleic acid sequence encoding a switch receptor (e.g., a PD1-CD28 switch receptor).

In some embodiments, a nucleic acid of the present disclosure provides for the production of a TCR as described herein, e.g., in a mammalian cell. In some embodiments, a nucleic acid of the present disclosure provides for amplification of the TCR-encoding nucleic acid.

As described herein, a TCR of the present disclosure comprises a TCR alpha chain and a TCR beta chain. Accordingly, the present disclosure provides a nucleic acid encoding a TCR alpha chain, and a nucleic acid encoding a TCR beta chain. In some embodiments, the nucleic acid encoding a TCR alpha chain is separate from the nucleic acid encoding a TCR beta chain. In an exemplary embodiment, the nucleic acid encoding a TCR alpha chain, and the nucleic acid encoding a TCR beta chain, resides within the same nucleic acid.

In some embodiments, a nucleic acid of the present disclosure comprises a nucleic acid comprising a TCR alpha chain coding sequence and a TCR beta chain coding sequence. In some embodiments, a nucleic acid of the present disclosure comprises a nucleic acid comprising a TCR alpha chain coding sequence and a TCR beta chain coding sequence that is separated by a linker. A linker for use in the present disclosure allows for multiple proteins to be encoded by the same nucleic acid sequence (e.g., a multi-cistronic or bicistronic sequence), which are translated as a polyprotein that is dissociated into separate protein components. For example, a linker for use in a nucleic acid of the present disclosure comprising a TCR alpha chain coding sequence and a TCR beta chain coding sequence, allows for the TCR alpha chain and TCR beta chain to be translated as a polyprotein that is dissociated into separate TCR alpha chain and TCR beta chain components.

In some embodiments, the linker comprises a nucleic acid sequence that encodes for an internal ribosome entry site (IRES). As used herein, "an internal ribosome entry site" or "IRES" refers to an element that promotes direct internal ribosome entry to the initiation codon, such as ATG, of a protein coding region, thereby leading to cap-independent translation of the gene. Various internal ribosome entry sites are known to those of skill in the art, including, without limitation, IRES obtainable from viral or cellular mRNA sources, e.g., immunogloublin heavy-chain binding protein (BiP); vascular endothelial growth factor (VEGF); fibroblast growth factor 2; insulin-like growth factor; translational initiation factor eIF4G; yeast transcription factors TFIID and HAP4; and IRES obtainable from, e.g., cardiovirus, rhinovirus, aphthovirus, HCV, Friend murine leukemia virus (FrMLV), and Moloney murine leukemia virus (MoMLV). Those of skill in the art would be able to select the appropriate IRES for use in the present invention.

In some embodiments, the linker comprises a nucleic acid sequence that encodes for a self-cleaving peptide. As used herein, a "self-cleaving peptide" or "2A peptide" refers to an oligopeptide that allows multiple proteins to be encoded as polyproteins, which dissociate into component proteins upon translation. Use of the term "self-cleaving" is not intended to imply a proteolytic cleavage reaction. Various self-cleaving or 2A peptides are known to those of skill in the art, including, without limitation, those found in members of the Picornaviridae virus family, e.g., foot-and-mouth disease virus (FMDV), equine rhinitis A virus (ERAV0, Thosea asigna virus (TaV), and porcine tescho virus-1 (PTV-1); and carioviruses such as Theilovirus and encephalomyocarditis viruses. 2A peptides derived from FMDV, ERAV, PTV-1, and TaV are referred to herein as "F2A," "E2A," "P2A," and "T2A," respectively. Those of skill in the art would be able to select the appropriate self-cleaving peptide for use in the present invention.

In some embodiments, a linker further comprises a nucleic acid sequence that encodes a furin cleavage site. Furin is a ubiquitously expressed protease that resides in the trans-golgi and processes protein precursors before their secretion. Furin cleaves at the COOH— terminus of its consensus recognition sequence. Various furin consensus recognition sequences (or "furin cleavage sites") are known to those of skill in the art, including, without limitation, Arg-X-Lys-Arg (SEQ ID NO:22) or Arg-X-Arg-Arg (SEQ ID NO:23), (Lys/Arg)-Arg-X-(Lys/Arg)-Arg (SEQ ID NO:24) and Arg-X-X-Arg (SEQ ID NO:25), such as an Arg-Gln-Lys-Arg (SEQ ID NO:26), where X is any naturally occurring amino acid. Those of skill in the art would be able to select the appropriate Furin cleavage site for use in the present invention.

In some embodiments, the linker comprises a nucleic acid sequence encoding a combination of a Furin cleavage site and a 2A peptide. Examples include, without limitation, a linker comprising a nucleic acid sequence encoding Furin and F2A, a linker comprising a nucleic acid sequence encoding Furin and E2A, a linker comprising a nucleic acid sequence encoding Furin and P2A, a linker comprising a nucleic acid sequence encoding Furin and T2A. Those of skill in the art would be able to select the appropriate combination for use in the present invention. In such embodiments, the linker may further comprise a spacer sequence between the Furin and 2A peptide. Various spacer sequences are known in the art, including, without limitation, glycine serine (GS) spacers such as (GS)n, (GSGGS)n (SEQ ID NO:27) and (GGGS)n (SEQ ID NO:28), where n represents an integer of at least 1. Exemplary spacer sequences can comprise amino acid sequences including, without limitation, GGSG (SEQ ID NO:29), GGSGG (SEQ ID NO:30), GSGSG (SEQ ID NO:31), GSGGG (SEQ ID NO:32), GGGSG (SEQ ID NO:33), GSSSG (SEQ ID NO:34), and the like. Those of skill in the art would be able to select the appropriate spacer sequence for use in the present invention.

In an exemplary embodiment, a nucleic acid of the present disclosure comprises a nucleic acid sequence comprising a TCR alpha chain coding sequence and a TCR beta chain coding sequence that is separated by a Furin-(G4S)2-T2A (F-GS2-T2A) linker. The F-GS2-T2A linker may be encoded by the nucleic acid sequence CGTGCGAAGAGGGGCGGCGGGGGCTCCGGCGGGG-GAGGCAGTGAGGGCCGCGGCTCC CTGCTGACCTGCGGAGATGTAGAAGAGAACCCA GGCCCC (SEQ ID NO:35), and may comprise the amino acid sequence RAKRGGGGSGGGGSEGRGSLLTCGD-VEENPGP (SEQ ID NO:36). Those of skill in the art would appreciate that linkers of the present invention may include tolerable sequence variations.

In some embodiments, the present disclosure provides a nucleic acid comprising a nucleic acid sequence encoding a switch receptor as described herein. In some embodiments, a nucleic acid comprises a nucleic acid sequence encoding a switch receptor and a nucleic acid sequence encoding a TCR (e.g., NY-ESO-1 TCR). In one embodiment, the nucleic acid sequence encoding the switch receptor and the nucleic acid sequence encoding the TCR resides on separate nucleic acids. In one embodiment, the nucleic acid sequence encoding the switch receptor and the nucleic acid sequence encoding the TCR resides within the same nucleic acid. In such an embodiment, the nucleic acid sequence encoding the switch receptor and the nucleic acid sequence encoding the TCR is separated by a linker as described herein.

For example, a nucleic acid of the present disclosure may comprise a nucleic acid sequence encoding a switch receptor, a linker, and a nucleic acid sequence encoding a TCR. In one embodiment, the linker comprises a nucleic acid sequence encoding a 2A peptide (e.g., F2A). In an exemplary embodiment, a nucleic acid of the present disclosure may comprise a nucleic acid sequence encoding a switch receptor and a nucleic acid sequence encoding a TCR separated by a nucleic acid sequence encoding F2A. In an exemplary embodiment, the nucleic acid sequence encoding a TCR comprises a TCR alpha chain coding sequence and a TCR beta chain coding sequence separated by a nucleic acid sequence encoding F-GS2-T2A.

Accordingly, in one embodiment, a nucleic acid of the present disclosure comprises from 5' to 3': a nucleic acid sequence encoding a switch receptor, a nucleic acid sequence encoding a linker, and a nucleic acid sequence encoding a TCR. In one embodiment, a nucleic acid of the present disclosure comprises from 5' to 3': a nucleic acid sequence encoding a TCR, a nucleic acid sequence encoding a linker, and a nucleic acid sequence encoding a switch receptor. In an exemplary embodiment, a nucleic acid of the present disclosure comprises from 5' to 3': a nucleic acid sequence encoding a switch receptor, a nucleic acid sequence encoding F2A, and a nucleic acid sequence encoding a TCR. In another exemplary embodiment, a nucleic acid of the present disclosure comprises from 5' to 3': a nucleic acid sequence encoding a switch receptor, a nucleic acid sequence encoding F2A, a nucleic acid sequence encoding a TCR alpha chain, a nucleic acid sequence encoding F-GS2-T2A, and a nucleic acid sequence encoding a TCR beta chain.

In some embodiments, a nucleic acid of the present disclosure may be operably linked to a transcriptional control element, e.g., a promoter, and enhancer, etc. Suitable promoter and enhancer elements are known to those of skill in the art.

For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some embodiments, the promoter is a CD8 cell-specific promoter, a CD4 cell-specific promoter, a neutrophil-specific promoter, or an NK-specific promoter. For example, a CD4 gene promoter can be used; see, e.g., Salmon et al. Proc. Natl. Acad. Sci. USA (1993) 90:7739; and Marodon et al. (2003) Blood 101:3416. As another example, a CD8 gene promoter can be used. NK cell-specific expression can be achieved by use of an NcrI (p46) promoter; see, e.g., Eckelhart et al. Blood (2011) 117:1565.

For expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHOS promoter, a CUP1 promoter, a GALT promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art. Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol. (1991) 173(1): 86-93; Alpuche-Aranda et al., Proc. Natl. Acad. Sci. USA (1992) 89(21): 10079-83), a nirB promoter (Harborne et al. Mol. Micro. (1992) 6:2805-2813), and the like (see, e.g., Dunstan et al., Infect. Immun. (1999) 67:5133-5141; McKelvie et al., Vaccine (2004) 22:3243-3255; and Chatfield et al., Biotechnol. (1992) 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al., Infect. Immun. (2002) 70:1087-1096); an rpsM promoter (see, e.g., Valdivia and Falkow Mol. Microbiol. (1996). 22:367); a tet promoter (see, e.g., Hillen, W. and Wissmann, A. (1989) In Saenger, W. and Heinemann, U. (eds), Topics in Molecular and Structural Biology, Protein-Nucleic Acid Interaction. Macmillan, London, UK, Vol. 10, pp. 143-162); an SP6 promoter (see, e.g., Melton et al., Nucl. Acids Res. (1984) 12:7035); and the like. Suitable strong promoters for use in prokaryotes such as *Escherichia coli* include, but are not limited to Trc, Tac, T5, T7, and PLambda. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, e.g., deBoer et al., Proc. Natl. Acad. Sci. U.S.A. (1983) 80:21-25).

Other examples of suitable promoters include the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to a simian virus 40 (SV40) early promoter, a mouse mammary tumor virus (MMTV) or human immunodeficiency virus (HIV) long terminal repeat (LTR) promoter, a MoMuLV promoter, an avian leukemia virus promoter, an Epstein-Barr virus immediate early promoter, a Rous sarcoma virus promoter, the EF-1 alpha promoter, as well as human gene promoters such as, but not limited to, an actin promoter, a myosin promoter, a hemoglobin promoter, and a creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the locus or construct or transgene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., Proc. Natl. Acad. Sci. USA (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. Annual Review of Biochemistry (2006) 567-605; and Tropp, Molecular Biology (2012) (Jones & Bartlett Publishers, Sudbury, Mass.), the disclosures of which are incorporated herein by reference.

In some embodiments, a nucleic acid of the present disclosure further comprises a nucleic acid sequence encoding a TCR inducible expression cassette. In one embodiment, the TCR inducible expression cassette is for the production of a transgenic polypeptide product that is released upon TCR signaling. See, e.g., Chmielewski and Abken, Expert Opin. Biol. Ther. (2015) 15(8): 1145-1154; and Abken, Immunotherapy (2015) 7(5): 535-544. In some embodiments, a nucleic acid of the present disclosure further comprises a nucleic acid sequence encoding a cytokine operably linked to a T-cell activation responsive promoter. In some embodiments, the cytokine operably linked to a T-cell activation responsive promoter is present on a separate nucleic acid sequence. In one embodiment, the cytokine is IL-12.

A nucleic acid of the present disclosure may be present within an expression vector and/or a cloning vector. An expression vector can include a selectable marker, an origin of replication, and other features that provide for replication and/or maintenance of the vector. Suitable expression vectors include, e.g., plasmids, viral vectors, and the like. Large numbers of suitable vectors and promoters are known to those of skill in the art; many are commercially available for generating a subject recombinant construct. The following vectors are provided by way of example, and should not be construed in anyway as limiting: Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest. Opthalmol. Vis. Sci. (1994) 35: 2543-2549; Borras et al., Gene Ther. (1999) 6: 515-524; Li and Davidson, Proc. Natl. Acad. Sci. USA (1995) 92: 7700-7704; Sakamoto et al., H. Gene Ther. (1999) 5: 1088-1097; WO 94/12649, WO 93/03769; WO 93/19191; WO 94/28938; WO 95/11984 and WO 95/00655); adeno-associated virus (see, e.g., Ali et al., Hum. Gene Ther. (1998) 9: 81-86, Flannery et al., Proc. Natl. Acad. Sci. USA (1997) 94: 6916-6921; Bennett et al., Invest. Opthalmol. Vis. Sci. (1997) 38: 2857-2863; Jomary et al., Gene Ther. (1997) 4:683 690, Rolling et al., Hum. Gene Ther. (1999) 10: 641-648; Ali et al., Hum. Mol. Genet. (1996) 5: 591-594; Srivastava in WO 93/09239, Samulski et al., J. Vir. (1989) 63: 3822-3828; Mendelson et al., Virol. (1988) 166: 154-165; and Flotte et al., Proc. Natl. Acad. Sci. USA (1993) 90: 10613-10617); SV40; herpes simplex virus; human immunodeficiency virus (see, e.g., Miyoshi et al., Proc. Natl. Acad. Sci. USA (1997) 94: 10319-23; Takahashi et al., J. Virol. (1999) 73: 7812-7816); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Additional expression vectors suitable for use are, e.g., without limitation, a lentivirus vector, a gamma retrovirus vector, a foamy virus vector, an adeno-associated virus vector, an adenovirus vector, a pox virus vector, a herpes virus vector, an engineered hybrid virus vector, a transposon mediated vector, and the like. Viral vector technology is well known in the art and is described, for example, in Sambrook et al., 2012, Molecular Cloning: A Laboratory Manual, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses.

In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

In some embodiments, an expression vector (e.g., a lentiviral vector) may be used to introduce the TCR and/or the switch receptor into an immune cell or precursor thereof (e.g., a T cell). Accordingly, an expression vector (e.g., a lentiviral vector) of the present invention may comprise a nucleic acid encoding for a TCR and/or a switch receptor. In some embodiments, the expression vector (e.g., lentiviral vector) will comprise additional elements that will aid in the functional expression of the TCR and/or switch receptor encoded therein. In some embodiments, an expression vector comprising a nucleic acid encoding for a TCR and/or a switch receptor further comprises a mammalian promoter. In one embodiment, the vector further comprises an elongation-factor-1-alpha promoter (EF-1a promoter). Use of an EF-1α promoter may increase the efficiency in expression of downstream transgenes (e.g., a TCR and/or a switch receptor encoding nucleic acid sequence). Physiologic promoters (e.g., an EF-1α promoter) may be less likely to induce integration mediated genotoxicity, and may abrogate the ability of the retroviral vector to transform stem cells. Other physiological promoters suitable for use in a vector (e.g., lentiviral vector) are known to those of skill in the art and may be incorporated into a vector of the present invention. In some embodiments, the vector (e.g., lentiviral vector) further comprises a non-requisite cis acting sequence that may improve titers and gene expression. One non-limiting example of a non-requisite cis acting sequence is the central polypurine tract and central termination sequence (cPPT/CTS) which is important for efficient reverse transcription and nuclear import. Other non-requisite cis acting sequences are known to those of skill in the art and may be incorporated into a vector (e.g., lentiviral vector) of the present invention.

In some embodiments, the vector further comprises a posttranscriptional regulatory element. Posttranscriptional regulatory elements may improve RNA translation, improve transgene expression and stabilize RNA transcripts. One example of a posttranscriptional regulatory element is the woodchuck hepatitis virus posttranscriptional regulatory element (WPRE). Accordingly, in some embodiments a vector for the present invention further comprises a WPRE sequence. Various posttranscriptional regulator elements are known to those of skill in the art and may be incorporated into a vector (e.g., lentiviral vector) of the present invention. A vector of the present invention may further comprise additional elements such as a rev response element (RRE) for RNA transport, packaging sequences, and 5' and 3' long terminal repeats (LTRs). The term "long terminal repeat" or "LTR" refers to domains of base pairs located at the ends of retroviral DNAs which comprise U3, R and U5 regions. LTRs generally provide functions required for the expression of retroviral genes (e.g., promotion, initiation and polyadenylation of gene transcripts) and to viral replication. In one embodiment, a vector (e.g., lentiviral vector) of the present invention includes a 3' U3 deleted LTR. Accordingly, a vector (e.g., lentiviral vector) of the present invention may comprise any combination of the elements described herein to enhance the efficiency of functional expression of transgenes. For example, a vector (e.g., lentiviral vector) of the present invention may comprise a WPRE sequence, cPPT sequence, RRE sequence, 5'LTR, 3' U3 deleted LTR' in addition to a nucleic acid encoding for a TCR and/or a switch receptor.

Vectors of the present invention may be self-inactivating vectors. As used herein, the term "self-inactivating vector" refers to vectors in which the 3' LTR enhancer promoter region (U3 region) has been modified (e.g., by deletion or substitution). A self-inactivating vector may prevent viral transcription beyond the first round of viral replication. Consequently, a self-inactivating vector may be capable of infecting and then integrating into a host genome (e.g., a mammalian genome) only once, and cannot be passed further. Accordingly, self-inactivating vectors may greatly reduce the risk of creating a replication-competent virus.

In some embodiments, a nucleic acid of the present invention may be RNA, e.g., in vitro synthesized RNA. Methods for in vitro synthesis of RNA are known to those of skill in the art; any known method can be used to synthesize RNA comprising a sequence encoding a TCR and/or switch receptor of the present disclosure. Methods for introducing RNA into a host cell are known in the art. See, e.g., Zhao et al. Cancer Res. (2010) 15: 9053. Introducing RNA comprising a nucleotide sequence encoding a TCR and/or switch receptor of the present disclosure into a host cell can be carried out in vitro or ex vivo or in vivo. For example, a host cell (e.g., an NK cell, a cytotoxic T lymphocyte, etc.) can be electroporated in vitro or ex vivo with RNA comprising a nucleotide sequence encoding a TCR and/or switch receptor of the present disclosure.

In order to assess the expression of a polypeptide or portions thereof, the expression vector to be introduced into a cell may also contain either a selectable marker gene or a reporter gene, or both, to facilitate identification and selection of expressing cells from the population of cells sought to be transfected or infected through viral vectors. In some embodiments, the selectable marker may be carried on a separate piece of DNA and used in a co-transfection procedure. Both selectable markers and reporter genes may be flanked with appropriate regulatory sequences to enable expression in the host cells. Useful selectable markers include, without limitation, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include, without limitation, genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82).

E. Modified Immune Cells

The present disclosure provides a modified immune cell or precursor thereof (e.g., a T cell) comprising an exogenous TCR and/or switch receptor as described herein. Accordingly, such modified cells possess the specificity directed by the TCR that is expressed therein. For example, a modified cell of the present disclosure comprising a NY-ESO-1 TCR possesses specificity for NY-ESO-1 on a target cell.

In some embodiments, a modified cell of the present disclosure comprises an exogenous TCR. In one embodiment, a modified cell of the present disclosure comprises an exogenous TCR having affinity for NY-ESO-1 on a target cell. In some embodiments, a modified cell of the present disclosure comprises an exogenous TCR and a switch receptor. In one embodiment, a modified cell of the present disclosure comprises an exogenous TCR having affinity for NY-ESO-1 on a target cell, and a switch receptor. Modified cells comprising a switch receptor of the present disclosure are able to activate inhibitory ligands in the microenvironment by virtue of the first domain of the switch receptor, and switch the otherwise inhibitory signal into a positive signal to the modified cell by way of signaling through the second domain of the switch receptor.

In an exemplary embodiment, a modified cell of the present disclosure comprises an exogenous TCR (e.g., a TCR having affinity for NY-ESO-1 on a target cell), and a PD1-CD28 switch receptor. Such modified cells (e.g., modified T cells) in addition to having affinity for NY-ESO-1 on a target cell, are capable of converting inhibitory signals from the microenvironment they reside in into activating signals in the T cell. Modified T cells comprising a PD1-CD28 switch receptor are capable of converting inhibitory PD-1 ligands in the microenvironment into activating signals by signaling through the CD28 domain of the switch receptor. As such, a modified cell comprising an exogenous TCR (having affinity for an antigen on a target cell) and a switch receptor of the present disclosure possesses specificity for the antigen on the target cell, and can bypass any inhibitory, immunosuppressive signals present in the microenvironment wherein the target cell resides. In an exemplary embodiment, a modified cell (e.g., T cell) comprises an exogenous TCR having affinity for NY-ESO-1 on a tumor cell, and a PD1-CD28 switch receptor capable of converting an inhibitory, immunosuppressive PD-1 ligand in the tumor microenvironment into an activating signal in the modified cell (resulting in an activated modified cell). As used herein, an "activated modified cell" or "activated modified T cell" refers to, among other things, modified cells that are undergoing cell division. Activation can also be associated with generating an immune response, and detectably unregulating surface markers. Upregulation of surface markers, such as CD25 (the IL-2 receptor), initiates a phosphorylation cascade involving p56lck, causes the release of cytokines and interleukins, increases DNA synthesis, and causes the cells to proliferate.

In an exemplary embodiment, a modified cell of the present disclosure comprises an exogenous TCR (e.g., a TCR having affinity for NY-ESO-1 on a target cell), and a TIM3-CD28 switch receptor. In an exemplary embodiment, a modified cell (e.g., T cell) comprises an exogenous TCR having affinity for NY-ESO-1 on a tumor cell, and a TIM3-CD28 switch receptor.

In an exemplary embodiment, a modified cell of the present disclosure comprises an exogenous TCR (e.g., a TCR having affinity for NY-ESO-1 on a target cell), and a PD1-41BB switch receptor. In an exemplary embodiment, a modified cell (e.g., T cell) comprises an exogenous TCR having affinity for NY-ESO-1 on a tumor cell, and a PD1-41BB switch receptor.

In an exemplary embodiment, a modified cell of the present disclosure comprises an exogenous TCR (e.g., a TCR having affinity for NY-ESO-1 on a target cell), and a $PD1^{A132L}$-41BB switch receptor. In an exemplary embodiment, a modified cell (e.g., T cell) comprises an exogenous TCR having affinity for NY-ESO-1 on a tumor cell, and a $PD1^{A132L}$-41BB switch receptor.

In an exemplary embodiment, a modified cell of the present disclosure comprises an exogenous TCR (e.g., a TCR having affinity for NY-ESO-1 on a target cell), and a $PD1^{A132L}$-CD28 switch receptor. In an exemplary embodiment, a modified cell (e.g., T cell) comprises an exogenous TCR having affinity for NY-ESO-1 on a tumor cell, and a $PD1^{A132L}$-CD28 switch receptor.

In an exemplary embodiment, a modified cell of the present disclosure comprises an exogenous TCR (e.g., a TCR having affinity for NY-ESO-1 on a target cell), and a TGFβRI-IL-12Rβ1 switch receptor. In an exemplary embodiment, a modified cell (e.g., T cell) comprises an exogenous TCR having affinity for NY-ESO-1 on a tumor cell, and a TGFβRI-IL-12Rβ1 switch receptor.

In an exemplary embodiment, a modified cell of the present disclosure comprises an exogenous TCR (e.g., a TCR having affinity for NY-ESO-1 on a target cell), and a TGFβRII-IL-12Rβ2 switch receptor. In an exemplary embodiment, a modified cell (e.g., T cell) comprises an exogenous TCR having affinity for NY-ESO-1 on a tumor cell, and a TGFβRII-IL-12Rβ2 switch receptor.

In an exemplary embodiment, a modified cell of the present disclosure comprises an exogenous TCR (e.g., a TCR having affinity for NY-ESO-1 on a target cell), and a TGFβRIIDN "switch receptor." In an exemplary embodiment, a modified cell (e.g., T cell) comprises an exogenous TCR having affinity for NY-ESO-1 on a tumor cell, and a TGFβRIIDN "switch receptor."

Gene Edited Immune Cells

The present disclosure provides gene edited modified cells. In some embodiments, a modified cell (e.g., a modified cell comprising an exogenous TCR and/or switch receptor) of the present disclosure is genetically edited to disrupt the expression of one or more endogenously expressed genes. In some embodiments, the gene-edited immune cells (e.g., T cells), having a reduction, deletion, elimination, knockout or disruption in expression of an endogenous receptor (e.g. an endogenous T cell receptor or immune checkpoint protein).

In certain embodiments, the modified cell of the present disclosure is genetically edited to disrupt the expression of endogenous TCR gene products (e.g., gene products of TRAC and TRBC). Without being bound to any theory, disrupting the expression of TRAC and/or TRBC results in 1) reduced endogenous TCR and exogenous TCR (e.g., an NY-ESO-1 TCR) mispairing, thus reducing the risk of autoreactivity; and 2) enhances exogenous TCR expression on the cell surface by reducing mispairing with endogenous TCR, thus increasing efficacy of the modified cells. In one embodiment, the modified cell of the present disclosure is genetically edited to disrupt the expression of endogenous PDCD1 gene products (Programmed Death 1 receptor; PD-1). Disrupting the expression of endogenous PD-1 may create "checkpoint" resistant modified cells, resulting in increased tumor control. Checkpoint resistant modified cells may also be created by disrupting the expression of, for example, without limitation, the Adenosine A2A receptor (A2AR), B7-H3 (CD276), B7-H4 (VTCN1), the B and T Lymphocyte Attenuator protein (BTLA/CD272), CD96, the Cytotoxic T-Lymphocyte Associated protein 4 (CTLA-4/CD152), Indoleamine 2,3-dioxygenase (IDO), the Killer-cell Immunoglobulin-like Receptor (KIR), the Lymphocyte Activation Gene-3 (LAG3), the T cell immunoreceptor with Ig and ITIM domains (TIGIT), T-cell Immunoglobulin domain and Mucin domain 3 (TIM-3), or the V-domain Ig suppressor of T cell activation (VISTA). Accordingly, in one embodiment, the modified cell of the present disclosure is genetically edited to disrupt the expression of endogenous CTLA-4.

In some embodiments, a modified cell of the present disclosure comprises an exogenous TCR and is genetically edited to disrupt the expression of one or more endogenously expressed genes. In one embodiment, a modified cell of the present disclosure comprises an exogenous TCR having affinity for NY-ESO-1 on a target cell, wherein the expression of one or more endogenous genes is downregulated. In one embodiment, a modified cell of the present disclosure is a modified T cell comprising an exogenous TCR having affinity for NY-ESO-1 on a target cell, wherein the expression of one or more of A2AR, B7-H3 (CD276), B7-H4 (VTCN1), BTLA (CD272), CD96, CTLA-4 (CD152), IDO, KIR, LAG3, TIGIT, TIM-3, and/or VISTA gene products are downregulated. In an exemplary embodiment, a modified cell of the present disclosure is a modified T cell comprising an exogenous TCR having affinity for NY-ESO-1 on a target cell, wherein the expression of TRAC, TRBC, and PDCD1 gene products are downregulated.

In some embodiments, a modified cell of the present disclosure comprises an exogenous TCR and a switch receptor, and is genetically edited to disrupt the expression of one or more endogenously expressed genes. In one embodiment, a modified cell of the present disclosure comprises, an exogenous TCR having affinity for NY-ESO-1 on a target cell, and a switch receptor, wherein the expression of one or more endogenous genes is downregulated. In one embodiment, a modified cell of the present disclosure is a modified T cell comprising an exogenous TCR having affinity for NY-ESO-1 on a target cell, and a switch receptor, wherein the expression of one or more of A2AR, B7-H3 (CD276), B7-H4 (VTCN1), BTLA (CD272), CD96, CTLA-4 (CD152), IDO, KIR, LAG3, TIGIT, TIM-3, and/or VISTA gene products are downregulated. In one embodiment, a modified cell of the present disclosure is a modified T cell comprising an exogenous TCR having affinity for NY-ESO-1 on a target cell, and a switch receptor, wherein the expression of TRAC and TRBC gene products are downregulated. In an exemplary embodiment, a modified cell of the present disclosure is a modified T cell comprising an exogenous TCR having affinity for NY-ESO-1 on a target cell, and a PD1-CD28 switch receptor, wherein the expression of TRAC and TRBC gene products are downregulated. In an exemplary embodiment, a modified cell of the present disclosure is a modified T cell comprising an exogenous TCR having affinity for NY-ESO-1 on a target cell, and a PD1-CD28 switch receptor, wherein the expression of TRAC, TRBC and TIM-3 gene products are downregulated.

A modified cell of the present disclosure can comprise various switch receptors described elsewhere herein, e.g., PD1-CD28, TIM3-CD28, PD1-41BB, PD1$^{A132L}$-41BB, PD1$^{A132L}$-CD28, TGFβRI-IL-12Rβ1, TGFβRII-IL-12Rβ2, TGFβRIIDN.

Various gene editing technologies are known to those skilled in the art. Gene editing technologies include, without limitation, homing endonucleases, zinc-finger nucleases (ZFNs), transcription activator-like effector (TALE) nucleases (TALENs), and clustered regularly interspaced short palindromic repeats (CRISPR) systems (e.g. CRISPR/CRISPR-associated protein 9 (Cas9)). Homing endonucleases generally cleave their DNA substrates as dimers, and do not have distinct binding and cleavage domains. ZFNs recognize target sites that consist of two zinc-finger binding sites that flank a 5- to 7-base pair (bp) spacer sequence recognized by the FokI cleavage domain. TALENs recognize target sites that consist of two TALE DNA-binding sites that flank a 12- to 20-bp spacer sequence recognized by the FokI cleavage domain. The Cas9 nuclease is targeted to DNA sequences complementary to the targeting sequence within the single guide RNA (gRNA) located immediately upstream of a compatible protospacer adjacent motif (PAM). Accordingly, one of skill in the art would be able to select the appropriate gene editing technology for the present invention.

In some aspects, the disruption is carried out by gene editing using an RNA-guided nuclease such as a clustered regularly interspersed short palindromic nucleic acid (CRISPR)-Cas system, such as CRISPR/Cas9 system, specific for the gene (e.g., TRAC, TRBC, PDCDI or TIM3) being disrupted. In some embodiments, an agent containing a Cas9 (e.g. Cas9 RNA) and a guide RNA (gRNA) containing a targeting domain, which targets a region of the genetic locus, is introduced into the cell. In some embodiments, the agent is or comprises a ribonucleoprotein (RNP) complex of Cas9 and gRNA containing the gene-targeted targeting domain (Cas9/gRNA RNP). In some embodiments, the introduction includes contacting the agent or portion thereof with the cells, in vitro, which can include cultivating or incubating the cell and agent for up to 24, 36 or 48 hours or 3, 4, 5, 6, 7, or 8 days. In some embodiments, the introduction further can include effecting delivery of the agent into the cells. In various embodiments, the methods, compositions and cells according to the present disclosure utilize direct delivery of ribonucleoprotein (RNP) complexes of Cas9 and gRNA to cells, for example by electroporation. In some embodiments, the RNP complexes include a gRNA that has been modified to include a 3' poly-A tail and a 5' Anti-Reverse Cap Analog (ARCA) cap.

The CRISPR/Cas9 system is a facile and efficient system for inducing targeted genetic alterations. Target recognition by the Cas9 protein requires a 'seed' sequence within the guide RNA (gRNA) and a conserved di-nucleotide containing protospacer adjacent motif (PAM) sequence upstream of the gRNA-binding region. The CRISPR/Cas9 system can thereby be engineered to cleave virtually any DNA sequence by redesigning the gRNA in cell lines (such as 293T cells), primary cells, and TCR T cells. The CRISPR/Cas9 system can simultaneously target multiple genomic loci by coexpressing a single Cas9 protein with two or more gRNAs, making this system suited for multiple gene editing or synergistic activation of target genes.

The Cas9 protein and guide RNA form a complex that identifies and cleaves target sequences. Cas9 is comprised of six domains: REC I, REC II, Bridge Helix, PAM interacting, HNH, and RuvC. The RecI domain binds the guide RNA, while the Bridge helix binds to target DNA. The HNH and RuvC domains are nuclease domains. Guide RNA is engineered to have a 5' end that is complementary to the target DNA sequence. Upon binding of the guide RNA to the Cas9 protein, a conformational change occurs activating the protein. Once activated, Cas9 searches for target DNA by binding to sequences that match its protospacer adjacent motif (PAM) sequence. A PAM is a two or three nucleotide base sequence within one nucleotide downstream of the region complementary to the guide RNA. In one non-limiting example, the PAM sequence is 5'-NGG-3'. When the Cas9 protein finds its target sequence with the appropriate PAM, it melts the bases upstream of the PAM and pairs them with the complementary region on the guide RNA. Then the RuvC and HNH nuclease domains cut the target DNA after the third nucleotide base upstream of the PAM.

One non-limiting example of a CRISPR/Cas system used to inhibit gene expression, CRISPRi, is described in U.S. Patent Appl. Publ. No. US20140068797. CRISPRi induces permanent gene disruption that utilizes the RNA-guided Cas9 endonuclease to introduce DNA double stranded breaks which trigger error-prone repair pathways to result in frame shift mutations. A catalytically dead Cas9 lacks endonuclease activity. When coexpressed with a guide RNA, a DNA recognition complex is generated that specifically interferes with transcriptional elongation, RNA polymerase binding, or transcription factor binding. This CRISPRi system efficiently represses expression of targeted genes.

CRISPR/Cas gene disruption occurs when a guide nucleic acid sequence specific for a target gene and a Cas endonuclease are introduced into a cell and form a complex that enables the Cas endonuclease to introduce a double strand break at the target gene. In certain embodiments, the CRISPR/Cas system comprises an expression vector, such as, but not limited to, an pAd5F35-CRISPR vector. In other embodiments, the Cas expression vector induces expression of Cas9 endonuclease. Other endonucleases may also be used, including but not limited to, T7, Cas3, Cas8a, Cas8b, Cas10d, Cse1, Csy1, Csn2, Cas4, Cas10, Csm2, Cmr5, Fok1, other nucleases known in the art, and any combinations thereof.

In certain embodiments, inducing the Cas expression vector comprises exposing the cell to an agent that activates an inducible promoter in the Cas expression vector. In such embodiments, the Cas expression vector includes an inducible promoter, such as one that is inducible by exposure to an antibiotic (e.g., by tetracycline or a derivative of tetracycline, for example doxycycline). Other inducible promoters known by those of skill in the art can also be used. The inducing agent can be a selective condition (e.g., exposure to an agent, for example an antibiotic) that results in induction of the inducible promoter. This results in expression of the Cas expression vector.

The guide RNA is specific for a genomic region of interest and targets that region for Cas endonuclease-induced double strand breaks. The target sequence of the guide RNA sequence may be within a locus of a gene or within a non-coding region of the genome. In certain embodiments, the guide nucleic acid sequence is at least 10, 11, 12, 13, 14, 15, 16, 17, 18, 19, 20, 21, 22, 23, 24, 25, 26, 27, 30, 31, 32, 33, 34, 35, 36, 37, 38, 39, 40 or more nucleotides in length.

Guide RNA (gRNA), also referred to as "short guide RNA" or "sgRNA", provides both targeting specificity and scaffolding/binding ability for the Cas9 nuclease. The gRNA can be a synthetic RNA composed of a targeting sequence and scaffold sequence derived from endogenous bacterial crRNA and tracrRNA. gRNA is used to target Cas9 to a specific genomic locus in genome engineering experiments. Guide RNAs can be designed using standard tools well known in the art.

In the context of formation of a CRISPR complex, "target sequence" refers to a sequence to which a guide sequence is designed to have some complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In certain embodiments, a target sequence is located in the nucleus or cytoplasm of a cell. In other embodiments, the target sequence may be within an organelle of a eukaryotic cell, for example, mitochondrion or nucleus. Typically, in the context of an endogenous CRISPR system, formation of a CRISPR complex (comprising a guide sequence hybridized to a target sequence and complexed with one or more Cas proteins) results in cleavage of one or both strands in or near (e.g., within about 1, 2, 3, 4, 5, 6, 7, 8, 9, 10, 20, 50 or more base pairs) the target sequence. As with the target sequence, it is believed that complete complementarity is not needed, provided this is sufficient to be functional.

In certain embodiments, one or more vectors driving expression of one or more elements of a CRISPR system are introduced into a host cell, such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In certain embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g., each in a different intron, two or more in at least one intron, or all in a single intron).

In certain embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Additional domains that may form part of a fusion protein comprising a CRISPR enzyme are described in U.S. Patent Appl. Publ. No. US20110059502, incorporated herein by reference. In certain embodiments, a tagged CRISPR enzyme is used to identify the location of a target sequence.

Conventional viral and non-viral based gene transfer methods can be used to introduce nucleic acids in mammalian and non-mammalian cells or target tissues. Such methods can be used to administer nucleic acids encoding components of a CRISPR system to cells in culture, or in a host organism. Non-viral vector delivery systems include DNA plasmids, RNA (e.g., a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell (Anderson, 1992, Science 256:808-813; and Yu, et al., 1994, Gene Therapy 1:13-26).

In some embodiments, the CRISPR/Cas is derived from a type II CRISPR/Cas system. In other embodiments, the CRISPR/Cas system is derived from a Cas9 protein. The Cas9 protein can be from *Streptococcus pyogenes, Streptococcus thermophilus*, or other species.

In general, Cas proteins comprise at least one RNA recognition and/or RNA binding domain. RNA recognition and/or RNA binding domains interact with the guiding RNA. Cas proteins can also comprise nuclease domains (i.e., DNase or RNase domains), DNA binding domains, helicase domains, RNAse domains, protein-protein interaction domains, dimerization domains, as well as other domains. The Cas proteins can be modified to increase nucleic acid binding affinity and/or specificity, alter an enzymatic activity, and/or change another property of the protein. In certain embodiments, the Cas-like protein of the fusion protein can be derived from a wild type Cas9 protein or fragment thereof. In other embodiments, the Cas can be derived from modified Cas9 protein. For example, the amino acid sequence of the Cas9 protein can be modified to alter one or more properties (e.g., nuclease activity, affinity, stability, and so forth) of the protein. Alternatively, domains of the Cas9 protein not involved in RNA-guided cleavage can be eliminated from the protein such that the modified Cas9 protein is smaller than the wild type Cas9 protein. In general, a Cas9 protein comprises at least two nuclease (i.e., DNase) domains. For example, a Cas9 protein can comprise a RuvC-like nuclease domain and a HNH-like nuclease domain. The RuvC and HNH domains work together to cut single strands to make a double-stranded break in DNA. (Jinek, et al., 2012, Science, 337:816-821). In certain embodiments, the Cas9-derived protein can be modified to contain only one functional nuclease domain (either a RuvC-like or a HNH-like nuclease domain). For example, the Cas9-derived protein can be modified such that one of the nuclease domains is deleted or mutated such that it is no longer functional (i.e., the nuclease activity is absent). In some embodiments in which one of the nuclease domains is inactive, the Cas9-derived protein is able to introduce a nick into a double-stranded nucleic acid (such protein is termed a "nickase"), but not cleave the double-stranded DNA. In any of the above-described embodiments, any or all of the nuclease domains can be inactivated by one or more deletion mutations, insertion mutations, and/or substitution mutations using well-known methods, such as site-directed mutagenesis, PCR-mediated mutagenesis, and total gene synthesis, as well as other methods known in the art.

In one non-limiting embodiment, a vector drives the expression of the CRISPR system. The art is replete with suitable vectors that are useful in the present invention. The vectors to be used are suitable for replication and, optionally, integration in eukaryotic cells. Typical vectors contain transcription and translation terminators, initiation sequences, and promoters useful for regulation of the expression of the desired nucleic acid sequence. The vectors of the present invention may also be used for nucleic acid standard gene delivery protocols. Methods for gene delivery are known in the art (U.S. Pat. Nos. 5,399,346, 5,580,859 & 5,589,466, incorporated by reference herein in their entireties).

Further, the vector may be provided to a cell in the form of a viral vector. Viral vector technology is well known in the art and is described, for example, in Sambrook et al. (4th Edition, Molecular Cloning: A Laboratory Manual, Cold Spring Harbor Laboratory, New York, 2012), and in other virology and molecular biology manuals. Viruses, which are useful as vectors include, but are not limited to, retroviruses, adenoviruses, adeno-associated viruses, herpes viruses, Sindbis virus, gammaretrovirus and lentiviruses. In general, a suitable vector contains an origin of replication functional in at least one organism, a promoter sequence, convenient restriction endonuclease sites, and one or more selectable markers (e.g., WO 01/96584; WO 01/29058; and U.S. Pat. No. 6,326,193).

In some embodiments, guide RNA(s) and Cas9 can be delivered to a cell as a ribonucleoprotein (RNP) complex (e.g., a Cas9/RNA-protein complex). RNPs are comprised of purified Cas9 protein complexed with gRNA and are well known in the art to be efficiently delivered to multiple types of cells, including but not limited to stem cells and immune cells (Addgene, Cambridge, Mass., Mirus Bio LLC, Madison, Wis.). In some embodiments, the Cas9/RNA-protein complex is delivered into a cell by electroporation.

In some embodiments, a gene edited modified cell of the present disclosure is edited using CRISPR/Cas9 to disrupt one or more endogenous genes in a modified cell (e.g., a modified T cell). In some embodiments, CRISPR/Cas9 is used to disrupt one or more of endogenous TRAC, TRBC, PDCD1, A2AR, B7-H3 (CD276), B7-H4 (VTCN1), BTLA (CD272), CD96, CTLA-4 (CD152), IDO, KIR, LAG3, TIGIT, TIM-3, and/or VISTA loci, thereby resulting in the downregulation of TRAC, TRBC, PD-1, A2AR, B7-H3 (CD276), B7-H4 (VTCN1), BTLA (CD272), CD96, CTLA-4 (CD152), IDO, KIR, LAG3, TIGIT, TIM-3, and/or VISTA. In some embodiments, CRISPR/Cas9 is used to disrupt one or more of endogenous TRAC, TRBC, PDCD1, and/or TIM-3. Suitable gRNAs for use in disrupting one or more of endogenous TRAC, TRBC, PDCD1, and/or TIM-3 is set forth in Table 1.

TABLE 1

| gRNA name | gRNA sequence | SEQ ID NO: |
|---|---|---|
| TRAC1-1 | GAGAATCAAAATCGGTGAAT | 37 |
| TRAC1-4 | TGTGCTAGACATGAGGTCTA | 38 |
| TRAC1-5 | AAAGTCAGATTTGTTGCTCC | 39 |
| TRAC1-9 | AGAGTCTCTCAGCTGGTACA | 40 |

TABLE 1-continued

| gRNA name | gRNA sequence | SEQ ID NO: |
|---|---|---|
| TRAC1-13 | AGCTGGTACACGGCAGGGTC | 41 |
| TRAC1-16 | ACAAAACTGTGCTAGACATG | 42 |
| TRAC2-1 | CTCGACCAGCTTGACATCAC | 43 |
| TRAC2-2 | AAGTTCCTGTGATGTCAAGC | 44 |
| TRAC3-1 | TTCGGAACCCAATCACTGAC | 45 |
| TRAC3-2 | TTAATCTGCTCATGACGCTG | 46 |
| TRAC3-3 | GATTAAACCCGGCCACTTTC | 47 |
| TRAC3-4 | CGTCATGAGCAGATTAAACC | 48 |
| TRAC3-5 | TAAACCCGGCCACTTTCAGG | 49 |
| TRBC11-1 | CAAACACAGCGACCTCGGGT | 50 |
| TRBC11-2 | GGCTCAAACACAGCGACCTC | 51 |
| TRBC11-3 | TCAAACACAGCGACCTCGGG | 52 |
| TRBC11-4 | TGGCTCAAACACAGCGACCT | 53 |
| TRBC12-1 | TCTCCGAGAGCCCGTAGAAC | 54 |
| TRBC12-2 | GGCTCTCGGAGAATGACGAG | 55 |
| TRBC12-3 | TGACAGCGGAAGTGGTTGCG | 56 |
| TRBC12-4 | AGTCCAGTTCTACGGGCTCT | 57 |
| TRBC12-5 | CGCTGTCAAGTCCAGTTCTA | 58 |
| TRBC12-6 | AGCTCAGCTCCACGTGGTCG | 59 |
| TRBC12-7 | ACTGGACTTGACAGCGGAAG | 60 |
| TRBC12-8 | TTGACAGCGGAAGTGGTTGC | 61 |
| TRBC12-9 | GACAGCGGAAGTGGTTGCGG | 62 |
| TRBC12-10 | TGACGAGTGGACCCAGGATA | 63 |
| TRBC12-11 | CGTAGAACTGGACTTGACAG | 64 |
| TRBC12-12 | ATGACGAGTGGACCCAGGAT | 65 |
| TRBC12-13 | CTTGACAGCGGAAGTGGTTG | 66 |
| TRBC12-14 | GCTGTCAAGTCCAGTTCTAC | 67 |
| TRBC13-1 | AGGCCTCGGCGCTGACGATC | 68 |
| TRBC13-2 | GGCCTCGGCGCTGACGATCT | 69 |
| TRBC13-3 | CACCCAGATCGTCAGCGCCG | 70 |
| TRBC13-4 | GACGATCTGGGTGACGGGTT | 71 |
| TRBC13-5 | GATCGTCAGCGCCGAGGCCT | 72 |
| TRBC13-6 | AGATCGTCAGCGCCGAGGCC | 73 |
| PD1.1-1 | TGTAGCACCGCCCAGACGAC | 74 |
| PD1.1-2 | CGTCTGGGCGGTGCTACAAC | 75 |
| PD1.1-3 | GTCTGGGCGGTGCTACAACT | 76 |
| PD1.1-4 | AGGCGCCCTGGCCAGTCGTC | 77 |
| PD1.1-5 | CACCGCCCAGACGACTGGCC | 78 |
| PD1.21-1 | ATGTGGAAGTCACGCCCGTT | 79 |
| PD1.21-2 | CATGTGGAAGTCACGCCCGT | 80 |
| PD1.21-3 | CACGAAGCTCTCCGATGTGT | 81 |
| PD1.21-4 | CGGAGAGCTTCGTGCTAAAC | 82 |
| PD1.21-5 | CCTGCTCGTGGTGACCGAAG | 83 |
| PD1.21-6 | CCCCTTCGGTCACCACGAGC | 84 |
| PD1.21-7 | AGGCGGCCAGCTTGTCCGTC | 85 |
| PD1.21-8 | GCCCTGCTCGTGGTGACCGA | 86 |
| PD1.21-9 | CCCTTCGGTCACCACGAGCA | 87 |
| PD1.21-10 | CCCTGCTCGTGGTGACCGAA | 88 |
| PD1.22-1 | GCGTGACTTCCACATGAGCG | 89 |
| PD1.22-2 | AGGTGCCGCTGTCATTGCGC | 90 |
| PD1.22-3 | ACTTCCACATGAGCGTGGTC | 91 |
| PD1.22-4 | GGTGCCGCTGTCATTGCGCC | 92 |
| PD1.3-1 | ACCCTGGTGGTTGGTGTCGT | 93 |
| PD1.3-2 | AGGGTTTGGAACTGGCCGGC | 94 |
| PD1.5-1 | ATTGTCTTTCCTAGCGGAAT | 95 |
| PD1.5-2 | TCAGTGGCTGGGCACTCCGA | 96 |
| PD1.5-3 | CATTGTCTTTCCTAGCGGAA | 97 |
| Tim3-1 | AATGTGACTCTAGCAGACAG | 98 |
| Tim3-2 | ATGAGAATACCCTAGTAAGG | 99 |
| Tim3-3 | TATGAGAATACCCTAGTAAG | 100 |
| Tim3-4 | TGGCCCAGGTAACTATGCAT | 101 |
| Tim3-5 | ATAGGCATCTACATCGGAGC | 102 |
| Tim3-6 | GCTGTGGAAATAAAGTGTTG | 103 |
| Tim3-7 | GTGGAATACAGAGCGGAGGT | 104 |
| Tim3-8 | ACAGTGGGATCTACTGCTGC | 105 |
| Tim3-9 | TCTCTCTGCCGAGTCGGTGC | 106 |
| Tim3-10 | TTATGCCTGGGATTTGGATC | 107 |
| Tim3-11 | ATCAGAATAGGCATCTACAT | 108 |
| Tim3-12 | TGAGTTACGGGACTCTAGAT | 109 |
| Tim3-13 | GCCAATGTGGATATTTGCTA | 110 |
| Tim3-14 | GTGAAGTCTCTCTGCCGAGT | 111 |
| Tim3-15 | TCAGGGACACATCTCCTTTG | 112 |
| Tim3-16 | GGGCACGAGGTTCCCTGGGG | 113 |
| Tim3-17 | AAATAAGGTGGTTGGATCTA | 114 |
| Tim3-18 | CTAAATGGGGATTTCCGCAA | 115 |
| Tim3-19 | AATGTGGCAACGTGGTGCTC | 116 |
| Tim3-20 | ATCCCCATTTAGCCAGTATC | 117 |
| Tim3-21 | TGCTGCCGGATCCAAATCCC | 118 |

TABLE 1-continued

| gRNA name | gRNA sequence | SEQ ID NO: |
|---|---|---|
| Tim3-22 | GAACCTCGTGCCCGTCTGCT | 119 |
| Tim3-23 | CAGACGGGCACGAGGTTCCC | 120 |
| Tim3-24 | AGACGGGCACGAGGTTCCCT | 121 |
| Tim3-25 | CTCTCTGCCGAGTCGGTGCA | 122 |
| Tim3-26 | TCTCTGCCGAGTCGGTGCAG | 123 |
| Tim3-27 | AGGTCACCCCTGCACCGACT | 124 |
| Tim3-28 | TAGGCATCTACATCGGAGCA | 125 |
| Tim3-29 | TAGATTGGCCAATGACTTAC | 126 |

Suitable gRNAs for use in disrupting one or more of endogenous TRAC, TRBC, and/or PDCD1 are set forth in Table 2 as Group I gRNAs and Group II gRNAs. In an exemplary embodiment, gene edited modified cells of the present disclosure are edited using any one of the Group I gRNAs targeted to TRAC, TRBC, and PD1. In an exemplary embodiment, gene modified cells of the present disclosure are edited using any one of the Group II gRNAs targeted to TRAC, TRBC, and PD1.

Table 2:

TABLE 2

| gRNA name | gRNA sequence | SEQ ID NO: |
|---|---|---|
| TRAC-Group 1 | TGTGCTAGACATGAGGTCTA | 38 |
| TRAC-Group 2 | CGTCATGAGCAGATTAAACC | 48 |
| TRBC-Group 1 | GGAGAATGACGAGTGGACCC | 131 |
| TRBC-Group 2 | ATGACGAGTGGACCCAGGAT | 65 |
| PD1-Group 1 | GGCGCCCTGGCCAGTCGTCT | 127 |
| PD1-Group 2 | GTCTGGGCGGTGCTACAACT | 76 |

Accordingly, a method of genetically editing a modified cell of the present disclosure comprises introducing into the cell one or more nucleic acids capable of downregulating gene expression of one or more endogenous genes selected from TRAC, TRBC, PDCD1, A2AR, B7-H3 (CD276), B7-H4 (VTCN1), BTLA (CD272), CD96, CTLA-4 (CD152), IDO, KIR, LAG3, TIGIT, TIM-3, and VISTA. In one embodiment, a method of genetically editing a modified cell of the present disclosure comprises introducing into the cell one or more nucleic acids capable of downregulating gene expression of one or more endogenous genes selected from TRAC, TRBC, PDCD1, and TIM-3. In one embodiment, a method for generating a modified cell of the present disclosure comprises 1) introducing into the cell a nucleic acid comprising a nucleic acid sequence encoding an exogenous TCR; and 2) introducing into the cell one or more nucleic acids capable of downregulating gene expression of one or more endogenous genes selected from TRAC, TRBC, PDCD1, A2AR, B7-H3 (CD276), B7-H4 (VTCN1), BTLA (CD272), CD96, CTLA-4 (CD152), IDO, KIR, LAG3, TIGIT, TIM-3, and VISTA. In one embodiment, a method for generating a modified cell of the present disclosure comprises 1) introducing into the cell a nucleic acid comprising a nucleic acid sequence encoding an exogenous TCR; and 2) introducing into the cell one or more nucleic acids capable of downregulating gene expression of one or more endogenous genes selected from TRAC, TRBC, PDCD1, and TIM-3. In an exemplary embodiment, a method for generating a modified T cell of the present disclosure comprises 1) introducing into the T cell a nucleic acid comprising a nucleic acid sequence encoding an exogenous TCR having affinity for NY-ESO-1 on a target cell; 2) introducing into the cell a nucleic acid capable of downregulating gene expression of TRAC (e.g., SEQ ID NOs: 37-49); 3) introducing into the cell a nucleic acid capable of downregulating gene expression of TRBC (e.g., SEQ ID NOs:50-73, or 131); and 4) introducing into the cell a nucleic acid capable of downregulating gene expression of PDCD1 (e.g., SEQ ID NOs:74-97, or 127). In an exemplary embodiment, a method for generating a modified T cell of the present disclosure comprises 1) introducing into the T cell a nucleic acid comprising a nucleic acid sequence encoding an exogenous TCR having affinity for NY-ESO-1 on a target cell; 2) introducing into the cell a nucleic acid capable of downregulating gene expression of TRAC (e.g., SEQ ID NOs:37-49); 3) introducing into the cell a nucleic acid capable of downregulating gene expression of TRBC (e.g., SEQ ID NOs:50-73, or 131); and 4) introducing into the cell a nucleic acid capable of downregulating gene expression of TIM-3 (e.g., SEQ ID NOs:98-126).

In one embodiment, a method for generating a modified cell of the present disclosure comprises 1) introducing into the cell a nucleic acid comprising a nucleic acid sequence encoding an exogenous TCR and a nucleic acid sequence encoding a switch receptor; and 2) introducing into the cell one or more nucleic acids capable of downregulating gene expression of one or more endogenous genes selected from TRAC, TRBC, PDCD1, and TIM-3. In an exemplary embodiment, a method for generating a modified T cell of the present disclosure comprises 1) introducing into the T cell a nucleic acid comprising a nucleic acid sequence encoding an exogenous TCR having affinity for NY-ESO-1 on a target cell, and a nucleic acid sequence encoding a PD1-CD28 switch receptor; 2) introducing into the cell a nucleic acid capable of downregulating gene expression of TRAC (e.g., SEQ ID NOs:37-49); and 3) introducing into the cell a nucleic acid capable of downregulating gene expression of TRBC (e.g., SEQ ID NOs:50-73, or 131). In an exemplary embodiment, a method for generating a modified T cell of the present disclosure comprises 1) introducing into the T cell a nucleic acid comprising a nucleic acid sequence encoding an exogenous TCR having affinity for NY-ESO-1 on a target cell, and a nucleic acid sequence encoding a PD1-CD28 switch receptor; 2) introducing into the cell a nucleic acid capable of downregulating gene expression of TRAC (e.g., SEQ ID NOs:37-49); 3) introducing into the cell a nucleic acid capable of downregulating gene expression of TRBC (e.g., SEQ ID NOs:50-73, or 131); and 4) introducing into the cell a nucleic acid capable of downregulating gene expression of TIM-3 (e.g., SEQ ID NOs:98-126).

In some embodiments, a gene edited modified cell of the present disclosure comprises at least one nucleotide substitution, deletion, insertion, and/or insertion/deletion in the endogenous TIM-3 coding sequence. In some embodiments, a gene edited modified cell of the present disclosure is edited by any one of the TIM-3-targeted nucleic acids described herein, e.g., SEQ ID NOs:98-126.

In some embodiments, a gene edited modified cell of the present disclosure comprises at least one nucleotide substitution, deletion, insertion, and/or insertion/deletion in the endogenous TCR alpha chain coding sequence (TRAC). In some embodiments, a gene edited modified cell of the present disclosure is edited by any one of the TRAC-targeted nucleic acids described herein, e.g., SEQ ID NOs:37-49. In some embodiments, a gene edited modified cell of the present disclosure is edited by a Group I or Group II TRAC-targeted nucleic acid, as described herein. In an exemplary embodiment, a gene edited modified cell of the present disclosure is edited by a Group I TRAC-targeted nucleic acid, and comprises at least one nucleotide substitution, deletion, insertion, and/or insertion/deletion in the endogenous TCR alpha chain coding sequence (TRAC) comprising the nucleic acid sequence:

(SEQ ID NO: 128)
AACAAATGTGTCACAAAGTAAGGATTCTGATGTGTATATCACAGACAAA
ACTGTGCTAGACATGAGGTCTATGGACTTCAAGAGCAACAGTGCTGTGG
CCT, resulting in downregulation of the expression of endogenous TCR alpha chain. For example, a gene edited modified cell of the present disclosure is edited by a Group I TRAC-targeted nucleic acid and may comprise any one of the edited endogenous TRAC coding sequences as shown in FIG. 1.

Figure 2:
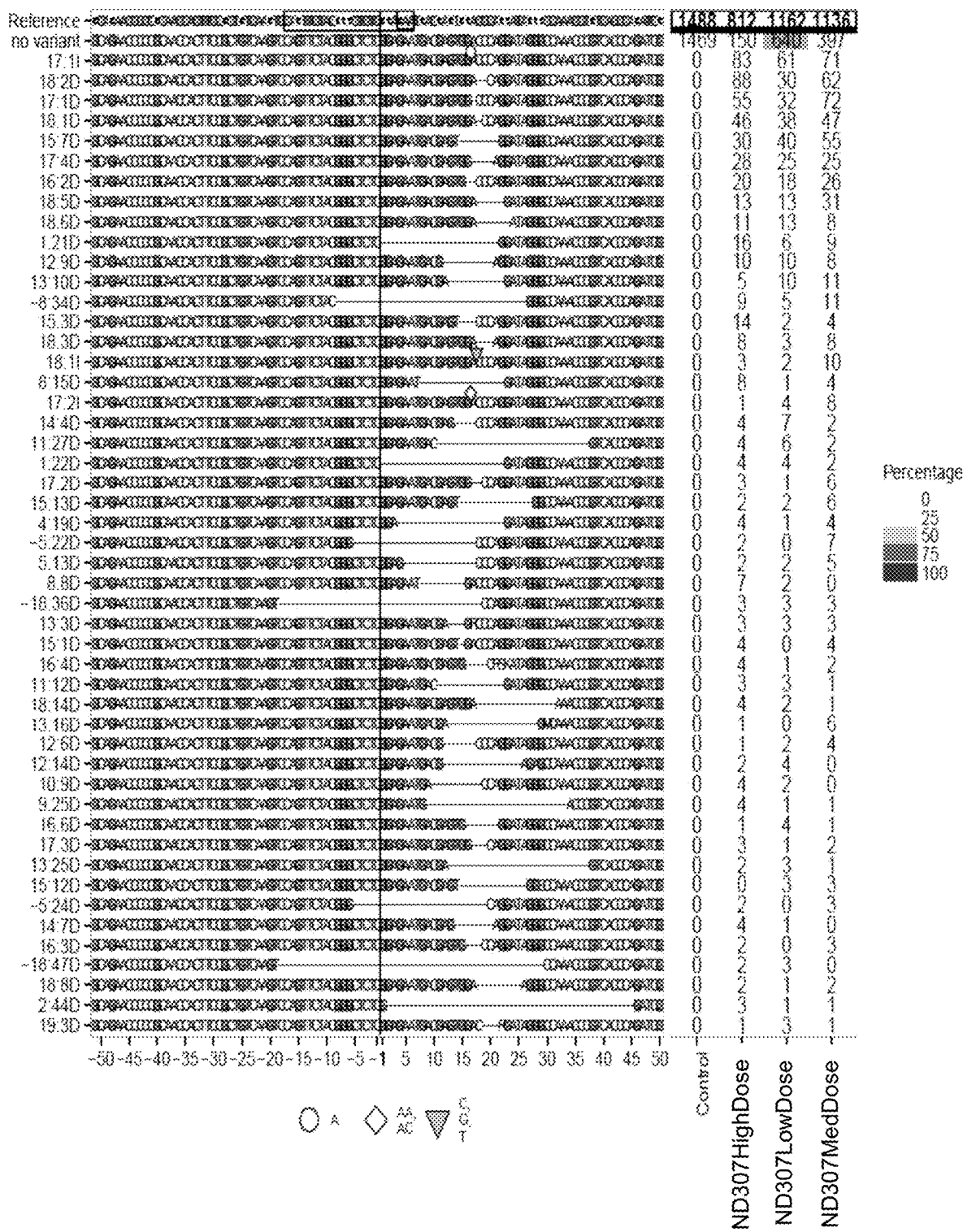
FIG. 2 depicts sequencing of a portion of the endogenous TRBC gene in cell clones targeted by the Group I TRBC gRNA (SEQ ID NOs: 191-241).

In some embodiments, a gene edited modified cell of the present disclosure comprises at least one nucleotide substitution, deletion, insertion, and/or insertion/deletion in the endogenous TCR beta chain coding sequence (TRBC). In some embodiments, a gene edited modified cell of the present disclosure is edited by any one of the TRBC-targeted nucleic acids described herein, e.g., SEQ ID NOs:50-73, or 131. In some embodiments, a gene edited modified cell of the present disclosure is edited by a Group I or Group II TRAC-targeted nucleic acid, as described herein. In an exemplary embodiment, a gene edited modified cell of the present disclosure is edited by a Group I TRBC-targeted nucleic acid, and comprises at least one nucleotide substitution, deletion, insertion, and/or insertion/deletion in the endogenous TCR beta coding sequence (TRBC) comprising the nucleic acid sequence:

(SEQ ID NO: 129)
GCAGAACCCCCGCAACCACTTCCGCTGTCAAGTCCAGTTCTACGGGCTC
TCGGAGAATGACGAGTGGACCCAGGATAGGGCCAAACCTGTCACCCAGA
TCG, resulting in downregulation of the expression of endogenous TCR beta chain. For example, a gene edited modified cell of the present disclosure is edited by a Group I TRBC-targeted nucleic acid and may comprise any one of the edited endogenous TRBC coding sequences as shown in FIG. 2.

Figure 3:
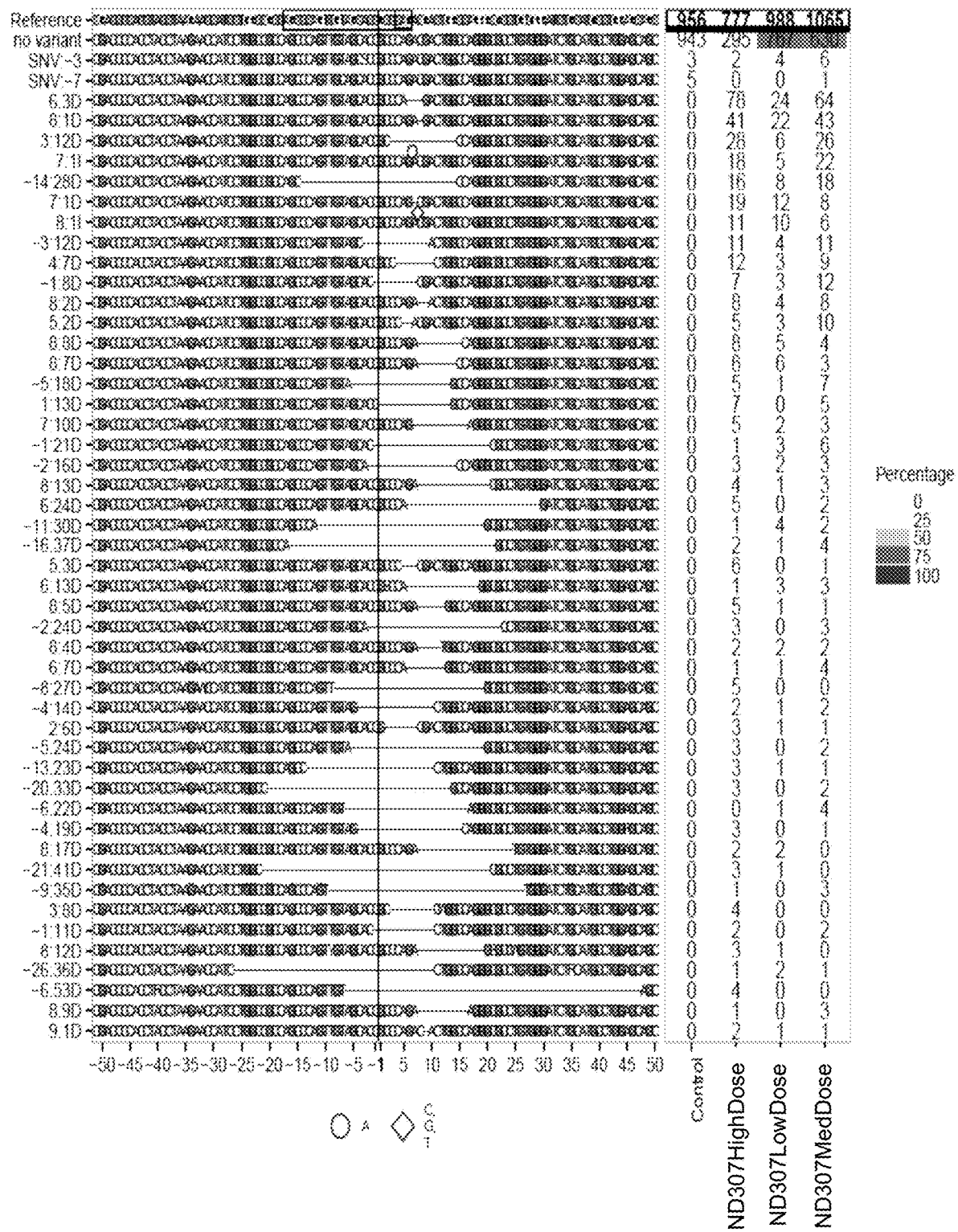
FIG. 3 depicts sequencing of a portion of the endogenous PDCD1 gene in cell clones targeted by the Group I PD1 gRNA (SEQ ID NOs: 242-292).

In some embodiments, a gene edited modified cell of the present disclosure comprises at least one nucleotide substitution, deletion, insertion, and/or insertion/deletion in the endogenous PD1 coding sequence. In some embodiments, a gene edited modified cell of the present disclosure is edited by any one of the PD1-targeted nucleic acids described herein, e.g., SEQ ID NOs:74-97, or 127. In some embodiments, a gene edited modified cell of the present disclosure is edited by a Group I or Group II PD1-targeted nucleic acid, as described herein. In an exemplary embodiment, a gene edited modified cell of the present disclosure is edited by a Group I PD1-targeted nucleic acid, and comprises at least one nucleotide substitution, deletion, insertion, and/or insertion/deletion in the PD1 coding sequence comprising the nucleic acid sequence:

(SEQ ID NO: 130)
GCTGCTCCAGGCATGCAGATCCCACAGGCGCCCTGGCCAGTCGTCTGGG
CGGTGCTACAACTGGGCTGGCGGCCAGGATGGTTCTTAGGTAGGTGGGG
TCG, resulting in downregulation of the expression of endogenous PD1. For example, a gene edited modified cell of the present disclosure is edited by a Group I PD1-targeted nucleic acid and may comprise any one of the edited endogenous PD1 coding sequences as shown in FIG. 3.

In some embodiments, a gene edited modified cell of the present disclosure comprises at least one nucleotide substitution, deletion, insertion, and/or insertion/deletion in the endogenous TCR alpha chain coding sequence (TRAC) comprising the nucleic acid sequence set forth in SEQ ID NO:128, in the endogenous TCR beta chain coding sequence (TRBC) comprising the nucleic acid sequence set forth in SEQ ID NO:129, and optionally in the endogenous PD1 coding sequence (PDCD1) comprising the nucleic acid sequence set forth in SEQ ID NO:130, resulting in downregulation of the expression of endogenous TCR alpha chain, endogenous TCR beta chain, and endogenous PD1.

In one embodiment, a modified cell of the present disclosure comprises an exogenous TCR, wherein the expression of an endogenous TCR alpha chain coding sequence, an endogenous TCR beta chain coding sequence, and an endogenous PD1 coding sequence is downregulated. In an exemplary embodiment, a modified cell of the present disclosure is a modified T cell comprising an exogenous TCR having affinity for NY-ESO-1 on a target cell, wherein the expression of an endogenous TCR alpha chain coding sequence, an endogenous TCR beta chain coding sequence, and an endogenous PD1 coding sequence are downregulated. In another exemplary embodiment, a modified cell of the present disclosure is a modified T cell comprising an exogenous TCR having affinity for NY-ESO-1 on a target cell, wherein at least one nucleotide substitution, deletion, insertion, and/or insertion/deletion is in the endogenous TCR alpha chain coding sequence comprising the nucleic acid sequence set forth in SEQ ID NO:128, wherein at least one nucleotide substitution, deletion, insertion, and/or insertion/deletion is in the endogenous TCR beta chain coding sequence comprising the nucleic acid sequence set forth in SEQ ID NO: 129, and wherein at least one nucleotide substitution, deletion, insertion, and/or insertion/deletion is in the endogenous PD1 coding sequence comprising the nucleic acid sequence set forth in SEQ ID NO:130, thereby resulting in the downregulation of the expression of endogenous TCR alpha chain, endogenous TCR beta chain, and endogenous PD1.

In one embodiment, a modified cell of the present disclosure comprises an exogenous TCR and a switch receptor (e.g., a PD1-CD28 switch receptor), wherein the expression of an endogenous TCR alpha chain coding sequence, and an endogenous TCR beta chain coding sequence are downregulated. In an exemplary embodiment, a modified cell of the present disclosure is a modified T cell comprising an exogenous TCR having affinity for NY-ESO-1 on a target cell and a switch receptor (e.g., a PD1-CD28 switch receptor), wherein the expression of an endogenous TCR alpha chain coding sequence, and an endogenous TCR beta chain coding sequence are downregulated. In another exemplary embodiment, a modified cell of the present disclosure is a modified T cell comprising an exogenous TCR having affinity for NY-ESO-1 on a target cell and a switch receptor (e.g., a PD1-CD28 switch receptor), wherein at least one nucleotide substitution, deletion, insertion, and/or insertion/deletion is in the endogenous TCR alpha chain coding sequence comprising the nucleic acid sequence set forth in SEQ ID NO:128, and wherein at least one nucleotide substitution, deletion, insertion, and/or insertion/deletion is in the endogenous TCR beta chain coding sequence comprising the nucleic acid sequence set forth in SEQ ID NO:129, thereby resulting in the downregulation of the expression of endogenous TCR alpha chain and endogenous TCR beta chain.

In some aspects, the provided compositions and methods include those in which at least or greater than about 50%, 60%, 65%, 70%, 75%, 80%, 85%, 90% or 95% of immune cells in a composition of immune cells contain the desired genetic modification. For example, about 50%, 60%, 65%, 70%, 75%, 80%, 85%, 90% or 95% of immune cells in a composition of cells into which an agent (e.g. gRNA/Cas9) for knockout or genetic disruption of endogenous gene (e.g., TRAC, TRBC, PDCD1 or TIM3) was introduced contain the genetic disruption, do not express the targeted endogenous polypeptide, or do not contain a contiguous and/or functional copy of the targeted gene. In some embodiments, the methods, compositions and cells according to the present disclosure include those in which at least or greater than about 50%, 60%, 65%, 70%. 75%, 80%, 85%, 90% or 95% of cells in a composition of cells into which an agent (e.g. gRNA/Cas9) for knockout or genetic disruption of a targeted gene was introduced do not express the targeted polypeptide, such as on the surface of the immune cells. In some embodiments, at least or greater than about 50%, 60%, 65%, 70%, 75%, 80%, 85%, 90% or 95% of cells in a composition of cells into which an agent (e.g. gRNA/Cas9) for knockout or genetic disruption of the targeted gene was introduced are knocked out in both alleles, i.e. comprise a biallelic deletion, in such percentage of cells.

In some embodiments, provided are compositions and methods in which the Cas9-mediated cleavage efficiency (% indel) in or near the targeted gene (e.g. within or about within 100 base pairs, within or about within 50 base pairs, or within or about within 25 base pairs or within or about within 10 base pairs upstream or downstream of the cut site) is at least or greater than about 50%, 60%, 65%, 70%, 75%, 80%, 85%, 90% or 95% in cells of a composition of cells into which an agent (e.g. gRNA/Cas9) for knockout or genetic disruption of a targeted gene has been introduced.

In some embodiments, the provided cells, compositions and methods results in a reduction or disruption of signals delivered via the endogenous gene in at least or greater than about 50%, 60%, 65%, 70%, 75%, 80%, 85%, 90% or 95% of cells in a composition of cells into which an agent (e.g. gRNA/Cas9) for knockout or genetic disruption of a targeted gene was introduced.

In some embodiments, compositions according to the provided disclosure that comprise cells engineered with a recombinant receptor and comprise the reduction, deletion, elimination, knockout or disruption in expression of an endogenous receptor (e.g. genetic disruption of a TRBC, TRAC or immune checkpoint gene) retain the functional property or activities of the receptor compared to the receptor expressed in engineered cells of a corresponding or reference composition comprising the receptor but do not comprise the genetic disruption of a gene or express the polypeptide when assessed under the same conditions. In some embodiments, the engineered cells of the provided compositions retain a functional property or activity compared to a corresponding or reference composition comprising engineered cells in which such are engineered with the recombinant receptor but do not comprise the genetic disruption or express the targeted polypeptide when assessed under the same conditions. In some embodiments, the cells retain cytotoxicity, proliferation, survival or cytokine secretion compared to such a corresponding or reference composition.

In some embodiments, the immune cells in the composition retain a phenotype of the immune cell or cells compared to the phenotype of cells in a corresponding or reference composition when assessed under the same conditions. In some embodiments, cells in the composition include naive cells, effector memory cells, central memory cells, stem central memory cells, effector memory cells, and long-lived effector memory cells. In some embodiments, the percentage of T cells, or T cells expressing the recombinant receptor (e.g. NY-ESO-1 TCR), and comprising the genetic disruption of a targeted gene (e.g., TRAC, TRBC, PDCD1, or TIM3) exhibit a non-activated, long-lived memory or central memory phenotype that is the same or substantially the same as a corresponding or reference population or composition of cells engineered with the recombinant receptor but not containing the genetic disruption or expressing the switch receptor. In some embodiments, such property, activity or phenotype can be measured in an in vitro assay, such as by incubation of the cells in the presence of the NY-ESO-1 antigen, a cell expressing the antigen and/or an antigen-receptor activating substance. In some embodiments, any of the assessed activities, properties or phenotypes can be assessed at various days following electroporation or other introduction of the agent, such as after or up to 3, 4, 5, 6, 7 days. In some embodiments, such activity, property or phenotype is retained by at least 80%, 85%, 90%, 95% or 100% of the cells in the composition compared to the activity of a corresponding composition containing cells engineered with the recombinant receptor but not comprising the genetic disruption of the targeted gene when assessed under the same conditions.

As used herein, reference to a "corresponding composition" or a "corresponding population of immune cells" (also called a "reference composition" or a "reference population of cells") refers to immune cells (e.g., T cells) obtained, isolated, generated, produced and/or incubated under the same or substantially the same conditions, except that the immune cells or population of immune cells were not introduced with the agent. In some aspects, except for not containing introduction of the agent, such immune cells are treated identically or substantially identically as immune cells that have been introduced with the agent, such that any one or more conditions that can influence the activity or properties of the cell, including the upregulation or expression of the inhibitory molecule, is not varied or not substantially varied between the cells other than the introduction of the agent.

Methods and techniques for assessing the expression and/or levels of T cell markers are known in the art. Antibodies and reagents for detection of such markers are well known in the art, and readily available. Assays and methods for detecting such markers include, but are not limited to, flow cytometry, including intracellular flow cytometry, ELISA, ELISPOT, cytometric bead array or other multiplex methods, Western Blot and other immunoaffinity-based methods. In some embodiments, antigen receptor (e.g. NY-ESO1 TCR)-expressing cells can be detected by flow cytometry or other immunoaffinity based method for expression of a marker unique to such cells, and then such cells can be co-stained for another T cell surface marker or markers.

In some embodiments, the cells, compositions and methods provide for the deletion, knockout, disruption, or reduction in expression of the target gene in immune cells (e.g. T cells) to be adoptively transferred (such as cells engineered to express exogenous NY-ESO-1 TCR). In some embodiments, the methods are performed ex vivo on primary cells, such as primary immune cells (e.g. T cells) from a subject. In some aspects, methods of producing or generating such genetically engineered T cells include introducing into a population of cells containing immune cells (e.g. T cells) one or more nucleic acids encoding a recombinant receptor (e.g. exogenous NY-ESO-1 TCR) and an agent or agents that is capable of disrupting, a gene that encode the endogenous receptor to be targeted. As used herein, the term "introducing" encompasses a variety of methods of introducing DNA into a cell, either in vitro or in vivo, such methods including transformation, transduction, transfection (e.g. electroporation), and infection. Vectors are useful for introducing DNA encoding molecules into cells. Possible vectors include plasmid vectors and viral vectors. Viral vectors include retroviral vectors, lentiviral vectors, or other vectors such as adenoviral vectors or adeno-associated vectors.

The population of cells containing T cells can be cells that have been obtained from a subject, such as obtained from a peripheral blood mononuclear cells (PBMC) sample, an unfractionated T cell sample, a lymphocyte sample, a white blood cell sample, an apheresis product, or a leukapheresis product. In some embodiments, T cells can be separated or selected to enrich T cells in the population using positive or negative selection and enrichment methods. In some embodiments, the population contains CD4+, CD8+ or CD4+ and CD8+ T cells. In some embodiments, the step of introducing the nucleic acid encoding a genetically engineered antigen receptor and the step of introducing the agent (e.g. Cas9/gRNA RNP) can occur simultaneously or sequentially in any order. In some embodiments, subsequent to introduction of the exogenous receptor and one or more gene editing agents (e.g. Cas9/gRNA RNP), the cells are cultured or incubated under conditions to stimulate expansion and/or proliferation of cells.

Thus, provided are cells, compositions and methods that enhance immune cell, such as T cell, function in adoptive cell therapy, including those offering improved efficacy, such as by increasing activity and potency of administered genetically engineered (e.g. anti-NY-ESO-1) cells, while maintaining persistence or exposure to the transferred cells over time. In some embodiments, the genetically engineered cells, exhibit increased expansion and/or persistence when administered in vivo to a subject, as compared to certain available methods. In some embodiments, the provided immune cells exhibit increased persistence when administered in vivo to a subject. In some embodiments, the persistence of genetically engineered immune cells, in the subject upon administration is greater as compared to that which would be achieved by alternative methods, such as those involving administration of cells genetically engineered by methods in which T cells were not introduced with an agent that reduces expression of or disrupts a gene encoding an endogenous receptor. In some embodiments, the persistence is increased at least or about at least 1.5-fold, 2-fold, 3-fold, 4-fold, 5-fold, 6-fold, 7-fold, 8-fold, 9-fold, 10-fold, 20-fold, 30-fold, 50-fold, 60-fold, 70-fold, 80-fold, 90-fold, 100-fold or more.

In some embodiments, the degree or extent of persistence of administered cells can be detected or quantified after administration to a subject. For example, in some aspects, quantitative PCR (qPCR) is used to assess the quantity of cells expressing the exogenous receptor (e.g., NY-ESO-1 TCR) in the blood or serum or organ or tissue (e.g., disease site) of the subject. In some aspects, persistence is quantified as copies of DNA or plasmid encoding the exogenous receptor per microgram of DNA, or as the number of receptor-expressing cells per microliter of the sample, e.g., of blood or serum, or per total number of peripheral blood mononuclear cells (PBMCs) or white blood cells or T cells per microliter of the sample. In some embodiments, flow cytometric assays detecting cells expressing the receptor generally using antibodies specific for the receptors also can be performed. Cell-based assays may also be used to detect the number or percentage of functional cells, such as cells capable of binding to and/or neutralizing and/or inducing responses, e.g., cytotoxic responses, against cells of the disease or condition or expressing the antigen recognized by the receptor. In any of such embodiments, the extent or level of expression of another marker associated with the exogenous receptor (e.g. exogenous NY-ESO-1 TCR) can be used to distinguish the administered cells from endogenous cells in a subject.

F. Methods of Producing Genetically Modified Immune Cells

The present disclosure provides methods for producing or generating a modified immune cell or precursor thereof (e.g., a T cell) of the invention for tumor immunotherapy, e.g., adoptive immunotherapy. The cells generally are engineered by introducing one or more genetically engineered nucleic acids encoding the exogenous receptors (e.g., a NY-ESO-1 receptor and/or a switch receptor). In some embodiments, the cells also are introduced, either simultaneously or sequentially with the nucleic acid encoding the exogenous receptor, with an agent (e.g. Cas9/gRNA RNP) that is capable of disrupting a targeted gene (e.g., a gene encoding TRAC, TRBC or an immune inhibitory molecule such as PD-1.

In some embodiments, the exogenous receptor (e.g., TCR and/or switch receptor) is introduced into a cell by an expression vector. Expression vectors comprising a nucleic acid sequence encoding a TCR and/or switch receptor of the present invention are provided herein. Suitable expression vectors include lentivirus vectors, gamma retrovirus vectors, foamy virus vectors, adeno associated virus (AAV) vectors, adenovirus vectors, engineered hybrid viruses, naked DNA, including but not limited to transposon mediated vectors, such as Sleeping Beauty, Piggybak, and Integrases such as Phi31. Some other suitable expression vectors include Herpes simplex virus (HSV) and retrovirus expression vectors.

Adenovirus expression vectors are based on adenoviruses, which have a low capacity for integration into genomic DNA but a high efficiency for transfecting host cells. Adenovirus expression vectors contain adenovirus sequences sufficient to: (a) support packaging of the expression vector and (b) to ultimately express the TCR and/or switch receptor in the host cell. In some embodiments, the adenovirus genome is a 36 kb, linear, double stranded DNA, where a foreign DNA sequence (e.g., a nucleic acid encoding an exogenous TCR and/or switch receptor) may be inserted to substitute large pieces of adenoviral DNA in order to make the expression vector of the present invention (see, e.g., Danthinne and Imperiale, Gene Therapy (2000) 7(20): 1707-1714).

Another expression vector is based on an adeno associated virus, which takes advantage of the adenovirus coupled systems. This AAV expression vector has a high frequency of integration into the host genome. It can infect nondividing cells, thus making it useful for delivery of genes into mammalian cells, for example, in tissue cultures or in vivo. The AAV vector has a broad host range for infectivity.

Details concerning the generation and use of AAV vectors are described in U.S. Pat. Nos. 5,139,941 and 4,797,368.

Retrovirus expression vectors are capable of integrating into the host genome, delivering a large amount of foreign genetic material, infecting a broad spectrum of species and cell types and being packaged in special cell lines. The retrovirus vector is constructed by inserting a nucleic acid (e.g., a nucleic acid encoding an exogenous TCR and/or switch receptor) into the viral genome at certain locations to produce a virus that is replication defective. Though the retrovirus vectors are able to infect a broad variety of cell types, integration and stable expression of the TCR and/or switch receptor requires the division of host cells.

Lentivirus vectors are derived from lentiviruses, which are complex retroviruses that, in addition to the common retroviral genes gag, pol, and env, contain other genes with regulatory or structural function (see, e.g., U.S. Pat. Nos. 6,013,516 and 5,994,136). Some examples of lentiviruses include the Human Immunodeficiency Viruses (HIV-1, HIV-2) and the Simian Immunodeficiency Virus (SIV). Lentivirus vectors have been generated by multiply attenuating the HIV virulence genes, for example, the genes env, vif, vpr, vpu and nef are deleted making the vector biologically safe. Lentivirus vectors are capable of infecting non-dividing cells and can be used for both in vivo and ex vivo gene transfer and expression, e.g., of a nucleic acid encoding a TCR and/or a switch receptor (see, e.g., U.S. Pat. No. 5,994,136).

Expression vectors including a nucleic acid of the present disclosure can be introduced into a host cell by any means known to persons skilled in the art. The expression vectors may include viral sequences for transfection, if desired. Alternatively, the expression vectors may be introduced by fusion, electroporation, biolistics, transfection, lipofection, or the like. The host cell may be grown and expanded in culture before introduction of the expression vectors, followed by the appropriate treatment for introduction and integration of the vectors. The host cells are then expanded and may be screened by virtue of a marker present in the vectors. Various markers that may be used are known in the art, and may include hprt, neomycin resistance, thymidine kinase, hygromycin resistance, etc. As used herein, the terms "cell," "cell line," and "cell culture" may be used interchangeably. In some embodiments, the host cell is an immune cell or precursor thereof, e.g., a T cell, an NK cell, or an NKT cell.

The present invention also provides genetically engineered cells which include and stably express a TCR and/or switch receptor of the present disclosure. In some embodiments, the genetically engineered cells are genetically engineered T-lymphocytes (T cells), naive T cells (TN), memory T cells (for example, central memory T cells (TCM), effector memory cells (TEM)), natural killer cells (NK cells), and macrophages capable of giving rise to therapeutically relevant progeny. In one embodiment, the genetically engineered cells are autologous cells.

Modified cells (e.g., comprising a TCR and/or a switch receptor) may be produced by stably transfecting host cells with an expression vector including a nucleic acid of the present disclosure. Additional methods to generate a modified cell of the present disclosure include, without limitation, chemical transformation methods (e.g., using calcium phosphate, dendrimers, liposomes and/or cationic polymers), non-chemical transformation methods (e.g., electroporation, optical transformation, gene electrotransfer and/or hydrodynamic delivery) and/or particle-based methods (e.g., impalefection, using a gene gun and/or magnetofection). Transfected cells expressing a TCR and/or switch receptor of the present disclosure may be expanded ex vivo.

Physical methods for introducing an expression vector into host cells include calcium phosphate precipitation, lipofection, particle bombardment, microinjection, electroporation, and the like. Methods for producing cells including vectors and/or exogenous nucleic acids are well-known in the art. See, e.g., Sambrook et al. (2001), Molecular Cloning: A Laboratory Manual, Cold Spring Harbor Laboratory, New York. Chemical methods for introducing an expression vector into a host cell include colloidal dispersion systems, such as macromolecule complexes, nanocapsules, microspheres, beads, and lipid-based systems including oil-in-water emulsions, micelles, mixed micelles, and liposomes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform may be used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). Compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, molecular biology assays well known to those of skill in the art, such as Southern and Northern blotting, RT-PCR and PCR; biochemistry assays, such as detecting the presence or absence of a particular peptide, e.g., by immunological means (ELISAs and Western blots) or by assays described herein to identify agents falling within the scope of the invention.

In one embodiment, the nucleic acids introduced into the host cell are RNA. In another embodiment, the RNA is mRNA that comprises in vitro transcribed RNA or synthetic RNA. The RNA may be produced by in vitro transcription using a polymerase chain reaction (PCR)-generated template. DNA of interest from any source can be directly converted by PCR into a template for in vitro mRNA synthesis using appropriate primers and RNA polymerase. The source of the DNA may be, for example, genomic DNA, plasmid DNA, phage DNA, cDNA, synthetic DNA sequence or any other appropriate source of DNA.

PCR may be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers may also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

In some embodiments, the RNA is electroporated into the cells, such as in vitro transcribed RNA. Any solutes suitable for cell electroporation, which can contain factors facilitating cellular permeability and viability such as sugars, peptides, lipids, proteins, antioxidants, and surfactants can be included.

In some embodiments, a nucleic acid encoding a TCR and/or a switch receptor of the present disclosure will be RNA, e.g., in vitro synthesized RNA. Methods for in vitro synthesis of RNA are known in the art; any known method can be used to synthesize RNA comprising a sequence encoding a TCR and/or a switch receptor. Methods for introducing RNA into a host cell are known in the art. See, e.g., Zhao et al. Cancer Res. (2010) 15: 9053. Introducing RNA comprising a nucleotide sequence encoding a TCR and/or a switch receptor into a host cell can be carried out in vitro or ex vivo or in vivo. For example, a host cell (e.g., an NK cell, a cytotoxic T lymphocyte, etc.) can be electroporated in vitro or ex vivo with RNA comprising a nucleotide sequence encoding a TCR and/or a switch receptor.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and a vector-free. A RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171, 264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993, 434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

In some embodiments, the immune cells (e.g. T cells) can be incubated or cultivated prior to, during and/or subsequent to introducing the nucleic acid molecule encoding the exogenous receptor (e.g., the exogenous NY-ESO-1 receptor and/or switch receptor) and the gene editing agent (e.g. CRISPR system, CRISPR/Cas9 system, Cas9/gRNA RNP). In some embodiments, the cells (e.g. T cells) can be incubated or cultivated prior to, during or subsequent to the introduction of the nucleic acid molecule encoding the exogenous receptor, such as prior to, during or subsequent to the transduction of the cells with a viral vector (e.g. lentiviral vector) encoding the exogenous receptor. In some embodiments, the cells (e.g. T cells) can be incubated or cultivated prior to, during or subsequent to the introduction of the gene editing agent (e.g. Cas9/gRNA RNP), such as prior to, during or subsequent to contacting the cells with the agent or prior to, during or subsequent to delivering the agent into the cells, e.g. via electroporation. In some embodiments, the incubation can be both in the context of introducing the nucleic acid molecule encoding the exogenous receptor and introducing the gene editing agent, e.g. Cas9/gRNA RNP. In some embodiments, the method includes activating or stimulating cells with a stimulating or activating agent (e.g. anti-CD3/anti-CD28 antibodies) prior to introducing the nucleic acid molecule encoding the exogenous receptor and the gene editing agent, e.g. Cas9/gRNA RNP.

In some embodiments, the introducing the gene editing agent, e.g. Cas9/gRNA RNP, is after introducing the nucleic acid molecule encoding the exogenous receptor. In some embodiments, prior to the introducing of the agent, the cells are rested, e.g. by removal of any stimulating or activating agent. In some embodiments, prior to introducing the agent, the stimulating or activating agent and/or cytokines are not removed.

G. Sources of Immune Cells

Prior to expansion, a source of immune cells is obtained from a subject for ex vivo manipulation. Sources of target cells for ex vivo manipulation may also include, e.g., autologous or heterologous donor blood, cord blood, or bone marrow. For example the source of immune cells may be from the subject to be treated with the modified immune cells of the invention, e.g., the subject's blood, the subject's cord blood, or the subject's bone marrow. Non-limiting examples of subjects include humans, dogs, cats, mice, rats, and transgenic species thereof. Preferably, the subject is a human.

Immune cells can be obtained from a number of sources, including blood, peripheral blood mononuclear cells, bone marrow, lymph node tissue, spleen tissue, umbilical cord, lymph, or lymphoid organs. Immune cells are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). In some aspects, the cells are human cells. With reference to the subject to be treated, the cells may be allogeneic and/or autologous. The cells typically are primary cells, such as those isolated directly from a subject and/or isolated from a subject and frozen.

In certain embodiments, the immune cell is a T cell, e.g., a CD8+ T cell (e.g., a CD8+ naive T cell, central memory T cell, or effector memory T cell), a CD4+ T cell, a natural killer T cell (NKT cells), a regulatory T cell (Treg), a stem cell memory T cell, a lymphoid progenitor cell a hematopoietic stem cell, a natural killer cell (NK cell) or a dendritic cell. In some embodiments, the cells are monocytes or granulocytes, e.g., myeloid cells, macrophages, neutrophils, dendritic cells, mast cells, eosinophils, and/or basophils. In an embodiment, the target cell is an induced pluripotent stem (iPS) cell or a cell derived from an iPS cell, e.g., an iPS cell generated from a subject, manipulated to alter (e.g., induce a mutation in) or manipulate the expression of one or more target genes, and differentiated into, e.g., a T cell, e.g., a CD8+ T cell (e.g., a CD8+ naive T cell, central memory T cell, or effector memory T cell), a CD4+ T cell, a stem cell memory T cell, a lymphoid progenitor cell or a hematopoietic stem cell.

In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. Among the sub-types and subpopulations of T cells and/or of CD4+ and/or of CD8+ T cells are naive T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. In certain embodiments, any number of T cell lines available in the art, may be used.

In some embodiments, the methods include isolating immune cells from the subject, preparing, processing, culturing, and/or engineering them. In some embodiments, preparation of the engineered cells includes one or more culture and/or preparation steps. The cells for engineering as described may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig. In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets. In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some aspects, a washing step is accomplished by tangential flow filtration (TFF) according to the manufacturer's instructions. In some embodiments, the cells are resuspended in a variety of biocompatible buffers after washing. In certain embodiments, components of a blood cell sample are removed and the cells directly resuspended in culture media. In some embodiments, the methods include density-based cell separation methods, such as the preparation of white blood cells from peripheral blood by lysing the red blood cells and centrifugation through a Percoll or Ficoll gradient.

In one embodiment, immune are obtained cells from the circulating blood of an individual by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution that lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population. The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

In some embodiments, one or more of the T cell populations is enriched for or depleted of cells that are positive for (marker+) or express high levels (marker$^{high}$) of one or more particular markers, such as surface markers, or that are negative for (marker-) or express relatively low levels (marker$^{low}$) of one or more markers. For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the CD8+ cells or the T cells, e.g., CD3+ cells) are enriched for (i.e., positively selected for) cells that are positive or expressing high surface levels of CD45RO, CCR7, CD28, CD27, CD44, CD 127, and/or CD62L and/or depleted of (e.g., negatively selected for) cells that are positive for or express high surface levels of CD45RA. In some embodiments, cells are enriched for or depleted of cells positive or expressing high surface levels of CD 122, CD95, CD25, CD27, and/or IL7-Ra (CD 127). In some examples, CD8+ T cells are enriched for cells positive for CD45RO (or negative for CD45RA) and for CD62L. For example, CD3+, CD28+ T cells can be positively selected using CD3/CD28 conjugated magnetic beads (e.g., DYNABEADS® M-450 CD3/CD28 T Cell Expander).

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations. In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such sub-populations. In some embodiments, combining TCM-enriched CD8+ T cells and CD4+ T cells further enhances efficacy.

In some embodiments, memory T cells are present in both CD62L+ and CD62L− subsets of CD8+ peripheral blood lymphocytes. PBMC can be enriched for or depleted of CD62L-CD8+ and/or CD62L+CD8+ fractions, such as using anti-CD8 and anti-CD62L antibodies. In some embodiments, a CD4+ T cell population and a CD8+ T cell sub-population, e.g., a sub-population enriched for central memory (TCM) cells. In some embodiments, the enrichment for central memory T (TCM) cells is based on positive or high surface expression of CD45RO, CD62L, CCR7, CD28, CD3, and/or CD127; in some aspects, it is based on negative selection for cells expressing or highly expressing CD45RA and/or granzyme B. In some aspects, isolation of a CD8+ population enriched for TCM cells is carried out by depletion of cells expressing CD4, CD14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

CD4+T helper cells are sorted into naive, central memory, and effector cells by identifying cell populations that have cell surface antigens. CD4+ lymphocytes can be obtained by standard methods. In some embodiments, naive CD4+T lymphocytes are CD45RO−, CD45RA+, CD62L+, CD4+ T cells. In some embodiments, central memory CD4+ cells are CD62L+ and CD45RO+. In some embodiments, effector CD4+ cells are CD62L− and CD45RO. In one example, to enrich for CD4+ cells by negative selection, a monoclonal antibody cocktail typically includes antibodies to CD14, CD20, CDI Ib, CD16, HLA-DR, and CD8. In some embodiments, the antibody or binding partner is bound to a solid support or matrix, such as a magnetic bead or paramagnetic bead, to allow for separation of cells for positive and/or negative selection.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In another embodiment, T cells are isolated from peripheral blood by lysing the red blood cells and depleting the monocytes, for example, by centrifugation through a PERCOLL™ gradient. Alternatively, T cells can be isolated from an umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19, and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11 b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° C. per minute and stored in the vapor phase of a liquid nitrogen storage tank. Other methods of controlled freezing may be used as well as uncontrolled freezing immediately at −20° C. or in liquid nitrogen.

In one embodiment, the population of T cells is comprised within cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

In certain embodiments, T regulatory cells (Tregs) can be isolated from a sample. The sample can include, but is not limited to, umbilical cord blood or peripheral blood. In certain embodiments, the Tregs are isolated by flow-cytometry sorting. The sample can be enriched for Tregs prior to isolation by any means known in the art. The isolated Tregs can be cryopreserved, and/or expanded prior to use. Methods for isolating Tregs are described in U.S. Pat. Nos. 7,754,482, 8,722,400, and 9,555,105, and U.S. patent application Ser. No. 13/639,927, contents of which are incorporated herein in their entirety.

H. Expansion of Immune Cells

Whether prior to or after modification of cells to express a TCR and/or a switch receptor, the cells can be activated and expanded in number using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Publication No. 20060121005. For example, the T cells of the invention may be expanded by contact with a surface having attached thereto an agent that stimulates a CD3/TCR complex associated signal and a ligand that stimulates a co-stimulatory molecule on the surface of the T cells. In particular, T cell populations may be stimulated by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, T cells can be contacted with an anti-CD3 antibody and an anti-CD28 antibody, under conditions appropriate for stimulating proliferation of the T cells. Examples of an anti-CD28 antibody include 9.3, B-T3, XR-CD28 (Diaclone, Besancon, France) and these can be used in the invention, as can other methods and reagents known in the art (see, e.g., ten Berge et al., Transplant Proc. (1998) 30(8): 3975-3977; Haanen et al., J. Exp. Med. (1999) 190(9): 1319-1328; and Garland et al., J. Immunol. Methods (1999) 227(1-2): 53-63).

Expanding T cells by the methods disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

Following culturing, the T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing nucleic acids into the T cell.

In another embodiment, the method comprises isolating T cells and expanding the T cells. In another embodiment, the invention further comprises cryopreserving the T cells prior to expansion. In yet another embodiment, the cryopreserved T cells are thawed for electroporation with the RNA encoding the TCR and/or switch receptor.

Another procedure for ex vivo expansion of cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-3 and c-kit ligand. In one embodiment, expanding the T cells comprises culturing the T cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. A cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more. In one embodiment, human T regulatory cells are expanded via anti-CD3 antibody coated KT64.86 artificial antigen presenting cells (aAPCs). Methods for expanding and activating T cells can be found in U.S. Pat. Nos. 7,754,482, 8,722,400, and 9,555, 105, contents of which are incorporated herein in their entirety.

In one embodiment, the method of expanding the T cells can further comprise isolating the expanded T cells for further applications. In another embodiment, the method of expanding can further comprise a subsequent electroporation of the expanded T cells followed by culturing. The subsequent electroporation may include introducing a nucleic acid encoding an agent, such as a transducing the expanded T cells, transfecting the expanded T cells, or electroporating the expanded T cells with a nucleic acid, into the expanded population of T cells, wherein the agent further stimulates the T cell. The agent may stimulate the T cells, such as by stimulating further expansion, effector function, or another T cell function.

I. Methods of Treatment

The modified cells (e.g., T cells) described herein may be included in a composition for immunotherapy. The composition may include a pharmaceutical composition and further include a pharmaceutically acceptable carrier. A therapeutically effective amount of the pharmaceutical composition comprising the modified T cells may be administered.

In one aspect, the invention includes a method for adoptive cell transfer therapy comprising administering to a subject in need thereof a modified T cell of the present invention. In another aspect, the invention includes a method of treating a disease or condition in a subject comprising administering to a subject in need thereof a population of modified T cells.

Also included is a method of treating a disease or condition in a subject in need thereof comprising administering to the subject a genetically edited modified cell (e.g., genetically edited modified T cell). In one embodiment, the method of treating a disease or condition in a subject in need thereof comprises administering to the subject a genetically edited modified cell comprising an exogenous TCR (e.g., a genetically modified T cell comprising an exogenous TCR having affinity for NY-ESO-1 on a target cell). In one embodiment, the method of treating a disease or condition in a subject in need thereof comprises administering to the subject a genetically editing modified cell comprising an exogenous TCR and a switch receptor (e.g., a genetically modified T cell comprising an exogenous TCR having affinity for NY-ESO-1 on a target cell and a PD1-CD28 switch receptor).

Also provided are methods of treating cancer in a subject in need thereof comprising administering to the subject a composition comprising any of the modified T cells of the present invention.

In one aspect, the invention includes a method of treating multiple myeloma in a subject in need thereof. The method comprises administering to the subject a lymphodepleting chemotherapy comprising an effective amount of cyclophosphamide and a modified T cell. The modified T cell comprises an exogenous T cell receptor (TCR) having affinity for NY-ESO-1 on a target cell. The exogenous TCR comprises a TCR alpha chain comprising the amino acid sequence set forth in SEQ ID NO:5 and a TCR beta chain comprising the amino acid sequence set forth in SEQ ID NO:12. The T cell also comprises at least one nucleotide substitution, deletion, insertion, and/or insertion/deletion in an endogenous TCR alpha chain coding sequence comprising the nucleic acid sequence set forth in SEQ ID NO:128, in an endogenous TCR beta chain coding sequence comprising the nucleic acid sequence set forth in SEQ ID NO:129, and in an endogenous PD1 coding sequence comprising the nucleic acid sequence set forth in SEQ ID NO:130. The expression of the endogenous TCR alpha chain coding sequence, the endogenous TCR beta chain coding sequence, and endogenous PD1 coding sequence are downregulated.

In another aspect, the invention includes a method of treating melanoma, synovial sarcoma, or myxoid/round cell liposarcoma in a subject in need thereof. The method comprises administering to the subject a lymphodepleting chemotherapy, which comprises an effective amount of cyclophosphamide and an effective amount of fludarabine, and a modified T cell. The modified T cell comprises an exogenous T cell receptor (TCR) having affinity for NY-ESO-1 on a target cell. The exogenous TCR comprises a TCR alpha chain comprising the amino acid sequence set forth in SEQ ID NO:5 and a TCR beta chain comprising the amino acid sequence set forth in SEQ ID NO:12. The T cell also comprises at least one nucleotide substitution, deletion, insertion, and/or insertion/deletion in an endogenous TCR alpha chain coding sequence comprising the nucleic acid sequence set forth in SEQ ID NO:128, in an endogenous TCR beta chain coding sequence comprising the nucleic acid sequence set forth in SEQ ID NO:129, and in an endogenous PD1 coding sequence comprising the nucleic acid sequence set forth in SEQ ID NO:130. The expression of the endogenous TCR alpha chain coding sequence, the endogenous TCR beta chain coding sequence, and endogenous PD1 coding sequence are downregulated.

Methods for administration of immune cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338. In some embodiments, the cell therapy, e.g., adoptive T cell therapy is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject has been treated with a therapeutic agent targeting the disease or condition, e.g. the tumor, prior to administration of the cells or composition containing the cells. In some aspects, the subject is refractory or non-responsive to the other therapeutic agent. In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

In some embodiments, the subject is responsive to the other therapeutic agent, and treatment with the therapeutic agent reduces disease burden. In some aspects, the subject is initially responsive to the therapeutic agent, but exhibits a relapse of the disease or condition over time. In some embodiments, the subject has not relapsed. In some such embodiments, the subject is determined to be at risk for relapse, such as at a high risk of relapse, and thus the cells are administered prophylactically, e.g., to reduce the likelihood of or prevent relapse. In some aspects, the subject has not received prior treatment with another therapeutic agent.

In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

The modified immune cells of the present invention can be administered to an animal, preferably a mammal, even more preferably a human, to treat a cancer. In addition, the cells of the present invention can be used for the treatment of any condition related to a cancer, especially a cell-mediated immune response against a tumor cell(s), where it is desirable to treat or alleviate the disease. The types of cancers to be treated with the modified cells or pharmaceutical compositions of the invention include, carcinoma, blastoma, and sarcoma, and certain leukemia or lymphoid malignancies, benign and malignant tumors, and malignancies e.g., sarcomas, carcinomas, and melanomas. Other exemplary cancers include but are not limited to breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like. The cancers may be non-solid tumors (such as hematological tumors) or solid tumors. Adult tumors/cancers and pediatric tumors/cancers are also included. In one embodiment, the cancer is a solid tumor or a hematological tumor. In one embodiment, the cancer is a carcinoma. In one embodiment, the cancer is a sarcoma. In one embodiment, the cancer is a leukemia. In one embodiment the cancer is a solid tumor.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma.

In certain exemplary embodiments, the modified immune cells of the invention are used to treat a myeloma, or a condition related to myeloma. Examples of myeloma or conditions related thereto include, without limitation, light chain myeloma, non-secretory myeloma, monoclonal gamopathy of undetermined significance (MGUS), plasmacytoma (e.g., solitary, multiple solitary, extramedullary plasmacytoma), amyloidosis, and multiple myeloma. In one embodiment, a method of the present disclosure is used to treat multiple myeloma. In one embodiment, a method of the present disclosure is used to treat refractory myeloma. In one embodiment, a method of the present disclosure is used to treat relapsed myeloma.

In certain exemplary embodiments, the modified immune cells of the invention are used to treat a melanoma, or a condition related to melanoma. Examples of melanoma or conditions related thereto include, without limitation, superficial spreading melanoma, nodular melanoma, lentigo maligna melanoma, acral lentiginous melanoma, amelanotic melanoma, or melanoma of the skin (e.g., cutaneous, eye, vulva, vagina, rectum melanoma). In one embodiment, a method of the present disclosure is used to treat cutaneous melanoma. In one embodiment, a method of the present disclosure is used to treat refractory melanoma. In one embodiment, a method of the present disclosure is used to treat relapsed melanoma.

In yet other exemplary embodiments, the modified immune cells of the invention are used to treat a sarcoma, or a condition related to sarcoma. Examples of sarcoma or conditions related thereto include, without limitation, angiosarcoma, chondrosarcoma, chordoma, Ewing's sarcoma, endotheliosarcoma, lymphangiosarcoma, lymphangioendotheliosarcoma, fibrosarcoma, gastrointestinal stromal tumor, leiomyosarcoma, liposarcoma, mesothelioma, malignant peripheral nerve sheath tumor, myxosarcoma, osteogenic sarcoma, osteosarcoma, pleomorphic sarcoma, rhabdomyosarcoma, synovial sarcoma, synovioma, and other soft tissue sarcomas. In one embodiment, a method of the present disclosure is used to treat synovial sarcoma. In one embodiment, a method of the present disclosure is used to treat liposarcoma such as myxoid/round cell liposarcoma, differentiated/dedifferentiated liposarcoma, and pleomorphic liposarcoma. In one embodiment, a method of the present disclosure is used to treat myxoid/round cell liposarcoma. In one embodiment, a method of the present disclosure is used to treat a refractory sarcoma. In one embodiment, a method of the present disclosure is used to treat a relapsed sarcoma.

In certain embodiments, the subject is provided a secondary treatment. Secondary treatments include but are not limited to chemotherapy, radiation, surgery, and medications.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

The cells of the invention to be administered may be autologous, with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as $CD8^+$ and $CD4^+$ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as $CD4^+$ to $CD8^+$ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or subtype, or minimum number of cells of the population or sub-type per unit of body weight. Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of $CD4^+$ to $CD8^+$ cells, and/or is based on a desired fixed or minimum dose of $CD4^+$ and/or $CD8^+$ cells.

In certain embodiments, the cells, or individual populations of sub-types of cells, are administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

In some embodiments, the dose of total cells and/or dose of individual sub-populations of cells is within a range of between at or about $1 \times 10^5$ cells/kg to about $1 \times 10^{11}$ cells/kg $10^4$ and at or about $10^{11}$ cells/kilograms (kg) body weight, such as between $10^5$ and $10^6$ cells/kg body weight, for example, at or about $1 \times 10^5$ cells/kg, $1.5 \times 10^5$ cells/kg, $2 \times 10^5$ cells/kg, or $1 \times 10^6$ cells/kg body weight. For example, in some embodiments, the cells are administered at, or within a certain range of error of, between at or about $10^4$ and at or about $10^9$ T cells/kilograms (kg) body weight, such as between $10^5$ and $10^6$ T cells/kg body weight, for example, at or about $1 \times 10^5$ T cells/kg, $1.5 \times 10^5$ T cells/kg, $2 \times 10^5$ T cells/kg, or $1 \times 10^6$ T cells/kg body weight. In other exemplary embodiments, a suitable dosage range of modified cells for use in a method of the present disclosure includes, without limitation, from about $1 \times 10^5$ cells/kg to about $1 \times 10^6$ cells/kg, from about $1 \times 10^6$ cells/kg to about $1 \times 10^7$ cells/kg, from about $1 \times 10^7$ cells/kg about $1 \times 10^8$ cells/kg, from about $1 \times 10^8$ cells/kg about $1 \times 10^9$ cells/kg, from about $1 \times 10^9$ cells/kg about $1 \times 10^{10}$ cells/kg, from about $1 \times 10^{10}$ cells/kg about $1 \times 10^{11}$ cells/kg. In an exemplary embodiment, a suitable dosage for use in a method of the present disclosure is about $1 \times 10^8$ cells/kg. In an exemplary embodiment, a suitable dosage for use in a method of the present disclosure is about $1 \times 10^7$ cells/kg. In other embodiments, a suitable dosage is from about $1 \times 10^7$ total cells to about $5 \times 10^7$ total cells. In some embodiments, a suitable dosage is from about $1 \times 10^8$ total cells to about $5 \times 10^8$ total cells. In some embodiments, a suitable dosage is from about $1.4 \times 10^7$ total cells to about $1.1 \times 10^9$ total cells. In an exemplary embodiment, a suitable dosage for use in a method of the present disclosure is about $7 \times 10^9$ total cells.

In some embodiments, the cells are administered at or within a certain range of error of between at or about $10^4$ and at or about $10^9$ CD4$^+$ and/or CD8$^+$ cells/kilograms (kg) body weight, such as between $10^5$ and $10^6$ CD4$^+$ and/or CD8$^+$ cells/kg body weight, for example, at or about $1 \times 10^5$ CD4$^+$ and/or CD8$^+$ cells/kg, $1.5 \times 10^5$ CD4$^+$ and/or CD8$^+$ cells/kg, $2 \times 10^5$ CD4$^+$ and/or CD8$^+$ cells/kg, or $1 \times 10^6$ CD4$^+$ and/or CD8$^+$ cells/kg body weight. In some embodiments, the cells are administered at or within a certain range of error of, greater than, and/or at least about $1 \times 10^6$, about $2.5 \times 10^6$, about $5 \times 10^6$, about $7.5 \times 10^6$, or about $9 \times 10^6$ CD4$^+$ cells, and/or at least about $1 \times 10^6$, about $2.5 \times 10^6$, about $5 \times 10^6$, about $7.5 \times 10^6$, or about $9 \times 10^6$ CD8+ cells, and/or at least about $1 \times 10^6$, about $2.5 \times 10^6$, about $5 \times 10^6$, about $7.5 \times 10^6$, or about $9 \times 10^6$ T cells. In some embodiments, the cells are administered at or within a certain range of error of between about $10^8$ and $10^{12}$ or between about $10^{10}$ and $10^{11}$ T cells, between about $10^9$ and $10^{12}$ or between about $10^{10}$ and $10^{11}$ CD4$^+$ cells, and/or between about $10^8$ and $10^{12}$ or between about $10^{10}$ and $10^{11}$ CD8$^+$ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios, for example, in some embodiments, the desired ratio (e.g., ratio of CD4$^+$ to CD8$^+$ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In some embodiments, a dose of modified cells is administered to a subject in need thereof, in a single dose or multiple doses. In some embodiments, a dose of modified cells is administered in multiple doses, e.g., once a week or every 7 days, once every 2 weeks or every 14 days, once every 3 weeks or every 21 days, once every 4 weeks or every 28 days. In an exemplary embodiment, a single dose of modified cells is administered to a subject in need thereof. In an exemplary embodiment, a single dose of modified cells is administered to a subject in need thereof by rapid intravenous infusion.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents includes a cytokine, such as IL-2, for example, to enhance persistence. In some embodiments, the methods comprise administration of a chemotherapeutic agent.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD 107a, IFNy, IL-2, and TNF. In some aspects the biological activity is measured by assessing clinical outcome, such as reduction in tumor burden or load.

In some exemplary embodiments, the methods of the invention employ specific dosage regimen to treat a subject in need thereof. In an exemplary embodiment, a suitable subject is an adult HLA-A*0201 positive patient with relapsed or refractory tumors expressing NY-ESO-1 antigen. In one embodiment, to identify such patients, a basket design enrolling patients with myeloma, synovial sarcoma, and myxoid/round cell liposarcoma (MRCL), and melanoma may be used. In one embodiment patients with multiple myeloma and sarcoma may be targeted for enrollment first, with the plan to expand enrollment to include melanoma patients once initial safety is established.

In some exemplary embodiments, a suitable subject is an HLA-A*0201 positive patient with tumors expressing NY-ESO-1 antigen. As described herein, the NY-ESO-1 derived peptide in complex with HLA-A*0201 is SLLMWITQC (NY-ESO$_{157-165}$; SEQ ID NO: 1). The Cancer Testis Antigen LAGE-1 is 90% homologous to NY-ESO-1, and has two transcript variants, LAGE-1S and LAGE-1L. The LAGE-1S transcript variant shares the same HLA-A*0201 epitope, SLLMWITQC (SEQ ID NO: 1), with NY-ESO-1. In some exemplary embodiments, the LAGE-1 HLA-A*0201 epitope is an equivalent target for NY-ESO-1 directed therapy. Accordingly, in some exemplary embodiments, a suitable subject for NY-ESO-1 directed therapy is an HLA-A*0201 positive patient with tumors expressing LAGE-1 antigen. See, e.g., Rapoport et al., Nature Medicine (2015) 21(8): 914-921; Rimoldi et al., J. Immunology (2000) 165 (12): 7253-7261; and Purbhoo et al., J. Immunology (2006) 176(12): 7308-7316.

In some exemplary embodiments, identification of a subject suitable for treatment comprises screening for HLA-A*0201 expression, and expression of NY-ESO-1 and/or LAGE-1. Screening methods are known in the art. For example, PCR, or RT-PCR can be performed to identify patients that are positive for expression of NY-ESO-1 and/or LAGE-1. In some cancers, e.g., multiple myeloma, both NY-ESO-1 and LAGE-1 are expressed by the cancer cells, and LAGE-1 is is commonly found to be expressed at a higher level than NY-ESO-1. In some cases, LAGE-1 expression frequency is approximately twice that of NY-ESO-1. Thus, in some exemplary embodiments, identifying a suitable subject may comprise first screening an HLA-A*0201 positive cancer patient for expression of LAGE-1, followed by further screening of the HLA-A*0201 positive, LAGE-1 positive patient for expression of NY-ESO-1.

In some embodiments, a specific dosage regimen includes administering to a subject in need thereof a modified cell of the present disclosure. In an exemplary embodiment, a specific dosage regimen includes administering to a subject in need thereof, e.g., autologous T cells transduced with a lentiviral vector to express NY-ESO-1 and electroporated with Cas9 and guide RNA to disrupt expression of endogenous receptor (e.g., TRAC, TRBC and/or PD1).

In some embodiments, a specific dosage regimen of the present disclosure includes a lymphodepletion step prior to the administration of the modified T cells. In an exemplary embodiment, the lymphodepletion step includes administration of cyclophosphamide and/or fludarabine. In an exemplary embodiment, for a subject having multiple myeloma, the subject receives lymphodepleting chemotherapy prior to the administration of the modified T cells. In an exemplary embodiment, for a subject having multiple myeloma, the subject receives lymphodepleting chemotherapy including about 1.5 g/m$^2$ of cyclophosphamide by intravenous infusion. In an exemplary embodiment, for a subject having multiple myeloma, the subject receives lymphodepleting chemotherapy including about 1.5 g/m$^2$ of cyclophosphamide by intravenous infusion about 2 days (±1 day) prior to administration of the modified T cells. In an exemplary embodiment, for a subject having a sarcoma or melanoma, the subject receives lymphodepleting chemotherapy prior to the administration of the modified T cells. In an exemplary embodiment, for a subject having a sarcoma or melanoma, the subject receives lymphodepleting chemotherapy including about 300 mg/m$^2$ of cyclophosphamide and 30 mg/m$^2$ fludarabine by intravenous infusion. In an exemplary embodiment, for a subject having a sarcoma or melanoma, the subject receives lymphodepleting chemotherapy including about 300 mg/m$^2$ of cyclophosphamide and 30 mg/m$^2$ fludarabine by intravenous infusion at 4 days, at 3 days, and at 2 days prior to administration of of the modified T cells.

In some embodiments, the methods of the invention involve selecting and treating a subject having failed at least one prior course of standard of cancer cancer therapy. For example, a suitable subject may have had a confirmed diagnosis of relapsed refractory multiple myeloma, melanoma, synovial sarcoma, or myxoid/round cell liposarcoma (MRCL).

In an exemplary embodiment, a suitable subject is a subject having had a confirmed prior diagnosis of active myeloma as defined by IMWG criteria. In one embodiment, a suitable subject has relapsed or refractory disease after either one of the following: 1) at least 3 prior regimens, which must have contained an alkylating agent, proteasome inhibitor, and immunomodulatory agent (IMiD); or 2) at least 2 prior regimens if "double-refractory" to a proteasome inhibitor and IMiD, defined as progression on or within 60 days of treatment with these agents. In some embodiments, induction therapy, stem cell transplant, and maintenance therapy, if given sequentially without intervening progression, should be considered as 1 "regimen." In some embodiments, a suitable subject is at least 90 days since autologous stem cell transplant, if performed. In some embodiments, a suitable subject may experience toxicities from prior therapies, with the exception of alopecia or peripheral neuropathy attributable to bortezomib. In such cases, toxicities from prior therapies must have recovered to grade 2 according to the CTC 4.0 criteria or to the subject's prior baseline. In one embodiment, a suitable subject has measurable disease per IMWG criteria on study entry, which must include at least 1 of the following: 1) serum M-spike ≥0.5 g/dL (patients with IgA myeloma in whom serum protein electrophoresis may be deemed unreliable, due to co-migration of normal serum proteins with the paraprotein in the beta region, may be considered eligible as long as total serum IgA level is elevated above normal range); 2) 24 hr urine M-spike ≥200 mg; 3) involved serum free light chain (FLC) ≥50 mg/L with abnormal ratio; 4) measurable plasmacytoma on exam or imaging; 5) bone marrow plasma cells ≥20%.

In an exemplary embodiment, a suitable subject is a subject having had a confirmed prior diagnosis of melanoma, progressed after at least 2 therapy lines, and/or has had measurable disease per RECIST 1.1 in order to allow assessment of an anti-tumor response. In an exemplary embodiment, a suitable subject is a subject having had a confirmed prior diagnosis of synovial sarcoma or MRCL, proven metastatic disease or surgically inoperable local recurrence that have failed first line treatment, and/or has measurable disease per RECIST 1.1 in order to allow assessment of an anti-tumor response.

In some embodiments, a suitable subject is a subject that has an ECOG performance status of 0-2.

In an exemplary embodiment, a suitable subject is a subject having documented NY-ESO-1 expression on tumor tissue. In an exemplary embodiment, a suitable subject is a subject that is HLA-A*201 positive.

In some embodiments, a suitable subject is a subject that has adequate vital organ function as defined by: 1) serum creatinine ≤2.5 or estimated creatinine clearance ≥30 ml/min and not dialysis-dependent; 2) absolute neutrophil count ≥1000/µl and platelet count ≥50,000/µl (≥30,000/µl bone marrow plasma cells are ≥50% of cellularity for MM patients); 3) SGOT ≤3×the upper limit of normal and total bilirubin ≤2.0 mg/dl (except for patients in whom hyperbilirubinemia is attributed to Gilbert's syndrome); and/or 4) left ventricular ejection fraction (LVEF) ≥45%, wherein the LVEF assessment is performed within 8 weeks of enrollment.

J. Pharmaceutical Compositions and Formulations

Also provided are populations of immune cells of the invention, compositions containing such cells and/or enriched for such cells, such as in which cells expressing the recombinant receptor make up at least 50%, 60%, 70%, 80%, 90%, 91%, 92%, 93%, 94%, 95%, 96%, 97%, 98%, 99%, or more of the total cells in the composition or cells of a certain type such as T cells or CD8+ or CD4+ cells. Among the compositions are pharmaceutical compositions and formulations for administration, such as for adoptive cell therapy. Also provided are therapeutic methods for administering the cells and compositions to subjects, e.g., patients.

Also provided are compositions including the cells for administration, including pharmaceutical compositions and formulations, such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection. Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXAMPLES

Example 1: Manufacture of NY-ESO-1 TCR Autologous T Cells with Disrupted Expression of Endogenous TRAC, TRBC, and PDCD1 (NYCE T Cells)

The disruption conditions for the triple knock-out system in which TRAC, TRBC and PDCD1 genes were targeted using Cas9 RNA and guide RNA (gRNA) specific for these genes were tested in vitro. PBMCs from two normal donors were isolated from whole blood by Ficoll extraction, and T cells were isolated from PBMCs by negative selection using the Pan T Cell Isolation Kit II (Miltenyi Biotec). Isolated T cells were stimulated overnight with Dynabeads Human T-Expander CD3/CD28 beads at a 3:1 bead:cell ratio. T cells were then transduced with lentivirus vector (LV) encoding NY-ESO-1 TCR at a virus concentration adjusted to an MOI of 1 and incubated overnight. On Day 3 after LV transduction, CD3/CD28 beads were removed and the pre-activated T cells were electroporated with Cas9 RNA followed by electroporation with three different concentrations of gRNA (H, M, and L) specific for the TCRα, TCRβ, and PD1 on Day 4. T cell expansion (FIG. 4), efficacy of gene disruption (FIGS. 5-8), cell functionality (FIGS. 9-11) and long term expansion (FIGS. 12 and 13) were tested.

Following LV transduction and Cas9 mRNA and gRNA electroporation, cells were diluted with fresh media every other day during expansion to maintain optimal growth. Total cell numbers were measured at multiple time points and used to determine the fold-expansion of T cells. Data graphed in FIG. 4 indicate that cells from both donors showed a dose-dependent decrease in T cell expansion as a function of increasing concentrations of gRNAs.

Figure 4:
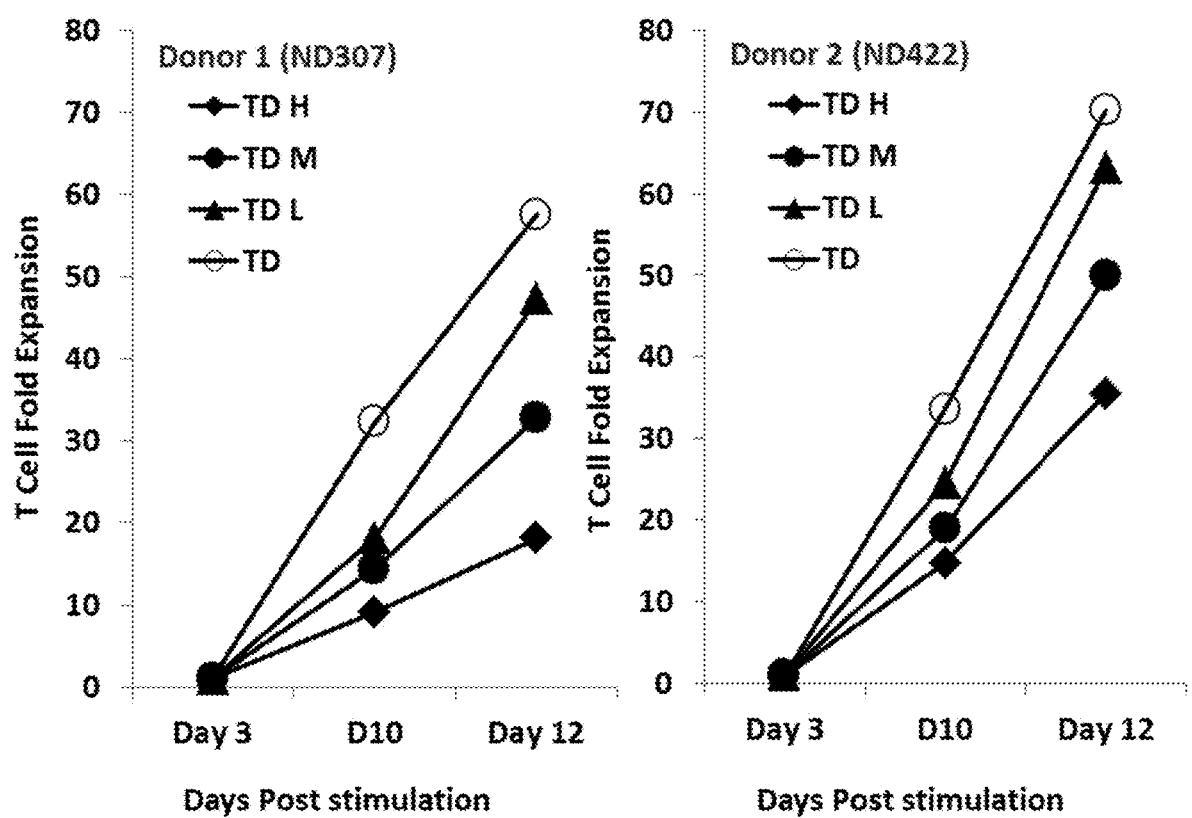
FIG. 4 depicts graphs demonstrating the expansion of NY-ESO-1 TCR transduced T cells with different concentrations of Cas9 RNA plus gRNAs for TCRα, β, and PD1.

Referring to FIG. 4, T cells were isolated from normal, healthy donors (Donor 1-ND307 and Donor2-ND422) and transduced with (solid shapes) or without (open circles) NY-ESO-1 LV at MOI=1. On Day 3, cells were electroporated with Cas9 RNA and on Day 4 cells were electroporated with gRNA at 3 different doses: L (Low, solid triangles), M (Medium/Standard, solid circle) and H (High, solid diamond). Cell electroporation was performed at a concentration range of $1$-$3 \times 10^8$/mL. Viable cells were counted on Day 3, 10, and 12 (x-axis) of culture and T cell fold expansion was calculated (y-axis).

To determine the efficiency of Cas9 gene editing of $TCR^{endo}$, the T cells were evaluated by flow cytometry for cell surface expression of NY-ESO-1 TCR and endogenous TCR (FIGS. 5 and 6) on culture day 11. Cells were stained with mAb specific to the Vβ8 (binding to NY-ESO-1 TCR) and CD3 (FIG. 5) or with a fluorescently labeled HLA-A2 dextramer folded around the NY-ESO-1 epitope (FIG. 6).

Analysis was done by first gating on cells with a lymphocyte scatter profile and then measuring expression of CD3 and Vβ8. The results showed, for both donors, a high level of NY-ESO-1-specific TCR expression was maintained across a range of gRNA concentrations, with NY-ESO-1 TCR expression ranging between 45-49% for one donor and 60-62% for the other donor T cells. Endogenous TCR gene editing was observed in 46% to 90% of untransduced T cells and was dependent on the gRNA concentration. Extrapolating from the data, at the medium dose of gRNA, 70% of the NY-ESO-1 TCR expressing cells would lack endogenous TCR (FIG. 5).

Referring to FIG. 5, T cells from Day 11 expansion cultures from two donors (ND307 and ND422) of NY-ESO-1 transduced cells, electroporated with three different concentrations (High, Medium, Low dose) of gRNAs for TCRα, TCRβ, and PD1 were analyzed by flow cytometry for CD3 and Vβ8 surface expression. Analysis was done by first gating on a lymphocyte scatter profile followed by analysis of CD3 (surrogate for TCR expression; x-axis) and Vβ8 (binds to NY-ESO-1 TCR; y-axis). Both donors exhibited low level background staining with the anti-Vβ8 mAb; hence, this mAb reliably identified NY-ESO-1 TCR-expressing transgenic T cells.

Figure 6:
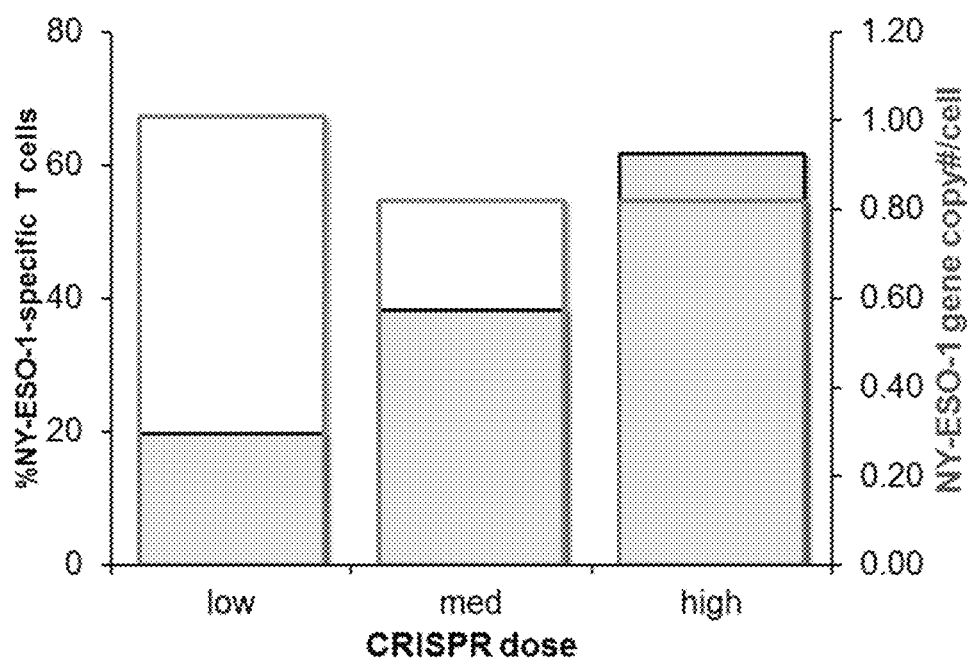
FIG. 6 depicts a graph demonstrating that surface expression of the NY-ESO-1 specific TCR is enhanced by increasing doses of endogenous TCR-targeting gRNAs.

The frequency of NY-ESO-1-specific T cells was confirmed by flow cytometry using a fluorescently labeled HLA-A2/NY-ESO-1 dextramer (FIG. 6, solid bars). Surface expression of the transduced TCR chains was dramatically enhanced with increasing concentrations of gRNAs indicating that antigen recognition by this TCR was enhanced when the endogenous TCR chains were knocked out, as previously reported for other transgenic TCRs. At the high concentrations of gRNA the % of T cells expressing NY-ESO-1 TCR was equivalent to that seen in FIG. 5 when NY-ESO-1 expression was assessed by Vβ8 mAb. Furthermore, transduction efficiency was assessed using a validated WPRE (for the Woodchuck Hepatitis Virus Posttranscriptional Regulatory Element) qPCR, (part of the lentiviral NY-ESO-1 TCR vector). This analysis revealed one or less copies of integration of the NY-ESO-1 viral vector per cell (FIG. 6, bars outlined in grey and right side y-axis).

Referring to FIG. 6, T cells from Day 11 expansion cultures from donor ND422 of NY-ESO-1 transduced cells, electroporated with three different concentrations (high, medium, low) of gRNAs for TCRα, TCRβ, and PD1 were analyzed by flow cytometry using fluorescently conjugated HLA-A*0201 dextramers folded around the NY-ESO-1 peptide SLLMWITQC (grey filled bars; SEQ ID NO:1) and also by qPCR specific for the WPRE (grey outlined bars). Shown is the expression of this TCR in total T cells.

Figure 7:
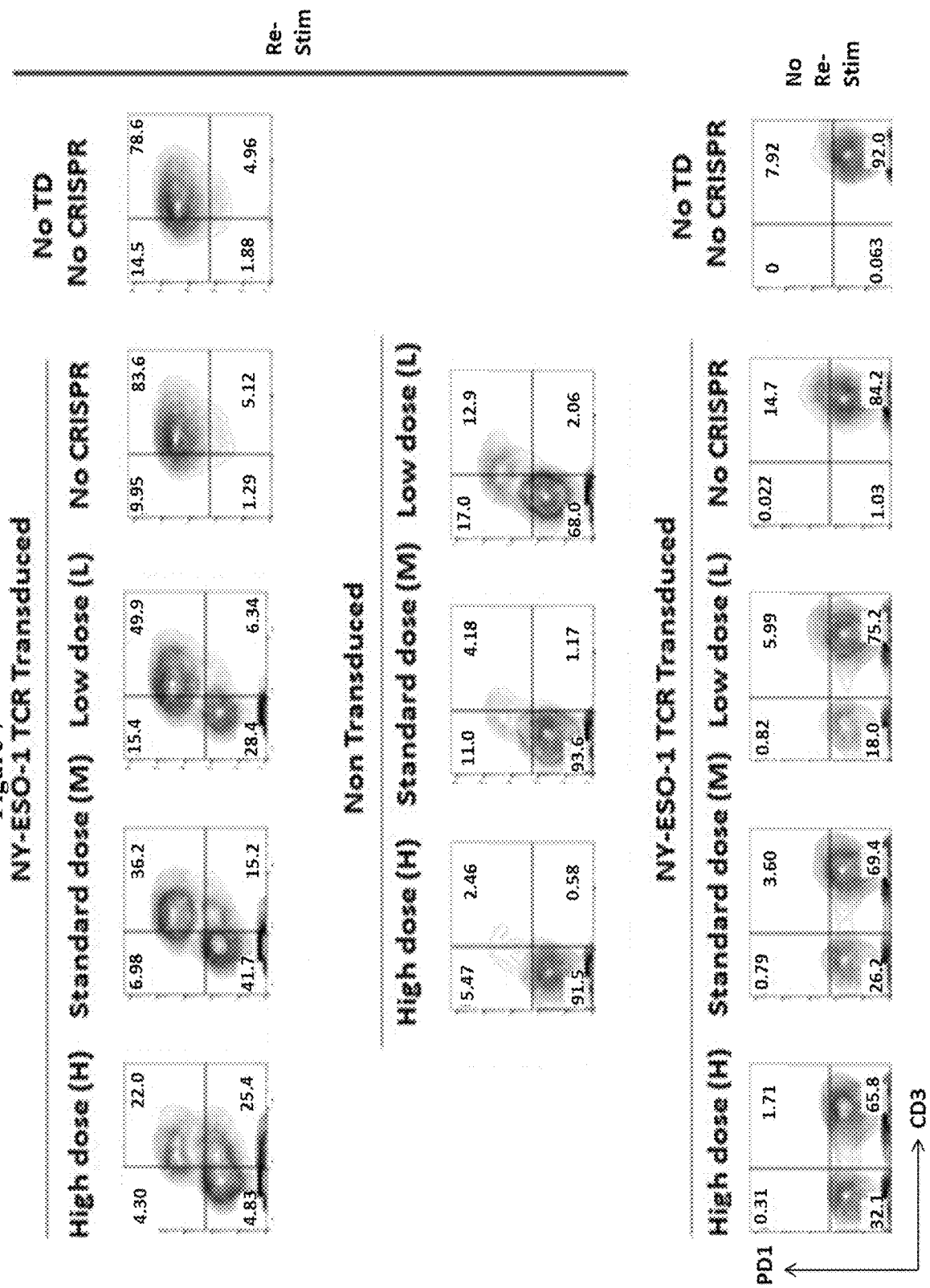
FIG. 7 depicts flow cytometry analysis demonstrating the efficiency of PD1 gene editing.

To determine the efficiency of PD1 gene editing, the same Day 11 cultures were restimulated with CD3/CD28 beads for 3 days to induce PD1 expression (FIG. 7). Without restimulation, NY-ESO-1 transduced but not edited cells had a background PD1 expression of 14.7%. With stimulation, in the absence of gene editing for PD1 in either LV transduced (No CRISPR) or non-LV transduced (No TD No CRISPR), greater than 95% of CD3 positive cells were induced to express PD1. The percentage of LV transfected T cells electroporated with gRNA and lacking PD1 expression dropped to 35%, 57%, and 74% for L, M, and H gRNA concentrations respectively. Thus, at the medium/standard dose of gRNA, 57% of the NY-ESO-1$^+$ T cells were deficient in the ability to express PD1 (PD1$^-$).

Referring to FIG. 7, T cells from Day 11 expansion culture of NY-ESO-1 transduced cells electroporated with three different concentrations (High, Standard, Low) of gRNAs for TCRα, TCRβ, and PD1 were analyzed by flow cytometry. T cells that were not transduced with NY-ESO-1 lentiviral vector (Non Transduced) but electroporated with the 3 concentrations of gRNAs were also prepared. Control cells that were not electroporated were prepared for each of the transduced and non-transduced cell populations. These cell populations were restimulated with CD3/CD28 beads (Re-stim) to induce PD1 expression or were left unstimulated (No Re-stim). Three days later, all cell populations were surface stained with mAb specific for CD3 and PD1. Analysis was done by first gating on a lymphocyte scatter profile and then analyzing for CD3 expression (surrogate for TCR expression; x-axis) and PD1 (y-axis).

In addition to flow cytometry analysis for protein expression, the frequency of targeted gene disruption was measured by a mismatch-selective surveyor nuclease assay on DNA amplified from the cells on day 12 of culture (FIG. 8). For each donor, a dose response was observed correlating the % of gene editing with the concentration of gRNA used. This was observed for all three genes: TCRα, TCRβ, and PD1 though the extent of gene editing varied by donor. This assay demonstrated efficient disruption for all the genes in donor 307. For donor 422 T cells, the disruption of TCRα was not optimal, however, the other genes were efficiently disrupted.

Referring to FIG. 8, primer sets for each gene (TCRα, TCRβ, and PD1) were used in regular, singular PCR reactions. PCR products were treated with endonuclease and run on polyacrylamide gels (left panel). The intensity of the intact and digested bands were measured and % gene knockout was calculated for both donors (right panel:dark grey bars=ND307; light grey bars=ND422). % gene knockout was calculated for four concentrations of gRNA (high, medium, low, none) for cells prepared as described in FIG. 4 above.

Functionality of NY-ESO-1 transduced T cells with TCR$^{endo}$ and PD1 gene edited was measured by the cells ability to degranulate (FIG. 9), release IL-2 and IFNγ (FIG. 10), and lyse (FIG. 11) upon co-culture with tumor cell lines expressing NY-ESO-1.

To determine the ability of NY-ESO-1 transduced cells to degranulate in response to Nalm6-HLA-A2-expressing NY-ESO-1 transfected tumor cell line (Nalm6-ESO), T cells from the above expansion cultures, from two donors, were assessed by flow cytometry for the appearance of expression of CD107a on the surface of the T cells. For both donors, only in the NY-ESO-1 transduced T cells was degranulation observed via surface expression of CD107a. The percentage of T cell degranulation was increased in the TCR$^{endo}$ and PD1 gene edited cells and was dose dependent (FIG. 9).

Referring to FIG. 9, T cells prepared as described in FIG. 4 were co-incubated with a Nalm6-HLA-A2-expressing NY-ESO-1 transfected tumor cell line (Nalm6-ESO) or a control cell line without NY-ESO-1 expression (Nalm6). Cells were surface stained with mAbs specific for CD8 and CD107a and analyzed by flow cytometry.

Next, the ability of NY-ESO-1 transduced T cells with TCR$^{endo}$ and PD1 gene edited to release IL-2 and IFNγ in the presence or absence of NY-ESO-1 presenting tumors was assessed. NY-ESO-1 transduced T cells released IFNγ and IL-2 in response to Nalm6-HLA-A2-expressing NY-ESO-1 transfected tumor cell line (Nalm6-ESO) and to a NY-ESO-1 expressing melanoma tumor cell line, but not when incubated with non-NY-ESO-1 expressing tumor (Nalm6). In addition, there was a clear dose dependence of cytokine production in response to the amount of gene editing. Cytokine production was superior for TCR$^{endo}$ and PD1 gene edited cells compared to NY-ESO-1 transduction alone for both donors which indicates a functional advantage to gene editing of TCR$^{endo}$ and PD1 (FIG. 10).

Figure 10:
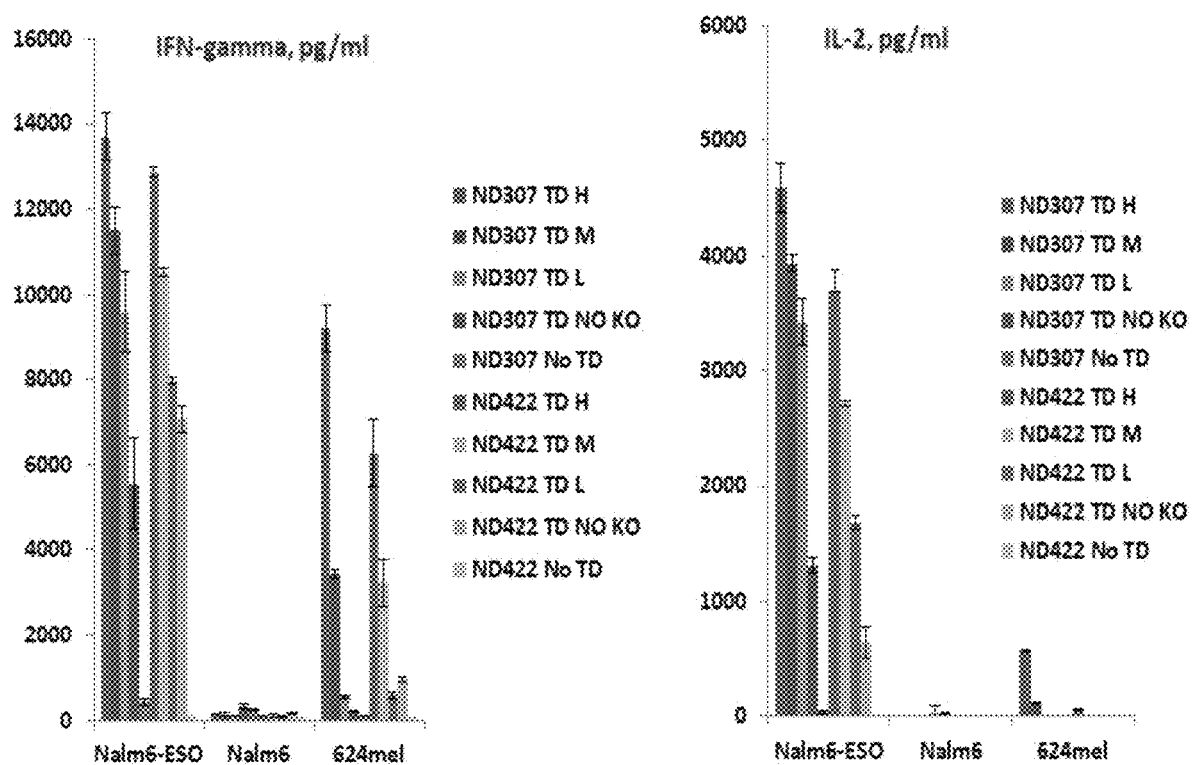
FIG. 10 depicts graphs demonstrating the ability of NY-ESO-1 transduced T cell with $TCR^{endo}$ and PD1 gene editing to release IFNγ or IL-2 in response to tumor.

Referring to FIG. 10, NY-ESO-1 transduced T cells (TD) or non-transduced (No TD) cells prepared as described in FIG. 4 were co-incubated overnight with a Nalm6-HLA-A2-expressing NY-ESO-1 transfected tumor cell line (Nalm6-ESO) or a control cell line without NY-ESO-1 expression (Nalm6) or with a melanoma cell line expressing NY-ESO-1 (624mel). Culture supernatant was collected and IFNγ or IL-2 measured by ELISA. The ability of NY-ESO-1 transduced T cells in the absence of gene editing (TD NO KO) to release cytokine in response to tumor was also evaluated. T cells from expansion cultures from two donors (307 and 422) were tested.

To determine the ability of NY-ESO-1 transduced or non-transduced T cells with or without gene editing of TCR$^{endo}$ and PD1 to kill a HLA-A2 NY-ESO-1 tumor cell line, a luminescence assay of tumor specific lysis was performed. Nalm6-ESO-CBG cells were resuspended at 1×10$^5$ cells/mL and incubated with different ratios of T cells (e.g. 30:1, 15:1, etc.) overnight at 37° C. 100 μl of the mixture was transferred to a 96 well white luminometer plate, 100 ul of substrate was added and the luminescence was immediately determined. Gene edited T cells transduced with NY-ESO-1 showed superior ability to lyse the tumor cell target across all E:T ratios above either non-transduced cells (No TD) or NY-ESO-1 transduced cells without gene editing (TD NO KO) (FIG. 11).

Figure 11:
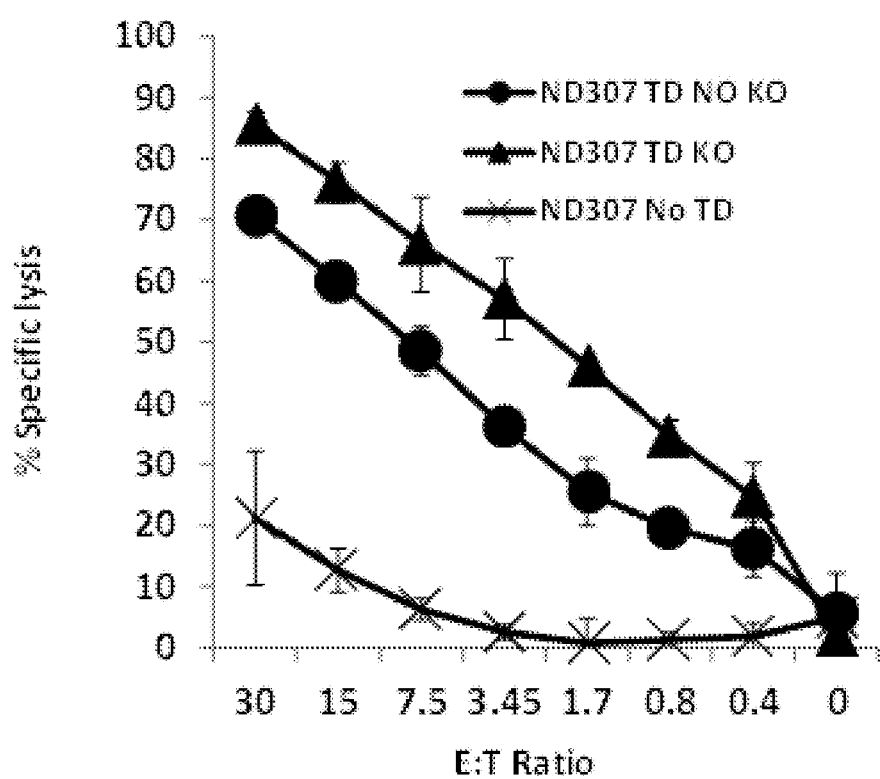
FIG. 11 depicts a graph demonstrating the ability of NY-ESO-1 transduced T cell with $TCR^{endo}$ and PD1 gene editing to lyse NY-ESO-1 expressing tumor.

Referring to FIG. 11, NY-ESO-1 transduced T cells (TD) or non-transduced (No TD) with (solid triangles) or without (solid circles or X) gene editing for TCR$^{endo}$ and PD1 were co-cultured with Nalm6-HLA-A2-expressing NY-ESO-1 transfected tumor cell line (Naml6-ESO). Tumor cell lysis was determined by luminescence assay and expressed as tumor specific lysis (y-axis) as a function of the effector to target ratio (E:T; x-axis). T cells from Day 12 cultures from donor 307 were tested. Results are reported as percent killing based on luciferase activity in wells with tumor, but no T cells. (% killing=100−((RLU from well with effector and target cell coculture)/(RLU from well with target cells)× 100)).

Without being bound by any theory, these data indicate that NY-ESO-1 TCR transduced and triple edited cells exert superior functional activity compared to the NY-ESO-1 TCR transduced cells only and that the disruption of the targeted genes does not negatively affect their functional potential.

Figure 12:
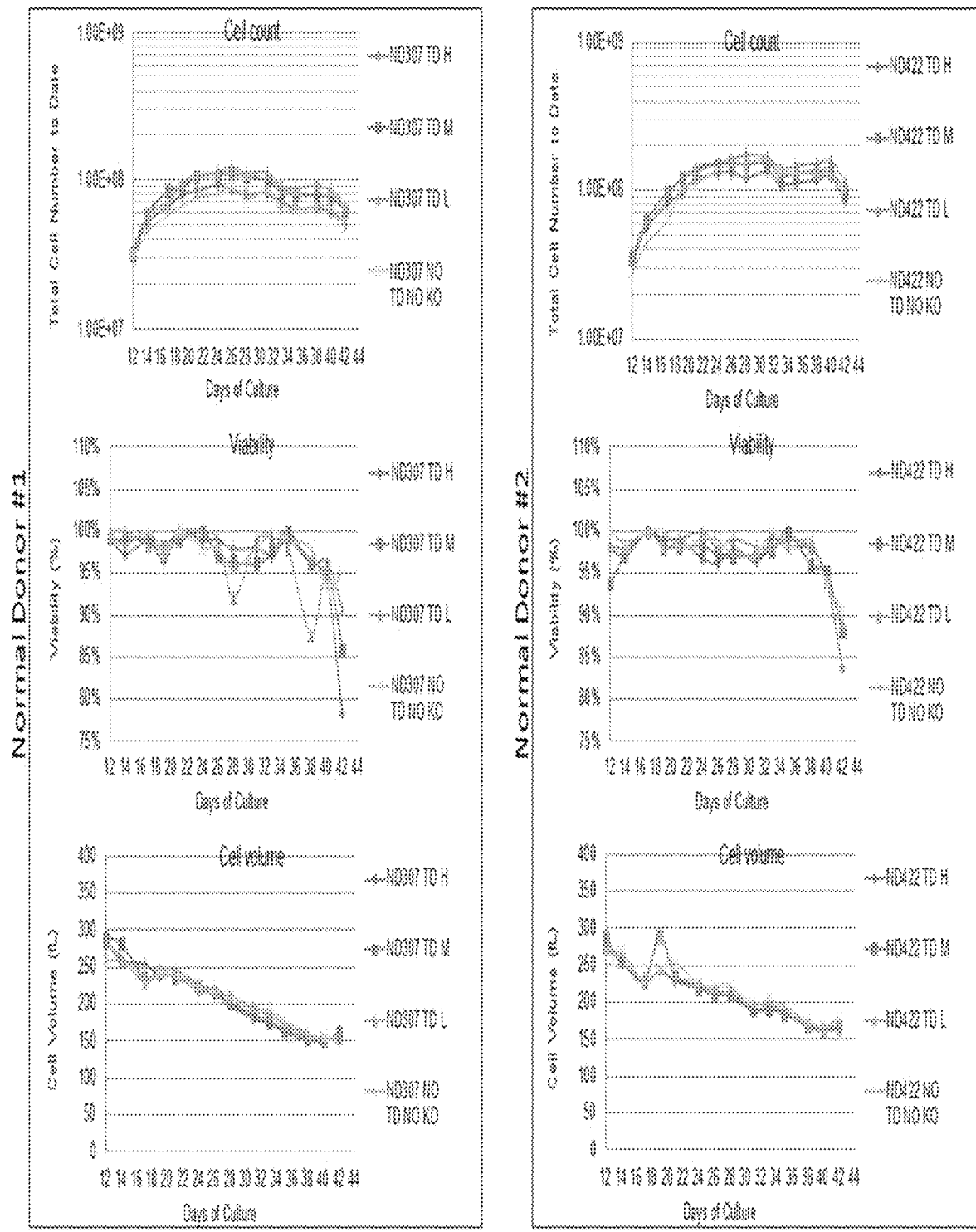
FIG. 12 depicts graphs demonstrating the long term culture of NY-ESO-1 transduced T cells with $TCR^{endo}$ and PD1 gene editing.

To determine if TCR$^{endo}$ and PD1 gene editing introduces off-target mutations that influence cell proliferation, Day 12 T cells were placed in culture without additional stimulation. After initial expansion, all conditions plateaued or contracted by day 42. Viability either remained stable or decreased. Cell size steadily decreased in all conditions (FIG. 12). The populations of NY-ESO-1 transduced T cells with TCR$^{endo}$ and PD1 gene editing are expected to continue to contract similarly to non-modified cells. These data demonstrate the absence of TCR$^{endo}$ and PD1 gene editing-associated transforming mutations.

Referring to FIG. 12, NY-ESO-1 transduced T cells with TCR$^{endo}$ and PD1 gene editing from Day 12 cultures were placed in long term culture. Initial long-term cultures were seeded with $2\times10^7$ cells per condition in RPMI10 medium with IL2 (100 IU/ml) at $1\times10^6$ cells/mL. Cell number, cell viability and cell size were measured throughout the culture on the days indicated. Cells were fed every other day with RPMI10 medium supplemented with IL2.

Surface expression of the NY-ESO-1 TCR was again assessed at day 38 using the aforementioned HLA-A2/NYESO1 dextramer staining. The data (FIG. 13) demonstrated that high level surface expression of this TCR was maintained throughout culture, and, again, both CD4+ and CD8+ T cells showed similarly high frequencies of NYESO1-specific TCR expression with the same titration effect as shown in FIG. 6.

Figure 13:
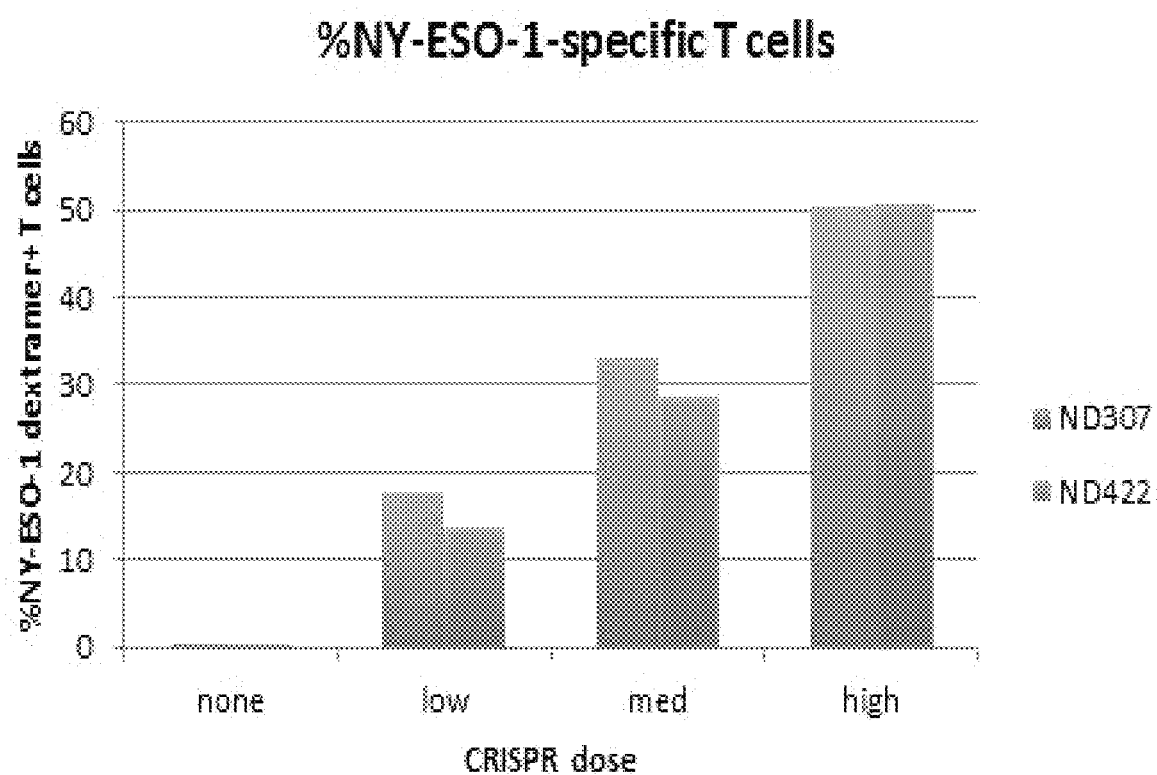
FIG. 13 depicts a graph showing NY-ESO-1 TCR expression at the end of long term cultures.

Referring to FIG. 13, cell populations at the end of long term cultures (day 38 in FIG. 9) were analyzed by flow cytometry for NY-ESO-1 TCR expression using the method described in FIG. 6. The graph represents % NY-ESO-1 expressing T cells (y-axis) as a function of gRNA concentration (none, low, medium, high; x-axis) for both donor T cells.

Without being bound by any theory, these data demonstrated that the triple CRISPR editing system combined with LV transduction of T cells was successful in redirecting T cells and provided a gain in function potential superior to that of LV transduced T cells only. The NY-ESO-1 TCR expressing T cells edited at the endogenous TCR and PD-1 loci were able to expand, secrete cytokine, degranulate and lyse antigen specific targets in vitro supporting their proposed clinical use.

Prophetic Example 1: Manufacture of Clinical NY-ESO-1 TCR Autologous T Cells with Disrupted Expression of Endogenous TRAC, TRBC, and PDCD1 (NYCE T Cells)

NYCE T cells are autologous NY-ESO-1-redirected and CRISPR TCR$^{endo}$ and PD1 edited T cells. Autologous T cells will be engineered using a lentiviral vector to express a TCR with specificity for NY-ESO-1 peptide (SLLMWITQC; SEQ ID NO:1) in complex with HLA-A*0201 in which the endogenous TCR (α and β chains) and PD1 have been disrupted. Without being bound to any theory, this is expected to enhance the potency of the transduced T cells toward NY-ESO-1 expressing targets since a) the negative checkpoint regulator PD1 is knocked out and b) surface dimerization of the transgenic TCRs is achieved in the absence of TCR$^{endo}$ expression. In addition, since the endogenous and introduced TCR chains can dimerize and create novel, unwanted, specificities, the knockout of the TCR$^{endo}$ will enhance the safety of NYCE T cells.

The NYCE T cells will be manufactured in the Clinical Cell and Vaccine Production Facility (CVPF) at the University of Pennsylvania. At the end of cell culture, the cells are cryopreserved in infusible cryomedia. Each bag will contain an aliquot (volume dependent upon dose) of cryomedia containing the following infusible grade reagents (% v/v): 31.25% plasmalyte-A, 31.25% dextrose (5%), 0.45% NaCl, 7.5% DMSO, 1% dextran 40, 5% human serum albumin. NYCE T cells will be administered as a single infusion. The target dose is $1\times10^8$ total cells/kg.

Absorption, distribution and metabolism. Lymphocytes have complex trafficking and survival kinetics, and after adoptive transfer several fates have been demonstrated: 1) margination; 2) exit from the peripheral blood and trafficking to lymphoid tissues; and 3) death by apoptosis. Following an intravenous dose, retrovirally modified and adoptively transferred T cells have been shown to persist in the circulation for at least 10 years in immunodeficient SCID patients due to the replicative competence of T cells. Human CD8 CTLs have an elimination half-life from the peripheral blood of about 8 days following intravenous infusion, and this increases to about 16 days when low doses of IL-2 are given. In patients with HIV infection, the mean half-life of lentivirally modified CD4 T cells in the circulation of 5 patients following a single infusion was 23.5 (±7.7) days in patients. Adoptively transferred human T cells have been shown to traffic to tumor and secondary lymphoid tissues. CD19 CAR T cells (CART19) have persisted beyond 5 years in patients with chronic lymphocytic leukemia and acute lymphocytic leukemia.

Drug interactions. Without being bound by any theory, NYCE T cells are expected to retain many of the properties of natural T cells. As such, they will be expected to be susceptible to immunosuppressive agents such as corticosteroids, calcineurin inhibitors such as cyclosporine and tacrolimus, anti-metabolite agents including methotrexate and mycophenolate mofetil, mTOR inhibitors such as sirolimus and everolimus, and lymphodepleting antibodies including, alemtuzumab, daclizumab, and denileukin diftitox. Lymphocytes are also susceptible to cytotoxic and chemotherapeutic agents that are commonly administered for hematologic malignancies such as cyclophosphamide and fludarabine.

Immune elimination. Without being bound by any theory, it is possible that the engineered NYCE T cells may be immunogenic, and that the patients will have an immune response directed against the cells, resulting in cell elimination. Immune responses may be directed towards the NY-ESO-1 transgenic TCR, however this was not observed in previous studies. It is also possible that immune responses may be directed against the edited gene products of the endogenous TCR or against edited PD1. Products from the CRISPR/Cas9 editing process may be partially translocated, not be displayed on the cell surface and yet trigger an immune response. Cas9 is a protein derived from *Streptococcus*; this is expected to be immunogenic. Since the gene-edited cells will undergo extensive proliferation following the initial editing, the Cas9 protein product is expected to be present at exceedingly low or undetectable levels in the infused cell product. Immunogenicity of the infused product will be monitored as a secondary correlative analysis. If it is found that the T cells have prolonged engraftment, then immunogenicity is not a major issue.

Rationale for lymphodepletion. Adoptive immunotherapy strategies may be able to capitalize on homeostatic T cell proliferation, a finding that naive T cells begin to proliferate and differentiate into memory-like T cells when total numbers of naive T cells are reduced below a certain threshold. Lymphodepletion reduces or eliminates regulatory T cells and other competing elements of the immune system that act as "cytokine sinks," enhancing the availability of cytokines such as IL-7 and IL-15 that promote expansion of adoptively transferred T cells. This hypothesis has been tested clinically in patients with metastatic melanoma refractory of conventional treatments. The patients received a lymphodepleting conditioning regimen consisting of cyclophosphamide (60 mg/kg×2 days) and fludarabine (25 mg/m$^2$×5 days) prior to adoptive transfer of T cells. Treated patients with myeloma and lymphoma after lymphodepleting chemotherapy have been observed to exhibit improved engraftment in lymphoma, as well as in randomized cohorts of myeloma and neuroblastoma patients. In this experiment NYCE T cells will be administered into subjects that are rendered lymphopenic as a result of cytotoxic chemotherapy. The chemotherapy regimen used for lymphodepletion will be disease specific.

Predicted cell populations generated during product manufacture. Based on the lentiviral gene transfer of the NY-ESO-1 TCR and the CRISPR/Cas9 editing targeting of PDCD1, TRAC and TRBC genes, there are 16 possible populations of autologous T cells that can be generated during the manufacturing process (Table 2).

TABLE 2

|         | NYESO1− TCR WT | NYESO1+ TCR WT | NYESO1− TCR A−B+ | NYESO1+ TCR A−B+ | NYESO1− TCR B−A+ | NYESO1+ TCR B−A+ | NYESO1− TCR A−B− | NYESO1+ TCR A−B− |          |
|---------|----------------|----------------|------------------|------------------|------------------|------------------|------------------|------------------|----------|
| PD1 WT  | 1              | 2              | 3                | 4                | 5                | 6                | 7                | 8                |          |
| PD1−    | 9              | 10             | 11               | 12               | 13               | 14               | 15               | 16               |          |
| CD3     | 1              | 2              | 3                | 4                | 5                | 6                | 7                | 8                | CD3 neg  |
| CD3     | 9              | 10             | 11               | 12               | 13               | 14               | 15               | 16               | CD3+     |
| Tetramer| 1              | 2              | 3                | 4                | 5                | 6                | 7                | 8                | Tetramer neg |
| Tetramer| 9              | 10             | 11               | 12               | 13               | 14               | 15               | 16               | Tetramer+|

These 16 cell types reduce down to 6 possible cell surface phenotypes as detected by staining with NY-ESO-1 tetramer, anti-CD3 and anti-PD-1 antibodies. Within those 6 possible cell surface phenotypes, there are different potential safety and efficacy profiles based on NY-ESO-1 TCR, PD-1, TCRα and TCRβ expression. A detailed breakdown of these profiles is outlined in Table 3.

TABLE 3

| Cell surface staining profile | Cell surface staining NY-ESO-1 | CD3 | PD1* | Gene status (intact+) or (disruption−) TCRα | TCRβ | PD1 | Cell Pop'n | Predicted safety and efficacy profile |
|---|---|---|---|---|---|---|---|---|
| 1 | − | + | + | + | + | + | 1 | Wild-type T cells that were not modified during manufacturing. Safety is expected while efficacy is not. |
| 2 | − | + | − | + | + | − | 9 | T cells with PD-1 disruption that retains endogenous TCR. These cells are anticipated to have a low toxicity risk based on data from systemic therapy with PD-1 antagonists, however they could mediate autoreactivity. These cells may facilitate "antigenic spreading" of an antitumor response. |
| 3 | − | − | + | − | + | + | 3 | T cells with endogenous TCR disruption. These cells are expected to be rare, have low potential for toxicity and should not persist after adoptive transfer. |
|   |   |   |   | + | − | + | 5 | |
|   |   |   |   | − | − | + | 7 | |
| 4 | − | − | − | − | + | − | 11 | T cells with endogenous TCR and PD-1 disruption; expected to be rare, have low potential for toxicity and should not persist after adoptive transfer. |
|   |   |   |   | + | − | − | 13 | |
|   |   |   |   | − | − | − | 15 | |
| 5 | + | + | + | + | + | + | 2 | NY-ESO-1 specific T cells without gene disruption. Previously tested in patients with multiple myeloma with demonstrated safety. |
|   |   |   |   | − | + | + | 4 | NY-ESO-1 specific T cells with endogenous TCR disruption. Expected enhanced anti-tumor activity compared to cell |
|   |   |   |   | + | − | + | 6 | |

TABLE 3-continued

| Cell surface staining profile | Cell surface staining NY-ESO-1 | CD3 | PD1* | Gene status (intact+) or (disruption−) TCRα | TCRβ | PD1 | Cell Pop'n | Predicted safety and efficacy profile |
|---|---|---|---|---|---|---|---|---|
|  |  |  |  |  |  |  |  | population 2, have reduced, but not absent potential for mispairing and susceptible to exhaustion by PD-1 expression. |
|  |  |  |  | − | − | + | 8 | NY-ESO-1 specific T cells with endogenous TCR disruption. Expected enhanced anti-tumor activity compared to population 2. Absent potential for mispairing, but susceptible to exhaustion by PD-1 expression. |
| 6 | + | + | − | + | + | − | 10 | NY-ESO-1 specific T cells with PD-1 disruption and retained endogenous TCR. Expected anti-tumor efficacy and less susceptible to exhaustion by PD-1 expression |
|  |  |  |  | − | + | − | 12 | NY-ESO-1 specific T cells with endogenous TCR and PD-1 disruption. Expected reduced potential for mispairing. May have enhanced effector function. Expected to be less susceptible to exhaustion by PD-1 expression. |
|  |  |  |  | + | − | − | 14 |  |
|  |  |  |  | − | − | − | 16 |  |

*after stimulation

Population #1 is wild type T cells that escaped transduction or editing during manufacturing. These autologous T cells are expected to be safe and have no antitumor activity based on previous trials. Population #2 are T cells with transgenic TCR and the retained endogenous TCR. These cells have been tested clinically and found to be safe and have antitumor efficacy in sarcoma, melanoma and myeloma. Population #9 are T cells with PD-1 disruption that retain endogenous TCR. These cells are anticipated to have a low toxicity risk based on data from systemic therapy with PD-1 antagonists, but may mediate autoreactivity. Without being bound by any theory it is possible that these cells may facilitate "antigenic spreading" of an antitumor response directed against tumor neo-epitopes. Populations #3, 5, 7, 11, 13, and 15 are T cells with endogenous TCR disruption. These cells are expected to be rare, have low potential for toxicity and should not persist after adoptive transfer because TCR signals are required for T cell survival in experimental settings. Populations #10, 12, 14, and 16 are NY-ESO-1 specific T cells with PD-1 disruption. These cells may have enhanced effector function and are expected to be less susceptible to exhaustion by PD-1 expression. A major rationale for this experiment is that it is a competitive repopulation experiment: the bulk cells will be infused with the expectation that the immune competition and tumor microenvironment will select the "winners," testing the hypothesis that T cells with NY-ESO-1 specificity and disrupted PD1 may have enhanced function.

Prophetic Example 2: Administration of NYCE T Cells to Patients

Figure 14:
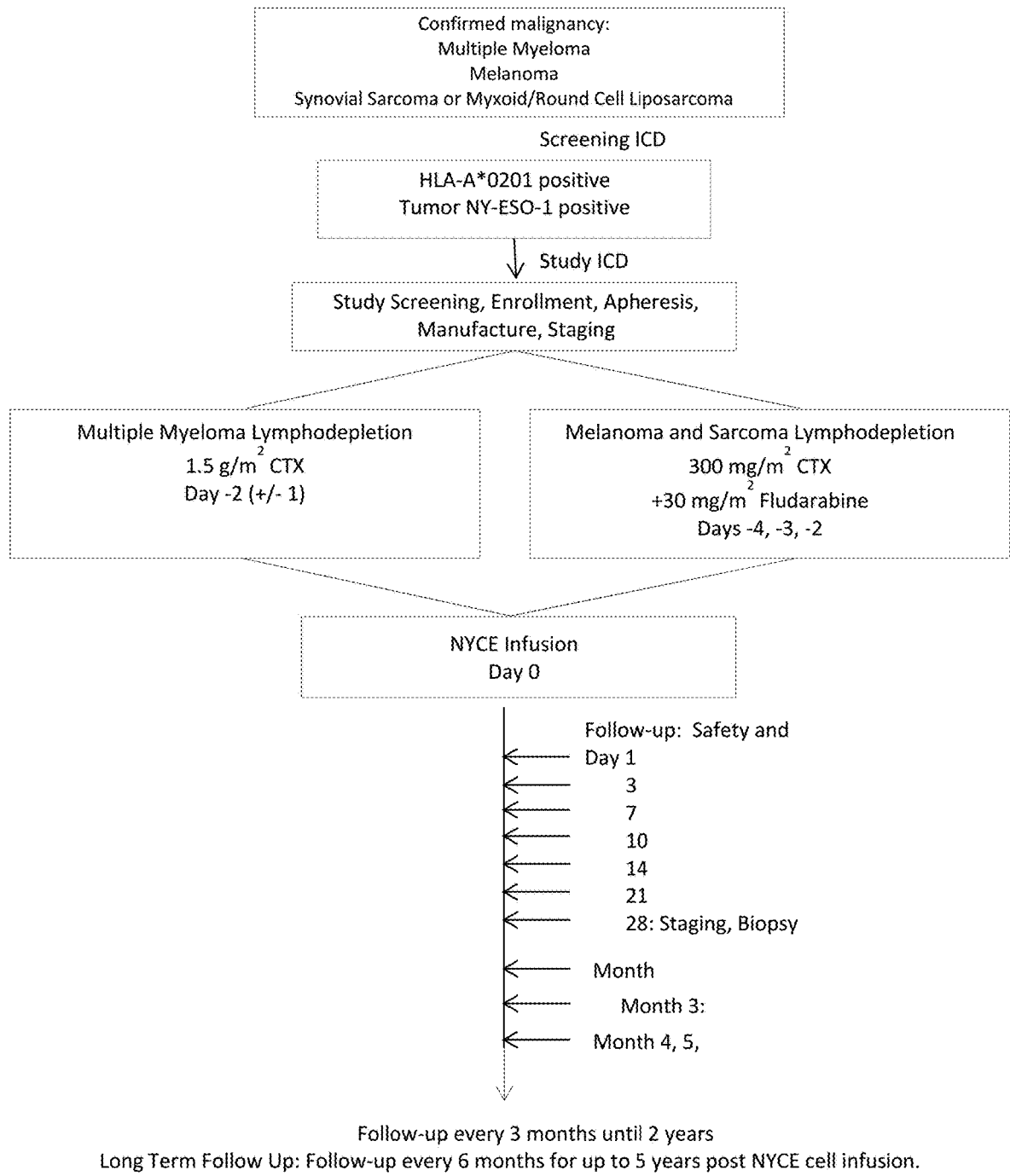
FIG. 14 depicts a schema describing a general protocol for the administration of NYCE T cells.

NYCE T cells are autologous NY-ESO-1-redirected and CRISPR TCR$^{endo}$ and PD1 edited T cells. Autologous T cells will be engineered using a lentiviral vector to express a TCR with specificity for NY-ESO-1 peptide (SLLMWITQC; SEQ ID NO:1) in complex with HLA-A*0201 in which A pilot trial will be done to determine if the infusion of autologous NYCE T cells (transduced to express NY-ESO-1 TCR and lacking endogenous TCR and PD-1) is safe. The primary goals of the trial are to determine the safety of NYCE T cells in relapsed and/or refractory multiple myeloma (MM), sarcoma and melanoma patients. The protocol consists of an open label pilot study. The general protocol schema is shown in FIG. 14.

As part of informed consent, patients will be asked for permission to test their HLA-A*201 status and their tumor for expression of NY-ESO-1. HLA-A*201 status will be confirmed first. Patients who are HLA-A*201 positive will then have their tumor tissue tested for NY-ESO-1 expression. Expression testing can be performed on historical samples if available (see Section 6.1 for additional details). Patients who are HLA-A*201+ and express NY-ESO-1 in their tumor samples may proceed to the next step and be presented the main informed consent form to undergo additional screening.

At study, entry subjects will undergo routine laboratory and imaging assessment of their disease. Eligible subjects will undergo steady-state apheresis to obtain large numbers of peripheral blood mononuclear cells (PBMC) for manufacturing. Cryopreserved historical apheresis products collected from the patient prior to study entry are usable for manufacturing if collected at an appropriately certified apheresis center and the product meets adequate mononuclear cell yields. If a historical apheresis product is not available, an apheresis procedure will be scheduled for cell procurement after study entry. The T cells will be purified from the PBMC, transduced with lentiviral vector to deliver the recombinant NY-ESO-1 TCR and electroporated with CRISPR/Cas9 complexes, expanded in vitro and then frozen for future administration. The number of subjects who have inadequate T cell collections, expansion or manufacturing compared to the number of subjects who have cells successfully manufactured will be recorded.

The manufacturing process and product release will take 4-5 weeks from time of apheresis until NYCE T cells are ready for infusion. Patients may receive additional specific anti-tumor therapy to keep their disease in check during this interval, at their physician's discretion. Patients must be off all therapy, however, during the 2 weeks prior to the planned infusion date.

Up to 18 evaluable subjects: 6 myeloma subjects, 6 sarcoma subjects and 6 melanoma subjects will be enrolled. Patients with multiple myeloma and sarcoma will be targeted for enrollment first, with the plan to expand enrollment to include melanoma patients once initial safety is established. Subjects will be enrolled serially. Infusions of the first 2 subjects in each disease indication will be staggered by 28 days to allow for observation of adverse events.

In the event that the clinical target dose is not met for a particular subject, the subject has the option of undergoing a second apheresis and manufacturing run. Alternatively, the subject can be treated with the available dose that is lower than the target dose. In this case, the subject will be evaluated for primary endpoints (safety and feasibility), but not for efficacy secondary endpoints. Subjects who do not receive NYCE T cells will be replaced.

All subjects will have evaluations, physical exams, and blood tests to assess safety and engraftment/persistence of the NYCE T cells at regular intervals.

Disease assessment will be performed at Day +28 and at 3 months post-infusion for all indications.

Formal myeloma response assessments will be made according to International Myeloma Working Group (IMWG) criteria at Days +14 and +28, then monthly until Day +180, then every 3 months thereafter, up to 2 years. Subjects with MM will undergo bone marrow aspirates/biopsies to assess the bone marrow plasma cell burden at day +28 and Month 3.

Melanoma response assessment will be made using (i) clinical exam for visible cutaneous tumors, (ii) radiological imaging (CT scan) with RECIST 1.1 criteria, (iii) pathological criteria for resected tumor tissue.

Sarcoma response assessment will be made using radiological imaging (CT scan) with RECIST 1.1 criteria. CT scans of the chest for synovial sarcoma and CT scans of the chest/abdomen/pelvis for MRCL. If there is locally unresectable disease in the extremity or pelvis, it will be assessed by MRI with/without gadolinium contrast (no lab studies applicable for tumor progression).

Subsequent biopsy collections (tumor, bone marrow) will be performed at Day 28 and as clinically indicated at the discretion of the treating physician; samples from these biopsies may be provided to TCSL for correlative studies.

Upon discontinuation from the primary follow-up phase, subjects will enter long-term follow-up for up to 5 years from their NYCE cell infusion. During long-term follow-up, subjects will be monitored for delayed adverse events that may be associated with the administration of the NYCE T cells, as well as T cell persistence and disease progression (as applicable).

Example 2: PD1-CD28 Switch Receptor Boosts NY-ESO-1 TCR T Cell Function Through Evading Suppression from Tumor Microenvironment Safety and potency are two major requirements for an effective adoptive immunotherapy of cancers using genetically TCR engineered T cells. Current therapies of treating cancers using TCR engineered T cells, especially for solid tumors, are limited by poor T cell function and poor T cell persistence, majorly due to tumor microenvironment induced T cell hypofunction and exhaustion, as well as safety concerns due to either mis-pairing of introduced TCR with endogenous TCR or using affinity enhanced TCRs that potentially cause un-predicted off target toxicities.

High efficient multiplex gene disruption of both TRAC and TRBC in a wild type NY-ESO-1 TCR transferred T cells using CRISPR/CAS9 gene editing was found to improve antigen specific T cell functions both in vitro and in vivo in tumor mouse models.

Figure 15A:
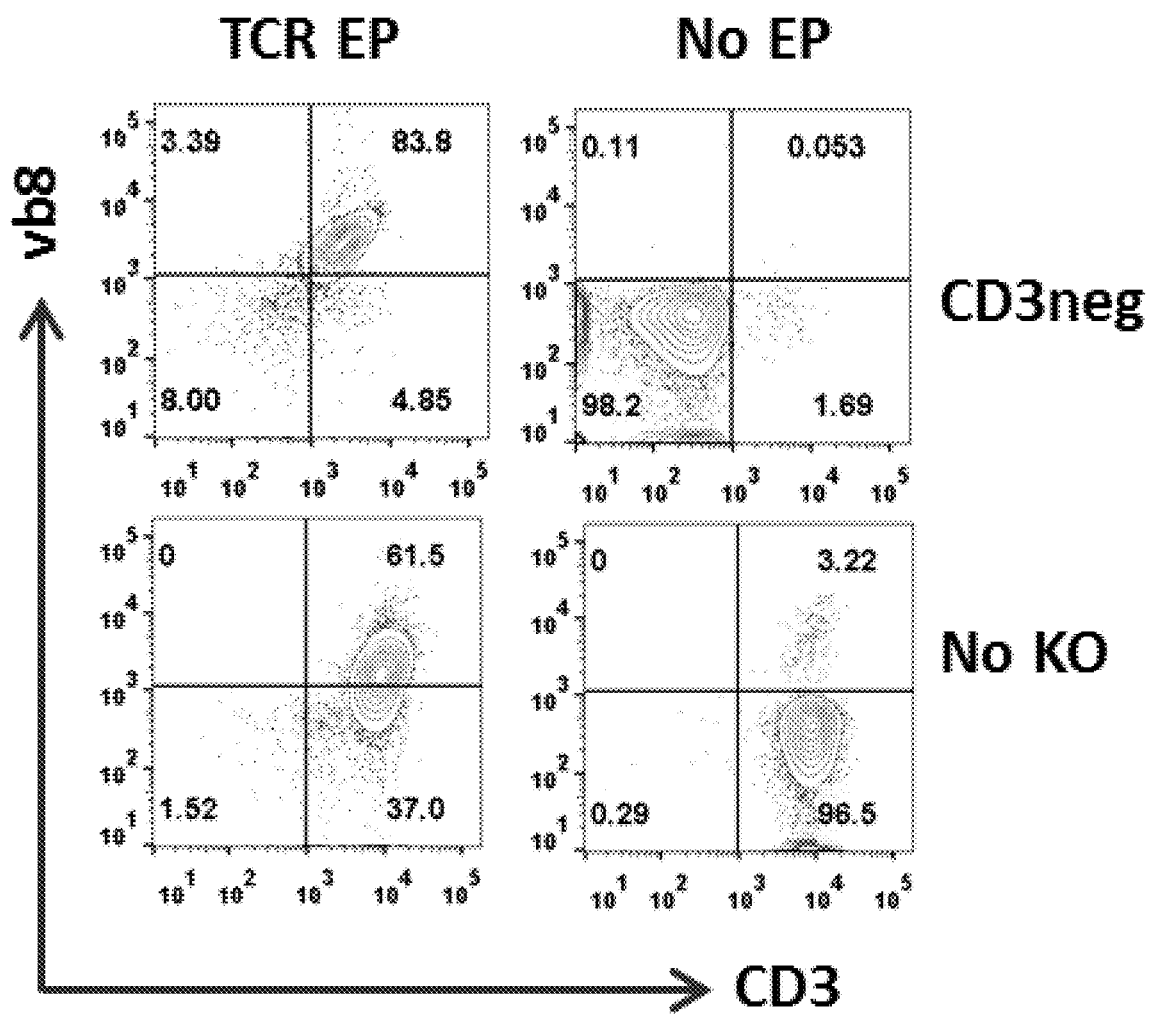
FIGS. 15A-15C depict the characterization of T cells transferred with 8F NY-ESO-1 TCR via electroporation.
Figure 15B:
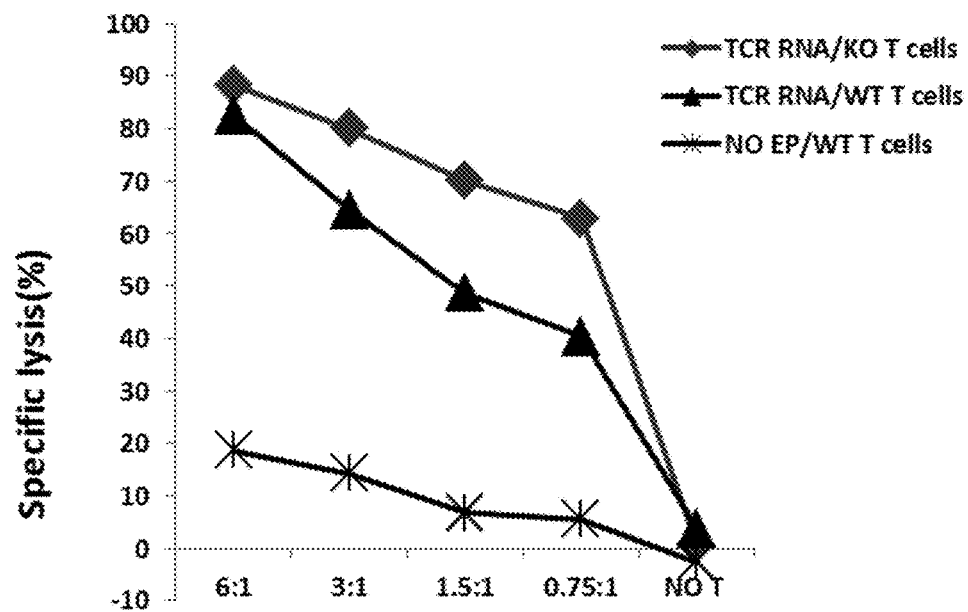
Figure 15C:
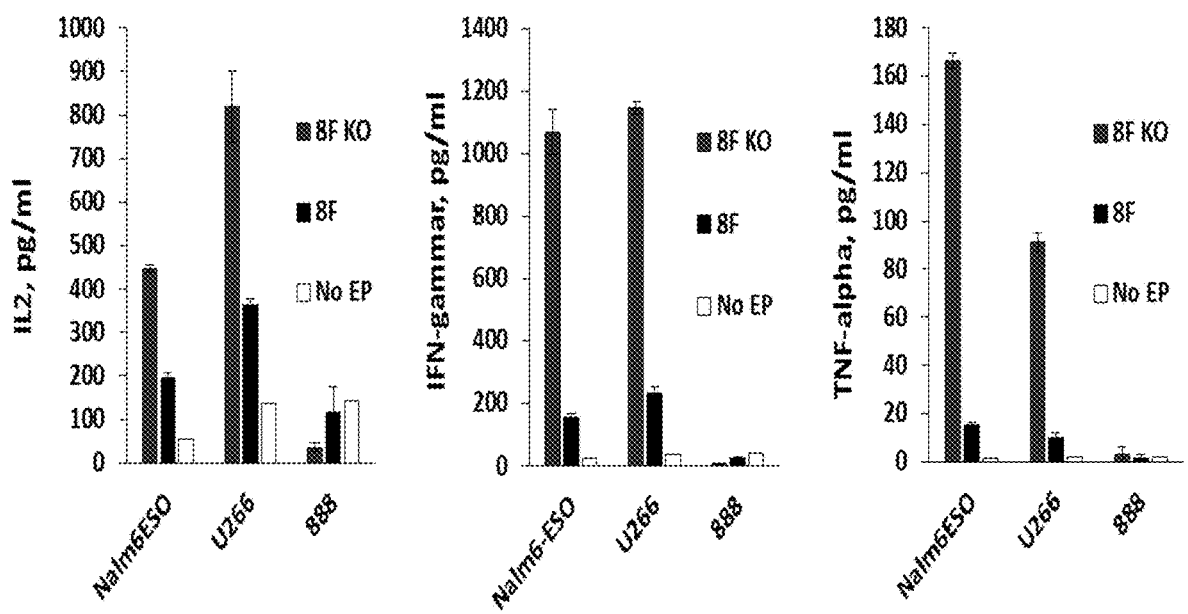

T cells transferred with 8F NY-ESO-1 TCR via electroporation were characterized (FIGS. 15A-15C). FIG. 15A shows CD3 and transferred TCR (vb8) expression of TRAC/TRBC disrupted CD3− T cells (CD3−) that were electroporated with RNAs for TCR alpha and beta of 8F NY-ESO-1 TCR (TCR EP). FIG. 15B shows the lytic activity of 8F NY-ESO-1 TCR transferred TRAC/TRBC CRISPR/CAS9 disrupted CD3 negative T cells (TCR EP/CD3−), compared with the same TCR transferred non-CRISPR/CAS9 gene edited regular CD3 positive T cells (TCR EP/CD3+). FIG. 15C shows the level of cytokine production of 8F NY-ESO-1 TCR transferred TRAC/TRBC CRISPR/CAS9 disrupted CD3 negative T cells (TCR EP/CD3−), compared with the same TCR transferred non-CRISPR/CAS9 gene edited regular CD3 positive T cells (TCR EP/CD3+).

Figure 16B:
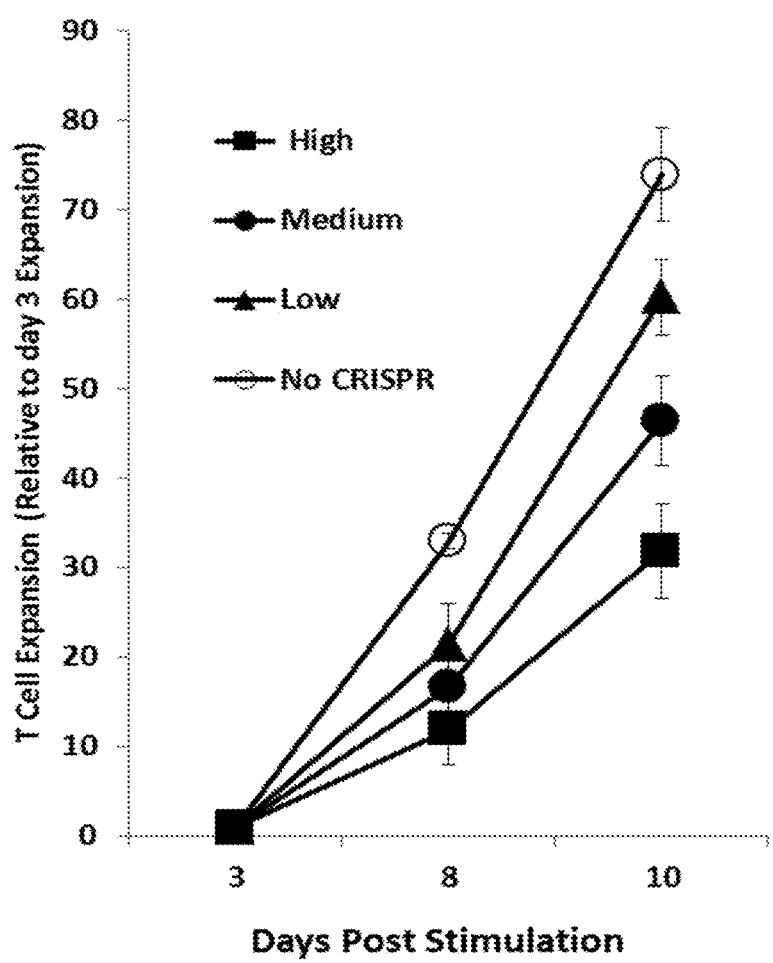

Stress tests were performed for CRISPR gene editing of NY-ESO-1 TCR transduced T cells (FIGS. 16A-16B). FIG. 16A shows the expression of TCR (vb8), CD3 and PD1 in the T cells transduced (TD) (or non-transduced (NO TD)) with 8F NY-ESO-1 TCR and subjected to different doses of CRISPR/CAS9 RNA. FIG. 16B shows the expansion of the T cells that were subjected to different doses of CRISPR/CAS9 RNA.

Figure 17:
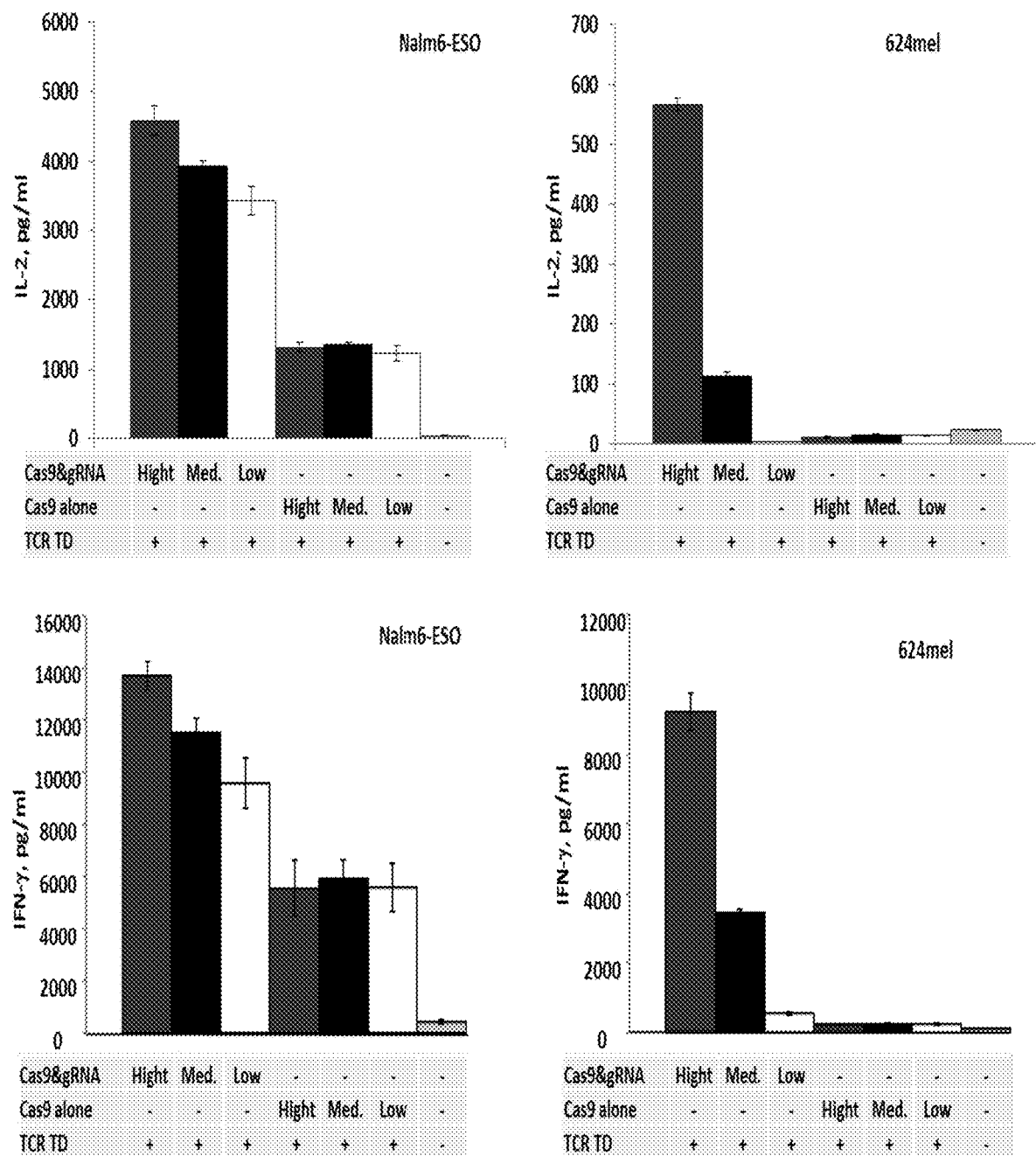
FIG. 17 depicts graphs showing the level of cytokine production in stimulated gene edited T cells.

Referring to FIG. 17, FIG. 17 shows the level of cytokine production of the NY-ESO-1/HLA-A2 positive cell lines Nalm6-ESO or 624mel stimulated with T cells that were transduced with 8F NY-ESO-1 TCR (TCR TD) and subjected to TRAC/TRBC/PD1 disruption with different doses of CAS9/gRNA.

Figure 18:
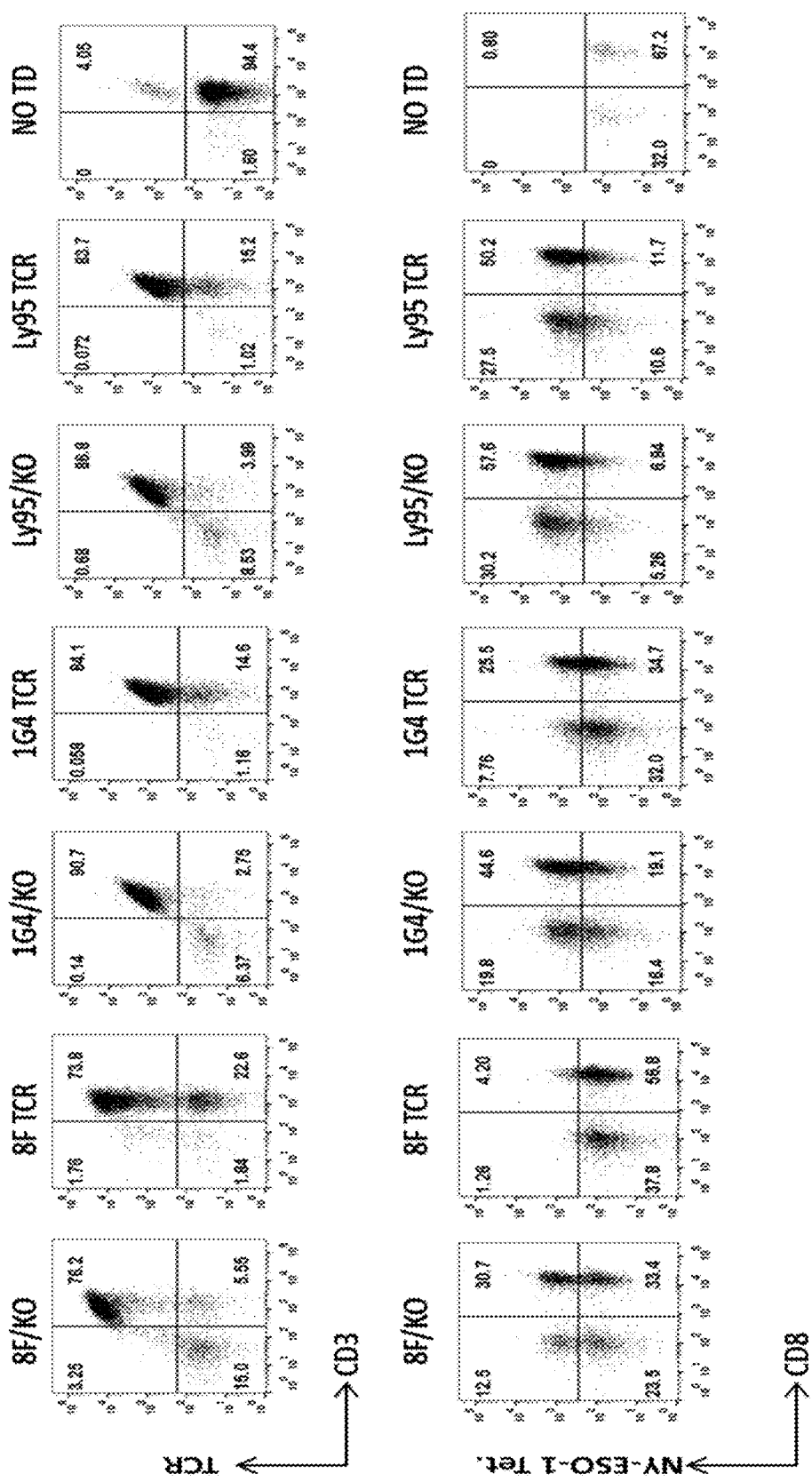
FIG. 18 depicts flow cytometry analysis of 8F, 1G4, or Ly95 transduced T cells.

TRAC/TRBC disruption was examined across T cells transduced with different TCRs (FIG. 18). FIG. 18 shows the transduced TCR expression and tetramer staining of TRAC and TRBC disrupted T cells that were transduced with either wild type NY-ESO-1 TCR (8F or 1G4) or affinity enhanced 1G4 NY-ESO-1 TCR for (Ly95).

Figure 19:
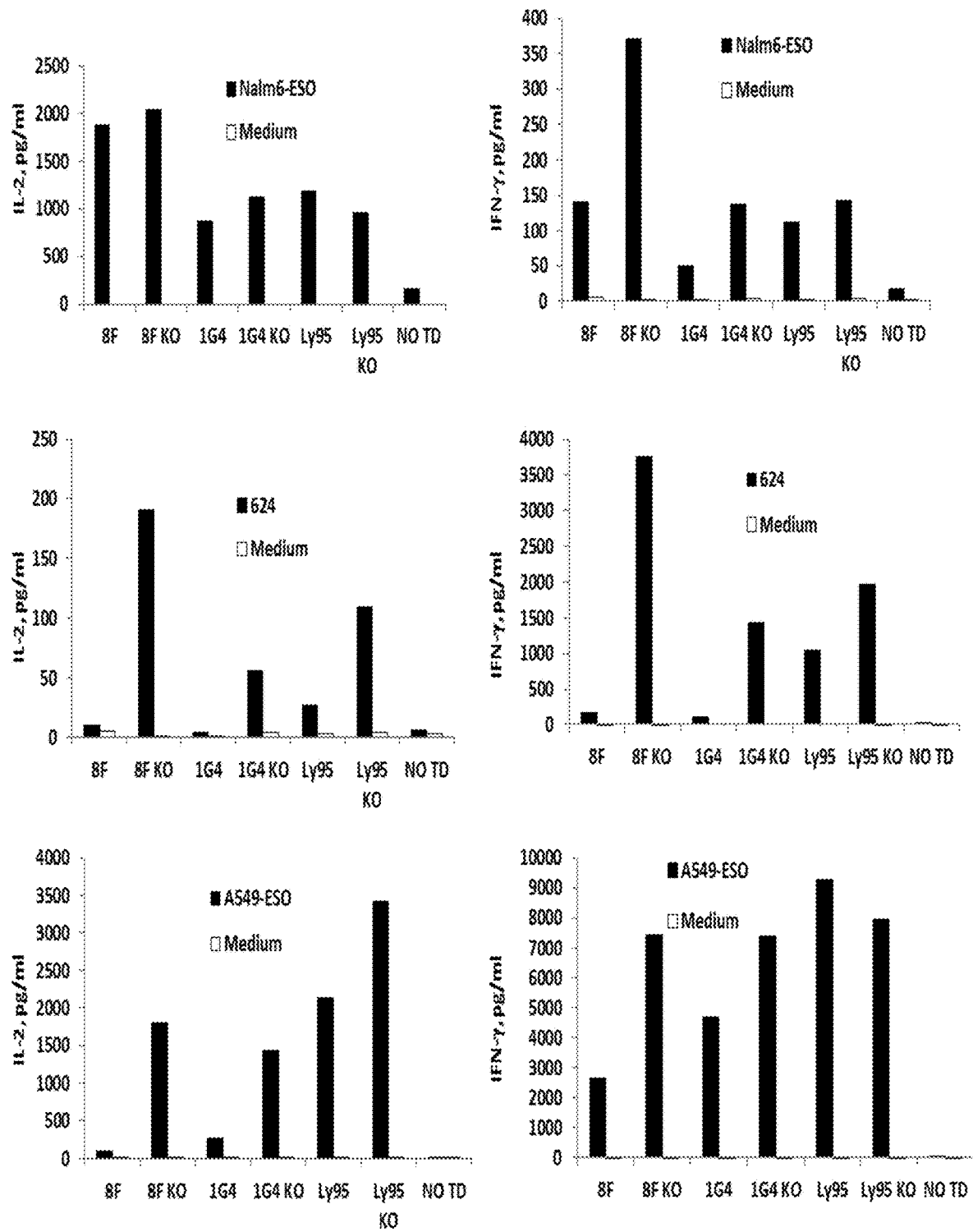
FIG. 19 depicts the level of cytokine production of different NY-ESO-1/HLA-A2 positive cell lines.

FIG. 19 shows the level of cytokine production of different NY-ESO-1/HLA-A2 positive cell lines (Nalm6-ESO, 624mel or A549-ESO) stimulated with TRAC and TRBC disrupted T cells that were transduced with either wild type NY-ESO-1 TCR (8F or 1G4) or affinity enhanced 1G4 NY-ESO-1 TCR (Ly95).

Figure 20:
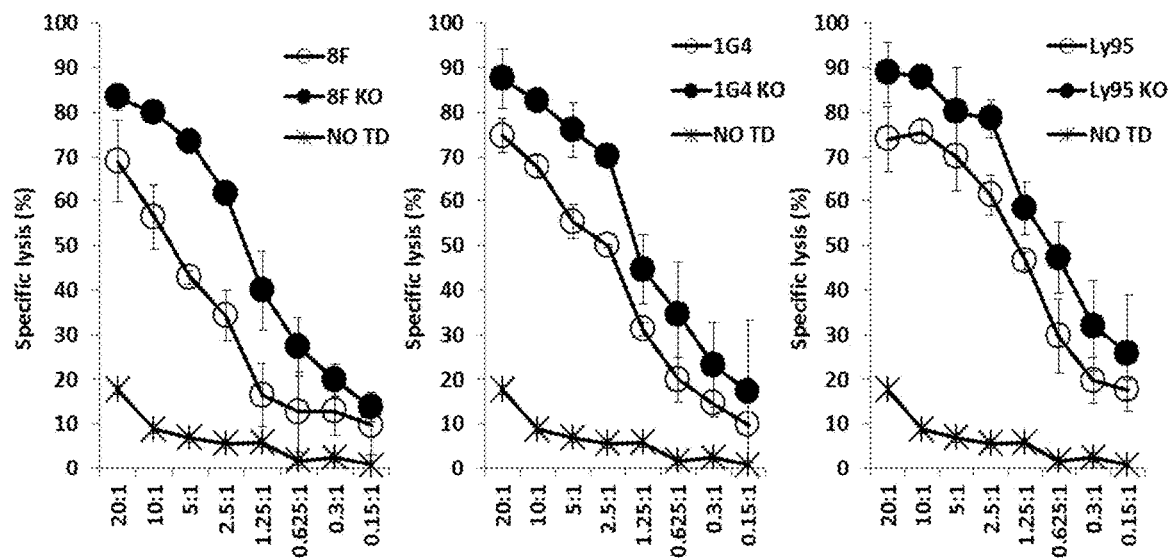
FIG. 20 depicts the lytic activity of different TRAC and TRBC disrupted T cells.

FIG. 20 shows the lytic activity of the TRAC and TRBC disrupted T cells that were transduced with either wild type NY-ESO-1 TCR (8F or 1G4) or affinity enhanced 1G4 NY-ESO-1 TCR (Ly95) against the A549-ESO tumor line.

Figure 21A:
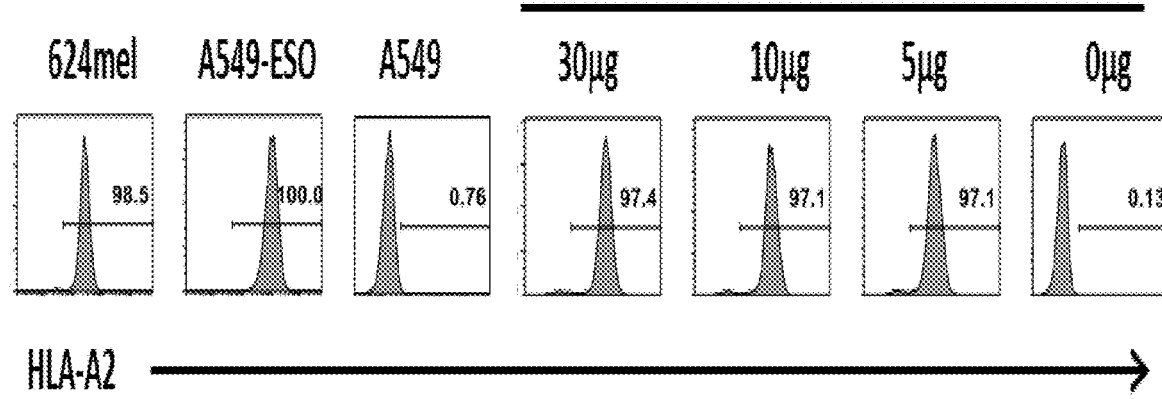

CRISPR/CAS9 disruption of TRAC and TRBC was found to improve the function of both wild type and affinity enhanced NY-ESO-1 TCR transduced T cells, while the specificity was only maintained for T cells with wild type TCRs (FIGS. 21A-21B). FIG. 21A shows HLA-A2 expression of K562 electroporated with different amount of HLA-A2 in vitro transcribed RNA. FIG. 21B shows CD107a expression of the TRAC and TRBC disrupted T cells that were transduced with either wild type NY-ESO-1 TCR (8F or 1G4) or affinity enhanced 1G4 NY-ESO-1 TCR (Ly95) stimulated by the NY-ESO-1/HLA-A2 positive tumor lines (624mel and A549-ESO), the NY-ESO-1/HLA-A2 negative tumor line A549, and the NY-ESO-1 negative K562 electroporated with different amounts of HLA-A2 RNA.

To further boost the in vivo anti-tumor activities of the NY-ESO-1 TCR transferred T cells, a PD1 switch receptor, comprising the truncated extracellular domain of PD1 and the transmembrane and cytoplasmic signaling domains of CD28 (PD1-CD28) was co-introduced into TRAC and TRBC disrupted NY-ESO-1 T cells.

The NYESO-1 TCR and PD1-CD28 switch receptor were cloned into the same lentivirus vector. As such, the lentivirus vector contained sequences for NYESO-1 TCR alpha chain, NYESO-1 TCR beta chain, and a PD1-CD28 switch receptor, as well as WPRE, cPPR, and a EF-1a promoter, as shown in FIG. 22.

Figure 22:
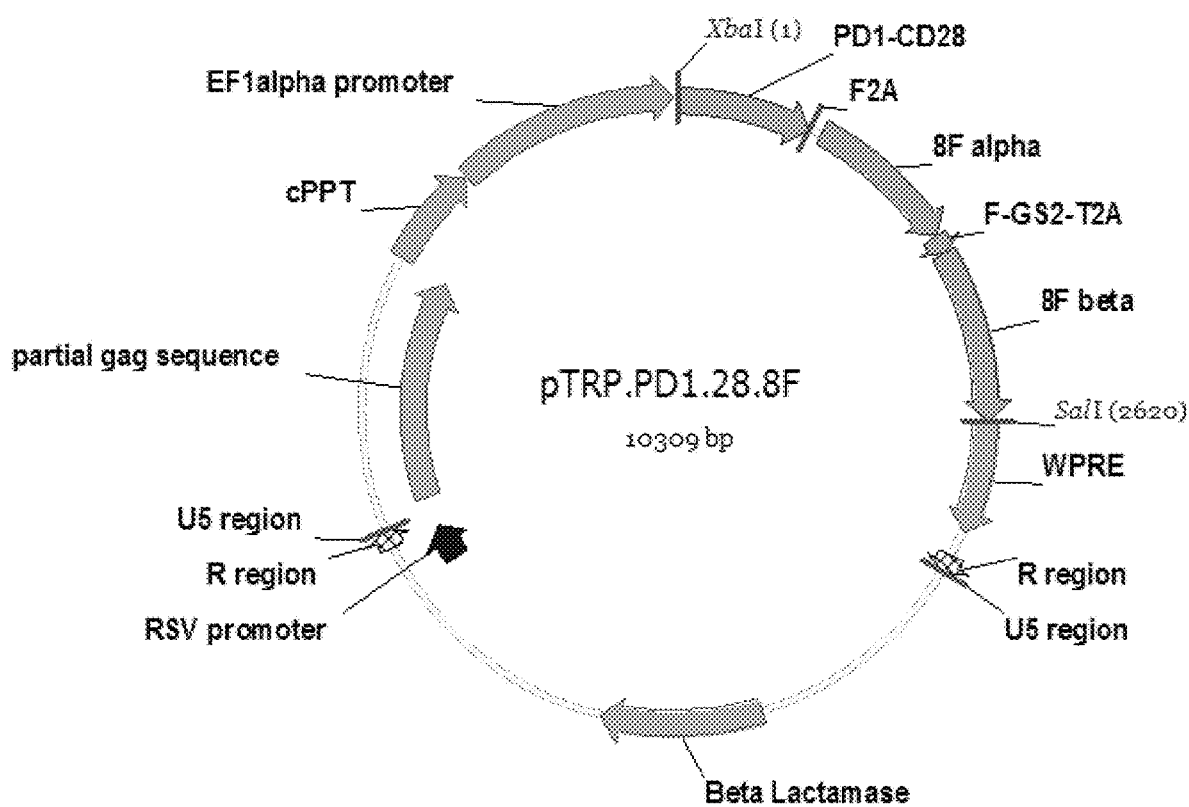
FIG. 22 depicts a lentiviral map comprising an NY-ESO-1 TCR and PD1-CD28 switch receptor.

FIG. 22 shows a lentivirus vector map. As shown, the PD1-CD28 sequence is separated from the NY-ESO-1 (8F) sequence by a F2A sequence as described herein. The NY-ESO-1 (8F) alpha and beta chain sequences are separated by an F-GS2-T2A sequence as described herein.

Figure 23A:
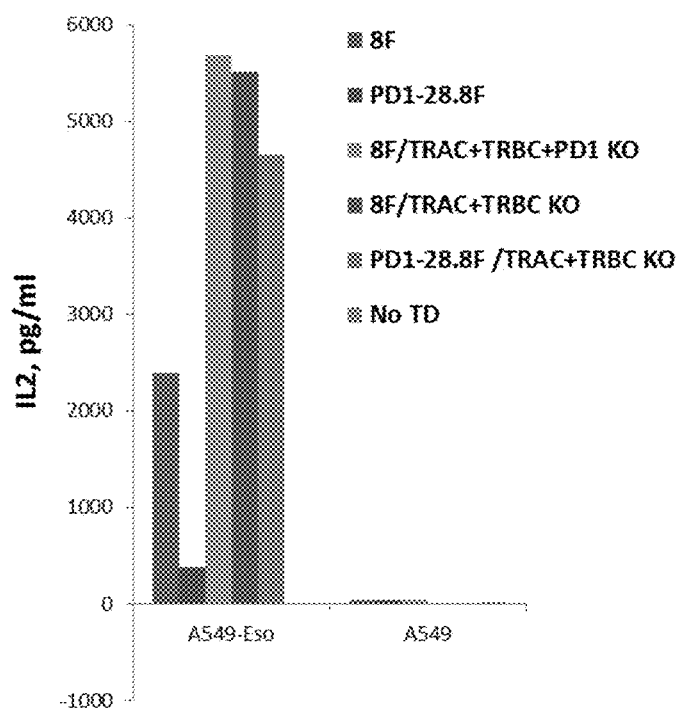
FIGS. 23A-23B depict data showing the in vitro function tests of CRISPR/CAS9 gene edited, NY-ESO-1 TCR (8F) transduced T cells, with or without co-expressing the PD1-CD28 switch receptor.
Figure 23B:
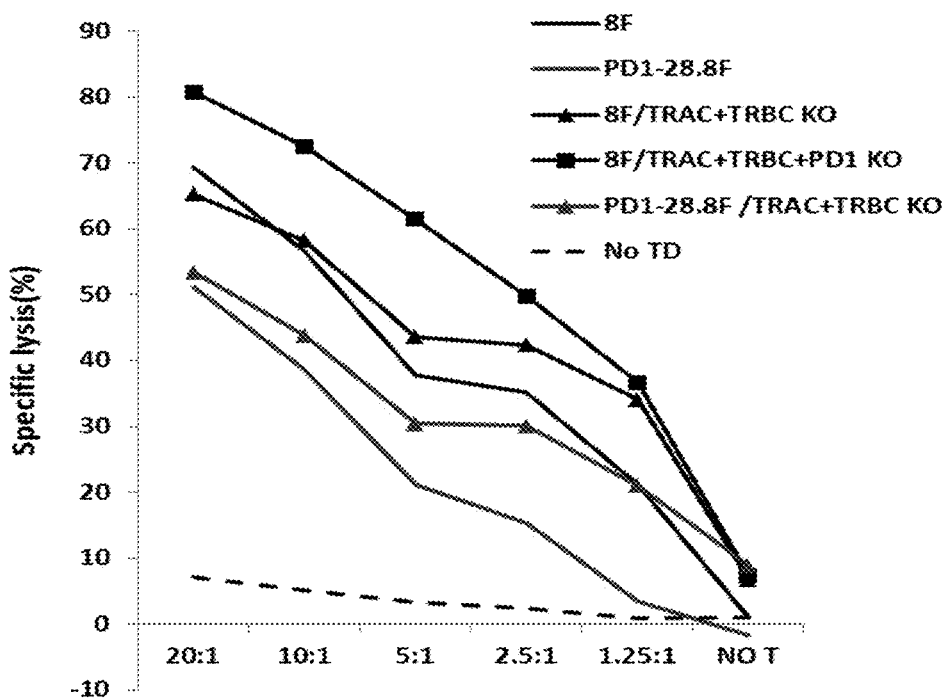

In vitro function tests of CRISPR/CAS9 gene edited, NY-ESO-1 TCR (8F) transduced T cells, with or without co-expressing the PD1-CD28 switch receptor were performed (FIGS. 23A-23B). FIG. 23 shows cytokine production (FIG. 23A) and tumor specific lysis (FIG. 23B) are dramatically increased in TCR KO T cells.

Treatment of mice bearing solid tumors with PD1-CD28, NY-ESO-1 T cells led to significant regression in tumor volume due to enhanced TIL infiltrating, decreased susceptibility to tumor-induced hypofunction, resistance of tumor derived suppression, such as from TGFβ, adenosine, IDO, hypoxia and Treg, compared to NY-ESO-1 T cells with TRAC/TRBC double disruption, or TRAC/TRBC/PD1 triple disruption (FIGS. 24A-25C).

Figure 24A:
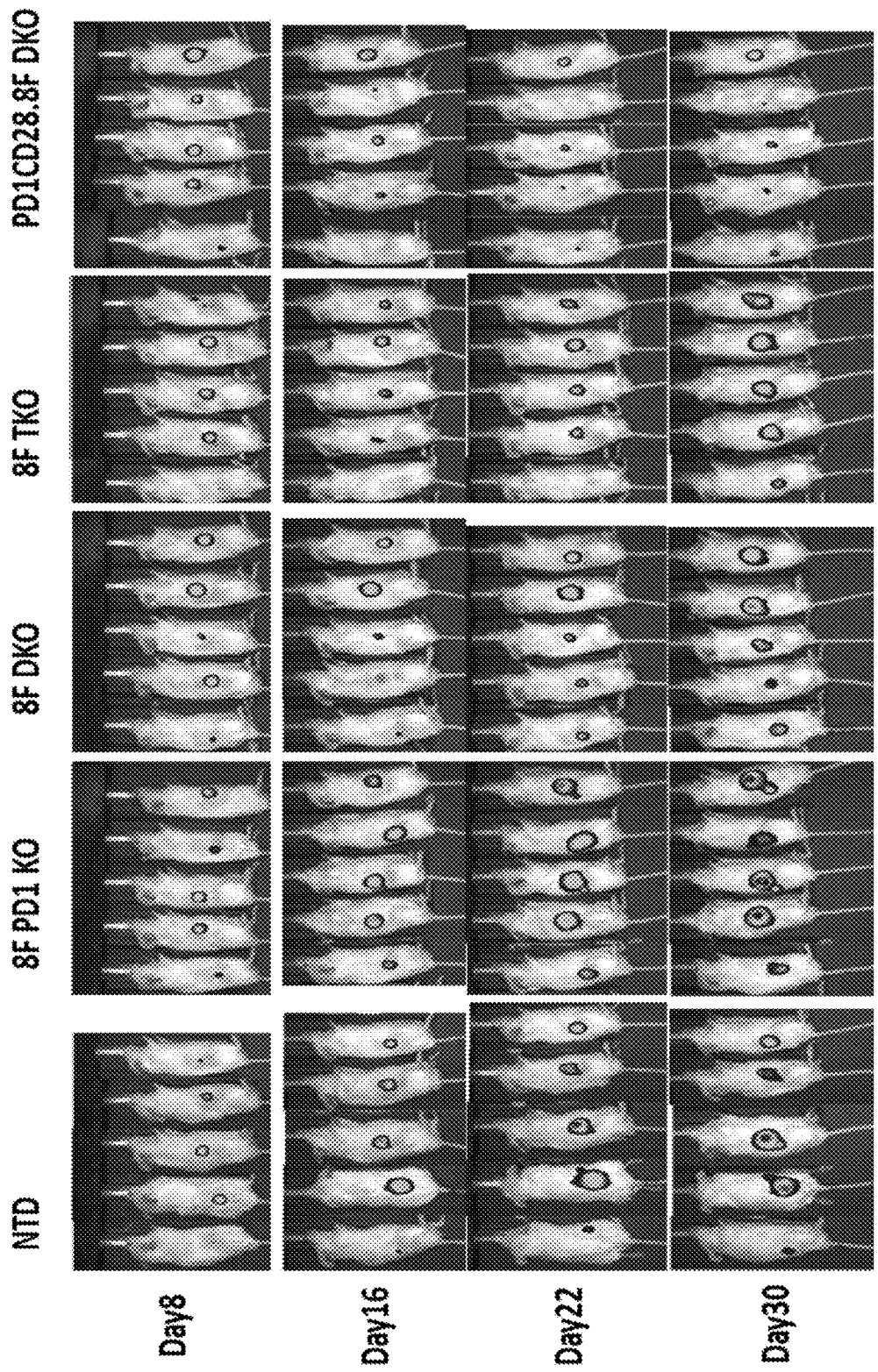
FIGS. 24A-24B depict bioluminescence imaging and data for a first set of mouse experiments.
Figure 24B:
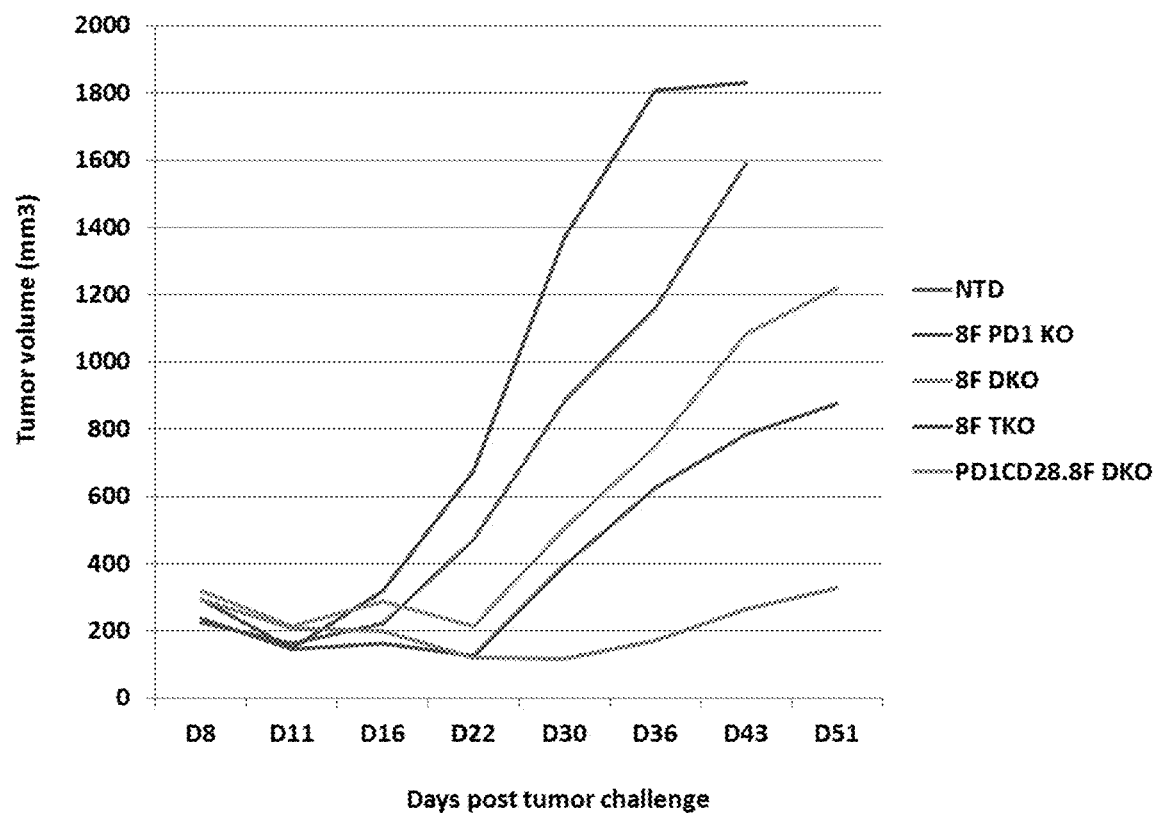

A549.ESO.CBG was subcutaneously injected at $5 \times 10^6$ cells/mouse at day 0. At day 9 tumor T cells injection (i.v.) at $1 \times 10^7$ cells/mouse (FIG. 24A-25B). FIG. 24A shows the BLI (bioluminescence imaging) that was conducted weekly. FIG. 24B shows a graph of tumor size that was measured one day prior to the T cell treatment, and weekly post-treatment. In FIG. 24B, NTD: non-transduced; 8F PD1 KO: 8F transduced T cells with disrupted PD1; 8F DKO: 8F transduced T cells with disrupted TRAC and TRBC; 8F TKO: 8F transduced T cells with disrupted TRAC, TRBC and PD1; PD1CD28.8F DKO: 8F and PD1-CD28 switch receptor transduced T cells with disrupted TRAC and TRBC.

Figures 25A, 25B:
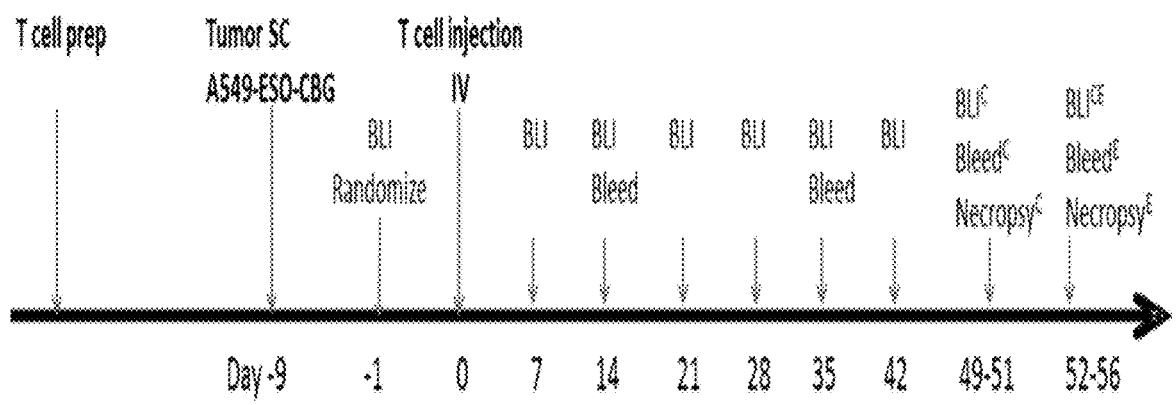
FIGS. 25A-25D depict bioluminescence imaging and data for a second set of mouse experiments.
Figure 25C:
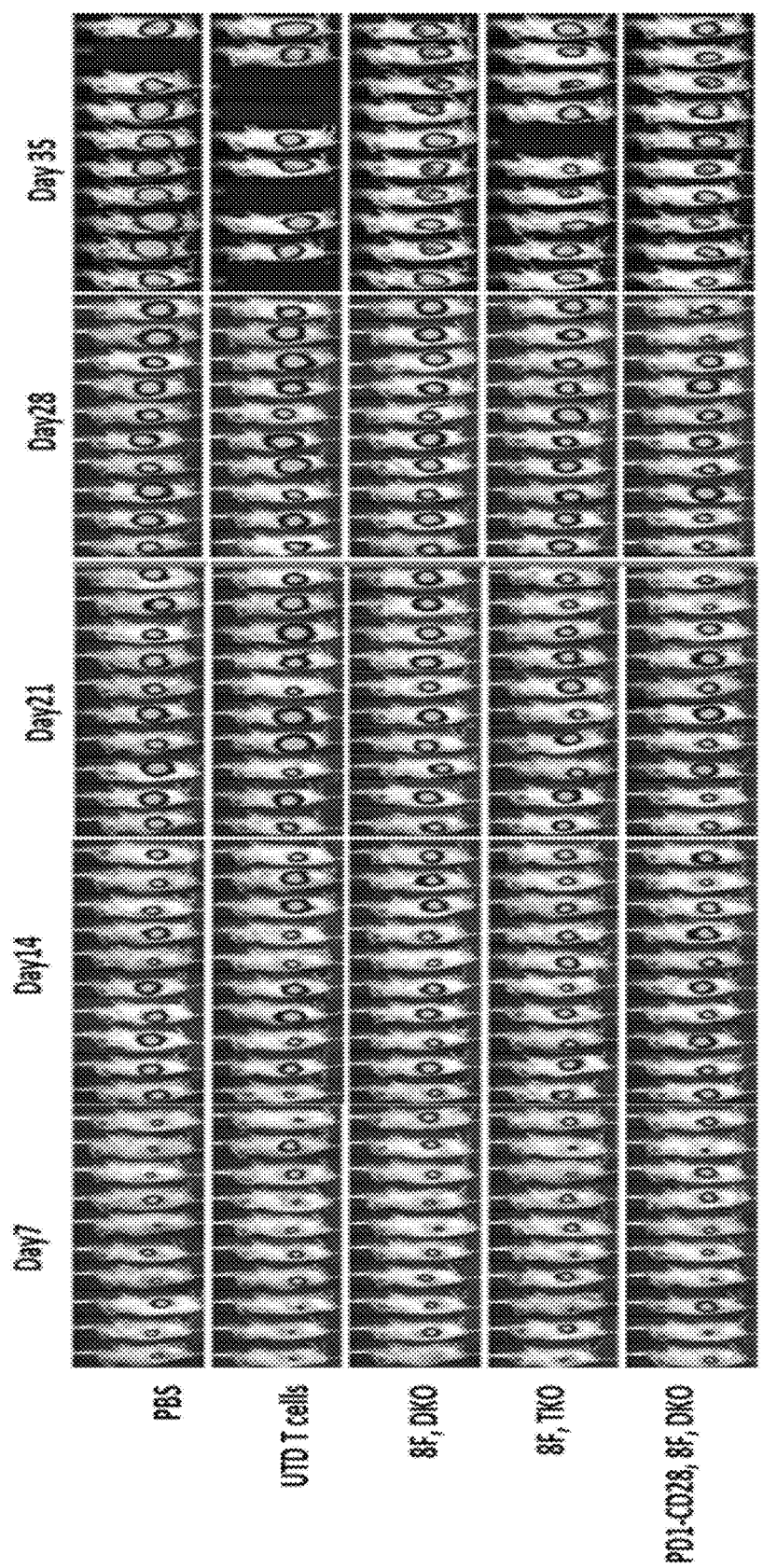
Figure 25D:
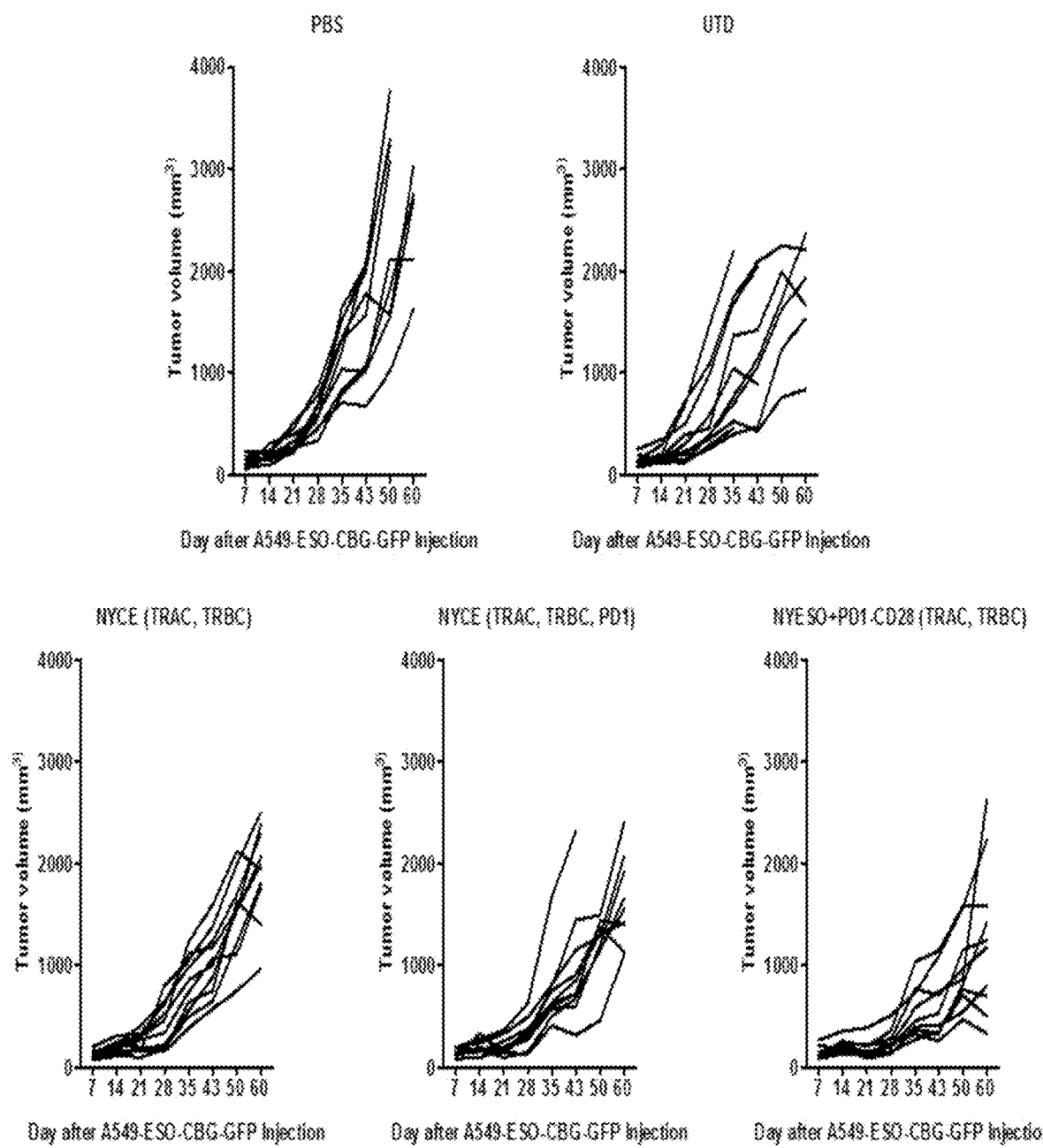

A second set of mouse experiments were performed (FIGS. 25A-25C). FIG. 25A shows a table of the experimental groups, with 10 mice/group. FIG. 25B shows a timeline of the mouse experiments. FIG. 25C shows BLI (bioluminescence imaging) of the mice. FIG. 25D shows a graph of tumor size that was measured one day prior to the T cell treatment, and weekly post-treatment.

Figure 26A:
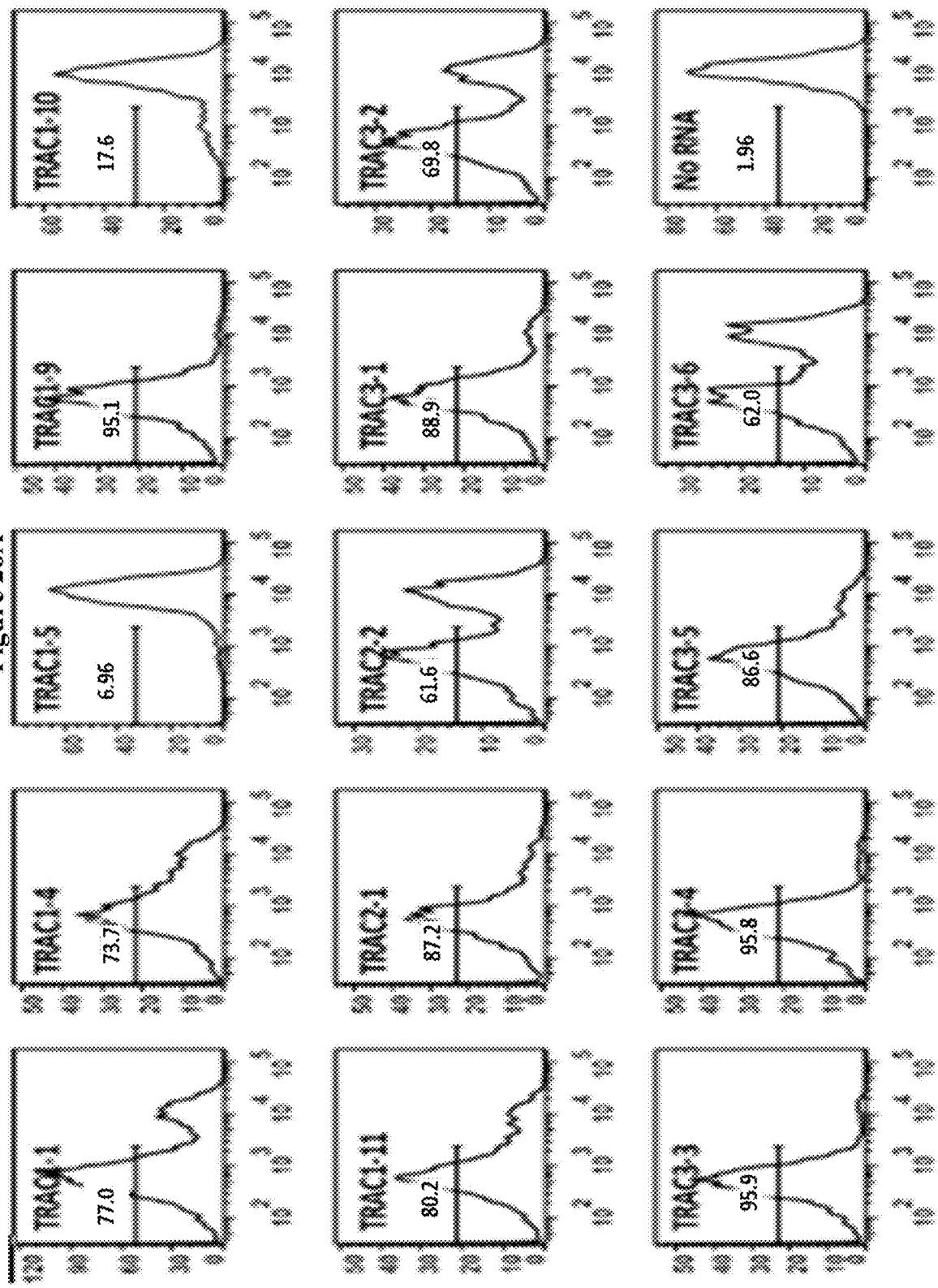
FIGS. 26A-26C depict a series of plots illustrating CRISPR/Cas9 gene disruption efficiency of T cells.
Figure 26B:
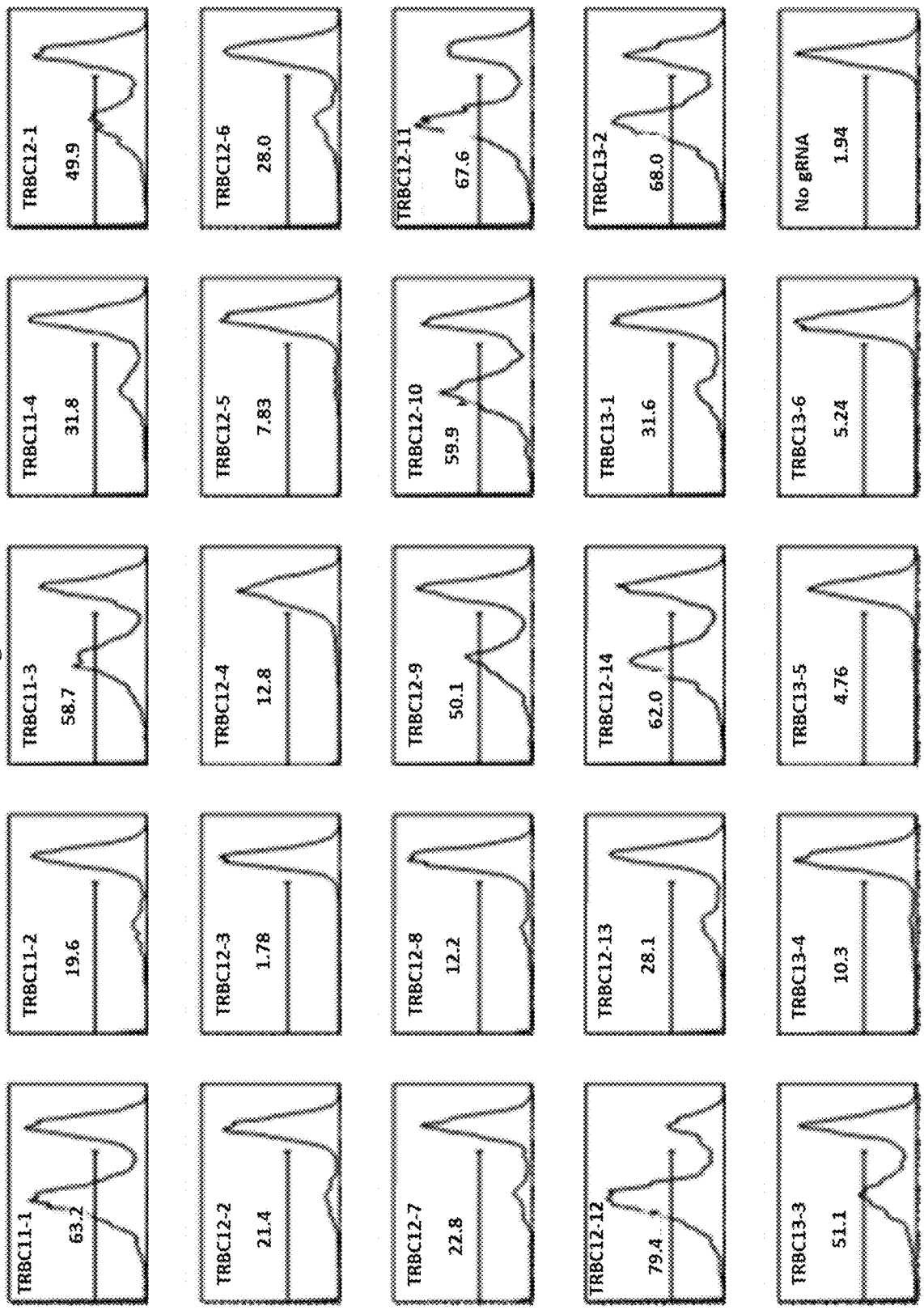
Figure 26C:
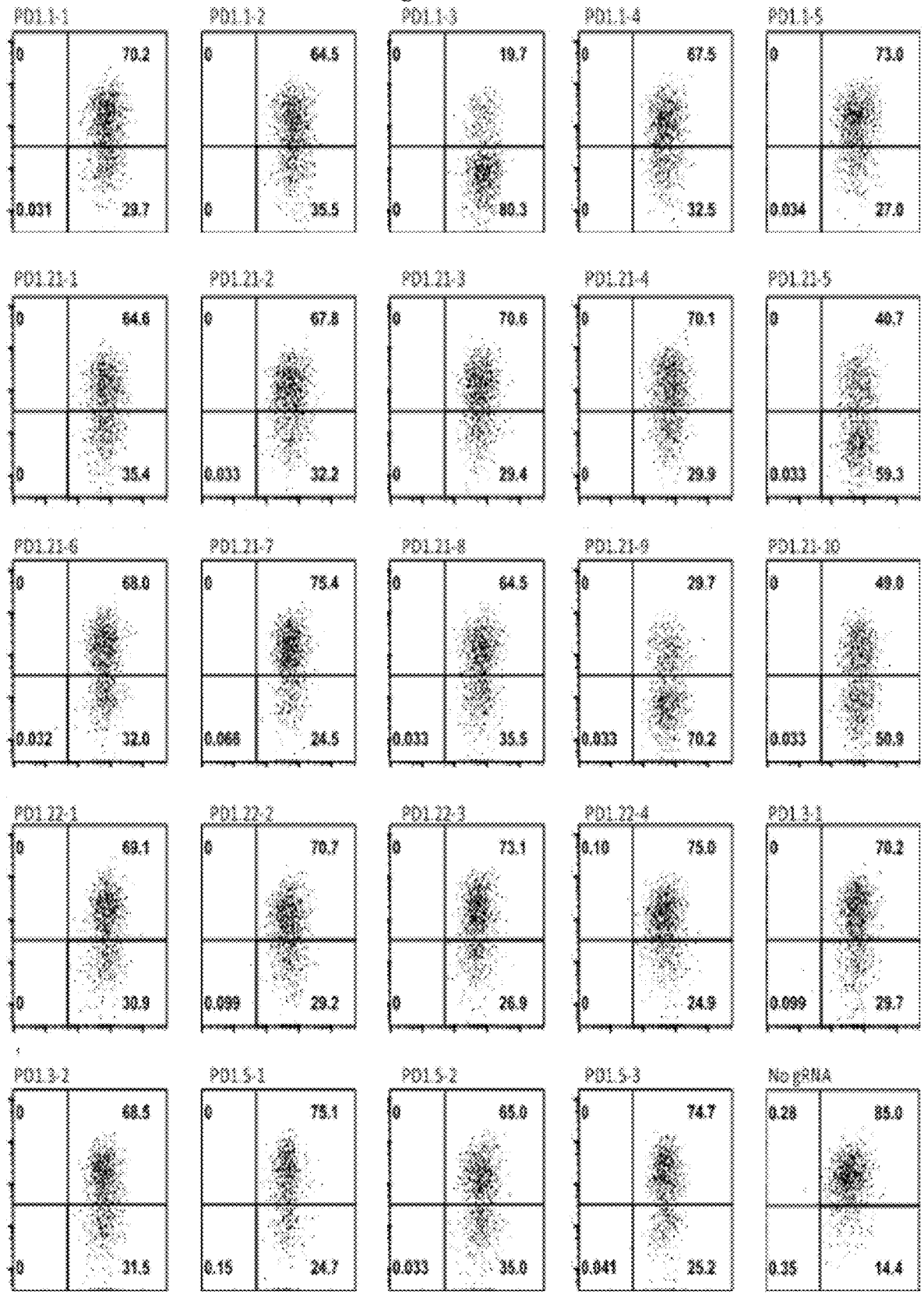

A screen was performed to identify effective gRNAs targeting TRAC, TRBC, and PD1 (FIGS. 26A-26C). FIGS. 26A-26C show a series of plots illustrating TRAC (FIG. 26A), TRBC (FIG. 26B), and PD1 (FIG. 26C) gene disruption efficiency in T cells screened by electroporation of CRISPR/CAS9 RNA for gRNAs targeting TRAC, TRBC, and PD1, respectively.

Figures 27C, 27D:
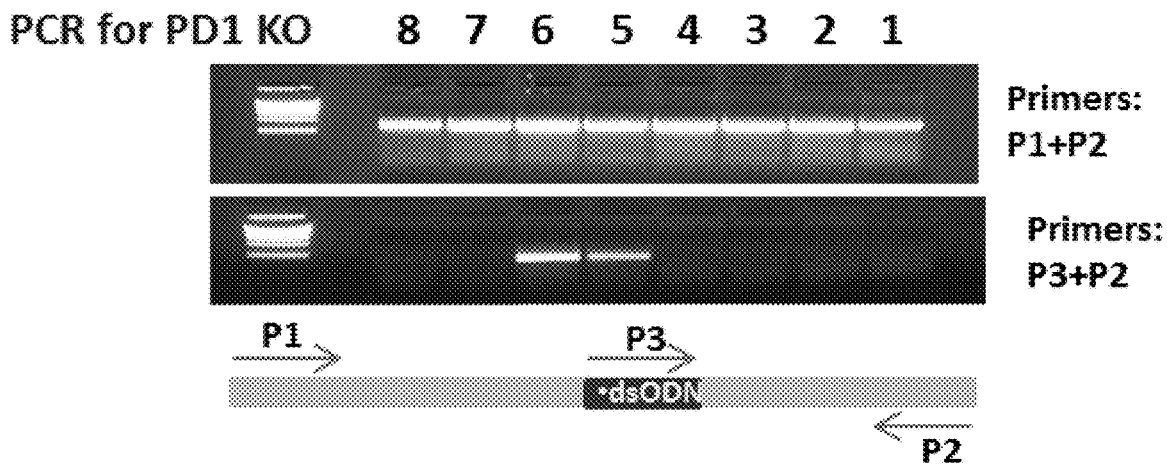

Off-Target detection by Guide-seq was performed (FIGS. 27A-27D). FIG. 27A shows a table of samples' treatment. FIG. 27B shows the expression of PD1 and CD3 in T cells of each sample. FIG. 27C shows the validation of capture of double-stranded oligodeoxynucleotides (dsODN) into DSBs. FIG. 27D shows a summary of the Guide-seq results for the off-target sites. The percent off-target sites was: Group I guide RNAs: 1.7%; Group II guide RNAs: 0.19%.

Figure 28B:
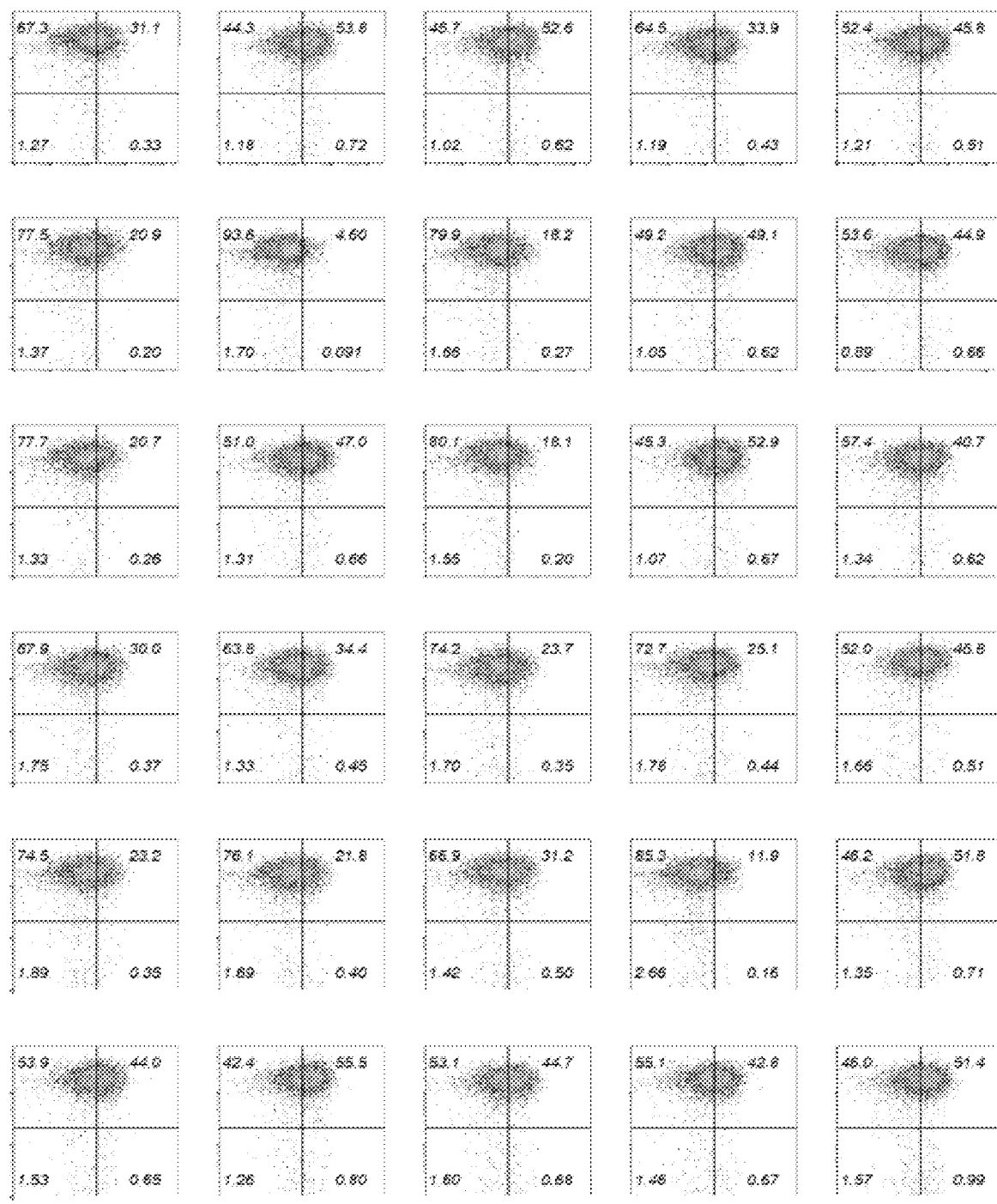
Figure 28D:
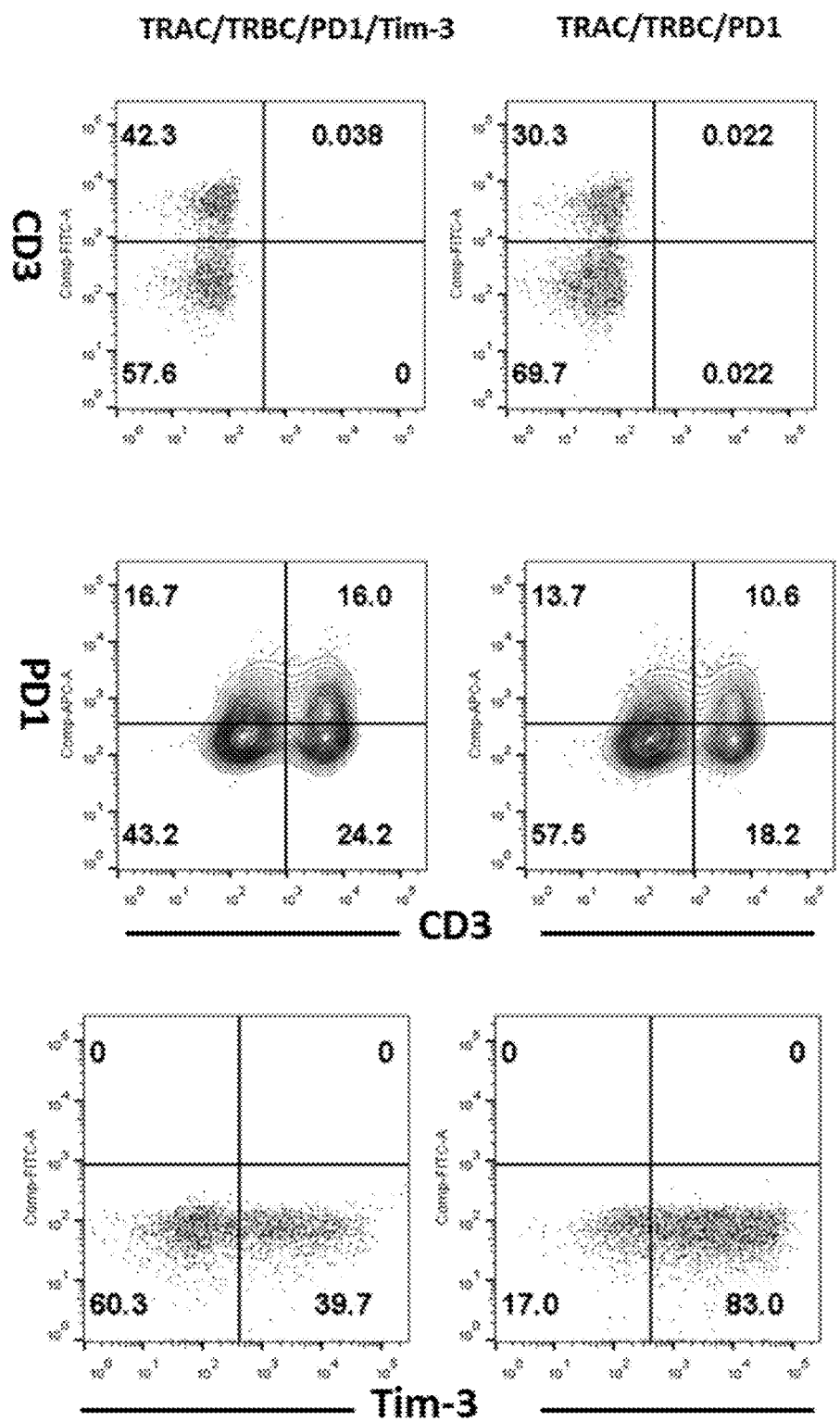

Additional disruption of Tim-3 for TRAC/TRBC double disrupted PD1-CD28 NY-ESO-1 T cells showed synergistic effect of controlling large, established solid tumors in mice. A screen was performed to identify effective gRNAs targeting the immune checkpoint protein TIM-3 (FIGS. 28A-28D). FIG. 28A shows the gRNA sequences used in the screen (SEQ ID NOs. 98-126). FIG. 28B shows the expression of TIM-3 in T cells disrupted by each TIM-3 gRNA. FIG. 28C shows the efficiency of TIM-3 knockout/knock-down for each gRNA tested. FIG. 28D shows the expression of CD3, PD1, or TIM-3 of T cells with TRAC/TRBC/PD1/TIM-3 disrupted, and T cells with TRAC/TRBC/PD1 disrupted.

Figure 29A:
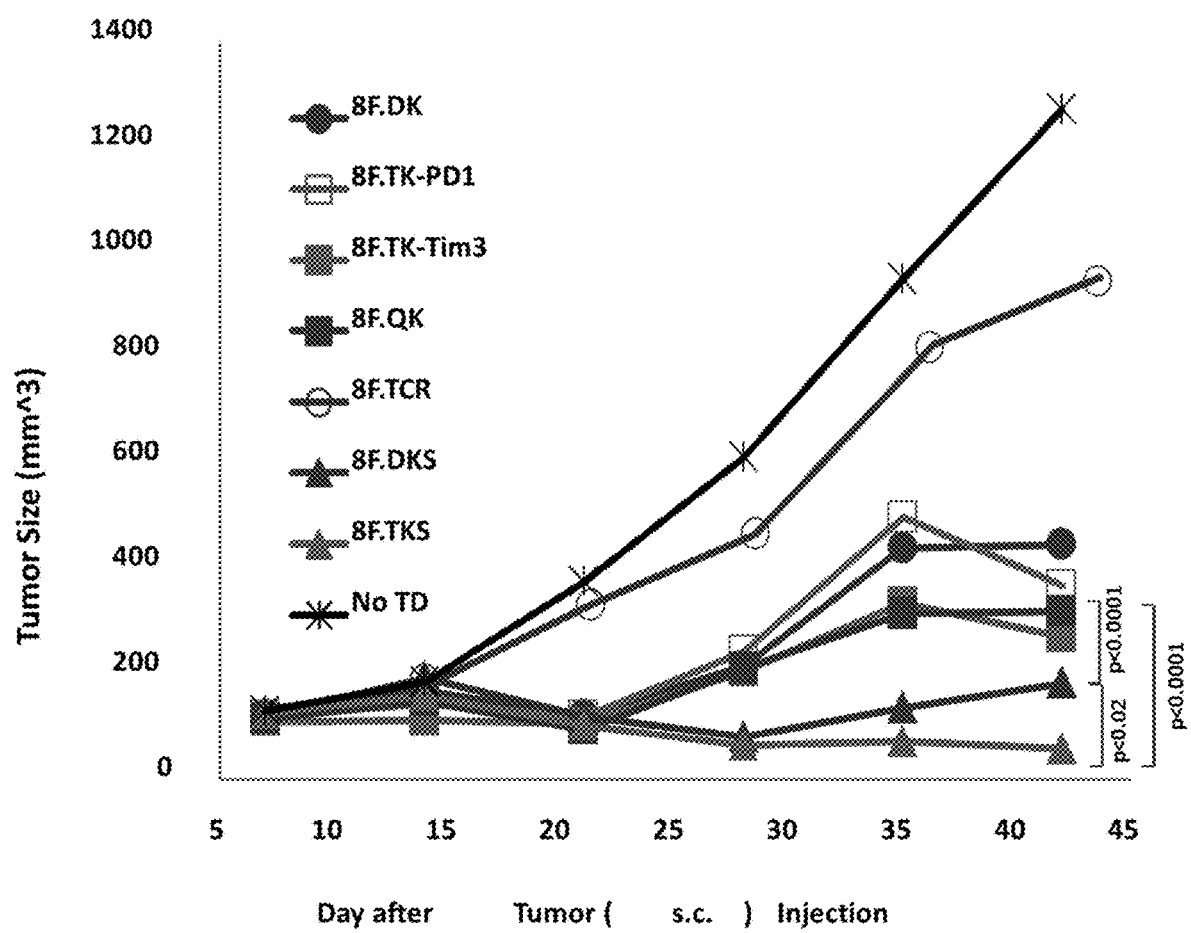
FIGS. 29A-29B depict data showing further efficacy in disrupting TIM-3.
Figure 29B:
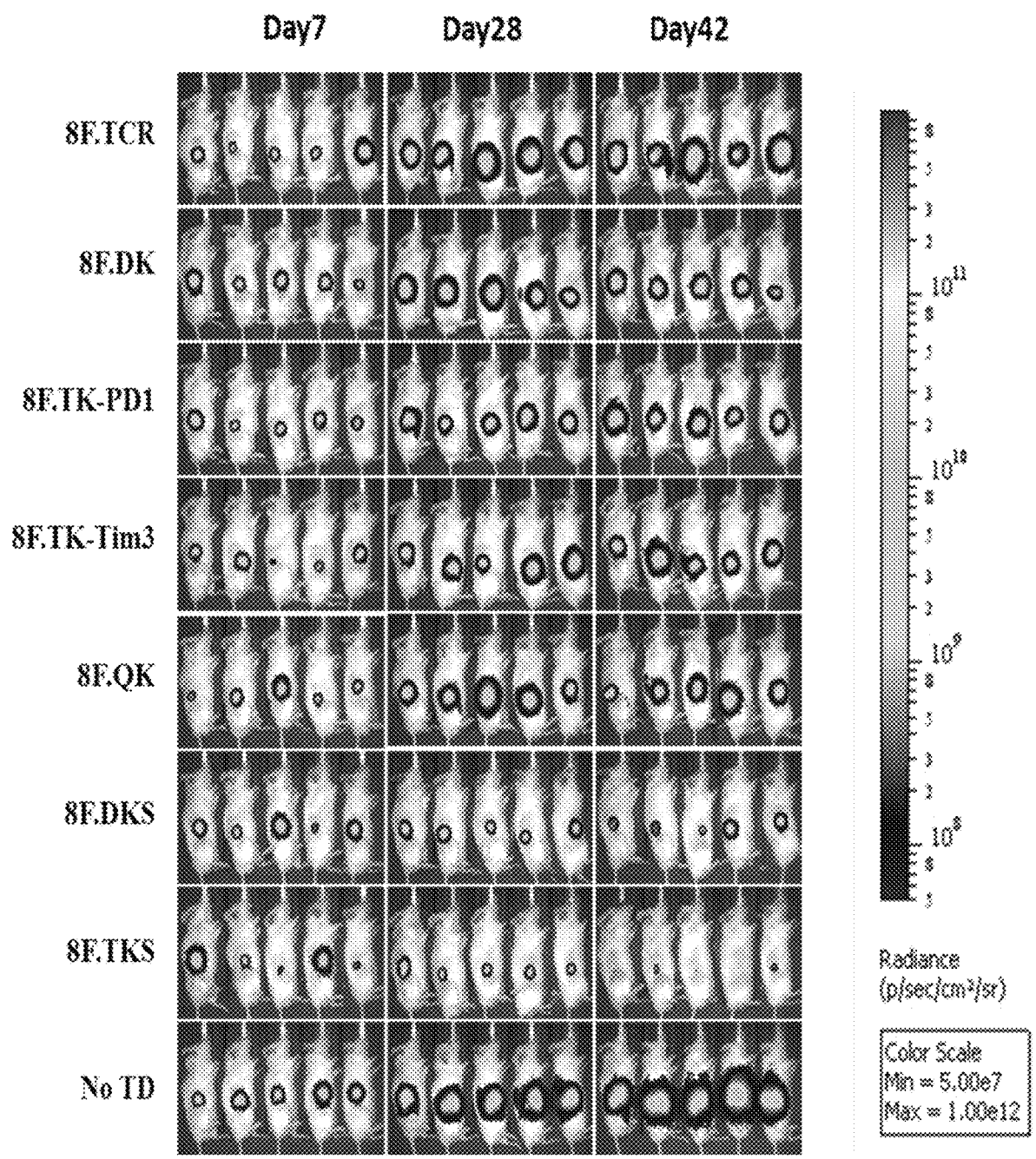

TIM-3 CRISPR disruption shows further efficacy (FIGS. 29A-29B). FIG. 29A shows a graph of tumor size of mice challenged with A549-ESO tumor (n=5) and treated with: TRAC/TRBC disrupted T cells transduced with 8F NY-ESO-1 TCR (8F.DK), TRAC/TRBC/PD1 disrupted T cells transduced with 8F NY-ESO-1 TCR (8F.TK-PD1), TRAC/TRBC/TIM-3 disrupted T cells transduced with 8F NY-ESO-1 TCR (8F.TK-Tim3), TRAC/TRBC/PD1/TIM-3 disrupted T cells transduced with 8F NY-ESO-1 TCR (8F.QK), T cells transduced with 8F NY-ESO-1 TCR (8F.TCR), TRAC/TRBC disrupted T cells transduced with 8F NY-ESO-1 TCR and PD1-CD28 switch receptor (8F.DKS), or TRAC/TRBC/TIM-3 disrupted T cells transduced with 8F NY-ESO-1 TCR and PD1-CD28 switch receptor (8F.TKS). No TD: non-transduced T cells. FIG. 29B shows bioluminescence imaging (BLI) of the treated mice.

Improved anti-tumor function of NY-ESO-1 TCR transduced T cells with PD1-CD28 switch receptor was found to be associated with significant gene expression profile changes (FIGS. 30A-30C). FIG. 30A shows the number of tumor infiltrating lymphocytes (TILs) isolated from mice with different treatments (n=3). Cont.: control; DK: treatment with TRAC/TRBC disrupted T cells transduced with 8F TCR; TK: treatment with TRAC/TRBC/PD1 disrupted T cells transduced with 8F TCR; DKS: TRAC/TRBC disrupted T cells transduced with 8F TCR and PD1-CD28 switch receptor. FIG. 30B shows the expression of CD137 of the TILs stimulated by A549-ESO tumor line. FIG. 30C shows the IFN-gamma secretion of the TILs stimulated with A549-ESO tumor line.

Figure 31A:
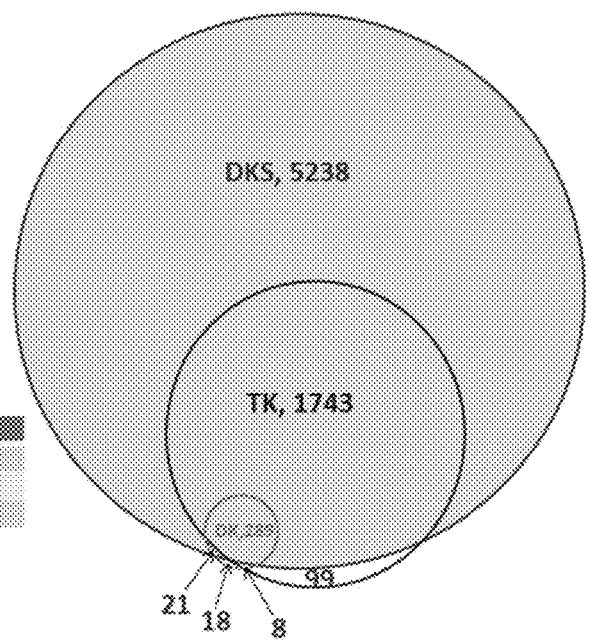
Figure 31B:
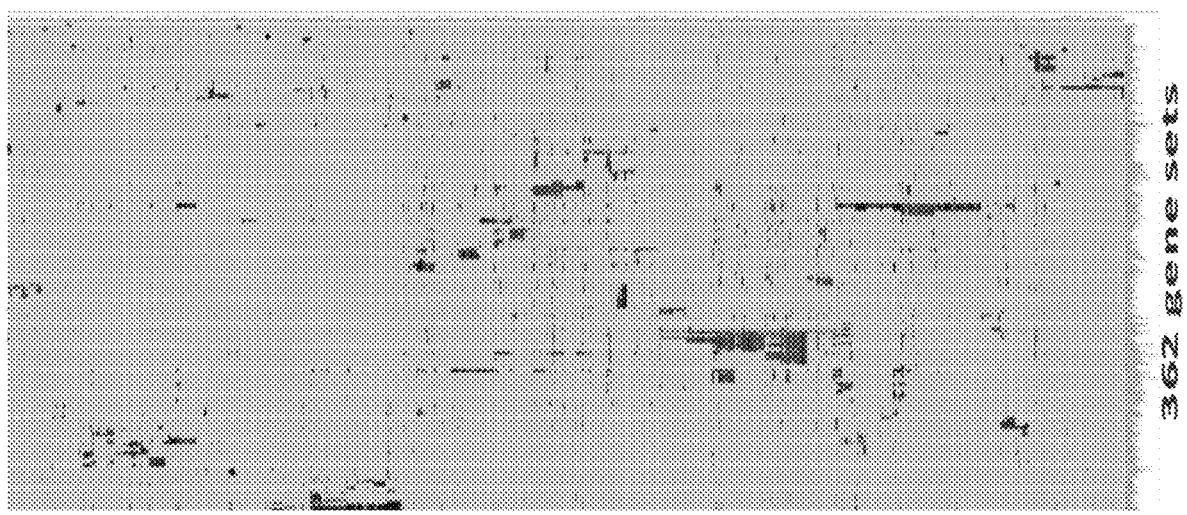
Figure 31D:
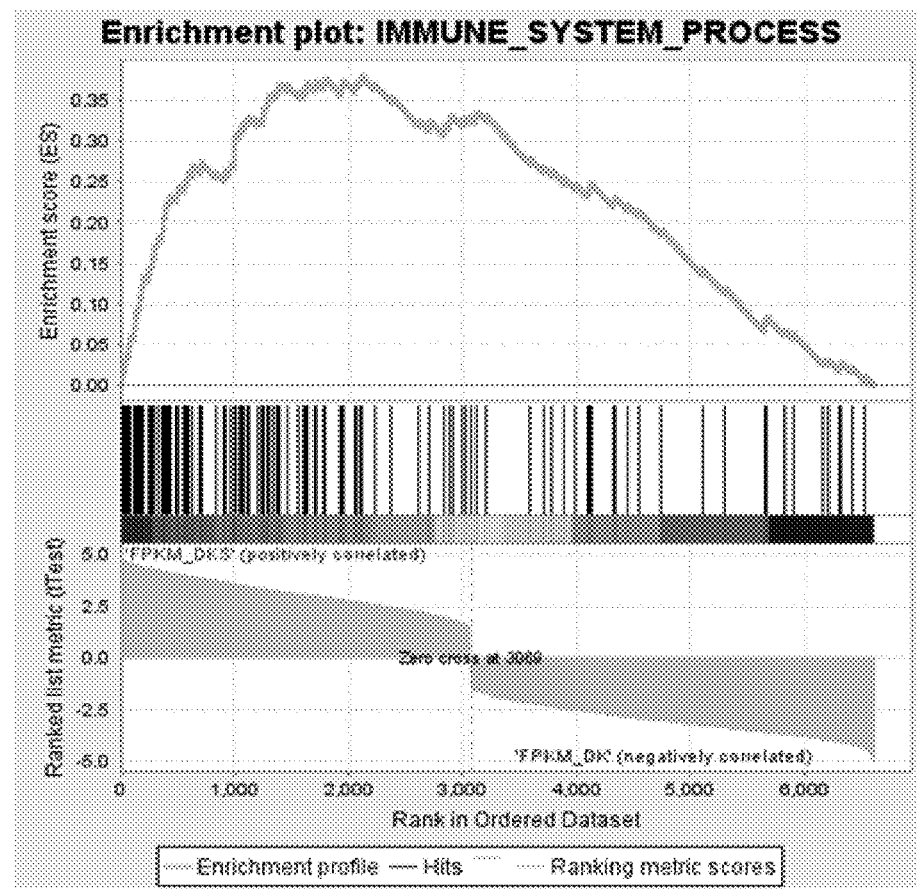
Figure 31E:
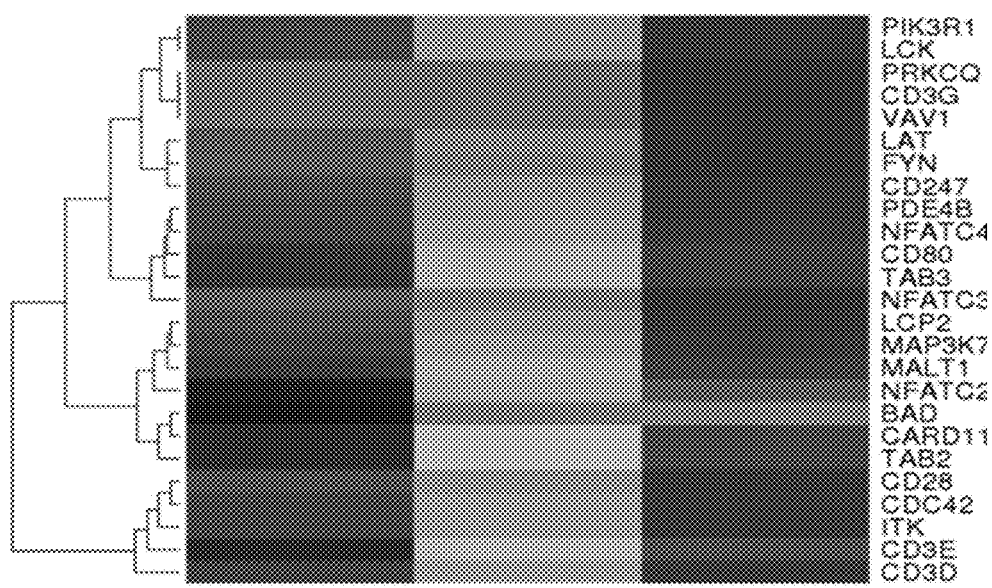
Figure 31F:
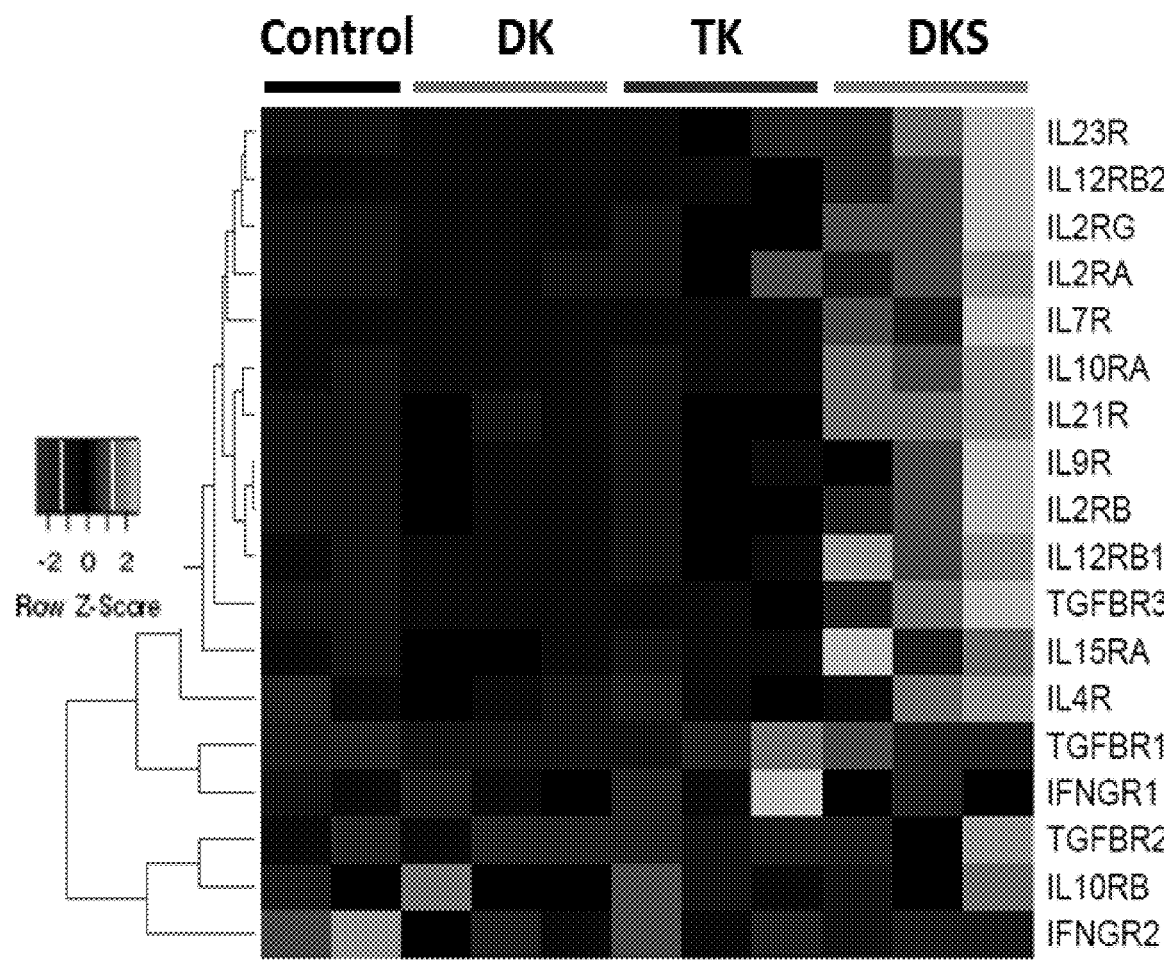

RNA-seq data showed massive gene expression profile changes in T cell activation, CD28 costimulatory signaling for PD1-CD28 NY-ESO-1 T cells with TRAC/TRBC double disruption (FIGS. 31A-31F). FIG. 31A provides an overview of the differentially expressed genes obtained from RNA-seq results. FIG. 31B shows the Gene Set Enrichment Analysis comparing TRAC/TRBC disrupted T cells transduced with 8F and PD1-CD28 switch (DKS) and TRAC/TRBC disrupted T cells transduced with 8F (DK). The Gene Set Enrichment Analysis revealed 1790 enriched genes involved in 362 gene sets. FIG. 31C shows that immune responses, T cell activation, nucleic acid metabolic processes, gene synthesis/expression, and cell cycle are among the top 20 ranked pathways. FIG. 31D shows Gene Set Enrichment Analysis of DK versus DKS for immune system process pathway. FIG. 31E shows a heat map for CD28 pathway associated genes. FIG. 31F shows a heat map for cytokine receptors that associate with T cell function. TK: TRAC/TRBC/PD1 disrupted T cells transduced with 8F TCR.

Figure 31H:
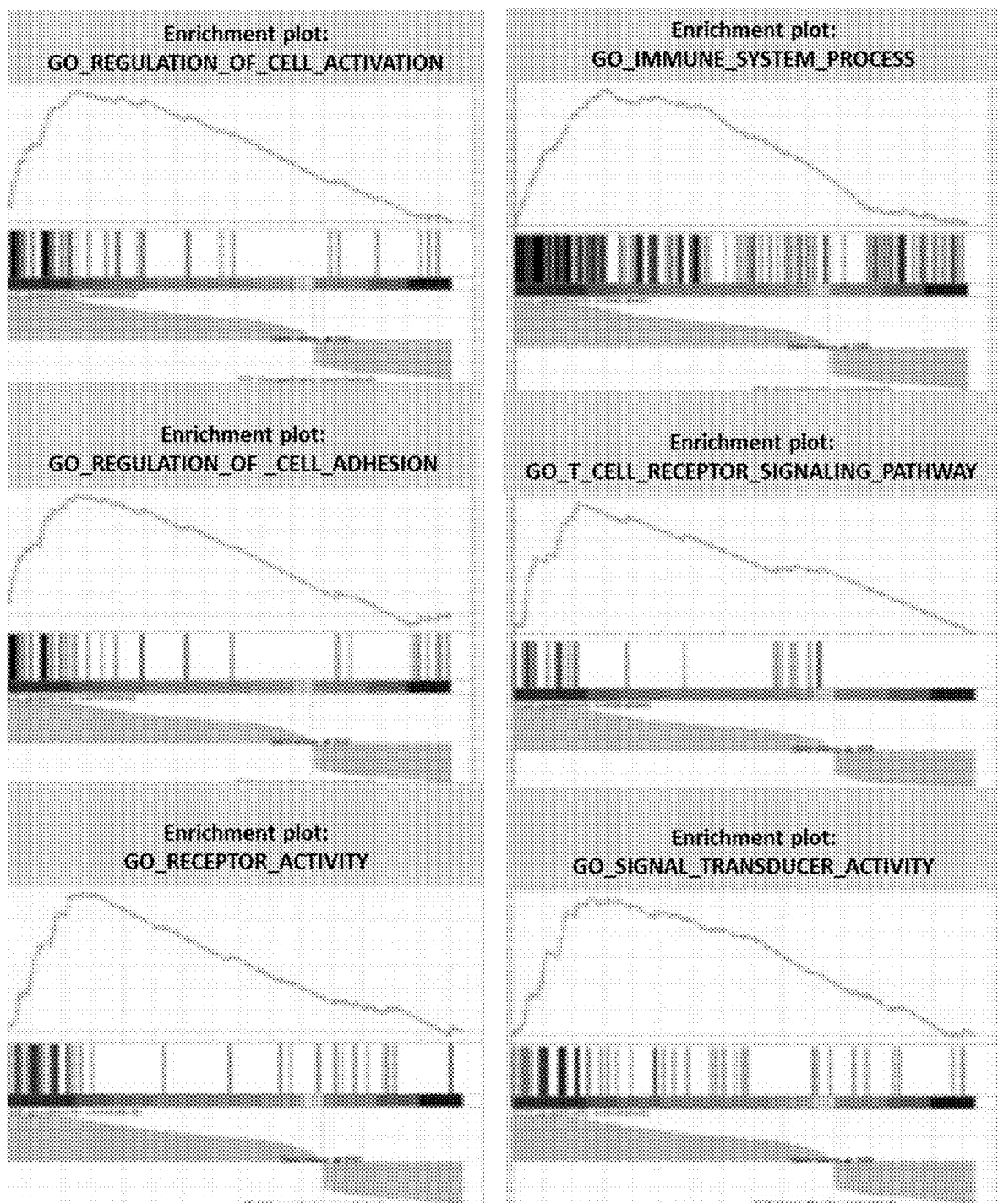

FIGS. 31G and 31H show that tumor-infiltrating lymphocytes (TILs) expressing NY-ESO-1 TCR and PD1-CD28 switch exhibit a unique distribution of gene expression. FIG. 31G shows the distribution of various TILs as indicated in an A549 tumor slice. As shown, NY-ESO-1 TILs expressing PD1-CD28 switch has higher distribution on the right side of the tumor slice. The bottom image is an overlay of all four distributions. DK: NY-ESO-1 TCR T cells with TRAC/TRBC disrupted; TK-PD1: NY-ESO-1 TCR T cells with TRAC/TRBC/PDCD1 disrupted; DKS: NY-ESO-1 TCR T cells with TRAC/TRBC disrupted and expressing PD1-CD28 switch; NTD: non-transduced. FIG. 31H shows Gene Set Enrichment Analysis of DK versus DKS for regulation of cell activation, immune system process, regulation of cell-cell adhesion, T cell receptor signaling pathway, receptor activity, and signal transducer activity as indicated.

Figure 32B:
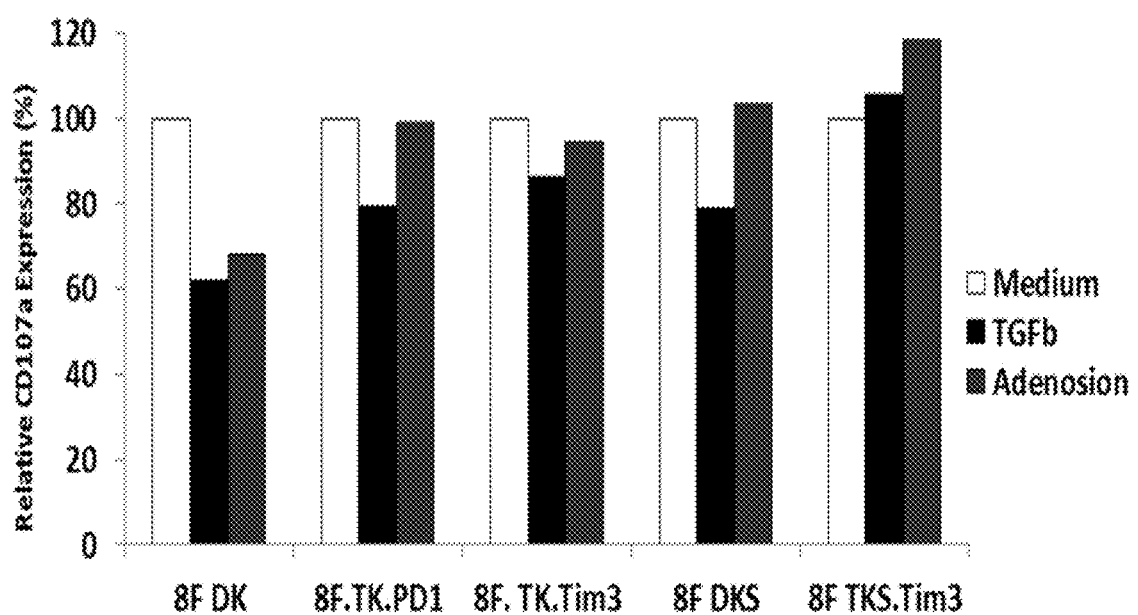

Example 3: PD1-CD28 Switch Receptor Boosts NY-ESO-1 TCR T Cell Function Through Evading Suppression from Tumor Microenvironment Transforming growth factor β (TGFβ) and adenosine are known immunosuppressive signals that reside within the tumor microenvironment. As shown in FIGS. 32A-32B, T cells transduced with NY-ESO-1 TCR (8F) and PD1-CD28 switch receptor exhibit increased resistance to TGFβ and adenosine, as compared to non-PD1-CD28 switch receptor transduced T cells. FIG. 32A shows the resistance to TGFβ and resistance to adenosine inhibition of NY-ESO-1 TCR T cells. FIG. 32B shows the expression of CD107a in different T cells stimulated with A549-ESO tumor line, in the presence of either TGFβ or Adenosine. 8F DK: TRAC/TRBC disrupted T cells transduced with 8F TCR; 8F.TK.PD1: TRAC/TRBC/PD1 disrupted T cells transduced with 8F TCR; 8F.TK.Tim3: TRAC/TRBC/TIM-3 disrupted T cells transduced with 8F TCR; 8F DKS: TRAC/TRBC disrupted T cells transduced with 8F TCR and PD1-CD28 switch receptor; 8F TKS.Tim3: TRAC/TRBC/TIM-3 disrupted T cells transduced with 8F TCR and PD1-CD28 switch receptor.

Figure 33A:
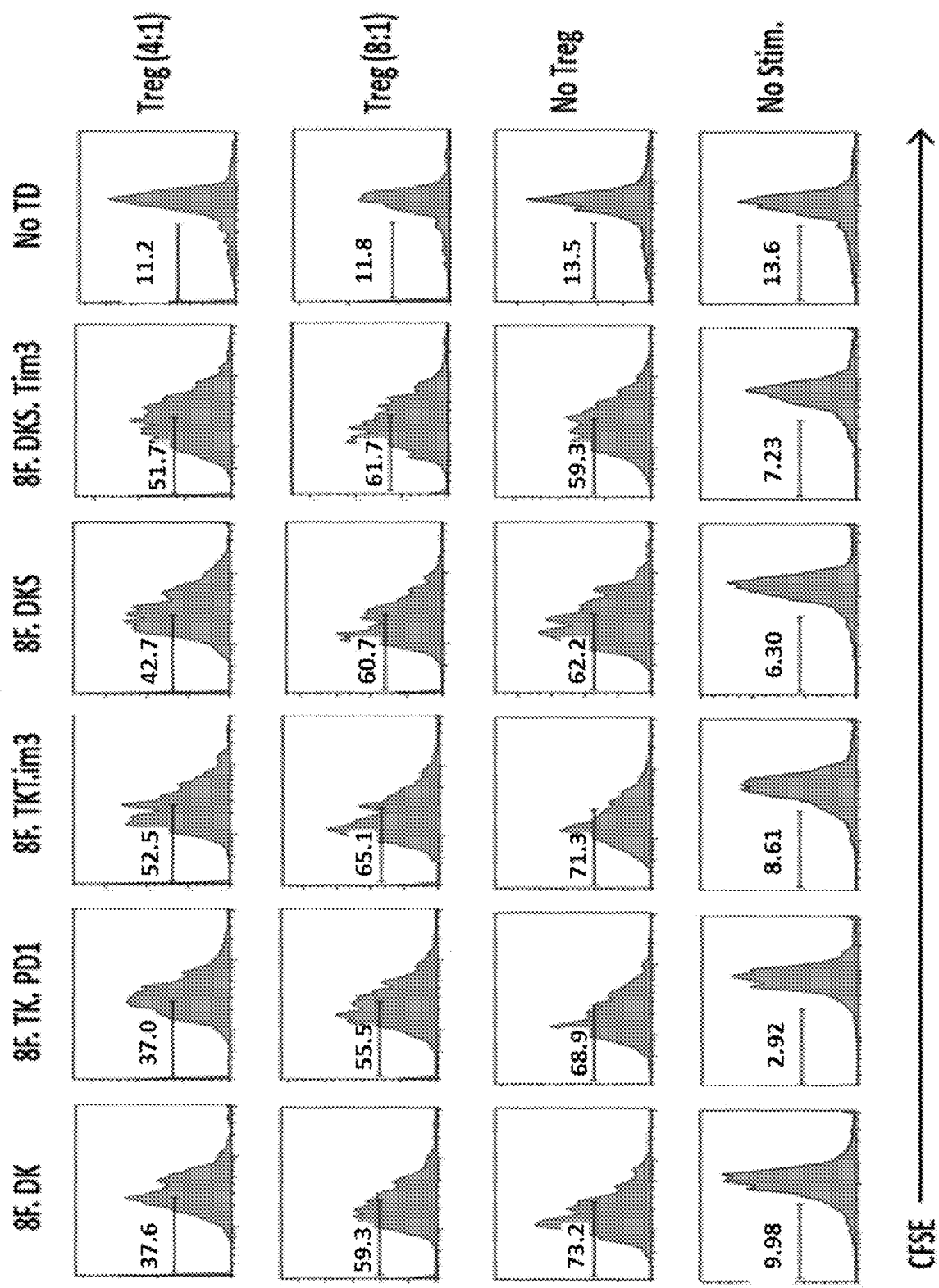
FIGS. 33A-33B depict data showing that T cells transduced with NY-ESO-1 TCR (8F) and PD1-CD28 switch receptor exhibit increased resistance Tregs.
Figure 33B:
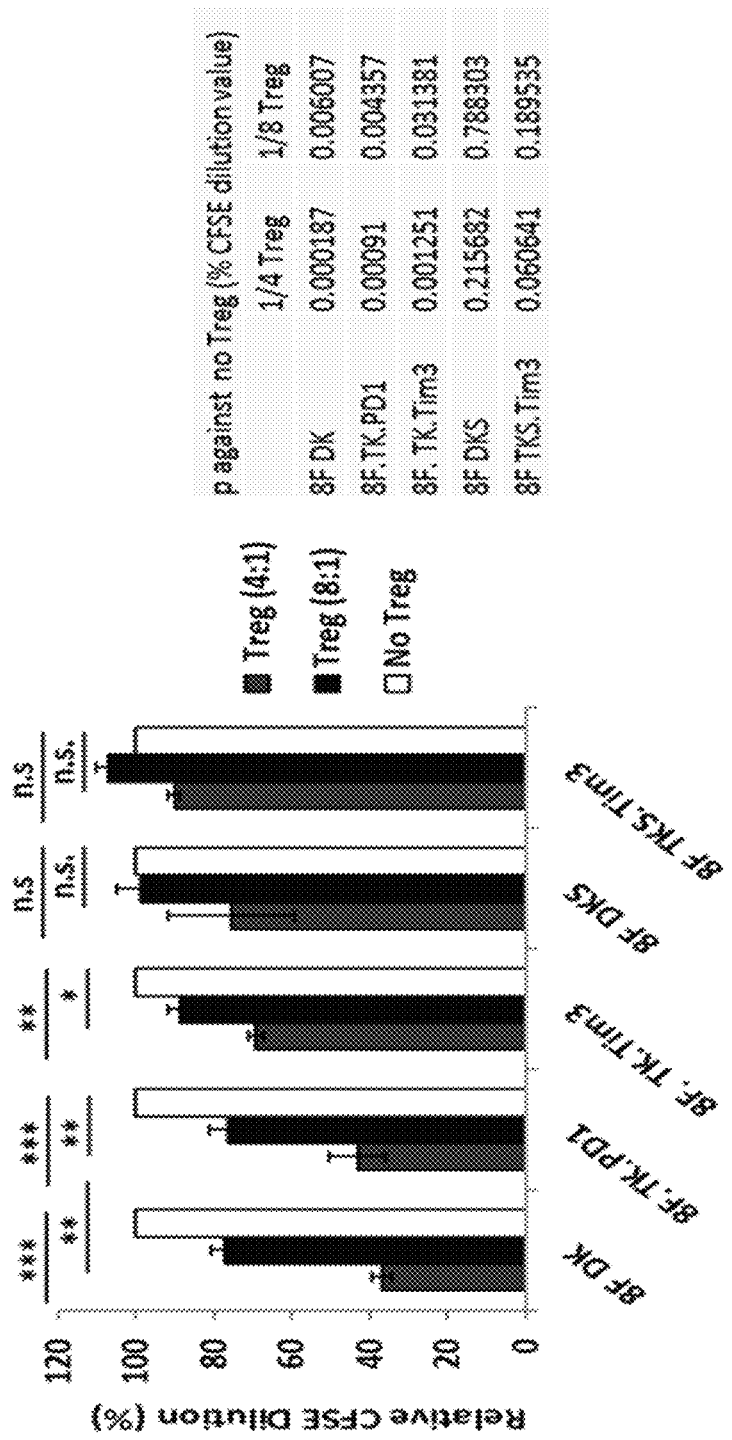

Regulatory T cells (Tregs) are known to inhibit the function of T cells. As shown in FIGS. 33A-33B, 8F DKS cells demonstrate enhanced resistance to Tregs, as compared to 8F DK and 8F.TK.PD1 cells. FIG. 33A shows the resistance to Treg inhibition of NY-ESO-1 TCR T cells. FIG. 33B shows carboxyfluorescein succinimidyl ester (CFSE) dilution of different T cells stimulated with A549-ESO tumor line, in the presence of different amount of Tregs.

Figure 33C:
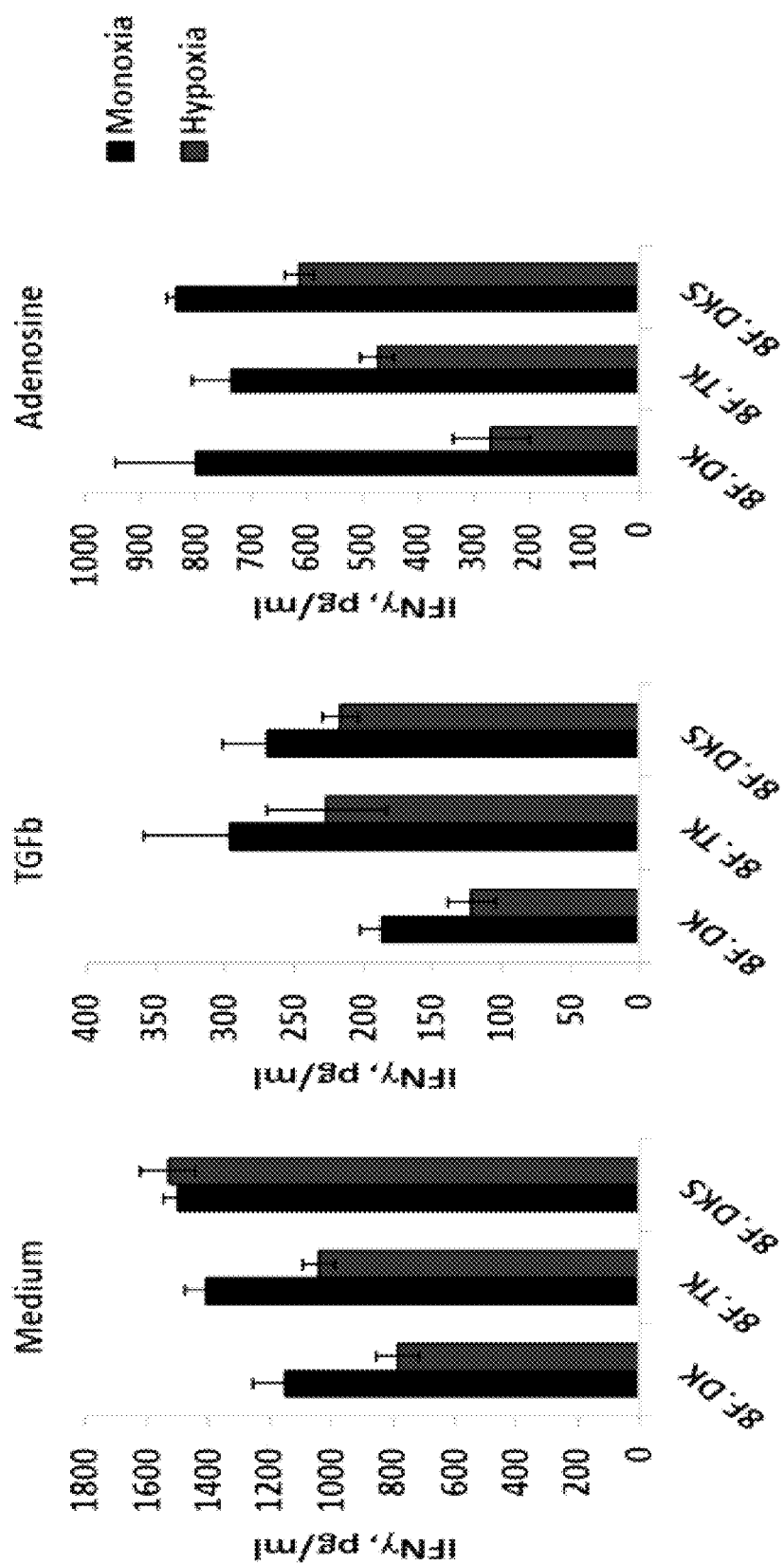
FIG. 33C depicts data demonstrating enhanced resistance of various NY-ESO-1 TCR (8F) T cells as indicated, to hypoxia inhibition.

The PD1-CD28 switch receptor was also found to confer NY-ESO-1 TCR T cells resistance to hypoxia inhibition. FIG. 33C demonstrates enhanced resistance of various 8F T cells (NY-ESO-1 TCR T cells) as indicated to hypoxia inhibition, by measuring IFNγ production in the various media as indicated. 8F.DK indicates 8F NY-ESO-1 TCR T cells with disrupted TRAC and TRBC; 8F.TK indicates 8F NY-ESO-1 TCR T cells with disrupted TRAC, TRBC, and PDCD1; 8F.DKS indicates 8F NY-ESO-1 TCR T cells with disrupted TRAC and TRBC, additionally expressing a switch receptor.

Example 4: TGFβR-IL12R Switch Receptor

Figures 34A, 34B:
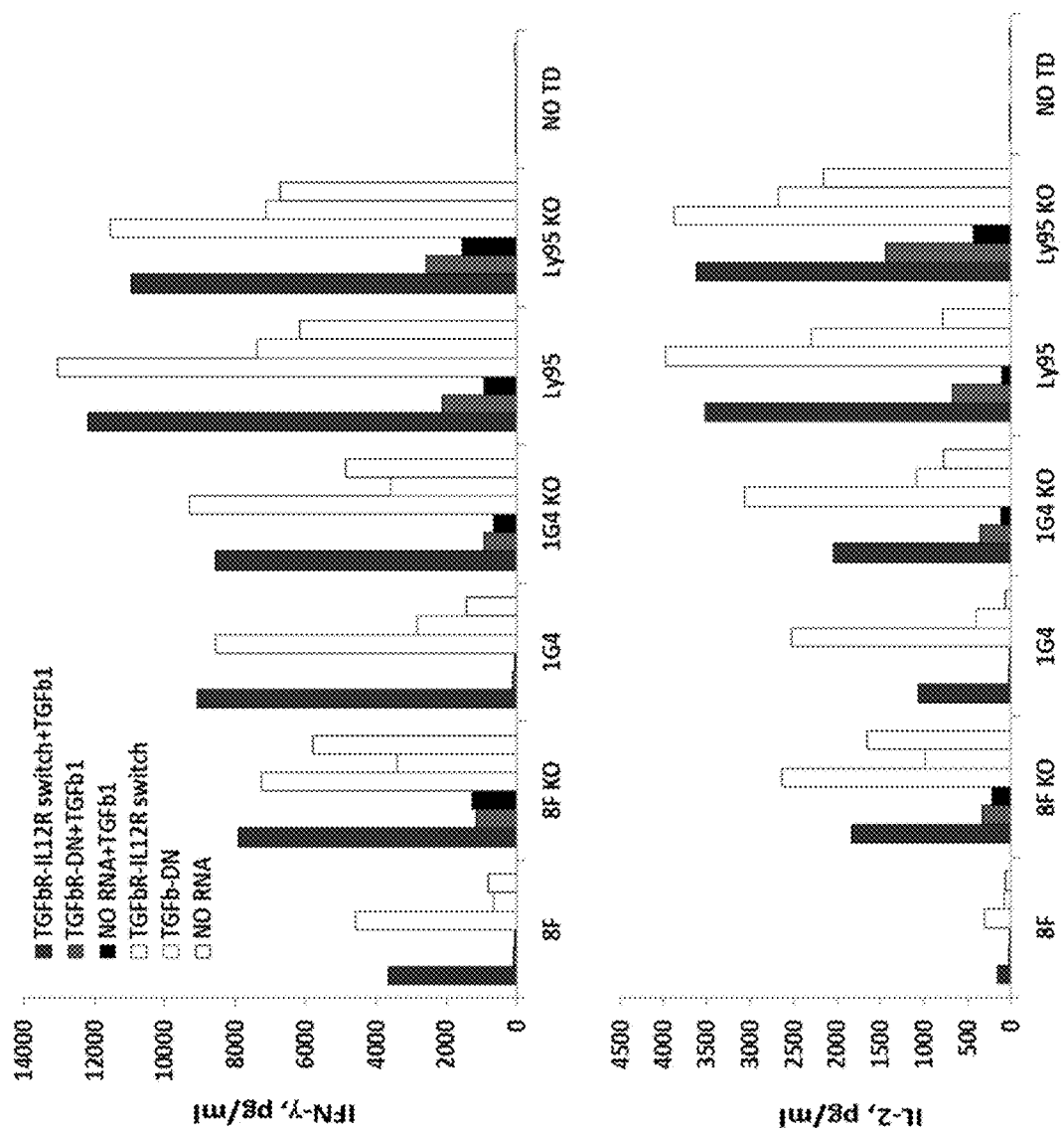
FIGS. 34A-34B depict data showing that a TGFβR-IL12R switch receptor improves NY-ESO-1 TCR transduced T cell function.

A TGFβR-IL12R switch receptor also further improves NY-ESO-1 TCR transduced T cell function. A TGFβR-IL12R switch receptor was found to boost T cell function (FIGS. 34A-34B). FIG. 34A shows a schematic of the TGFβR-IL12R switch receptor. FIG. 34B shows the level of cytokine production of different NY-ESO-1 TCR transferred T cells that were co-transferred with TGFβR-IL12R switch receptor, or dominant negative TGFβR(DN), in the presence or absence of TGFβ1.

Example 5: High Affinity PD1 Switch Receptor Enhances NY-ESO-1 TCR T Cell Function Several switch receptors were generated using methods known in the art, and using sequences described elsewhere herein. The high affinity PD1 switch receptor, PD1$^{A132L}$-41BB, comprises a variant PD1 extracellular domain having an A132L substitution relative to the full length amino acid sequence of PD1, a CD8alpha transmembrane domain, and a 4-1BB cytoplasmic domain. The PD1 A132L substitution increases its affinity for PD-L1. See, e.g., Zhang et al. Immunity 2004, 20:337-347. PD1-41BB, TIM3-CD28 and PD1$^{A132L}$-CD28 switch receptors were also generated using methods known in the art, and using sequences described elsewhere herein.

Figure 35B:
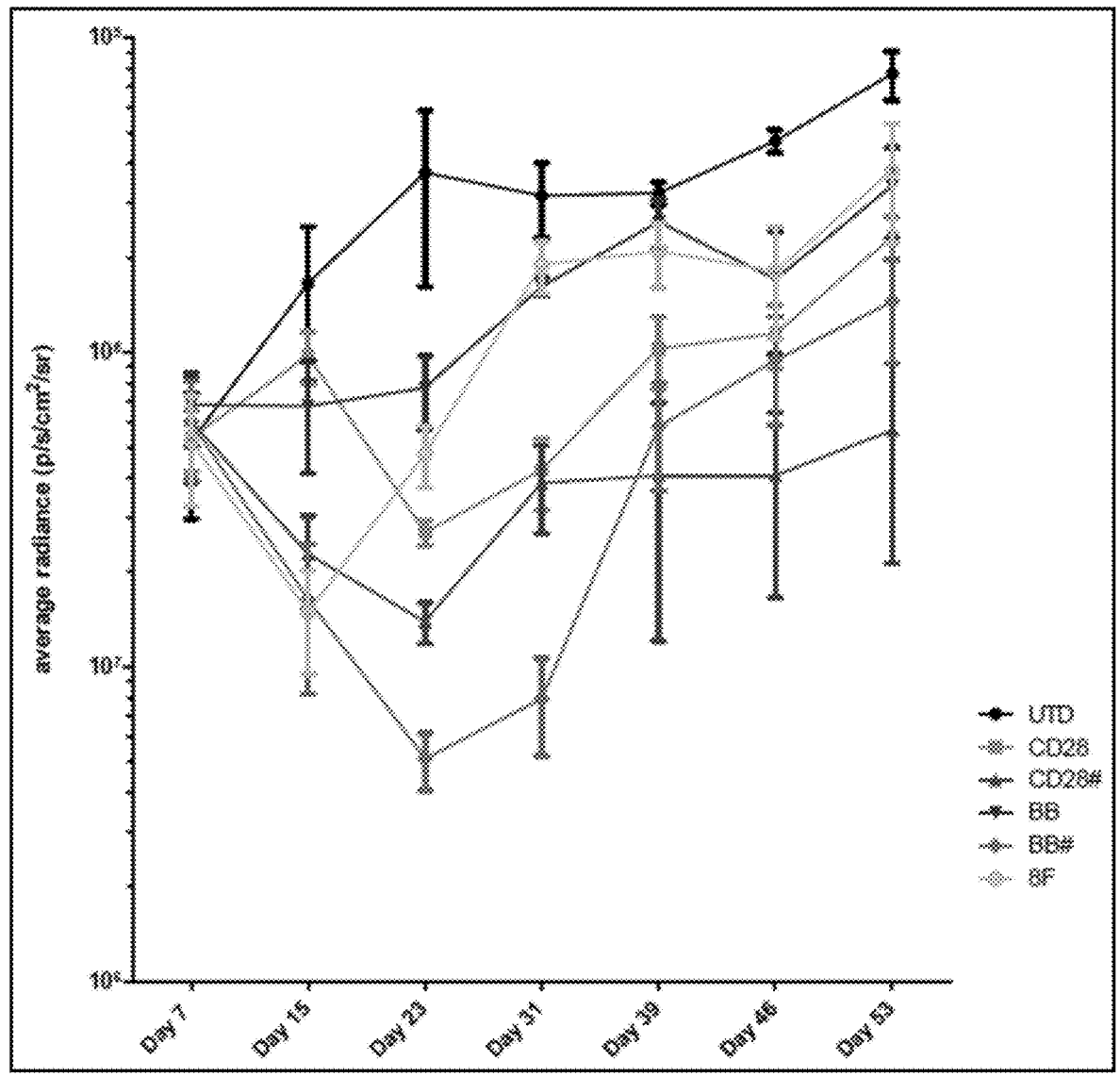
Figure 35C:
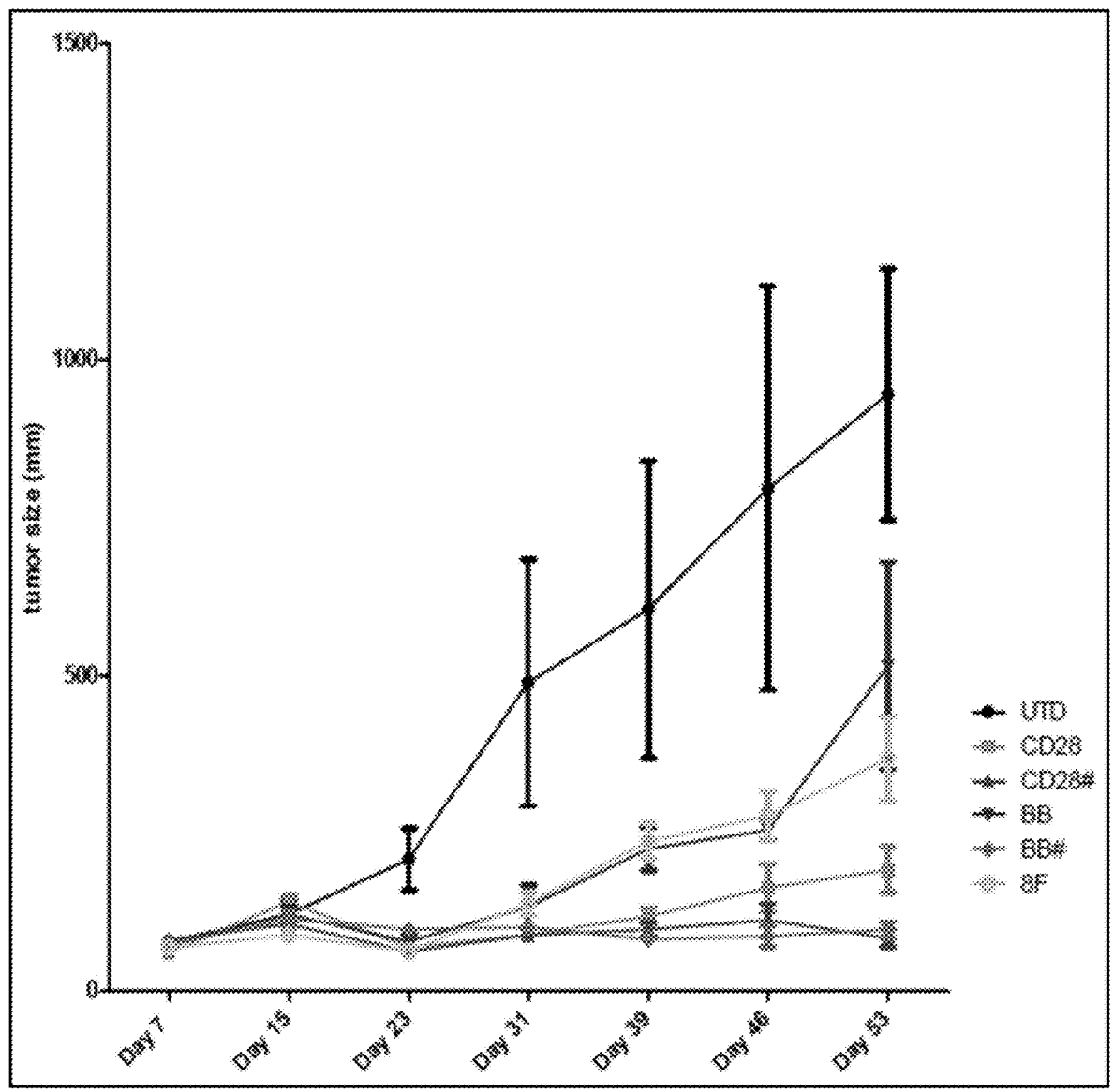

$5 \times 10^6$ tumor (A549ESO) cells in Matrigel™ were injected (s.c.) on day 0. On day 8, $10 \times 10^6$ 8F-Vβ8 positive T cells were injected intravenously. Tumor growth was monitored by bioluminescence imaging (BLI) weekly. NY-ESO-1 TCR (8F) positive T cells had the following phenotypes: NY-ESO-1 TCR (8F) only; NY-ESO-1 TCR (8F) and PD1.CD28 switch (PD1-CD28); NY-ESO-1 TCR (8F) and PD1*.CD28 switch (PD1$^{A132L}$-CD28); NY-ESO-1 TCR (8F) and PD1.BB switch (PD1-41BB); or NY-ESO-1 TCR (8F) and PD1*.BB switch (PD1$^{A132L}$-41BB). Untransduced T cells (UTD) were used as a control. In FIG. 35A, BLI of mice injected with T cells as indicated shows that the high affinity PD1 switches (i.e., PD1*.CD28 and PD1*.BB) enhance the anti-tumor activity of NY-ESO-1 redirected T cells. FIG. 35B shows the quantification of average radiance for the indicated groups. FIG. 35C shows a plot of tumor size measured weekly post-injection with T cells for the various groups as indicated. UTD: untransduced; CD28: NY-ESO-1 TCR (8F) and PD1.CD28 switch (PD1-CD28); CD28 #: NY-ESO-1 TCR (8F) and PD1*.CD28 switch (PD1$^{A132L}$-CD28); BB: NY-ESO-1 TCR (8F) and PD1.BB switch (PD1-41BB); or BB #: NY-ESO-1 TCR (8F) and PD1*.BB switch (PD1$^{A132L}$-41 BB).

Figure 36A:
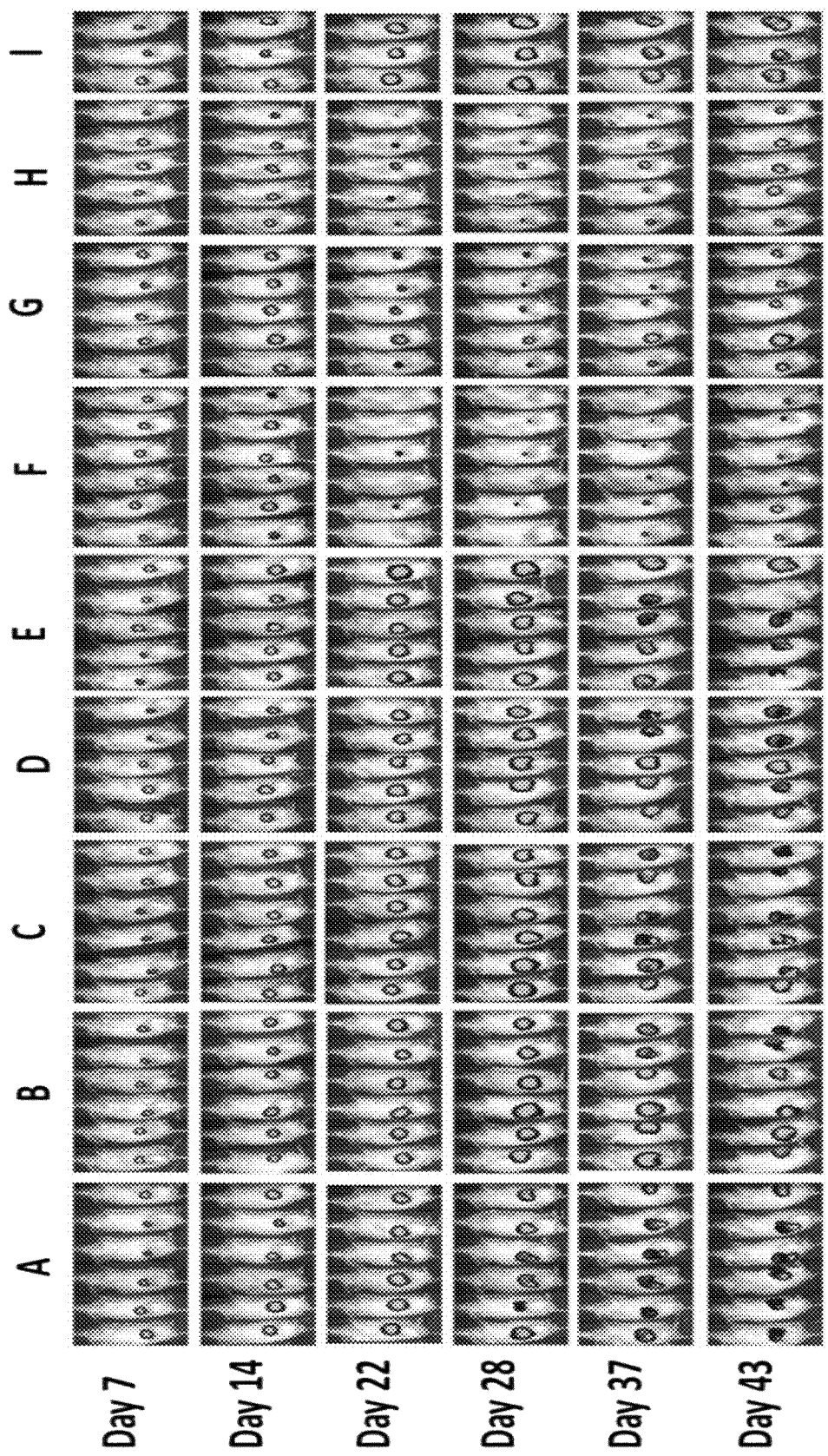
FIGS. 36A-36E depict data showing that a high affinity PD1 switch receptor enhances NY-ESO-1 TCR anti-tumor activity.
Figure 36B:
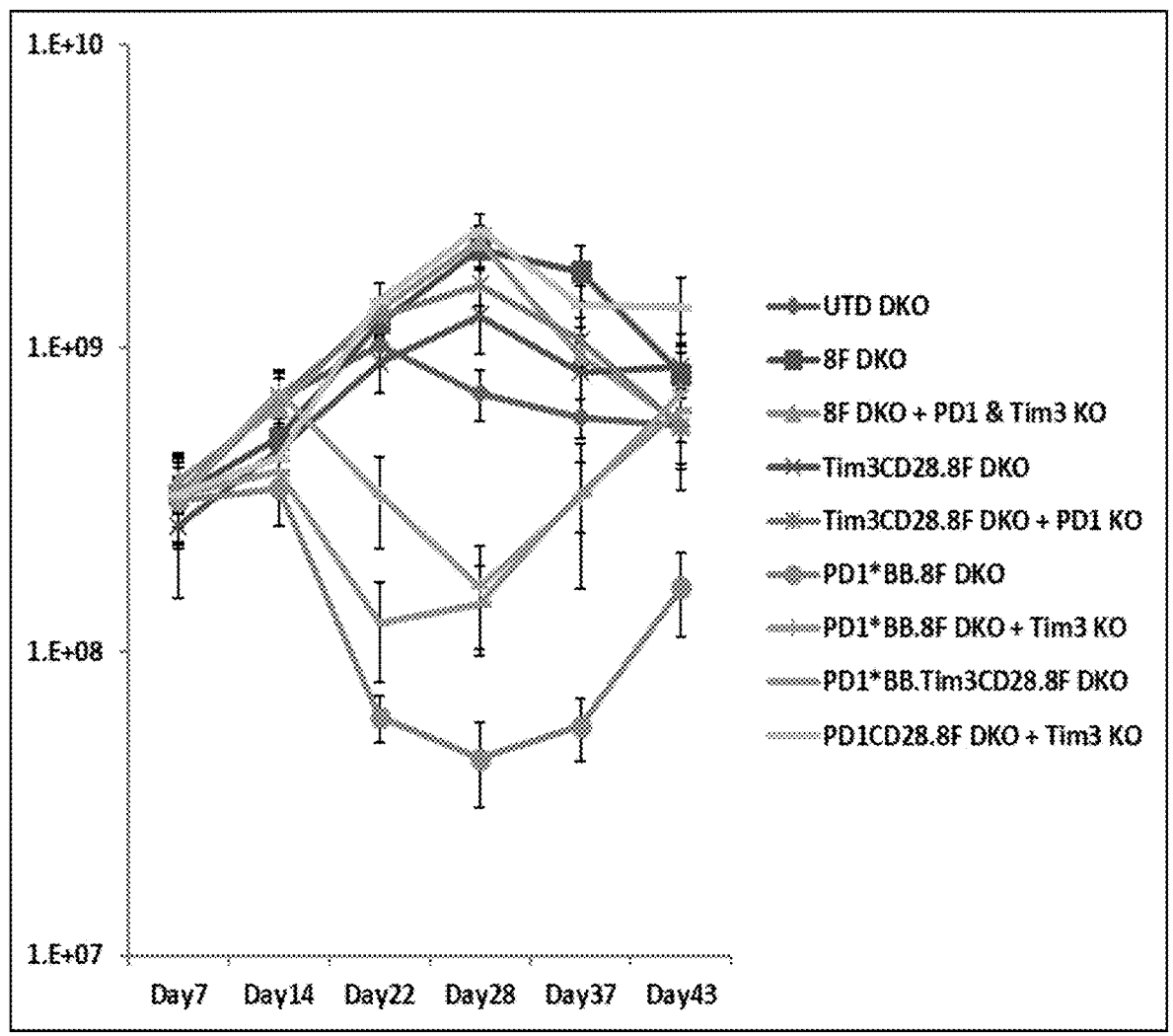
Figure 36C:
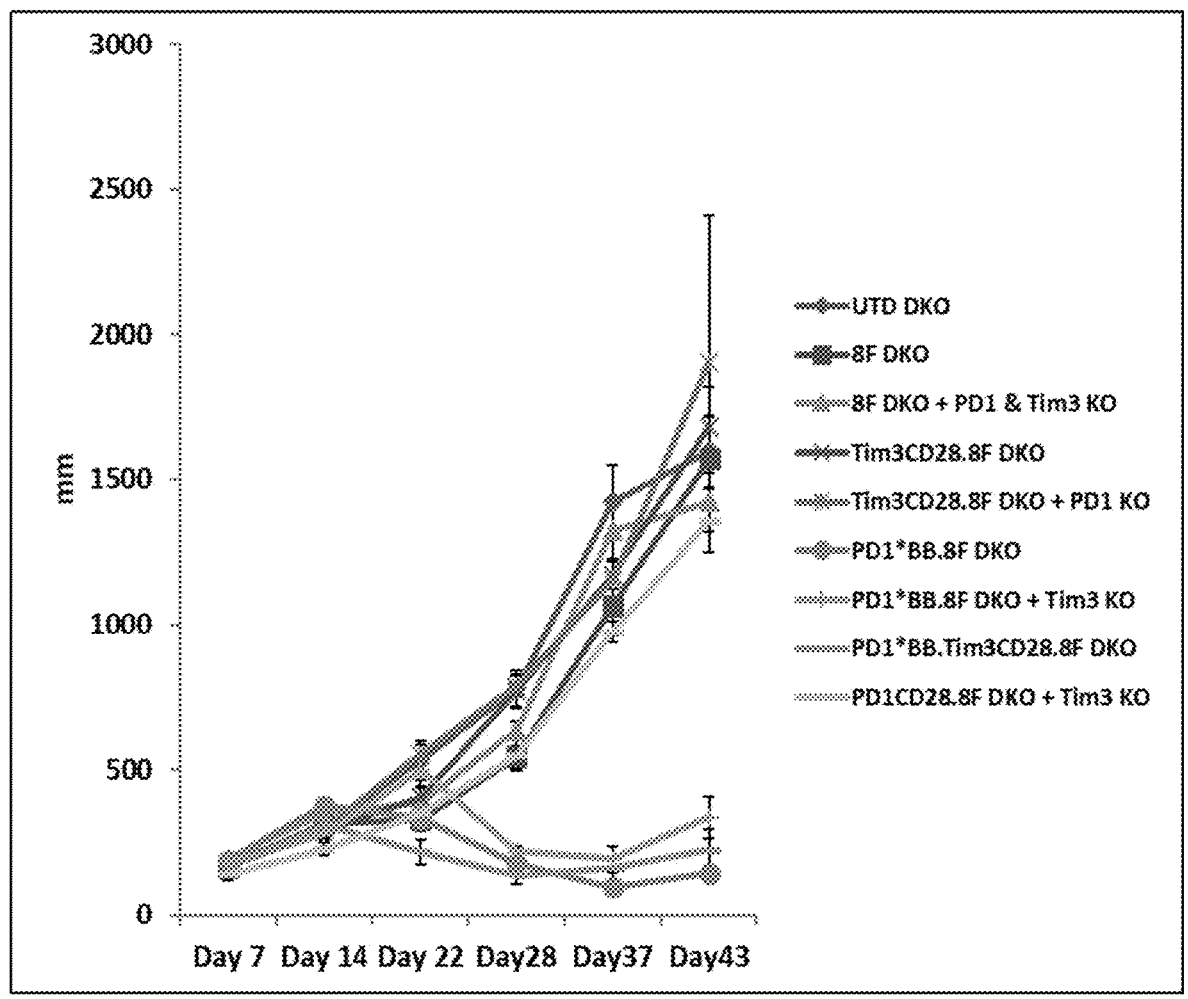
Figure 36D:
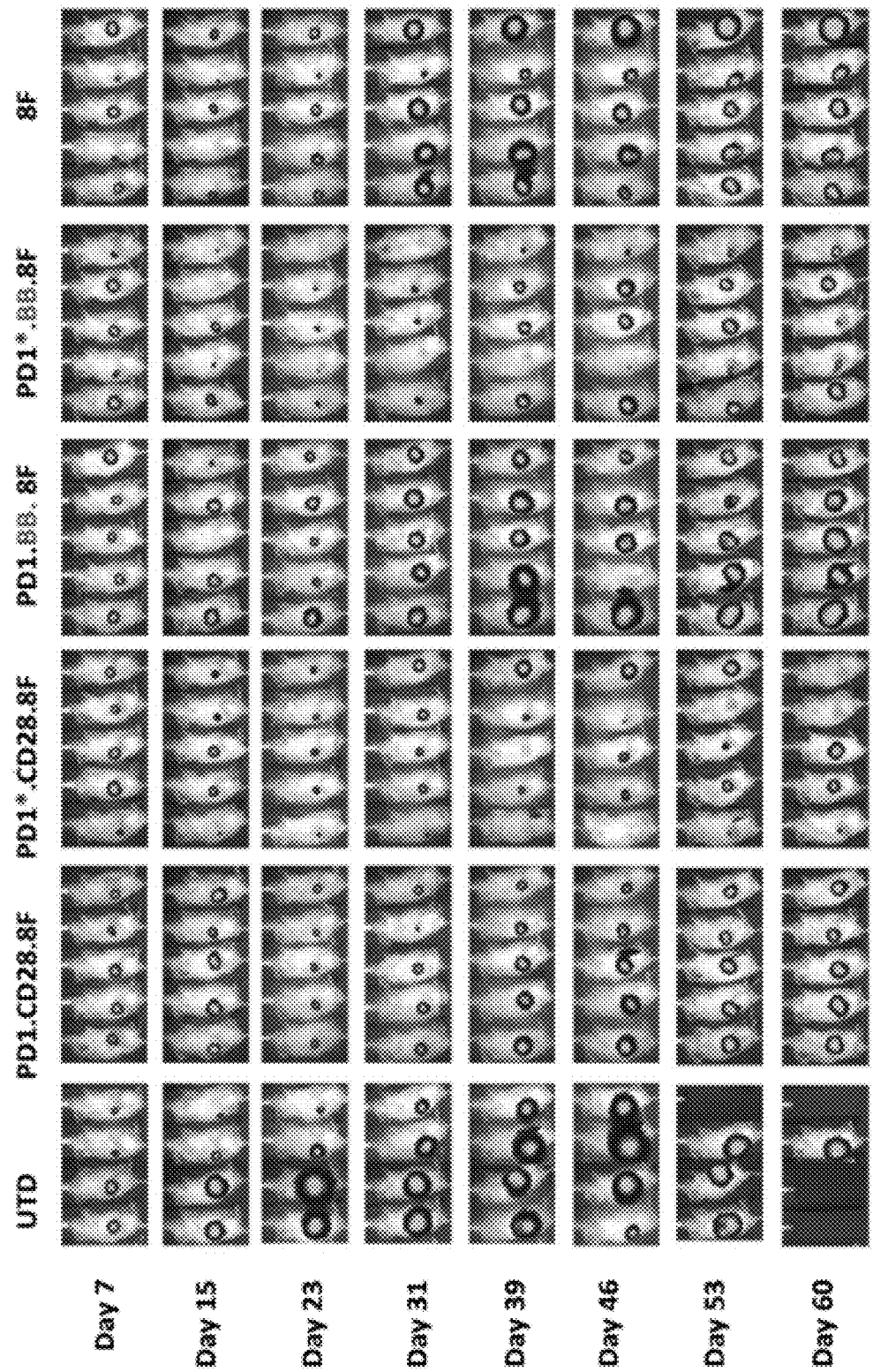
Figure 36E:
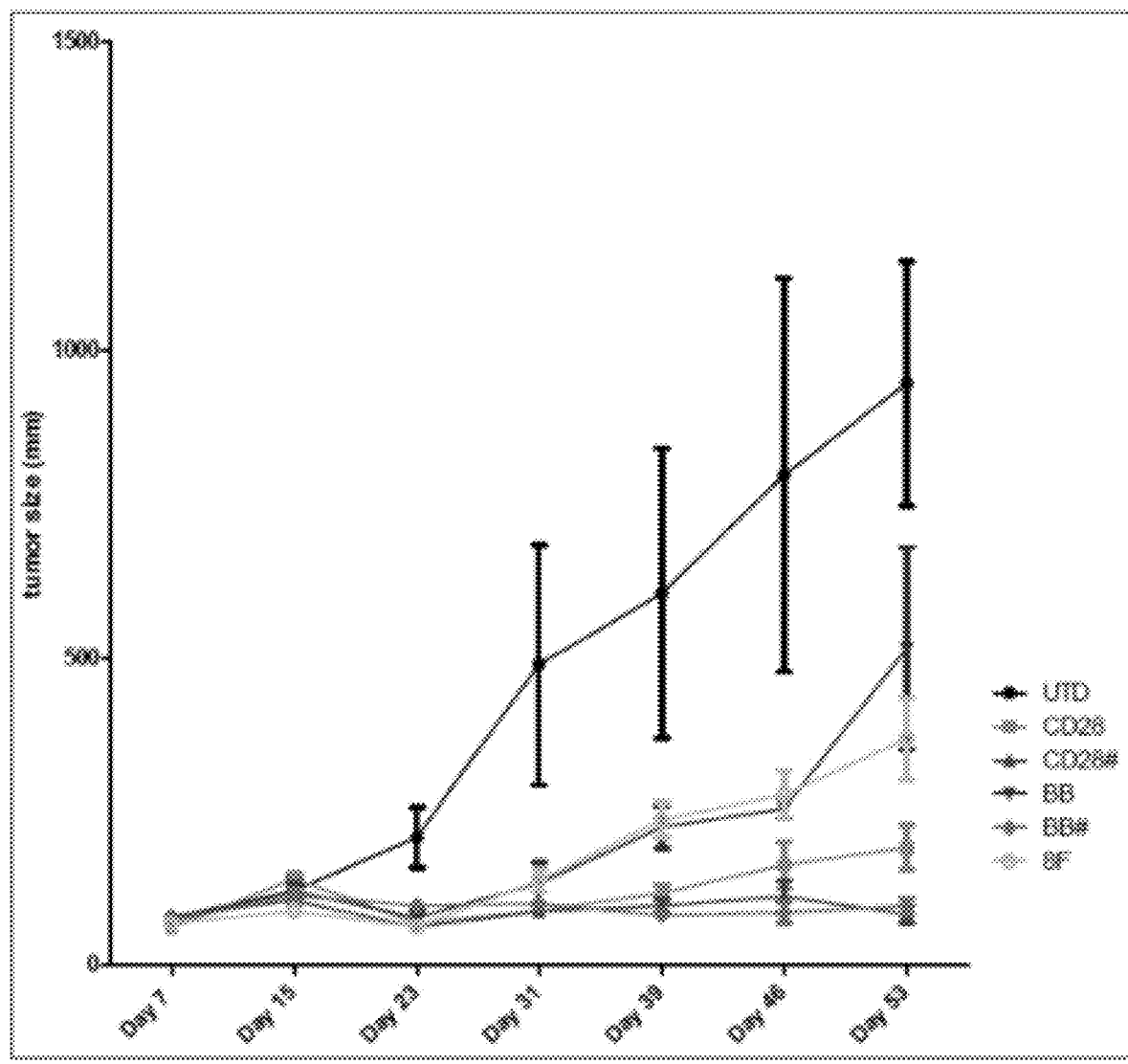

In FIG. 36A, BLI of mice injected with T cells as indicated showed that the high affinity PD1 switches (i.e., PD1*.CD28 and PD1*.BB) enhanced the anti-tumor activity of NY-ESO-1 redirected T cells. FIG. 36B shows the quantification of average radiance for the indicated groups. FIG. 36C shows a plot of tumor size measured weekly post-injection with T cells for the various groups as indicated. The various groups are as follows: from top to bottom, A: untransduced, TRAC/TRBC disrupted T cells (UTD DKO); B: NY-ESO-1 TCR (8F), TRAC/TRBC disrupted T cells (8F DKO); C: NY-ESO-1 TCR (8F), TRAC/TRBC/PDCD1/TIM3 disrupted T cells (8F DKO+PD1 & Tim3 KO); D: NY-ESO-1 TCR (8F), TIM3-CD28 switch, TRAC/TRBC disrupted T cells (Tim3CD28.8F DKO); E: NY-ESO-1 TCR (8F), TIM3-CD28 switch, TRAC/TRBC/PDCD1 disrupted T cells (Tim3CD28.8F DKO+PD1 KO); F: NY-ESO-1 TCR (8F), PD1$^{A132L}$-41BB switch, TRAC/TRBC disrupted T cells (PD1*BB.8F DKO); G: NY-ESO-1 TCR (8F), PD1$^{A132L}$-41BB switch, TRAC/TRBC/TIM3 disrupted T cells (PD1*BB.8F DKO+Tim3 KO); H: NY-ESO-1 TCR (8F), PD1$^{A132L}$-41BB switch, TIM3-CD28 switch, TRAC/TRBC disrupted T cells (PD1*BB.Tim3CD28.8F DKO); and I: NY-ESO-1 TCR (8F), PD1-CD28 switch, TRAC/TRBC/TIM3 disrupted T cells (PD1CD28.8F DKO+Tim3 KO). FIG. 36D shows BLI of mice injected with T cells as indicated, demonstrating that high affinity PD1 switch receptors enhanced 8F NY-ESO-1 TCR re-directed anti-tumor activity. FIG. 36E shows a plot of tumor size measured at various time points as indicated post-injection with T cells for the various groups as indicated. In FIGS. 36D and 36E, UTD: untransduced T cells; PD1.CD28.8F (CD28 in FIG. 36E): 8F NY-ESO-1 TCR T cells with PD1-CD28 switch; PD1*.CD28.8F (CD28 # in FIG. 36E): 8F NY-ESO-1 TCR T cells with PD1$^{A132L}$-CD28 switch; PD1.BB.8F (BB in FIG. 36E): 8F NY-ESO-1 TCR T cells with PD1-41BB switch; PD1*.BB.8F (BB # in FIG. 36E): 8F NY-ESO-1 TCR T cells with PD1$^{A132L}$-41BB switch; 8F: 8F NY-ESO-1 TCR T cells.

---

What is claimed is:

1. A modified T cell comprising:
   (a) an exogenous T cell receptor (TCR) having affinity for NY-ESO-1 on a target cell, wherein the exogenous TCR comprises:
      (i) a TCR α chain comprising a variable region having the amino acid sequence set forth in SEQ ID NO:2; and
      (ii) a TCR β chain comprising a variable region having the amino acid sequence set forth in SEQ ID NO:7;
   (b) an endogenous TCR α chain coding sequence comprising the nucleic acid sequence set forth in SEQ ID NO:128, wherein SEQ ID NO:128 comprises at least one nucleotide substitution, deletion, insertion, or insertion and deletion;
   (c) an endogenous TCR β chain coding sequence comprising the nucleic acid sequence set forth in SEQ ID NO:129, wherein SEQ ID NO:129 comprises at least one nucleotide substitution, deletion, insertion, or insertion and deletion; and
   (d) a switch receptor comprising:
      (i) a first domain comprising at least a portion of the extracellular domain of a human PD-1 comprising an amino acid sequence set forth at positions 1-170 of SEQ ID NO: 134, wherein the human PD-1 is a variant PD-1 comprising an alanine to leucine substitution at amino acid position 132 of SEQ ID NO: 134;
      (ii) a second domain comprising a switch receptor transmembrane domain; and
      (iii) a third domain comprising the intracellular domain of CD28 or 4-1BB;
   wherein the expression of the endogenous TCR α and β chain coding sequences are downregulated;
   wherein the modified T cell exhibits increased resistance to a PD1 immunosuppressive signal or a non-PD1 immunosuppressive signal; enhanced tumor-infiltrating lymphocytes (TIL) infiltration and enhanced secretion of a cytokine selected from CD107, IFNγ, IL-2, or TNF; and
   wherein the non-PD1 immunosuppressive signal is selected from the group consisting of TGFβ, adenosine, Indoleamine 2,3-dioxygenase (IDO), hypoxia, T regulatory cells (Tregs), and combinations thereof.

2. The modified T cell of claim 1, wherein the non-PD1 immunosuppressive signal is T regulatory cells (Tregs).

3. The modified T cell of claim 2, wherein the T cell comprises an endogenous PD1 coding sequence comprising the nucleic acid sequence set forth in SEQ ID NO:130, wherein SEQ ID NO:130 comprises at least one nucleotide substitution, deletion, insertion, or insertion and deletion.

4. The modified T cell of claim 2, wherein
   the switch receptor transmembrane domain comprises at least a portion of the transmembrane domain of CD28; and
   the third domain comprises at least a portion of the intracellular domain of CD28.

5. The modified T cell of claim 2, wherein
   the switch receptor transmembrane domain comprises at least a portion of the transmembrane domain of CD8alpha; and
   the third domain comprises at least a portion of the intracellular domain of 4-1BB.

6. The modified T cell of claim 2, wherein
   the switch receptor transmembrane domain comprising at least a portion of the transmembrane domain of CD8alpha; and
   the third domain comprises at least a portion of the intracellular domain of CD28.

7. The modified T cell of claim 2, wherein the switch receptor comprises the amino acid sequence set forth in any one of SEQ ID NOs: 136 or 138.

8. The modified T cell of claim 1, wherein the modified T cell is an autologous T cell derived from a human.

9. A method of treating a cancer in a subject in need thereof, the method comprising administering a therapeutically effective composition comprising the modified T cell of claim 1 to the subject.

10. The method of claim 9, further comprising administering to the subject a lymphodepleting chemotherapy.

11. The method of claim 10, wherein the lymphodepleting chemotherapy comprises administering to the subject an effective amount of cyclophosphamide, and an effective amount of fludarabine.

12. The method of claim 9, wherein the cancer is selected from the group consisting of multiple myeloma, melanoma, synovial sarcoma, and myxoid/round cell liposarcoma.

13. A modified T cell comprising:
   (a) an exogenous T cell receptor (TCR) having affinity for NY-ESO-1 on a target cell, wherein the exogenous TCR comprises:
      (i) a TCR α chain comprising a variable region having the amino acid sequence set forth in SEQ ID NO:2; and
      (ii) a TCR β chain comprising a variable region having the amino acid sequence set forth in SEQ ID NO:7;
   (b) an endogenous TCR α chain coding sequence comprising the nucleic acid sequence set forth in SEQ ID NO:128, wherein SEQ ID NO:128 comprises at least one nucleotide substitution, deletion, insertion, or insertion and deletion;
   (c) an endogenous TCR β chain coding sequence comprising the nucleic acid sequence set forth in SEQ ID NO:129, wherein SEQ ID NO:129 comprises at least one nucleotide substitution, deletion, insertion, or insertion and deletion;
   (d) an endogenous PD1 coding sequence comprising the nucleic acid sequence set forth in SEQ ID NO:130, wherein SEQ ID NO:130 comprises at least one nucleotide substitution, deletion, insertion, or insertion and deletion; and
   (e) a switch receptor comprising:
      (i) a first domain comprising at least a portion of the extracellular domain of a human PD-1 comprising an amino acid sequence set forth at positions 1-170 of SEQ ID NO: 134, wherein the human PD1 is a variant of human PD-1 comprising an alanine to leucine substitution at amino acid position 132 of SEQ ID NO: 134;
      (ii) a second domain comprising a switch receptor transmembrane domain; and
      (iii) a third domain comprising the intracellular domain of CD28 or 4-1BB;
   wherein the expression of the endogenous TCR α chain, TCR β chain, and PD1 coding sequences are downregulated;
   wherein the modified T cell exhibits increased resistance to a PD1 immunosuppressive signal or a non-PD1 immunosuppressive signal; enhanced tumor-infiltrating lymphocytes (TIL) infiltration and enhanced secretion of a cytokine selected from CD107, IFNγ, IL-2, or TNF; and
   wherein the non-PD1 immunosuppressive signal is selected from the group consisting of TGFβ, adenosine, Indoleamine 2,3-dioxygenase (IDO), hypoxia, T regulatory cells (Tregs), and combinations thereof.

14. The modified T cell of claim 13, wherein the modified T cell is an autologous T cell derived from a human.

15. The modified T cell of claim 13, wherein the non-PD1 immunosuppressive signal is T regulatory cells (Tregs).

16. A method of treating a cancer in a subject in need thereof, the method comprising administering a therapeutically effective composition comprising the modified T cell of claim 13 to the subject, wherein the cancer is selected from the group consisting of multiple myeloma, melanoma, synovial sarcoma, and myxoid/round cell liposarcoma.

17. A modified T cell comprising:
 (a) an exogenous T cell receptor (TCR) having affinity for NY-ESO-1 on a target cell, wherein the exogenous TCR comprises:
  (i) a TCR α chain comprising a variable region having the amino acid sequence set forth in SEQ ID NO:2; and
  (ii) a TCR β chain comprising a variable region having the amino acid sequence set forth in SEQ ID NO:7;
 (b) an endogenous TCR α chain coding sequence comprising the nucleic acid sequence set forth in SEQ ID NO:128, wherein SEQ ID NO:128 comprises at least one nucleotide substitution, deletion, insertion, or insertion and deletion;
 (c) an endogenous TCR β chain coding sequence comprising the nucleic acid sequence set forth in SEQ ID NO:129, wherein SEQ ID NO:129 comprises at least one nucleotide substitution, deletion, insertion, or insertion and deletion; and
 (d) a switch receptor comprising the amino acid sequence set forth in any one of SEQ ID NOs: 136 or 138,
 wherein the expression of the endogenous TCR α chain coding sequence and the expression of the endogenous TCR β chain coding sequence are downregulated;
 wherein the modified T cell exhibits increased resistance to a PD1 immunosuppressive signal or a non-PD1 immunosuppressive signal; enhanced tumor-infiltrating lymphocytes (TIL) infiltration; and enhanced secretion of a cytokine selected from CD107, IFNγ, IL-2, or TNF; and
 wherein the non-PD1 immunosuppressive signal is selected from the group consisting of TGFβ, adenosine, Indoleamine 2,3-dioxygenase (IDO), hypoxia, T regulatory cells (Tregs), and combinations thereof.

18. The modified T cell of claim 17, wherein the modified T cell is an autologous T cell derived from a human.

19. The modified T cell of claim 17, wherein the non-PD1 immunosuppressive signal is T regulatory cells (Tregs).

20. A method of treating a cancer in a subject in need thereof, the method comprising administering a therapeutically effective composition comprising the modified T cell of claim 17 to the subject, wherein the cancer is selected from the group consisting of multiple myeloma, melanoma, synovial sarcoma, and myxoid/round cell liposarcoma.

* * * * *